(12) United States Patent
Kondou et al.

(10) Patent No.: US 10,590,487 B2
(45) Date of Patent: Mar. 17, 2020

(54) LIVER CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoshi Kondou, Kamakura (JP); Hitoshi Nobumasa, Kamakura (JP); Satoko Kozono, Kamakura (JP); Hiroko Sudo, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 289 days.

(21) Appl. No.: 15/319,585

(22) PCT Filed: Jun. 18, 2015

(86) PCT No.: PCT/JP2015/067552
§ 371 (c)(1),
(2) Date: Dec. 16, 2016

(87) PCT Pub. No.: WO2015/194615
PCT Pub. Date: Dec. 23, 2015

(65) Prior Publication Data
US 2017/0166975 A1    Jun. 15, 2017

(30) Foreign Application Priority Data

Jun. 18, 2014 (JP) ................. 2014-124880

(51) Int. Cl.
| C12Q 1/68 | (2018.01) |
| C12P 19/34 | (2006.01) |
| C12Q 1/6886 | (2018.01) |
| G01N 33/574 | (2006.01) |
| G01N 37/00 | (2006.01) |
| G01N 33/53 | (2006.01) |
| C12N 15/09 | (2006.01) |
| C12Q 1/04 | (2006.01) |
| C12M 1/34 | (2006.01) |

(52) U.S. Cl.
CPC ............. *C12Q 1/6886* (2013.01); *C12M 1/34* (2013.01); *C12N 15/09* (2013.01); *C12Q 1/04* (2013.01); *G01N 33/53* (2013.01); *G01N 33/574* (2013.01); *G01N 37/00* (2013.01); *C12Q 2600/118* (2013.01); *C12Q 2600/158* (2013.01); *C12Q 2600/178* (2013.01)

(58) Field of Classification Search
CPC ........ C12Q 2600/158; C12Q 2600/178; C12Q 1/6886; C12Q 1/68; C12Q 1/6876
See application file for complete search history.

(56) References Cited

U.S. PATENT DOCUMENTS

| 2001/0053519 | A1* | 12/2001 | Fodor .................. B01J 19/0046 435/6.11 |
| 2011/0003704 | A1 | 1/2011 | Skog et al. |
| 2012/0115139 | A1 | 5/2012 | Kuroda et al. |
| 2014/0200261 | A1 | 7/2014 | Hoge et al. |

FOREIGN PATENT DOCUMENTS

| CN | 102816861 A | 12/2012 |
| EP | 3 150 707 A1 | 4/2017 |
| EP | 3 156 483 A1 | 4/2017 |
| EP | 3 159 416 A1 | 4/2017 |
| JP | 2013-538583 A | 10/2013 |
| WO | WO 2009/156507 A1 | 12/2009 |
| WO | WO 2010/054386 A9 | 5/2010 |
| WO | WO 2010/055488 A2 | 5/2010 |
| WO | WO 2010/123043 A1 | 10/2010 |
| WO | WO 2011/012074 A1 | 2/2011 |
| WO | WO 2011/076141 A1 | 6/2011 |
| WO | WO 2011/076142 A1 | 6/2011 |
| WO | WO 2012/151212 A1 | 11/2012 |
| WO | WO 2012/151736 A1 | 11/2012 |
| WO | WO 2012/174282 A2 | 12/2012 |
| WO | WO 2014/048441 A1 | 4/2014 |
| WO | WO 2014/114802 A1 | 7/2014 |

OTHER PUBLICATIONS

MiScript™ miRNA PCR Array (384-well, 384HC), Human miRBase Profiler HC Plate 4, Qiagen, pritned pp. 1-10 from https://b2b.qiagen.com/~/media/genetable/mi/hs/34/mihs-3404z (Year: 2012).*
Hoshikawa, Y. et al. Physiol Genomics 12: 209-219, (Year: 2003).*
Chenug V.G. et al. Nature Genetics, p. 422-425vol. 33, Mar., (Year: 2003).*
Cobb, J. P. et al. Crit Care Med,p. 2711-2721, vol. 30, No. 12 (Year: 2002).*
GenBank Locus NR_039836 "Homo sapiens microRNA 1343 (MIR1343), microRNA", (Feb. 27, 2014), from www.ncbi.nlm.nih.gov, pp. 1-3. (Year: 2014).*
Shen, J. et al. "Exploration of Genome-Wide Circulating MicroRNA in Hepatocellular Carcinoma: MiR-483-5p as a Potential Biomarker", Cancer Epidemiol Biomarkers Prev; 22(12), Dec. 2013; 2364-73. (Year: 2013).*
American Cancer Society, "Liver Cancer". 2013, total 58 pages, pp. 5-8, 14-15, 17-23,and 27-41.
Eguchi et al., "Usefulness of microRNA in peripheral blood as tumor marker for liver cancer", Journal of Japan Society of Clinical Oncology, 2011, vol. 46, No. 2, pp. 606, OS66-2.

(Continued)

*Primary Examiner* — Stephen T Kapushoc
(74) *Attorney, Agent, or Firm* — Birch, Stewart, Kolasch & Birch, LLP

(57) ABSTRACT

It is intended to provide a kit or device for the detection of liver cancer and a method for detecting liver cancer. The present invention relates to a kit or device for the detection of liver cancer, comprising a nucleic acid capable of specifically binding to miRNA in a sample of a subject, and a method for detecting liver cancer, comprising measuring the miRNA in vitro.

6 Claims, 4 Drawing Sheets

Specification includes a Sequence Listing.

(56) References Cited

OTHER PUBLICATIONS

Eto et al., "Prospect of microRNA toward laboratory medicine Gastrointestinal Cancer and microRNA", Clinical Chemistry, Apr. 2014, vol. 43, No. 2, pp. 99-105.
International Search Report, issued in PCT/JP2015/067552, dated Sep. 8, 2015.
Li et al., "Expression of serum miR-221 in human hepatocellular carcinoma and its prognostic significance", Biochemical and Biophysical Research Communications, 2011, vol. 406, No. 1, pp. 70-73.
NCCN Guidelines, "Hepatobiliary Cancers, the 2nd edition", 2014, MS-4.
Sobin et al., "TNM Classification of Malignant Tumours, the 7th edition", 2010, pp. 104-107.
Takahashi et al., "Case of clear-cell hepatocellular carcinoma that developed in the normal liver of a middle-aged woman", World Journal of Gastroenterology, 2008, vol. 14 (1), pp. 129-131.
Takizawa et al., "miRNA Profiling in Serum Samples Using DNA Chip 3D-Gene®", Bio Clinica, Jun. 10, 2014, vol. 29, No. 6, pp. 588-589.
Turato et al., "MicroRNAs and SerpinB3 in hepatocellular carcinoma", Life Sciences, Mar. 2014. vol. 100, No. 1, pp. 9-17.
Written Opinion of the International Searching Authority, issued in PCT/JP2015/067552, dated Sep. 8, 2015.
Zhang et al., "Combined . fetoprotein testing and ultrasonography as a screening test for primary liver cancer", Journal of Medical Screening, 1999, vol. 6 (2), pp. 108-110.
"*Homo sapiens* microRNA hsa-miR-1343-3p," EBI Database Accession No. FR772692, (Jan. 13, 2011), sequence.

Anonymous: "Mature sequence hsa-miR-1343-3p," Accession No. MIMAT0091776, miRBase (Jan. 1, 2011), ID hsa-miR-1343-3P, Databse EMBL XP055431878 (Cancer Res. 71:78-86 (2011)).
Anonymous: "miRNA Search Results," miRBase (Jan. 1, 2011), PMID 2119979, XP055431877 (Cancer Res. 71:78-86 (2011)).
Extended European Search Report dated Dec. 15, 2017, in European Patent Application No. 15810147.7.
Persson et al., "Identification of New MicroRNAs in Paired Normal and Tumor Breast Tissue Suggests a Dual Role for the ERBB2/Her2 Gene," Cancer Res. (2011), vol. 71, No. 1, pp. 78-86.
Anonymous: "miRNA Search Results," miRBase (Jan. 1, 2011), PMID 21199797, XP055431877 (Cancer Res. 71:78-86 (2011)).
Office Action dated Apr. 8, 2018, in Chinese Patent Application No. 201580032544.9.
Fu et al., "Circulating microRNA-101 as a potential biomarker for hepatitis B virus-related hepatocellular carcinoma," Oncology Letters (2013), vol. 6, pp. 1811-1815.
Office Action dated Nov. 20, 2018, in Chinese Patent Application No. 201580032544.9.
Estal et al., "MicroRNA signatures in hereditary breast cancer," Breast Cancer Res. Treat. (2013), vol. 142, pp. 19-30.
*Homo sapiens* microRNA 1343 (MIR1343), NCBI[online] (2014), URL, https://ncbi.nlm.nih.gov/nuccore/337756711?sat=18&satkey=18652513.
Office Action dated May 14, 2019, in Japanese Patent Application No. 2016-529424.
Office Action dated May 22, 2019, in Chinese Patent Application No. 201580032544.9.
Zhu, Kai (2012). Study on Role and Mechanism of Angiogenesis-Related microRNAs in Infestation and Metastasis of Hepatocellular Carcinoma (Doctoral Dissertation). Shanghai Medical College, Fudan University, China.

\* cited by examiner

SEQUENCE LISTING

<160> NUMBER OF SEQ ID NOS: 765

<210> SEQ ID NO 1
<211> LENGTH: 22
<212> TYPE: RNA
<213> ORGANISM: Homo sapiens

<400> SEQUENCE: 1
cuccuggggc ccgcacucuc gc                                              22

<210> SEQ ID NO 2
<211> LENGTH: 21
<212> TYPE: RNA
<213> ORGANISM: Homo sapiens

<400> SEQUENCE: 2
cgggagcugg ggucugcagg u                                               21

<210> SEQ ID NO 3
<211> LENGTH: 20
<212> TYPE: RNA
<213> ORGANISM: Homo sapiens

<400> SEQUENCE: 3
ucucuucauc uacccccag                                                  20

<210> SEQ ID NO 4
<211> LENGTH: 20
<212> TYPE: RNA
<213> ORGANISM: Homo sapiens

<400> SEQUENCE: 4
cggggugggu gaggucgggc                                                 20

<210> SEQ ID NO 5
<211> LENGTH: 18
<212> TYPE: RNA
<213> ORGANISM: Homo sapiens

<400> SEQUENCE: 5
ccagaggugg ggacugag                                                   18

<210> SEQ ID NO 6
<211> LENGTH: 23
<212> TYPE: RNA
<213> ORGANISM: Homo sapiens

<400> SEQUENCE: 6
agaggcuuug ugcggauacg ggg                                             23

<210> SEQ ID NO 7
<211> LENGTH: 19
<212> TYPE: RNA
<213> ORGANISM: Homo sapiens

<400> SEQUENCE: 7
ggcuggucag augggagug                                                  19

<210> SEQ ID NO 8
<211> LENGTH: 22
<212> TYPE: RNA
<213> ORGANISM: Homo sapiens

<400> SEQUENCE: 8
ugauugucuu cccccacccu ca                                    22

<210> SEQ ID NO 9
<211> LENGTH: 19
<212> TYPE: RNA
<213> ORGANISM: Homo sapiens

<400> SEQUENCE: 9
uugaucucgg aagcuaagc                                        19

<210> SEQ ID NO 10
<211> LENGTH: 22
<212> TYPE: RNA
<213> ORGANISM: Homo sapiens

<400> SEQUENCE: 10
acgcccuucc cccccuucuu ca                                    22

<210> SEQ ID NO 11
<211> LENGTH: 22
<212> TYPE: RNA
<213> ORGANISM: Homo sapiens

<400> SEQUENCE: 11 cuuccccca guaaucuuca uc                                     22

<210> SEQ ID NO 12
<211> LENGTH: 22
<212> TYPE: RNA
<213> ORGANISM: Homo sapiens

<400> SEQUENCE: 12
uggcgggggu agagcuggcu gc                                    22

<210> SEQ ID NO 13
<211> LENGTH: 20
<212> TYPE: RNA
<213> ORGANISM: Homo sapiens

<400> SEQUENCE: 13
ggauccgagu cacggcacca                                       20

<210> SEQ ID NO 14
<211> LENGTH: 22
<212> TYPE: RNA
<213> ORGANISM: Homo sapiens

<400> SEQUENCE: 14
ggcuggagcg agugcagugg ug                                    22

<210> SEQ ID NO 15
<211> LENGTH: 21
<212> TYPE: RNA
<213> ORGANISM: Homo sapiens

<400> SEQUENCE: 15
ucaccuggcu ggcccgccca g                                     21

<210> SEQ ID NO 16
<211> LENGTH: 18
<212> TYPE: RNA
<213> ORGANISM: Homo sapiens

<400> SEQUENCE: 16
auccuaguca cggcacca                                                   18

<210> SEQ ID NO 17
<211> LENGTH: 21
<212> TYPE: RNA
<213> ORGANISM: Homo sapiens

<400> SEQUENCE: 17
gcugggaagg caaagggacg u                                               21

<210> SEQ ID NO 18
<211> LENGTH: 18
<212> TYPE: RNA
<213> ORGANISM: Homo sapiens

<400> SEQUENCE: 18
uucccagcca acgcacca                                                   18

<210> SEQ ID NO 19
<211> LENGTH: 21
<212> TYPE: RNA
<213> ORGANISM: Homo sapiens

<400> SEQUENCE: 19
ugggggugug gggagagaga g                                               21

<210> SEQ ID NO 20
<211> LENGTH: 22
<212> TYPE: RNA
<213> ORGANISM: Homo sapiens

<400> SEQUENCE: 20
aggcgaugug gggauguaga ga                                              22

<210> SEQ ID NO 21
<211> LENGTH: 19
<212> TYPE: RNA
<213> ORGANISM: Homo sapiens

<400> SEQUENCE: 21 uggggggagau ggggguuga                                                 19

<210> SEQ ID NO 22
<211> LENGTH: 22
<212> TYPE: RNA
<213> ORGANISM: Homo sapiens

<400> SEQUENCE: 22
gguggcccgg ccgugccuga gg                                              22

<210> SEQ ID NO 23
<211> LENGTH: 21
<212> TYPE: RNA
<213> ORGANISM: Homo sapiens

<400> SEQUENCE: 23
ugagggaccc aggacaggag a                                               21

<210> SEQ ID NO 24
<211> LENGTH: 20
<212> TYPE: RNA
<213> ORGANISM: Homo sapiens

```
<400> SEQUENCE: 24
ggcggcgggg agguaggcag                                               20

<210> SEQ ID NO 25
<211> LENGTH: 21
<212> TYPE: RNA
<213> ORGANISM: Homo sapiens

<400> SEQUENCE: 25 ugggggcgggg caggucccug c                                            21

<210> SEQ ID NO 26
<211> LENGTH: 18
<212> TYPE: RNA
<213> ORGANISM: Homo sapiens

<400> SEQUENCE: 26
gggucccggg gaggggggg                                                18

<210> SEQ ID NO 27
<211> LENGTH: 22
<212> TYPE: RNA
<213> ORGANISM: Homo sapiens

<400> SEQUENCE: 27
ugggcgaggg cggcugagcg gc                                            22

<210> SEQ ID NO 28
<211> LENGTH: 23
<212> TYPE: RNA
<213> ORGANISM: Homo sapiens

<400> SEQUENCE: 28
ggaugguugg gggcggucgg cgu                                           23

<210> SEQ ID NO 29
<211> LENGTH: 25
<212> TYPE: RNA
<213> ORGANISM: Homo sapiens

<400> SEQUENCE: 29
agcggggagg aagugggcgc ugcuu                                         25

<210> SEQ ID NO 30
<211> LENGTH: 21
<212> TYPE: RNA
<213> ORGANISM: Homo sapiens

<400> SEQUENCE: 30
guguggccgg caggcgggug g                                             21

<210> SEQ ID NO 31
<211> LENGTH: 21
<212> TYPE: RNA
<213> ORGANISM: Homo sapiens

<400> SEQUENCE: 31
caggaguggg ggguggacg u                                              21

<210> SEQ ID NO 32
<211> LENGTH: 21
<212> TYPE: RNA
```

```
<213> ORGANISM: Homo sapiens

<400> SEQUENCE: 32
caggcaggug uaggguggag c                                             21

<210> SEQ ID NO 33
<211> LENGTH: 22
<212> TYPE: RNA
<213> ORGANISM: Homo sapiens

<400> SEQUENCE: 33
uuggggauug ggucaggcca gu                                            22

<210> SEQ ID NO 34
<211> LENGTH: 17
<212> TYPE: RNA
<213> ORGANISM: Homo sapiens

<400> SEQUENCE: 34 gugggccag gcggugg                                                   17

<210> SEQ ID NO 35
<211> LENGTH: 22
<212> TYPE: RNA
<213> ORGANISM: Homo sapiens

<400> SEQUENCE: 35
gugggugcug gugggagccg ug                                            22

<210> SEQ ID NO 36
<211> LENGTH: 22
<212> TYPE: RNA
<213> ORGANISM: Homo sapiens

<400> SEQUENCE: 36
aaaccguuac cauuacugag uu                                            22

<210> SEQ ID NO 37
<211> LENGTH: 22
<212> TYPE: RNA
<213> ORGANISM: Homo sapiens

<400> SEQUENCE: 37
ucaaaaucag gagucggggc uu                                            22

<210> SEQ ID NO 38
<211> LENGTH: 22
<212> TYPE: RNA
<213> ORGANISM: Homo sapiens

<400> SEQUENCE: 38
caggcacggg agcucaggug ag                                            22

<210> SEQ ID NO 39
<211> LENGTH: 22
<212> TYPE: RNA
<213> ORGANISM: Homo sapiens

<400> SEQUENCE: 39 ggggguccccc ggugcucgga uc                                           22

<210> SEQ ID NO 40
<211> LENGTH: 23
```

-continued

<212> TYPE: RNA
<213> ORGANISM: Homo sapiens

<400> SEQUENCE: 40
cggggccgua gcacugucug aga                                         23

<210> SEQ ID NO 41
<211> LENGTH: 22
<212> TYPE: RNA
<213> ORGANISM: Homo sapiens

<400> SEQUENCE: 41 ugggaggug uggagucagc au                                           22

<210> SEQ ID NO 42
<211> LENGTH: 19
<212> TYPE: RNA
<213> ORGANISM: Homo sapiens

<400> SEQUENCE: 42
aucccaccac ugccaccau                                              19

<210> SEQ ID NO 43
<211> LENGTH: 21
<212> TYPE: RNA
<213> ORGANISM: Homo sapiens

<400> SEQUENCE: 43
acaggagugg ggugggaca u                                            21

<210> SEQ ID NO 44
<211> LENGTH: 23
<212> TYPE: RNA
<213> ORGANISM: Homo sapiens

<400> SEQUENCE: 44 cuggggacg cgugagcgcg agc                                          23

<210> SEQ ID NO 45
<211> LENGTH: 21
<212> TYPE: RNA
<213> ORGANISM: Homo sapiens

<400> SEQUENCE: 45
aagggacagg gagggucgug g                                           21

<210> SEQ ID NO 46
<211> LENGTH: 21
<212> TYPE: RNA
<213> ORGANISM: Homo sapiens

<400> SEQUENCE: 46 cggcgggac ggcgauuggu c                                            21

<210> SEQ ID NO 47
<211> LENGTH: 22
<212> TYPE: RNA
<213> ORGANISM: Homo sapiens

<400> SEQUENCE: 47
gcccaggacu uugugcgggg ug                                          22

<210> SEQ ID NO 48

```
<211> LENGTH: 25
<212> TYPE: RNA
<213> ORGANISM: Homo sapiens

<400> SEQUENCE: 48
gugaggcggg gccaggaggg ugugu                                          25

<210> SEQ ID NO 49
<211> LENGTH: 21
<212> TYPE: RNA
<213> ORGANISM: Homo sapiens

<400> SEQUENCE: 49 agggccccccc cucaauccug u                                             21

<210> SEQ ID NO 50
<211> LENGTH: 22
<212> TYPE: RNA
<213> ORGANISM: Homo sapiens

<400> SEQUENCE: 50
caucucuaag gaacuccccc aa                                             22

<210> SEQ ID NO 51
<211> LENGTH: 21
<212> TYPE: RNA
<213> ORGANISM: Homo sapiens

<400> SEQUENCE: 51
cgggccggag gucaagggcg u                                              21

<210> SEQ ID NO 52
<211> LENGTH: 23
<212> TYPE: RNA
<213> ORGANISM: Homo sapiens

<400> SEQUENCE: 52
ugaggggcag agagcgagac uuu                                            23

<210> SEQ ID NO 53
<211> LENGTH: 23
<212> TYPE: RNA
<213> ORGANISM: Homo sapiens

<400> SEQUENCE: 53
ugagcaccac acaggccggg cgc                                            23

<210> SEQ ID NO 54
<211> LENGTH: 20
<212> TYPE: RNA
<213> ORGANISM: Homo sapiens

<400> SEQUENCE: 54
gccggggcuu ugggugaggg                                                20

<210> SEQ ID NO 55
<211> LENGTH: 22
<212> TYPE: RNA
<213> ORGANISM: Homo sapiens

<400> SEQUENCE: 55
ucgggccugg gguugggga gc                                              22
```

```
<210> SEQ ID NO 56
<211> LENGTH: 20
<212> TYPE: RNA
<213> ORGANISM: Homo sapiens

<400> SEQUENCE: 56
gugucugggc ggacagcugc                                               20

<210> SEQ ID NO 57
<211> LENGTH: 21
<212> TYPE: RNA
<213> ORGANISM: Homo sapiens

<400> SEQUENCE: 57
agcggugcuc cugcgggccg a                                             21

<210> SEQ ID NO 58
<211> LENGTH: 23
<212> TYPE: RNA
<213> ORGANISM: Homo sapiens

<400> SEQUENCE: 58
uggggaaggc uuggcaggga aga                                           23

<210> SEQ ID NO 59
<211> LENGTH: 23
<212> TYPE: RNA
<213> ORGANISM: Homo sapiens

<400> SEQUENCE: 59 gugagugggga gccgguggg cug                                           23

<210> SEQ ID NO 60
<211> LENGTH: 23
<212> TYPE: RNA
<213> ORGANISM: Homo sapiens

<400> SEQUENCE: 60
ugaggauaug gcagggaagg gga                                           23

<210> SEQ ID NO 61
<211> LENGTH: 24
<212> TYPE: RNA
<213> ORGANISM: Homo sapiens

<400> SEQUENCE: 61
ugaggggccu cagaccgagc uuuu                                          24

<210> SEQ ID NO 62
<211> LENGTH: 20
<212> TYPE: RNA
<213> ORGANISM: Homo sapiens

<400> SEQUENCE: 62
gcggaaggcg gagcggcgga                                               20

<210> SEQ ID NO 63
<211> LENGTH: 23
<212> TYPE: RNA
<213> ORGANISM: Homo sapiens

<400> SEQUENCE: 63
ugggcagggg cuuauuguag gag                                           23
```

```
<210> SEQ ID NO 64
<211> LENGTH: 22
<212> TYPE: RNA
<213> ORGANISM: Homo sapiens

<400> SEQUENCE: 64
ccccuggggc ugggcaggcg ga                                              22

<210> SEQ ID NO 65
<211> LENGTH: 23
<212> TYPE: RNA
<213> ORGANISM: Homo sapiens

<400> SEQUENCE: 65
agaagaaggc ggucggucug cgg                                             23

<210> SEQ ID NO 66
<211> LENGTH: 18
<212> TYPE: RNA
<213> ORGANISM: Homo sapiens

<400> SEQUENCE: 66
aucccaccuc ugccacca                                                   18

<210> SEQ ID NO 67
<211> LENGTH: 23
<212> TYPE: RNA
<213> ORGANISM: Homo sapiens

<400> SEQUENCE: 67
ggaggcgcag gcucggaaag gcg                                             23

<210> SEQ ID NO 68
<211> LENGTH: 19
<212> TYPE: RNA
<213> ORGANISM: Homo sapiens

<400> SEQUENCE: 68
cggggccaga gcagagagc                                                  19

<210> SEQ ID NO 69
<211> LENGTH: 23
<212> TYPE: RNA
<213> ORGANISM: Homo sapiens

<400> SEQUENCE: 69
uggggggaca gauggagagg aca                                             23

<210> SEQ ID NO 70
<211> LENGTH: 23
<212> TYPE: RNA
<213> ORGANISM: Homo sapiens

<400> SEQUENCE: 70 cgaggguag aagagcacag ggg                                              23

<210> SEQ ID NO 71
<211> LENGTH: 21
<212> TYPE: RNA
<213> ORGANISM: Homo sapiens

<400> SEQUENCE: 71
cccaugccuc cugccgcggu c                                               21
```

```
<210> SEQ ID NO 72
<211> LENGTH: 17
<212> TYPE: RNA
<213> ORGANISM: Homo sapiens

<400> SEQUENCE: 72
cuccgggacg gcugggc                                                    17

<210> SEQ ID NO 73
<211> LENGTH: 24
<212> TYPE: RNA
<213> ORGANISM: Homo sapiens

<400> SEQUENCE: 73
guggguaggg uuuggggag agcg                                             24

<210> SEQ ID NO 74
<211> LENGTH: 19
<212> TYPE: RNA
<213> ORGANISM: Homo sapiens

<400> SEQUENCE: 74
ugcggcagag cugggguca                                                  19

<210> SEQ ID NO 75
<211> LENGTH: 23
<212> TYPE: RNA
<213> ORGANISM: Homo sapiens

<400> SEQUENCE: 75
acggggaguc aggcaguggu gga                                             23

<210> SEQ ID NO 76
<211> LENGTH: 20
<212> TYPE: RNA
<213> ORGANISM: Homo sapiens

<400> SEQUENCE: 76
gcucggacug agcagguggg                                                 20

<210> SEQ ID NO 77
<211> LENGTH: 20
<212> TYPE: RNA
<213> ORGANISM: Homo sapiens

<400> SEQUENCE: 77
gggcuggggc gcgggaggu                                                  20

<210> SEQ ID NO 78
<211> LENGTH: 17
<212> TYPE: RNA
<213> ORGANISM: Homo sapiens

<400> SEQUENCE: 78
accccacucc ugguacc                                                    17

<210> SEQ ID NO 79
<211> LENGTH: 22
<212> TYPE: RNA
<213> ORGANISM: Homo sapiens

<400> SEQUENCE: 79
```
agggccgaag gguggaagcu gc    22

<210> SEQ ID NO 80
<211> LENGTH: 22
<212> TYPE: RNA
<213> ORGANISM: Homo sapiens

<400> SEQUENCE: 80
ugagccccug ugccgccccc ag    22

<210> SEQ ID NO 81
<211> LENGTH: 20
<212> TYPE: RNA
<213> ORGANISM: Homo sapiens

<400> SEQUENCE: 81
agagaugaag cggggggggcg    20

<210> SEQ ID NO 82
<211> LENGTH: 21
<212> TYPE: RNA
<213> ORGANISM: Homo sapiens

<400> SEQUENCE: 82
guaggugaca gucaggggcg g    21

<210> SEQ ID NO 83
<211> LENGTH: 19
<212> TYPE: RNA
<213> ORGANISM: Homo sapiens

<400> SEQUENCE: 83
aauggauuuu uggagcagg    19

<210> SEQ ID NO 84
<211> LENGTH: 22
<212> TYPE: RNA
<213> ORGANISM: Homo sapiens

<400> SEQUENCE: 84
uggcggcggu aguuaugggc uu    22

<210> SEQ ID NO 85
<211> LENGTH: 18
<212> TYPE: RNA
<213> ORGANISM: Homo sapiens

<400> SEQUENCE: 85
gaggcugaag gaagaugg    18

<210> SEQ ID NO 86
<211> LENGTH: 22
<212> TYPE: RNA
<213> ORGANISM: Homo sapiens

<400> SEQUENCE: 86
ggaggggucc cgcacuggga gg    22

<210> SEQ ID NO 87
<211> LENGTH: 23
<212> TYPE: RNA
<213> ORGANISM: Homo sapiens

<400> SEQUENCE: 87
gagggcagcg ugggugugge gga                                           23

<210> SEQ ID NO 88
<211> LENGTH: 22
<212> TYPE: RNA
<213> ORGANISM: Homo sapiens

<400> SEQUENCE: 88
accuugccuu gcugcccggg cc                                            22

<210> SEQ ID NO 89
<211> LENGTH: 20
<212> TYPE: RNA
<213> ORGANISM: Homo sapiens

<400> SEQUENCE: 89
guggguuggg gcgggcucug                                               20

<210> SEQ ID NO 90
<211> LENGTH: 22
<212> TYPE: RNA
<213> ORGANISM: Homo sapiens

<400> SEQUENCE: 90
auauacaggg ggagacucuc au                                            22

<210> SEQ ID NO 91
<211> LENGTH: 22
<212> TYPE: RNA
<213> ORGANISM: Homo sapiens

<400> SEQUENCE: 91
ccgggagaag gagguggccu gg                                            22

<210> SEQ ID NO 92
<211> LENGTH: 24
<212> TYPE: RNA
<213> ORGANISM: Homo sapiens

<400> SEQUENCE: 92
agggcuggac ucagcggcgg agcu                                          24

<210> SEQ ID NO 93
<211> LENGTH: 21
<212> TYPE: RNA
<213> ORGANISM: Homo sapiens

<400> SEQUENCE: 93
gugggcgggg gcaggugugu g                                             21

<210> SEQ ID NO 94
<211> LENGTH: 21
<212> TYPE: RNA
<213> ORGANISM: Homo sapiens

<400> SEQUENCE: 94
guuggggugc aggggucugc u                                             21

<210> SEQ ID NO 95
<211> LENGTH: 19
<212> TYPE: RNA
<213> ORGANISM: Homo sapiens

```
<400> SEQUENCE: 95
ggcuugcaug ggggacugg                                              19

<210> SEQ ID NO 96
<211> LENGTH: 21
<212> TYPE: RNA
<213> ORGANISM: Homo sapiens

<400> SEQUENCE: 96
acucggcugc gguggacaag u                                           21

<210> SEQ ID NO 97
<211> LENGTH: 20
<212> TYPE: RNA
<213> ORGANISM: Homo sapiens

<400> SEQUENCE: 97
ggggaggugu gcagggcugg                                             20

<210> SEQ ID NO 98
<211> LENGTH: 22
<212> TYPE: RNA
<213> ORGANISM: Homo sapiens

<400> SEQUENCE: 98
acuggguagg ugggcucca gg                                           22

<210> SEQ ID NO 99
<211> LENGTH: 23
<212> TYPE: RNA
<213> ORGANISM: Homo sapiens

<400> SEQUENCE: 99
cucggggcag gcggcuggga gcg                                         23

<210> SEQ ID NO 100
<211> LENGTH: 22
<212> TYPE: RNA
<213> ORGANISM: Homo sapiens

<400> SEQUENCE: 100
agacugacgg cuggaggccc au                                          22

<210> SEQ ID NO 101
<211> LENGTH: 23
<212> TYPE: RNA
<213> ORGANISM: Homo sapiens

<400> SEQUENCE: 101
uugcucugcu ccccgcccc cag                                          23

<210> SEQ ID NO 102
<211> LENGTH: 22
<212> TYPE: RNA
<213> ORGANISM: Homo sapiens

<400> SEQUENCE: 102
caggcaggga ggugggacca ug                                          22

<210> SEQ ID NO 103
<211> LENGTH: 22
<212> TYPE: RNA
<213> ORGANISM: Homo sapiens
```

```
<400> SEQUENCE: 103
cgucccgggg cugcgcgagg ca                                      22

<210> SEQ ID NO 104
<211> LENGTH: 20
<212> TYPE: RNA
<213> ORGANISM: Homo sapiens

<400> SEQUENCE: 104
ccugagcccg ggccgcgcag                                         20

<210> SEQ ID NO 105
<211> LENGTH: 17
<212> TYPE: RNA
<213> ORGANISM: Homo sapiens

<400> SEQUENCE: 105 guggggaga ggcuguc                                             17

<210> SEQ ID NO 106
<211> LENGTH: 18
<212> TYPE: RNA
<213> ORGANISM: Homo sapiens

<400> SEQUENCE: 106
cggugagcgc ucgcuggc                                           18

<210> SEQ ID NO 107
<211> LENGTH: 17
<212> TYPE: RNA
<213> ORGANISM: Homo sapiens

<400> SEQUENCE: 107
uuggaggcgu ggguuuu                                            17

<210> SEQ ID NO 108
<211> LENGTH: 19
<212> TYPE: RNA
<213> ORGANISM: Homo sapiens

<400> SEQUENCE: 108
uaaggagggg gaugagggg                                          19

<210> SEQ ID NO 109
<211> LENGTH: 23
<212> TYPE: RNA
<213> ORGANISM: Homo sapiens

<400> SEQUENCE: 109
ucaauaggaa agagguggga ccu                                     23

<210> SEQ ID NO 110
<211> LENGTH: 22
<212> TYPE: RNA
<213> ORGANISM: Homo sapiens

<400> SEQUENCE: 110
gugagccagu ggaauggaga gg                                      22

<210> SEQ ID NO 111
<211> LENGTH: 18
<212> TYPE: RNA
```

```
<213> ORGANISM: Homo sapiens

<400> SEQUENCE: 111
cuggcagggg gagaggua                                                   18

<210> SEQ ID NO 112
<211> LENGTH: 17
<212> TYPE: RNA
<213> ORGANISM: Homo sapiens

<400> SEQUENCE: 112
ggauggagga ggggucu                                                    17

<210> SEQ ID NO 113
<211> LENGTH: 22
<212> TYPE: RNA
<213> ORGANISM: Homo sapiens

<400> SEQUENCE: 113
caggaaggau uuagggacag gc                                              22

<210> SEQ ID NO 114
<211> LENGTH: 24
<212> TYPE: RNA
<213> ORGANISM: Homo sapiens

<400> SEQUENCE: 114
ugggcgaggg gugggcucuc agag                                            24

<210> SEQ ID NO 115
<211> LENGTH: 21
<212> TYPE: RNA
<213> ORGANISM: Homo sapiens

<400> SEQUENCE: 115 gggggaugu gcaugcuggu u                                                21

<210> SEQ ID NO 116
<211> LENGTH: 20
<212> TYPE: RNA
<213> ORGANISM: Homo sapiens

<400> SEQUENCE: 116
ccccagggcg acgcggcggg                                                 20

<210> SEQ ID NO 117
<211> LENGTH: 17
<212> TYPE: RNA
<213> ORGANISM: Homo sapiens

<400> SEQUENCE: 117
gggagaaggg ucggggc                                                    17

<210> SEQ ID NO 118
<211> LENGTH: 18
<212> TYPE: RNA
<213> ORGANISM: Homo sapiens

<400> SEQUENCE: 118
ggugggcuuc ccggaggg                                                   18

<210> SEQ ID NO 119
<211> LENGTH: 22
```

```
<212> TYPE: RNA
<213> ORGANISM: Homo sapiens

<400> SEQUENCE: 119
agacacauuu ggagagggac cc                                          22

<210> SEQ ID NO 120
<211> LENGTH: 19
<212> TYPE: RNA
<213> ORGANISM: Homo sapiens

<400> SEQUENCE: 120
gagggcgggu ggaggagga                                              19

<210> SEQ ID NO 121
<211> LENGTH: 22
<212> TYPE: RNA
<213> ORGANISM: Homo sapiens

<400> SEQUENCE: 121
uucagauccc agcggugccu cu                                          22

<210> SEQ ID NO 122
<211> LENGTH: 23
<212> TYPE: RNA
<213> ORGANISM: Homo sapiens

<400> SEQUENCE: 122 uggggcugg gaugggccau ggu                                          23

<210> SEQ ID NO 123
<211> LENGTH: 25
<212> TYPE: RNA
<213> ORGANISM: Homo sapiens

<400> SEQUENCE: 123
aagggaggag gagcggaggg gcccu                                       25

<210> SEQ ID NO 124
<211> LENGTH: 22
<212> TYPE: RNA
<213> ORGANISM: Homo sapiens

<400> SEQUENCE: 124
ccaggaggcg gaggaggugg ag                                          22

<210> SEQ ID NO 125
<211> LENGTH: 21
<212> TYPE: RNA
<213> ORGANISM: Homo sapiens

<400> SEQUENCE: 125
cgggggcggg gccgaagcgc g                                           21

<210> SEQ ID NO 126
<211> LENGTH: 22
<212> TYPE: RNA
<213> ORGANISM: Homo sapiens

<400> SEQUENCE: 126
gaggguuggg uggaggcucu cc                                          22

<210> SEQ ID NO 127
```

```
<211> LENGTH: 26
<212> TYPE: RNA
<213> ORGANISM: Homo sapiens

<400> SEQUENCE: 127
cucggccgcg gcgcguagcc cccgcc                                          26

<210> SEQ ID NO 128
<211> LENGTH: 21
<212> TYPE: RNA
<213> ORGANISM: Homo sapiens

<400> SEQUENCE: 128 gcgugggc cggaggggcg u                                                 21

<210> SEQ ID NO 129
<211> LENGTH: 17
<212> TYPE: RNA
<213> ORGANISM: Homo sapiens

<400> SEQUENCE: 129
ccccgccacc gccuugg                                                    17

<210> SEQ ID NO 130
<211> LENGTH: 22
<212> TYPE: RNA
<213> ORGANISM: Homo sapiens

<400> SEQUENCE: 130
cagcagggga gagagaggag uc                                              22

<210> SEQ ID NO 131
<211> LENGTH: 22
<212> TYPE: RNA
<213> ORGANISM: Homo sapiens

<400> SEQUENCE: 131
uggggagcgg cccccgggug gg                                              22

<210> SEQ ID NO 132
<211> LENGTH: 24
<212> TYPE: RNA
<213> ORGANISM: Homo sapiens

<400> SEQUENCE: 132
ccccgggaac gucgagacug gagc                                            24

<210> SEQ ID NO 133
<211> LENGTH: 22
<212> TYPE: RNA
<213> ORGANISM: Homo sapiens

<400> SEQUENCE: 133 uaggggcgg cuuguggagu gu                                               22

<210> SEQ ID NO 134
<211> LENGTH: 17
<212> TYPE: RNA
<213> ORGANISM: Homo sapiens

<400> SEQUENCE: 134
ggggcugggc gcgcgcc                                                    17
```

```
<210> SEQ ID NO 135
<211> LENGTH: 22
<212> TYPE: RNA
<213> ORGANISM: Homo sapiens

<400> SEQUENCE: 135
cucggcgcgg ggcgcgggcu cc                                              22

<210> SEQ ID NO 136
<211> LENGTH: 20
<212> TYPE: RNA
<213> ORGANISM: Homo sapiens

<400> SEQUENCE: 136
cgggcguggu gguggggug                                                  20

<210> SEQ ID NO 137
<211> LENGTH: 22
<212> TYPE: RNA
<213> ORGANISM: Homo sapiens

<400> SEQUENCE: 137
gugaggaggg gcuggcaggg ac                                              22

<210> SEQ ID NO 138
<211> LENGTH: 23
<212> TYPE: RNA
<213> ORGANISM: Homo sapiens

<400> SEQUENCE: 138
acaggcggcu guagcaaugg ggg                                             23

<210> SEQ ID NO 139
<211> LENGTH: 24
<212> TYPE: RNA
<213> ORGANISM: Homo sapiens

<400> SEQUENCE: 139 ugggggagcug aggcucuggg ggug                                           24

<210> SEQ ID NO 140
<211> LENGTH: 17
<212> TYPE: RNA
<213> ORGANISM: Homo sapiens

<400> SEQUENCE: 140
ggcgggugcg gggugg                                                     17

<210> SEQ ID NO 141
<211> LENGTH: 22
<212> TYPE: RNA
<213> ORGANISM: Homo sapiens

<400> SEQUENCE: 141
ugcggggcua gggcuaacag ca                                              22

<210> SEQ ID NO 142
<211> LENGTH: 21
<212> TYPE: RNA
<213> ORGANISM: Homo sapiens

<400> SEQUENCE: 142
uggcuguugg aggggggcagg c                                              21
```

```
<210> SEQ ID NO 143
<211> LENGTH: 24
<212> TYPE: RNA
<213> ORGANISM: Homo sapiens

<400> SEQUENCE: 143
aggcaggggc uggugcuggg cggg                                          24

<210> SEQ ID NO 144
<211> LENGTH: 22
<212> TYPE: RNA
<213> ORGANISM: Homo sapiens

<400> SEQUENCE: 144
gugggcuggg cuggcuggg cc                                             22

<210> SEQ ID NO 145
<211> LENGTH: 17
<212> TYPE: RNA
<213> ORGANISM: Homo sapiens

<400> SEQUENCE: 145
cgcgccgggc ccggguu                                                  17

<210> SEQ ID NO 146
<211> LENGTH: 22
<212> TYPE: RNA
<213> ORGANISM: Homo sapiens

<400> SEQUENCE: 146
uggggguggu cucuagccaa gg                                            22

<210> SEQ ID NO 147
<211> LENGTH: 23
<212> TYPE: RNA
<213> ORGANISM: Homo sapiens

<400> SEQUENCE: 147
gccccggcgc gggcggguuc ugg                                           23

<210> SEQ ID NO 148
<211> LENGTH: 22
<212> TYPE: RNA
<213> ORGANISM: Homo sapiens

<400> SEQUENCE: 148
agacacauuu ggagagggaa cc                                            22

<210> SEQ ID NO 149
<211> LENGTH: 23
<212> TYPE: RNA
<213> ORGANISM: Homo sapiens

<400> SEQUENCE: 149
ccucccugcc cgccucucug cag                                           23

<210> SEQ ID NO 150
<211> LENGTH: 23
<212> TYPE: RNA
<213> ORGANISM: Homo sapiens

<400> SEQUENCE: 150 ugggaggga gaggcagcaa gca                                            23
```

```
<210> SEQ ID NO 151
<211> LENGTH: 21
<212> TYPE: RNA
<213> ORGANISM: Homo sapiens

<400> SEQUENCE: 151
auccaguucu cugaggggc u                                          21

<210> SEQ ID NO 152
<211> LENGTH: 22
<212> TYPE: RNA
<213> ORGANISM: Homo sapiens

<400> SEQUENCE: 152
auauacaggg ggagacucuu au                                        22

<210> SEQ ID NO 153
<211> LENGTH: 25
<212> TYPE: RNA
<213> ORGANISM: Homo sapiens

<400> SEQUENCE: 153
acuugggcag gagggacccu guaug                                     25

<210> SEQ ID NO 154
<211> LENGTH: 22
<212> TYPE: RNA
<213> ORGANISM: Homo sapiens

<400> SEQUENCE: 154
ggggaacugu agaugaaaag gc                                        22

<210> SEQ ID NO 155
<211> LENGTH: 23
<212> TYPE: RNA
<213> ORGANISM: Homo sapiens

<400> SEQUENCE: 155
ucgaggacug guggaagggc cuu                                       23

<210> SEQ ID NO 156
<211> LENGTH: 21
<212> TYPE: RNA
<213> ORGANISM: Homo sapiens

<400> SEQUENCE: 156
cguggaggac gaggaggagg c                                         21

<210> SEQ ID NO 157
<211> LENGTH: 17
<212> TYPE: RNA
<213> ORGANISM: Homo sapiens

<400> SEQUENCE: 157
gagacugggg uggggcc                                              17

<210> SEQ ID NO 158
<211> LENGTH: 23
<212> TYPE: RNA
<213> ORGANISM: Homo sapiens

<400> SEQUENCE: 158
```

```
gggggccgau acacuguacg aga                                          23

<210> SEQ ID NO 159
<211> LENGTH: 17
<212> TYPE: RNA
<213> ORGANISM: Homo sapiens

<400> SEQUENCE: 159
gcggggcugg gcgcgcg                                                 17

<210> SEQ ID NO 160
<211> LENGTH: 24
<212> TYPE: RNA
<213> ORGANISM: Homo sapiens

<400> SEQUENCE: 160
uguaggcaug aggcagggcc cagg                                         24

<210> SEQ ID NO 161
<211> LENGTH: 22
<212> TYPE: RNA
<213> ORGANISM: Homo sapiens

<400> SEQUENCE: 161 uggggagga aggacaggcc au                                            22

<210> SEQ ID NO 162
<211> LENGTH: 25
<212> TYPE: RNA
<213> ORGANISM: Homo sapiens

<400> SEQUENCE: 162 uaggguggg ggaauucagg ggugu                                         25

<210> SEQ ID NO 163
<211> LENGTH: 22
<212> TYPE: RNA
<213> ORGANISM: Homo sapiens

<400> SEQUENCE: 163
gcugcgggcu gcggucaggg cg                                           22

<210> SEQ ID NO 164
<211> LENGTH: 23
<212> TYPE: RNA
<213> ORGANISM: Homo sapiens

<400> SEQUENCE: 164
uuagggagua gaagguggg gag                                           23

<210> SEQ ID NO 165
<211> LENGTH: 22
<212> TYPE: RNA
<213> ORGANISM: Homo sapiens

<400> SEQUENCE: 165
gugaacgggc gccaucccga gg                                           22

<210> SEQ ID NO 166
<211> LENGTH: 22
<212> TYPE: RNA
<213> ORGANISM: Homo sapiens

<400> SEQUENCE: 166
```

```
gggggguguq gagccagggg gc                              22

<210> SEQ ID NO 167
<211> LENGTH: 23
<212> TYPE: RNA
<213> ORGANISM: Homo sapiens

<400> SEQUENCE: 167
cugggcccgc ggcgggcgug ggg                             23

<210> SEQ ID NO 168
<211> LENGTH: 21
<212> TYPE: RNA
<213> ORGANISM: Homo sapiens

<400> SEQUENCE: 168
aucacauugc cagggauuac c                               21

<210> SEQ ID NO 169
<211> LENGTH: 21
<212> TYPE: RNA
<213> ORGANISM: Homo sapiens

<400> SEQUENCE: 169
aucacauugc cagggauuuc c                               21

<210> SEQ ID NO 170
<211> LENGTH: 22
<212> TYPE: RNA
<213> ORGANISM: Homo sapiens

<400> SEQUENCE: 170
gacuauagaa cuuucccccu ca                              22

<210> SEQ ID NO 171
<211> LENGTH: 20
<212> TYPE: RNA
<213> ORGANISM: Homo sapiens

<400> SEQUENCE: 171
ucacaccugc cucgccccccc                                20

<210> SEQ ID NO 172
<211> LENGTH: 23
<212> TYPE: RNA
<213> ORGANISM: Homo sapiens

<400> SEQUENCE: 172
gaacgccugu ucuugccagg ugg                             23

<210> SEQ ID NO 173
<211> LENGTH: 22
<212> TYPE: RNA
<213> ORGANISM: Homo sapiens

<400> SEQUENCE: 173
ucugcccccu ccgcugcugc ca                              22

<210> SEQ ID NO 174
<211> LENGTH: 22
<212> TYPE: RNA
<213> ORGANISM: Homo sapiens
```

<400> SEQUENCE: 174 gguggggau uguugcauu ac                                          22

<210> SEQ ID NO 175
<211> LENGTH: 22
<212> TYPE: RNA
<213> ORGANISM: Homo sapiens

<400> SEQUENCE: 175
ggcuacaaca caggacccgg gc                                        22

<210> SEQ ID NO 176
<211> LENGTH: 22
<212> TYPE: RNA
<213> ORGANISM: Homo sapiens

<400> SEQUENCE: 176
uagcagcacg uaaauauugg cg                                        22

<210> SEQ ID NO 177
<211> LENGTH: 22
<212> TYPE: RNA
<213> ORGANISM: Homo sapiens

<400> SEQUENCE: 177
uauugcacuc gucccggccu cc                                        22

<210> SEQ ID NO 178
<211> LENGTH: 22
<212> TYPE: RNA
<213> ORGANISM: Homo sapiens

<400> SEQUENCE: 178
cugguacagg ccuggggac ag                                         22

<210> SEQ ID NO 179
<211> LENGTH: 19
<212> TYPE: RNA
<213> ORGANISM: Homo sapiens

<400> SEQUENCE: 179
aggcacggug ucagcaggc                                            19

<210> SEQ ID NO 180
<211> LENGTH: 22
<212> TYPE: RNA
<213> ORGANISM: Homo sapiens

<400> SEQUENCE: 180
acaggugagg uucuugggag cc                                        22

<210> SEQ ID NO 181
<211> LENGTH: 22
<212> TYPE: RNA
<213> ORGANISM: Homo sapiens

<400> SEQUENCE: 181
agggacggga cgcggugcag ug                                        22

<210> SEQ ID NO 182
<211> LENGTH: 22
<212> TYPE: RNA
<213> ORGANISM: Homo sapiens

```
<400> SEQUENCE: 182
uauugcacuu gucccggccu gu                                         22

<210> SEQ ID NO 183
<211> LENGTH: 22
<212> TYPE: RNA
<213> ORGANISM: Homo sapiens

<400> SEQUENCE: 183
aggcggggcg ccgcgggacc gc                                         22

<210> SEQ ID NO 184
<211> LENGTH: 22
<212> TYPE: RNA
<213> ORGANISM: Homo sapiens

<400> SEQUENCE: 184
uaggggcagc agaggaccug gg                                         22

<210> SEQ ID NO 185
<211> LENGTH: 20
<212> TYPE: RNA
<213> ORGANISM: Homo sapiens

<400> SEQUENCE: 185
ugugggacug caaaugggag                                            20

<210> SEQ ID NO 186
<211> LENGTH: 19
<212> TYPE: RNA
<213> ORGANISM: Homo sapiens

<400> SEQUENCE: 186
aaggggcugg gggagcaca                                             19

<210> SEQ ID NO 187
<211> LENGTH: 18
<212> TYPE: RNA
<213> ORGANISM: Homo sapiens

<400> SEQUENCE: 187
gugaaggccc ggcggaga                                              18

<210> SEQ ID NO 188
<211> LENGTH: 22
<212> TYPE: RNA
<213> ORGANISM: Homo sapiens

<400> SEQUENCE: 188
ugguggagga agagggcagc uc                                         22

<210> SEQ ID NO 189
<211> LENGTH: 23
<212> TYPE: RNA
<213> ORGANISM: Homo sapiens

<400> SEQUENCE: 189
gggggggcag gaggggcuca ggg                                        23

<210> SEQ ID NO 190
<211> LENGTH: 23
<212> TYPE: RNA
```

<213> ORGANISM: Homo sapiens

<400> SEQUENCE: 190
cacacaggaa aagcggggcc cug                                    23

<210> SEQ ID NO 191
<211> LENGTH: 19
<212> TYPE: RNA
<213> ORGANISM: Homo sapiens

<400> SEQUENCE: 191 ugggcggag cuuccggag                                          19

<210> SEQ ID NO 192
<211> LENGTH: 18
<212> TYPE: RNA
<213> ORGANISM: Homo sapiens

<400> SEQUENCE: 192
ugaggcgggg gggcgagc                                          18

<210> SEQ ID NO 193
<211> LENGTH: 21
<212> TYPE: RNA
<213> ORGANISM: Homo sapiens

<400> SEQUENCE: 193
accacugcac uccagccuga g                                      21

<210> SEQ ID NO 194
<211> LENGTH: 22
<212> TYPE: RNA
<213> ORGANISM: Homo sapiens

<400> SEQUENCE: 194
guggguacgg cccagugggg gg                                     22

<210> SEQ ID NO 195
<211> LENGTH: 18
<212> TYPE: RNA
<213> ORGANISM: Homo sapiens

<400> SEQUENCE: 195
cggggcggca ggggccuc                                          18

<210> SEQ ID NO 196
<211> LENGTH: 22
<212> TYPE: RNA
<213> ORGANISM: Homo sapiens

<400> SEQUENCE: 196
caggaggcag ugggcgagca gg                                     22

<210> SEQ ID NO 197
<211> LENGTH: 20
<212> TYPE: RNA
<213> ORGANISM: Homo sapiens

<400> SEQUENCE: 197 uaggggugg caggcuggcc                                         20

<210> SEQ ID NO 198
<211> LENGTH: 25

<212> TYPE: RNA
<213> ORGANISM: Homo sapiens

<400> SEQUENCE: 198
agggaucgcg ggcggguggc ggccu    25

<210> SEQ ID NO 199
<211> LENGTH: 23
<212> TYPE: RNA
<213> ORGANISM: Homo sapiens

<400> SEQUENCE: 199
caggggcugg gguuucaggu ucu    23

<210> SEQ ID NO 200
<211> LENGTH: 20
<212> TYPE: RNA
<213> ORGANISM: Homo sapiens

<400> SEQUENCE: 200
accaggaggc ugaggccccu    20

<210> SEQ ID NO 201
<211> LENGTH: 21
<212> TYPE: RNA
<213> ORGANISM: Homo sapiens

<400> SEQUENCE: 201
cggggcagcu caguacagga u    21

<210> SEQ ID NO 202
<211> LENGTH: 18
<212> TYPE: RNA
<213> ORGANISM: Homo sapiens

<400> SEQUENCE: 202
gggugcgggc cggcgggg    18

<210> SEQ ID NO 203
<211> LENGTH: 22
<212> TYPE: RNA
<213> ORGANISM: Homo sapiens

<400> SEQUENCE: 203
cugggagagg guuguuuacu cc    22

<210> SEQ ID NO 204
<211> LENGTH: 20
<212> TYPE: RNA
<213> ORGANISM: Homo sapiens

<400> SEQUENCE: 204
cgcgggucgg ggucugcagg    20

<210> SEQ ID NO 205
<211> LENGTH: 22
<212> TYPE: RNA
<213> ORGANISM: Homo sapiens

<400> SEQUENCE: 205
aaggggcagg gacggguggc cc    22

<210> SEQ ID NO 206

```
<211> LENGTH: 22
<212> TYPE: RNA
<213> ORGANISM: Homo sapiens

<400> SEQUENCE: 206
cugggacagg aggaggaggc ag                                              22

<210> SEQ ID NO 207
<211> LENGTH: 23
<212> TYPE: RNA
<213> ORGANISM: Homo sapiens

<400> SEQUENCE: 207
cgggcugucc ggaggggucg gcu                                             23

<210> SEQ ID NO 208
<211> LENGTH: 22
<212> TYPE: RNA
<213> ORGANISM: Homo sapiens

<400> SEQUENCE: 208
gggaccaucc ugccugcugu gg                                              22

<210> SEQ ID NO 209
<211> LENGTH: 22
<212> TYPE: RNA
<213> ORGANISM: Homo sapiens

<400> SEQUENCE: 209
guaggggagg uugggccagg ga                                              22

<210> SEQ ID NO 210
<211> LENGTH: 22
<212> TYPE: RNA
<213> ORGANISM: Homo sapiens

<400> SEQUENCE: 210 uggggagug cagugauugu gg                                               22

<210> SEQ ID NO 211
<211> LENGTH: 20
<212> TYPE: RNA
<213> ORGANISM: Homo sapiens

<400> SEQUENCE: 211
acucaaacug uggggcacu                                                  20

<210> SEQ ID NO 212
<211> LENGTH: 18
<212> TYPE: RNA
<213> ORGANISM: Homo sapiens

<400> SEQUENCE: 212
agggggcggg cuccggcg                                                   18

<210> SEQ ID NO 213
<211> LENGTH: 22
<212> TYPE: RNA
<213> ORGANISM: Homo sapiens

<400> SEQUENCE: 213
agugggaggc cagggcacgg ca                                              22
```

```
<210> SEQ ID NO 214
<211> LENGTH: 24
<212> TYPE: RNA
<213> ORGANISM: Homo sapiens

<400> SEQUENCE: 214 uggggagcc augagauaag agca                                            24

<210> SEQ ID NO 215
<211> LENGTH: 22
<212> TYPE: RNA
<213> ORGANISM: Homo sapiens

<400> SEQUENCE: 215
uggcucaguu cagcaggaac ag                                             22

<210> SEQ ID NO 216
<211> LENGTH: 23
<212> TYPE: RNA
<213> ORGANISM: Homo sapiens

<400> SEQUENCE: 216
gugaguggga gccccagugu gug                                            23

<210> SEQ ID NO 217
<211> LENGTH: 17
<212> TYPE: RNA
<213> ORGANISM: Homo sapiens

<400> SEQUENCE: 217
gccggacaag agggagg                                                   17

<210> SEQ ID NO 218
<211> LENGTH: 22
<212> TYPE: RNA
<213> ORGANISM: Homo sapiens

<400> SEQUENCE: 218
ggaggaaccu uggagcuucg gc                                             22

<210> SEQ ID NO 219
<211> LENGTH: 20
<212> TYPE: RNA
<213> ORGANISM: Homo sapiens

<400> SEQUENCE: 219
ugggaauggg gguaagggcc                                                20

<210> SEQ ID NO 220
<211> LENGTH: 24
<212> TYPE: RNA
<213> ORGANISM: Homo sapiens

<400> SEQUENCE: 220
ggaggccggg gugggggcggg gcgg                                          24

<210> SEQ ID NO 221
<211> LENGTH: 20
<212> TYPE: RNA
<213> ORGANISM: Homo sapiens

<400> SEQUENCE: 221
gggaaaagga aggggagga                                                 20
```

```
<210> SEQ ID NO 222
<211> LENGTH: 22
<212> TYPE: RNA
<213> ORGANISM: Homo sapiens

<400> SEQUENCE: 222
agugggagga caggaggcag gu                                              22

<210> SEQ ID NO 223
<211> LENGTH: 23
<212> TYPE: RNA
<213> ORGANISM: Homo sapiens

<400> SEQUENCE: 223
guuugcacgg gugggccuug ucu                                             23

<210> SEQ ID NO 224
<211> LENGTH: 19
<212> TYPE: RNA
<213> ORGANISM: Homo sapiens

<400> SEQUENCE: 224
ggggagcgag gggcggggc                                                  19

<210> SEQ ID NO 225
<211> LENGTH: 84
<212> TYPE: RNA
<213> ORGANISM: Homo sapiens

<400> SEQUENCE: 225
gcuggcgucg gugcugggga gcggcccccg gguggccuc ugcucuggcc ccuccugggg      60
cccgcacucu cgcucugggc ccgc                                            84

<210> SEQ ID NO 226
<211> LENGTH: 61
<212> TYPE: RNA
<213> ORGANISM: Homo sapiens

<400> SEQUENCE: 226
gggggcggga gcuggggucu gcagguucgc acugaugccu gcucgcccug ucuccgcua      60 g                                                                     61

<210> SEQ ID NO 227
<211> LENGTH: 57
<212> TYPE: RNA
<213> ORGANISM: Homo sapiens

<400> SEQUENCE: 227
cauuggaggg uguggaagac aucugggcca acucugaucu cuucaucuac cccccag        57

<210> SEQ ID NO 228
<211> LENGTH: 73
<212> TYPE: RNA
<213> ORGANISM: Homo sapiens

<400> SEQUENCE: 228
cggcgacggc gggguggug aggucgggcc ccaagacucg ggguuugccg ggcgccucag      60
uucaccgcgg ccg                                                        73

<210> SEQ ID NO 229
<211> LENGTH: 86
```

```
<212> TYPE: RNA
<213> ORGANISM: Homo sapiens

<400> SEQUENCE: 229
ggcuuagaaa caguccccuag guaggauuug gggaggagcu aagaagcccc uacagggccc    60
agaggugggg acugagccuu aguugg                                         86

<210> SEQ ID NO 230
<211> LENGTH: 85
<212> TYPE: RNA
<213> ORGANISM: Homo sapiens

<400> SEQUENCE: 230
ggcgccuccu gcucugcugu gccgccaggg ccuccccuag cgcgccuucu ggagaggcuu    60
ugugcggaua cggggcugga ggccu                                          85

<210> SEQ ID NO 231
<211> LENGTH: 109
<212> TYPE: RNA
<213> ORGANISM: Homo sapiens

<400> SEQUENCE: 231
ucccgcauuc ccucugcuuu ggucaggugg ugcccuccuu ccauggguag agccagagau    60
gguggguucu ggcuggucag auggagugg acagagaccc gggguccuc                109

<210> SEQ ID NO 232
<211> LENGTH: 72
<212> TYPE: RNA
<213> ORGANISM: Homo sapiens

<400> SEQUENCE: 232
augagcgggu gggagcagau cuuauugaga guuccuucuc cugcuccuga uugucuuccc    60 ccaccccucac ag                                                       72

<210> SEQ ID NO 233
<211> LENGTH: 61
<212> TYPE: RNA
<213> ORGANISM: Homo sapiens

<400> SEQUENCE: 233
ucucguuuga ucucggaagc uaagcagggu ugggccuggu aguacuuggg augggaaacu    60
u                                                                    61

<210> SEQ ID NO 234
<211> LENGTH: 53
<212> TYPE: RNA
<213> ORGANISM: Homo sapiens

<400> SEQUENCE: 234
guuugaucuc ggaagcuaag cagggucggg ccugguuagu acuuggaugg gag           53

<210> SEQ ID NO 235
<211> LENGTH: 66
<212> TYPE: RNA
<213> ORGANISM: Homo sapiens

<400> SEQUENCE: 235
gggaggaggg aggagauggg ccaaguuccc ucuggcugga acgcccuucc ccccuucuu    60 caccug                                                               66
```

```
<210> SEQ ID NO 236
<211> LENGTH: 68
<212> TYPE: RNA
<213> ORGANISM: Homo sapiens

<400> SEQUENCE: 236
cguggugagg auauggcagg gaaggggagu uucccucuau ucccuucccc ccaguaaucu    60
ucaucaug                                                            68

<210> SEQ ID NO 237
<211> LENGTH: 61
<212> TYPE: RNA
<213> ORGANISM: Homo sapiens

<400> SEQUENCE: 237
ucggcuggcg ggguagagc uggcugcagg cccggcccu cucagcugcu gcccucucca     60
g                                                                   61

<210> SEQ ID NO 238
<211> LENGTH: 55
<212> TYPE: RNA
<213> ORGANISM: Homo sapiens

<400> SEQUENCE: 238
ccggauccga gucacggcac caaauuucau gcguguccgu gugaagagac cacca         55

<210> SEQ ID NO 239
<211> LENGTH: 68
<212> TYPE: RNA
<213> ORGANISM: Homo sapiens

<400> SEQUENCE: 239
ugcccaggcu ggagcgagug caguggugca gucaguccua gcucacugca gccucgaacu   60
ccugggcu                                                            68

<210> SEQ ID NO 240
<211> LENGTH: 87
<212> TYPE: RNA
<213> ORGANISM: Homo sapiens

<400> SEQUENCE: 240
gugaggcggg gccaggaggg uguguggcgu gggugcugcg gggccgucag ggugccugcg   60
ggacgcucac cuggcuggcc cgcccag                                       87

<210> SEQ ID NO 241
<211> LENGTH: 68
<212> TYPE: RNA
<213> ORGANISM: Homo sapiens

<400> SEQUENCE: 241
gugcaaagag caggaggaca ggggauuuau cucccaaggg aggucccug auccaguca     60 cggcacca                                                            68

<210> SEQ ID NO 242
<211> LENGTH: 110
<212> TYPE: RNA
<213> ORGANISM: Homo sapiens

<400> SEQUENCE: 242
ggcuacaguc uuucuucaug ugacucgugg acuucccuuu gucauccuau gccugagaau   60
```

```
auaugaagga ggcugggaag gcaaagggac guucaauugu caucacuggc                    110
```

<210> SEQ ID NO 243
<211> LENGTH: 49
<212> TYPE: RNA
<213> ORGANISM: Homo sapiens

<400> SEQUENCE: 243

```
uucccagcca acgcaccaaa aaugauaugg gucuguuguc uggagaaac                     49
```

<210> SEQ ID NO 244
<211> LENGTH: 86
<212> TYPE: RNA
<213> ORGANISM: Homo sapiens

<400> SEQUENCE: 244

```
ggggcugggg guguggggag agagagugca cagccagcuc agggauuaaa gcucuuucuc         60
ucucucucuc ucccacuucc cugcag                                              86
```

<210> SEQ ID NO 245
<211> LENGTH: 73
<212> TYPE: RNA
<213> ORGANISM: Homo sapiens

<400> SEQUENCE: 245

```
cugguguuug aggcgaugug gggauguaga gacaacuucc cagucucauu uccucauccu         60
gccaggccac cau                                                            73
```

<210> SEQ ID NO 246
<211> LENGTH: 60
<212> TYPE: RNA
<213> ORGANISM: Homo sapiens

<400> SEQUENCE: 246

```
caaggugggg gagauggggg uugaacuuca uuucucaugc ucaucccau cuccuuucag          60
```

<210> SEQ ID NO 247
<211> LENGTH: 115
<212> TYPE: RNA
<213> ORGANISM: Homo sapiens

<400> SEQUENCE: 247

```
ggugccgagg gccguccggc auccuaggcg ggucgcugcg guaccucccu ccugucugug         60 gcgguggau cccguggccg uguuuccug guggcccggc cgugccgag guuuc                115
```

<210> SEQ ID NO 248
<211> LENGTH: 72
<212> TYPE: RNA
<213> ORGANISM: Homo sapiens

<400> SEQUENCE: 248

```
gagucugagg gacccaggac aggagaaggc cuauggugau uugcauucuu ccugcccugg         60
cuccauccuc ag                                                             72
```

<210> SEQ ID NO 249
<211> LENGTH: 80
<212> TYPE: RNA
<213> ORGANISM: Homo sapiens

<400> SEQUENCE: 249

```
gcgucaagau ggcggcgggg agguaggcag agcaggacgc cgcugcugcc gccgccaccg    60
ccgccuccgc uccagucgcc                                                80

<210> SEQ ID NO 250
<211> LENGTH: 66
<212> TYPE: RNA
<213> ORGANISM: Homo sapiens

<400> SEQUENCE: 250
ccgagugggg cggggcaggu cccugcaggg acugugacac ugaaggaccu gcaccuucgc    60
ccacag                                                               66

<210> SEQ ID NO 251
<211> LENGTH: 62
<212> TYPE: RNA
<213> ORGANISM: Homo sapiens

<400> SEQUENCE: 251
gcuggggguc ccccgacagu guggagcugg ggccgggucc cggggagggg gguucugggc    60
ag                                                                   62

<210> SEQ ID NO 252
<211> LENGTH: 65
<212> TYPE: RNA
<213> ORGANISM: Homo sapiens

<400> SEQUENCE: 252
gagggugggc gagggcggcu gagcggcucc auccccggc cugcucaucc cccucgcccu     60
cucag                                                                65

<210> SEQ ID NO 253
<211> LENGTH: 86
<212> TYPE: RNA
<213> ORGANISM: Homo sapiens

<400> SEQUENCE: 253
cgccugagcg ugcagcagga caucuuccug accugguaau aauuagguga gaaggauggu    60 uggggcggu cggcguaacu caggga                                          86

<210> SEQ ID NO 254
<211> LENGTH: 82
<212> TYPE: RNA
<213> ORGANISM: Homo sapiens

<400> SEQUENCE: 254
gcuacgggga gcgggagga aguggcgcu gcuucugcgu uaucuggaag gagcagccca      60
cuccuguccu gggcucugug gu                                             82

<210> SEQ ID NO 255
<211> LENGTH: 87
<212> TYPE: RNA
<213> ORGANISM: Homo sapiens

<400> SEQUENCE: 255
guguggccgg caggcgggug ggcggggcg gccgguggga acccgcccc gccccgcgcc      60 cgcacucacc cgcccgucuc cccacag                                        87

<210> SEQ ID NO 256
<211> LENGTH: 102
```

```
<212> TYPE: RNA
<213> ORGANISM: Homo sapiens

<400> SEQUENCE: 256
uguguucccu auccuccuua ugucccaccc ccacuccugu uugaauauuu caccagaaac    60
aggagugggg gguggggacgu aaggaggaug ggggaaagaa ca                     102

<210> SEQ ID NO 257
<211> LENGTH: 69
<212> TYPE: RNA
<213> ORGANISM: Homo sapiens

<400> SEQUENCE: 257
ccgggcaggc agguguaggg uggagcccac ugggcuccu gacucagccc ugcugccuuc    60
accugccag                                                           69

<210> SEQ ID NO 258
<211> LENGTH: 93
<212> TYPE: RNA
<213> ORGANISM: Homo sapiens

<400> SEQUENCE: 258
gcuuguuggg gauuggguca ggccaguguu caagggcccc uccucuagua cucccuguuu    60
guguucugcc acugacugag cuucuccca cag                                  93

<210> SEQ ID NO 259
<211> LENGTH: 88
<212> TYPE: RNA
<213> ORGANISM: Homo sapiens

<400> SEQUENCE: 259
guggggccag gcgguggugg gcacugcugg gguggggcaca gcagccaugc agagcgggca    60
uuugaccccg ugccacccuu uuccccag                                       88

<210> SEQ ID NO 260
<211> LENGTH: 63
<212> TYPE: RNA
<213> ORGANISM: Homo sapiens

<400> SEQUENCE: 260
aauggguggg ugcugguggg agccgugccc uggccacuca uucggcucuc ucccucaccc    60
uag                                                                   63

<210> SEQ ID NO 261
<211> LENGTH: 72
<212> TYPE: RNA
<213> ORGANISM: Homo sapiens

<400> SEQUENCE: 261
cuugggaaug gcaaggaaac cguuaccauu acugaguuua guaaugguaa ugguucucuu    60
gcuauaccca ga                                                        72

<210> SEQ ID NO 262
<211> LENGTH: 81
<212> TYPE: RNA
<213> ORGANISM: Homo sapiens

<400> SEQUENCE: 262
uagaggcagu uucaacagau guguagacuu uugauaugag aaauuggu uu caaaaucagg    60
```
agucggggcu uuacugcuuu u                                             81

<210> SEQ ID NO 263
<211> LENGTH: 83
<212> TYPE: RNA
<213> ORGANISM: Homo sapiens

<400> SEQUENCE: 263
aauagagggu gcacaggcac gggagcucag gugaggcagg gagcugagcu caccugaccu    60
cccaugccug ugcacccucu auu                                           83

<210> SEQ ID NO 264
<211> LENGTH: 96
<212> TYPE: RNA
<213> ORGANISM: Homo sapiens

<400> SEQUENCE: 264
cucgggaggg gcgggagggg ggucccccggu gcucggaucu cgagggugcu uauuguucgg    60
uccgagccug ggucucccuc uuccccccaa cccccc                             96

<210> SEQ ID NO 265
<211> LENGTH: 82
<212> TYPE: RNA
<213> ORGANISM: Homo sapiens

<400> SEQUENCE: 265
ugagcuguug gauucggggc cguagcacug ucgagaggu uuacauuucu cacagugaac    60
cggucucuuu uucagcugcu uc                                            82

<210> SEQ ID NO 266
<211> LENGTH: 66
<212> TYPE: RNA
<213> ORGANISM: Homo sapiens

<400> SEQUENCE: 266
gggcaugggg aggugguggag ucagcauggg gcuaggaggc cccgcgcuga cccgccuucu    60
ccgcag                                                              66

<210> SEQ ID NO 267
<211> LENGTH: 89
<212> TYPE: RNA
<213> ORGANISM: Homo sapiens

<400> SEQUENCE: 267
ucuccguuua ucccaccacu gccaccauua uugcuacugu ucagcaggug cugcuggugg    60
ugauggugau agucuggugg gggcggugg                                     89

<210> SEQ ID NO 268
<211> LENGTH: 81
<212> TYPE: RNA
<213> ORGANISM: Homo sapiens

<400> SEQUENCE: 268
cauccuccuu acgucccacc ccccacuccu guuucuggug aaauauucaa acaggagugg    60
gggugggaca uaaggaggau a                                             81

<210> SEQ ID NO 269
<211> LENGTH: 79
<212> TYPE: RNA
<213> ORGANISM: Homo sapiens

```
<400> SEQUENCE: 269
cucgaggugc uggggggacgc gugagcgcga gccgcuuccu cacggcucgg ccgcggcgcg        60
uagcccccgc cacaucggg                                                     79

<210> SEQ ID NO 270
<211> LENGTH: 99
<212> TYPE: RNA
<213> ORGANISM: Homo sapiens

<400> SEQUENCE: 270
gcaagggaca gggagggucg uggcgacacu cgcgccagcu cccgggacgg cugggcucgg        60
gcuggucgcc gaccuccgac ccuccacuag augccuggc                               99

<210> SEQ ID NO 271
<211> LENGTH: 80
<212> TYPE: RNA
<213> ORGANISM: Homo sapiens

<400> SEQUENCE: 271
cgggaaugcc gcggcgggga cggcgauugg uccguaugug uggugccacc ggccgccggc        60
uccgccccgg ccccgcccc                                                     80

<210> SEQ ID NO 272
<211> LENGTH: 71
<212> TYPE: RNA
<213> ORGANISM: Homo sapiens

<400> SEQUENCE: 272
ugaccacccc cgggcaaaga ccugcagauc cccuguuaga cacgggccca ggacuuugug        60
cggggugccc a                                                             71

<210> SEQ ID NO 273
<211> LENGTH: 80
<212> TYPE: RNA
<213> ORGANISM: Homo sapiens

<400> SEQUENCE: 273
aggacccuuc cagagggccc ccccucaauc cuguugugcc uaauucagag gguugggugg        60
aggcucuccu gaagggcucu                                                    80

<210> SEQ ID NO 274
<211> LENGTH: 73
<212> TYPE: RNA
<213> ORGANISM: Homo sapiens

<400> SEQUENCE: 274
ggaugauaag uuaugggggcu ucuguagaga uuucuaugag aacaucucua aggaacuccc       60
ccaaacugaa uuc                                                           73

<210> SEQ ID NO 275
<211> LENGTH: 64
<212> TYPE: RNA
<213> ORGANISM: Homo sapiens

<400> SEQUENCE: 275
aaccccgggc cggaggucaa gggcgucgcu ucucccuaau guugccucuu uuccacggcc        60
ucag                                                                     64
```

```
<210> SEQ ID NO 276
<211> LENGTH: 94
<212> TYPE: RNA
<213> ORGANISM: Homo sapiens

<400> SEQUENCE: 276
auaaaggaag uuaggcugag gggcagagag cgagacuuuu cuauuuucca aaagcucggu      60
cugaggcccc ucagucuugc uuccuaaccc gcgc                                 94

<210> SEQ ID NO 277
<211> LENGTH: 97
<212> TYPE: RNA
<213> ORGANISM: Homo sapiens

<400> SEQUENCE: 277
cccgggaccu ugguccaggc gcuggucugc guggugcucg gguggauaag ucgaucuga      60 gcaccacaca ggccgggcgc cgggaccaag ggggcuc                              97

<210> SEQ ID NO 278
<211> LENGTH: 67
<212> TYPE: RNA
<213> ORGANISM: Homo sapiens

<400> SEQUENCE: 278
uacaggccgg ggcuuugggu gagggacccc cggagucugu cacggcucca ccccaacucu     60
gccccag                                                               67

<210> SEQ ID NO 279
<211> LENGTH: 69
<212> TYPE: RNA
<213> ORGANISM: Homo sapiens

<400> SEQUENCE: 279
ggcccucggg ccugggguug ggggagcucu guccugucuc acucauugcu ccucccugc      60 cuggcccag                                                             69

<210> SEQ ID NO 280
<211> LENGTH: 92
<212> TYPE: RNA
<213> ORGANISM: Homo sapiens

<400> SEQUENCE: 280
gucagugucu gggcggacag cugcaggaaa gggaagacca aggcuugcug ucuguccagu     60
cugccacccu acccugucug uucuugccac ag                                   92

<210> SEQ ID NO 281
<211> LENGTH: 71
<212> TYPE: RNA
<213> ORGANISM: Homo sapiens

<400> SEQUENCE: 281
gugucugugc cggucccagg agaaccugca gaggcaucgg gucagcggug cuccugcggg     60
ccgacacuca c                                                          71

<210> SEQ ID NO 282
<211> LENGTH: 79
<212> TYPE: RNA
<213> ORGANISM: Homo sapiens

<400> SEQUENCE: 282
``` cagccuggggg aaggcuuggc agggaagaca caugagcagu gccuccacuu cacgccucuc    60 ccugucucc uucccuag                                                    79

<210> SEQ ID NO 283
<211> LENGTH: 71
<212> TYPE: RNA
<213> ORGANISM: Homo sapiens

<400> SEQUENCE: 283 ggugagugggg agccgguggg gcuggaguaa gggcacgccc ggggcugccc caccugcuga    60
ccacccuccc c                                                          71

<210> SEQ ID NO 284
<211> LENGTH: 75
<212> TYPE: RNA
<213> ORGANISM: Homo sapiens

<400> SEQUENCE: 284
aagcaagacu gaggggccuc agaccgagcu uuggaaaau agaaaagucu cgcucucugc     60
cccucagccu aacuu                                                      75

<210> SEQ ID NO 285
<211> LENGTH: 96
<212> TYPE: RNA
<213> ORGANISM: Homo sapiens

<400> SEQUENCE: 285
gcucuggggc gugccgccgc cgucgcugcc accuccccua ccgcuagugg aagaagaugg    60
cggaaggcgg agcggcggau cuggacaccc agcggu                              96

<210> SEQ ID NO 286
<211> LENGTH: 87
<212> TYPE: RNA
<213> ORGANISM: Homo sapiens

<400> SEQUENCE: 286
cccucaucuc ugggcagggg cuuauuguag gagucucuga agagagcugu ggacugaccu    60
gcuuuaaccc uuccccaggu ucccauu                                        87

<210> SEQ ID NO 287
<211> LENGTH: 67
<212> TYPE: RNA
<213> ORGANISM: Homo sapiens

<400> SEQUENCE: 287
ccagaccccu gggcugggc aggcggaaag aggucugaac ugccucugcc uccuuggucu    60
ccggcag                                                              67

<210> SEQ ID NO 288
<211> LENGTH: 68
<212> TYPE: RNA
<213> ORGANISM: Homo sapiens

<400> SEQUENCE: 288
gaauggaaga agaaggcggu cggucugcgg gagccaggcc gcagagccau ccgccuucug    60
uccauguc                                                             68

<210> SEQ ID NO 289

```
<211> LENGTH: 73
<212> TYPE: RNA
<213> ORGANISM: Homo sapiens

<400> SEQUENCE: 289
accuuuccag cucaucccac cucugccacc aaaacacuca ucgcggguc agagggagug    60 ccaaaaaagg uaa                                                    73

<210> SEQ ID NO 290
<211> LENGTH: 73
<212> TYPE: RNA
<213> ORGANISM: Homo sapiens

<400> SEQUENCE: 290
ggcgagggga ggcgcaggcu cggaaaggcg cgcgaggcuc caggcuccuu cccgauccac    60
cgcucuccuc gcu                                                    73

<210> SEQ ID NO 291
<211> LENGTH: 61
<212> TYPE: RNA
<213> ORGANISM: Homo sapiens

<400> SEQUENCE: 291
aacugcgggg ccagagcaga gagcccuugc acaccaccag ccucuccucc cugugcccca    60
g                                                                 61

<210> SEQ ID NO 292
<211> LENGTH: 65
<212> TYPE: RNA
<213> ORGANISM: Homo sapiens

<400> SEQUENCE: 292
gagaaugggg ggacagaugg agaggacaca ggcuggcacu gagguccccu ccacuuuccu    60
ccuag                                                             65

<210> SEQ ID NO 293
<211> LENGTH: 64
<212> TYPE: RNA
<213> ORGANISM: Homo sapiens

<400> SEQUENCE: 293
gaaggcgagg gguagaagag cacaggggu cugauaaacc cuucugccug cauucuacuc    60
ccag                                                              64

<210> SEQ ID NO 294
<211> LENGTH: 62
<212> TYPE: RNA
<213> ORGANISM: Homo sapiens

<400> SEQUENCE: 294
gugggucucg caucaggagg caaggccagg acccgcugac ccaugccucc ugccgcgguc    60
ag                                                                62

<210> SEQ ID NO 295
<211> LENGTH: 89
<212> TYPE: RNA
<213> ORGANISM: Homo sapiens

<400> SEQUENCE: 295
accuccggga cggcugggcg ccggcggccg ggagauccgc gcuuccugaa ucccggccgg    60
```

```
cccgcccggc gcccguccgc ccgcggguc                              89
```

<210> SEQ ID NO 296
<211> LENGTH: 69
<212> TYPE: RNA
<213> ORGANISM: Homo sapiens

<400> SEQUENCE: 296

```
guggguaggg uuuggggag agcgugggcu gggguucagg gacacccucu caccacugcc   60
cucccacag                                                         69
```

<210> SEQ ID NO 297
<211> LENGTH: 62
<212> TYPE: RNA
<213> ORGANISM: Homo sapiens

<400> SEQUENCE: 297

```
ccuucugcgg cagagcuggg gucaccagcc cucauguacu ugugacuucu ccccugccac   60
ag                                                                62
```

<210> SEQ ID NO 298
<211> LENGTH: 66
<212> TYPE: RNA
<213> ORGANISM: Homo sapiens

<400> SEQUENCE: 298

```
ucaagacggg gagucaggca gugguggaga uggagagccc ugagccucca cucuccuggc   60
ccccag                                                            66
```

<210> SEQ ID NO 299
<211> LENGTH: 93
<212> TYPE: RNA
<213> ORGANISM: Homo sapiens

<400> SEQUENCE: 299

```
ggcgcuuuug ugcgcgcccg ggucuguugg ugcucagagu guggucaggc ggcucggacu   60
gagcaggugg gugcggggcu cggaggaggc ggc                              93
```

<210> SEQ ID NO 300
<211> LENGTH: 55
<212> TYPE: RNA
<213> ORGANISM: Homo sapiens

<400> SEQUENCE: 300

```
gggggcuggg gcgcgggag gugcuagguc ggccucggcu cccgcgccgc acccc         55
```

<210> SEQ ID NO 301
<211> LENGTH: 93
<212> TYPE: RNA
<213> ORGANISM: Homo sapiens

<400> SEQUENCE: 301

```
uacuuauggc accccacucc ugguaccaua gucauaaguu aggagauguu agagcuguga   60
guaccaugac uuaagugugg uggcuuaaac aug                              93
```

<210> SEQ ID NO 302
<211> LENGTH: 64
<212> TYPE: RNA
<213> ORGANISM: Homo sapiens

<400> SEQUENCE: 302
aguucagggc cgaagggugg aagcugcugg ugcucaucuc agccucugcc cuuggccucc    60
ccag                                                                64

<210> SEQ ID NO 303
<211> LENGTH: 90
<212> TYPE: RNA
<213> ORGANISM: Homo sapiens

<400> SEQUENCE: 303
guggguacgg cccagugggg gggagaggga cacgcccugg gcucugccca gggugcagcc    60
ggacugacug agccccugug ccgccccag                                     90

<210> SEQ ID NO 304
<211> LENGTH: 51
<212> TYPE: RNA
<213> ORGANISM: Homo sapiens

<400> SEQUENCE: 304
agagaugaag cgggggggcg gggucuugcu cuauugccua cgcugaucuc a             51

<210> SEQ ID NO 305
<211> LENGTH: 82
<212> TYPE: RNA
<213> ORGANISM: Homo sapiens

<400> SEQUENCE: 305
accuguaggu gacagucagg ggcggggugu ggugggcug ggcuggccc ccuccucaca      60 ccucuccugg caucgccccc ag                                            82

<210> SEQ ID NO 306
<211> LENGTH: 73
<212> TYPE: RNA
<213> ORGANISM: Homo sapiens

<400> SEQUENCE: 306
uguauccuug aauggauuuu uggagcagga guggacaccu gacccaaagg aaaucaaucc    60
auaggcuagc aau                                                      73

<210> SEQ ID NO 307
<211> LENGTH: 63
<212> TYPE: RNA
<213> ORGANISM: Homo sapiens

<400> SEQUENCE: 307
ugguggcggc gguaguuaug ggcuucucuu ucucaccagc agccccuggg ccgccgccuc    60
ccu                                                                 63

<210> SEQ ID NO 308
<211> LENGTH: 68
<212> TYPE: RNA
<213> ORGANISM: Homo sapiens

<400> SEQUENCE: 308
cucaggcuca guggugcaug cuuauagucc cagccacucu ggaggcugaa ggaagauggc    60
uugagccu                                                            68

<210> SEQ ID NO 309
<211> LENGTH: 80

```
<212> TYPE: RNA
<213> ORGANISM: Homo sapiens

<400> SEQUENCE: 309
cgugugagcc cgcccugugc ccggcccacu ucugcuuccu cuuagcgcag gaggggucccc    60 gcacugggag gggcccucac                                                 80

<210> SEQ ID NO 310
<211> LENGTH: 61
<212> TYPE: RNA
<213> ORGANISM: Homo sapiens

<400> SEQUENCE: 310
gagggcagcg uggugugggc ggaggcaggc gugaccguuu gccgcccucu cgcugcucua    60
g                                                                     61

<210> SEQ ID NO 311
<211> LENGTH: 80
<212> TYPE: RNA
<213> ORGANISM: Homo sapiens

<400> SEQUENCE: 311
ugagaggccg caccuugccu ugcugcccgg gccgugcacc cgugggcccc agggcgacgc    60
ggcgggggcg gcccuagcga                                                 80

<210> SEQ ID NO 312
<211> LENGTH: 102
<212> TYPE: RNA
<213> ORGANISM: Homo sapiens

<400> SEQUENCE: 312
gcuuaucgag gaaaagaucg aggugggguug gggcgggcuc uggggauuug gucucacagc    60
ccggauccca gcccacuuac cuugguuacu cuccuuccuu cu                       102

<210> SEQ ID NO 313
<211> LENGTH: 86
<212> TYPE: RNA
<213> ORGANISM: Homo sapiens

<400> SEQUENCE: 313
uuugguacuu aaagagagga uacccuuugu auguucacuu gauuaauggc gaauauacag    60
ggggagacuc ucauuugcgu aucaaa                                          86

<210> SEQ ID NO 314
<211> LENGTH: 63
<212> TYPE: RNA
<213> ORGANISM: Homo sapiens

<400> SEQUENCE: 314
cuugcccggg agaaggaggu ggccuggaga gcugcugucu ccagccgccg ccugucucca    60
cag                                                                   63

<210> SEQ ID NO 315
<211> LENGTH: 100
<212> TYPE: RNA
<213> ORGANISM: Homo sapiens

<400> SEQUENCE: 315
agcucagggc ggcugcgcag agggcuggac ucagcggcgg agcuggcugc uggccucagu    60
```
ucugccucug uccagguccu ugugacccgc ccgcucuccu                    100

<210> SEQ ID NO 316
<211> LENGTH: 73
<212> TYPE: RNA
<213> ORGANISM: Homo sapiens

<400> SEQUENCE: 316
gugggcgggg gcaggugugu gguggugggu ggccugcggu gagcagggcc cucacaccug    60
ccucgccccc cag                                                       73

<210> SEQ ID NO 317
<211> LENGTH: 137
<212> TYPE: RNA
<213> ORGANISM: Homo sapiens

<400> SEQUENCE: 317
agccagacaa gagggucaug gggagucacu gucaacccag agcaggcacu gccccugcga    60
ccagccuggg gcaucgguug ggugcaggg gucugcuggu gaugcuuucc aucucuuugc    120
uuuguccuga uuguagc                                                  137

<210> SEQ ID NO 318
<211> LENGTH: 85
<212> TYPE: RNA
<213> ORGANISM: Homo sapiens

<400> SEQUENCE: 318
ggccugggua ggcuugcaug ggggacuggg aagagaccau gaacagguua guccagggag    60
uucucaucaa gccuuuacuc aguag                                          85

<210> SEQ ID NO 319
<211> LENGTH: 68
<212> TYPE: RNA
<213> ORGANISM: Homo sapiens

<400> SEQUENCE: 319
gacucggcug cgguggacaa guccggcucc agaaccugga caccgcucag ccggccgcgg    60
caggggguc                                                            68

<210> SEQ ID NO 320
<211> LENGTH: 69
<212> TYPE: RNA
<213> ORGANISM: Homo sapiens

<400> SEQUENCE: 320
gaggagggga ggugugcagg gcuggggguca cugacucugc uuccccugcc cugcaugguc    60
uccccacag                                                            69

<210> SEQ ID NO 321
<211> LENGTH: 64
<212> TYPE: RNA
<213> ORGANISM: Homo sapiens

<400> SEQUENCE: 321
gaggcacugg guaggugggg cuccagggcu ccugacaccu ggaccucucc uccccaggcc    60
caca                                                                 64

<210> SEQ ID NO 322
<211> LENGTH: 65

<210> SEQ ID NO 322
<211> LENGTH: (not shown)
<212> TYPE: RNA
<213> ORGANISM: Homo sapiens

<400> SEQUENCE: 322
gggugcucgg ggcaggcggc ugggagcggc ccucacauug auggcuccug ccaccuccuc    60
cgcag                                                                65

<210> SEQ ID NO 323
<211> LENGTH: 86
<212> TYPE: RNA
<213> ORGANISM: Homo sapiens

<400> SEQUENCE: 323
auucuaggug gggagacuga cggcuggagg cccauaagcu gucuaaaacu ucggccccca    60
gauuucuggu cuccccacuu cagaac                                         86

<210> SEQ ID NO 324
<211> LENGTH: 62
<212> TYPE: RNA
<213> ORGANISM: Homo sapiens

<400> SEQUENCE: 324
uggccuaggg ggcggcuugu ggaguguaug ggcugagccu ugcucugcuc ccccgccccc    60
ag                                                                   62

<210> SEQ ID NO 325
<211> LENGTH: 59
<212> TYPE: RNA
<213> ORGANISM: Homo sapiens

<400> SEQUENCE: 325
ggggccaggc agggaggugg gaccaugggg gccuugcugu gugaccaccg uuccugcag     59

<210> SEQ ID NO 326
<211> LENGTH: 66
<212> TYPE: RNA
<213> ORGANISM: Homo sapiens

<400> SEQUENCE: 326
agcagcccuc ggcggcccgg ggggcgggcg gcggugcccg ucccggggcu gcgcgaggca    60
caggcg                                                               66

<210> SEQ ID NO 327
<211> LENGTH: 119
<212> TYPE: RNA
<213> ORGANISM: Homo sapiens

<400> SEQUENCE: 327
agccugcgcc ggagccgggg ccugagcccg ggccgcgcag gccgugaacu cgucgagcug    60
cgcgugcggc cggugcucaa ccugccgggu ccuggccccg cgcucccgcg cgcccugga   119

<210> SEQ ID NO 328
<211> LENGTH: 80
<212> TYPE: RNA
<213> ORGANISM: Homo sapiens

<400> SEQUENCE: 328
ccucugugag aaagggugug ggggagaggc ugucuugugu cguaaguau gccaaacuua    60 uuuuccccaa ggcagaggga                                                80

```
<210> SEQ ID NO 329
<211> LENGTH: 74
<212> TYPE: RNA
<213> ORGANISM: Homo sapiens

<400> SEQUENCE: 329
gcagcccggu gagcgcucgc uggccuggca gugcgucgga agaacagggc gggugggggcc      60 gcgcacaucu cugc                                                        74

<210> SEQ ID NO 330
<211> LENGTH: 53
<212> TYPE: RNA
<213> ORGANISM: Homo sapiens

<400> SEQUENCE: 330
gguggggguu ggaggcgugg guuuuagaac cuaucccuuu cuagcccuga gca             53

<210> SEQ ID NO 331
<211> LENGTH: 93
<212> TYPE: RNA
<213> ORGANISM: Homo sapiens

<400> SEQUENCE: 331
guaaggaggg ggaugagggg ucauaucucu ucucagggaa agcaggagcc cuucagcagg      60
gucagggccc cucaucuucc ccuccuuucc cag                                   93

<210> SEQ ID NO 332
<211> LENGTH: 98
<212> TYPE: RNA
<213> ORGANISM: Homo sapiens

<400> SEQUENCE: 332
cuuggucaau aggaaagagg ugggaccucc uggcuuuucc ucugcagcau ggcucggacc      60
uagugcaaug uuuaagcucc ccucucuuuc cguucag                               98

<210> SEQ ID NO 333
<211> LENGTH: 92
<212> TYPE: RNA
<213> ORGANISM: Homo sapiens

<400> SEQUENCE: 333
gugagccagu ggaauggaga ggcugugggc agggggagau gugaaggaaa gaacuaggac      60
ccauucaucc acugcauucc ugcuuggccc ag                                    92

<210> SEQ ID NO 334
<211> LENGTH: 94
<212> TYPE: RNA
<213> ORGANISM: Homo sapiens

<400> SEQUENCE: 334
cacggugucc ccugguggaa ccuggcaggg ggagagguaa ggucuuucag ccucuccaaa      60 gcccauugguc agguacucag gugggggagc ccug                                 94

<210> SEQ ID NO 335
<211> LENGTH: 60
<212> TYPE: RNA
<213> ORGANISM: Homo sapiens

<400> SEQUENCE: 335
ugugaaugac ccccuuccag agccaaaauc accagggaug gaggagggu cuugggguacu      60
```

<210> SEQ ID NO 336
<211> LENGTH: 70
<212> TYPE: RNA
<213> ORGANISM: Homo sapiens

<400> SEQUENCE: 336
aaaagccugu cccuaagucc cucccagccu uccagaguug gugccaggaa ggauuuaggg      60
acaggcuuug                                                            70

<210> SEQ ID NO 337
<211> LENGTH: 64
<212> TYPE: RNA
<213> ORGANISM: Homo sapiens

<400> SEQUENCE: 337
ucugggcgag ggugggcuc ucagagggc uggcaguacu gcucugaggc cugccucucc       60
ccag                                                                  64

<210> SEQ ID NO 338
<211> LENGTH: 75
<212> TYPE: RNA
<213> ORGANISM: Homo sapiens

<400> SEQUENCE: 338
gucagagggg ggaugugcau gcugguuggg gugggcugcc uguggaccaa ucagcgugca      60
cuuccccacc cugaa                                                      75

<210> SEQ ID NO 339
<211> LENGTH: 86
<212> TYPE: RNA
<213> ORGANISM: Homo sapiens

<400> SEQUENCE: 339
agggagaagg gucggggcag ggagggcagg gcaggcucug ggguggggg ucugugaguc       60 agccacggcu cugcccacgu cucccc                                          86

<210> SEQ ID NO 340
<211> LENGTH: 73
<212> TYPE: RNA
<213> ORGANISM: Homo sapiens

<400> SEQUENCE: 340
gaaaacaacc agguggcuu cccggagggc ggaacaccca gccccagcau ccagggcuca      60
ccuaccacgu uug                                                        73

<210> SEQ ID NO 341
<211> LENGTH: 77
<212> TYPE: RNA
<213> ORGANISM: Homo sapiens

<400> SEQUENCE: 341
gaguugggag guucccucuc caaaugguguc uugauccccc accccaagac acauuggag     60 agggacccuc ccaacuc                                                    77

<210> SEQ ID NO 342
<211> LENGTH: 61
<212> TYPE: RNA
<213> ORGANISM: Homo sapiens

```
<400> SEQUENCE: 342
ucacccggug agggcgggug gaggaggagg gucccacca ucagccuuca cugggacggg    60
a                                                                   61

<210> SEQ ID NO 343
<211> LENGTH: 119
<212> TYPE: RNA
<213> ORGANISM: Homo sapiens

<400> SEQUENCE: 343
ccaugaggag cuggcagugg gauggccugg ggguaggagc guggcuucug gagcuagacc    60
acauggguuc agaucccagc ggugccucua acuggccaca ggaccuuggg cagucagcu   119

<210> SEQ ID NO 344
<211> LENGTH: 70
<212> TYPE: RNA
<213> ORGANISM: Homo sapiens

<400> SEQUENCE: 344
gucccugggg gcugggaugg gccaugugu gcucugaucc cccguggguc ucuuggcccc     60
caggaacucc                                                          70

<210> SEQ ID NO 345
<211> LENGTH: 74
<212> TYPE: RNA
<213> ORGANISM: Homo sapiens

<400> SEQUENCE: 345
gggaggaaga agggaggagg agcggagggg cccuugucuu cccagagccu cucccuuccu    60 ccccucccc uccc                                                      74

<210> SEQ ID NO 346
<211> LENGTH: 66
<212> TYPE: RNA
<213> ORGANISM: Homo sapiens

<400> SEQUENCE: 346
acccaggagg cggaggaggu ggagguugca gugagccaag aucguggcac ugacuccagc    60
cugggg                                                              66

<210> SEQ ID NO 347
<211> LENGTH: 102
<212> TYPE: RNA
<213> ORGANISM: Homo sapiens

<400> SEQUENCE: 347
gugggagggc ccaggcgcgg gcaggggugg ggguggcaga gcgcuguccc gggggcgggg    60
ccgaagcgcg gcgaccguaa cuccuucugc uccgucccc ag                      102

<210> SEQ ID NO 348
<211> LENGTH: 113
<212> TYPE: RNA
<213> ORGANISM: Homo sapiens

<400> SEQUENCE: 348
gccggguggg gcgggcggc cucaggaggg gcccagcucc ccuggaugug cugcggguggg    60 gccggagggg cgucacgugc acccaaguga cgcccuucu gauucugccu cag          113
```

```
<210> SEQ ID NO 349
<211> LENGTH: 91
<212> TYPE: RNA
<213> ORGANISM: Homo sapiens

<400> SEQUENCE: 349 acgcccccg cccgccacc gccuuggagg cugaccucuu acuuucgguc ggcuucuuc    60 ccugggcuug guuuggggc gggggagugu c                                 91

<210> SEQ ID NO 350
<211> LENGTH: 54
<212> TYPE: RNA
<213> ORGANISM: Homo sapiens

<400> SEQUENCE: 350
agcagcaggg gagagagagg aguccucuag acaccgacuc ugucuccugc agau       54

<210> SEQ ID NO 351
<211> LENGTH: 136
<212> TYPE: RNA
<213> ORGANISM: Homo sapiens

<400> SEQUENCE: 351
ccgcuugccu cgcccagcgc agccccggcc gcugggcgca cccgucccgu ucgucccgg  60 acguugcucu cuaccccggg aacgucgaga cuggagcgcc cgaacugagc caccuucgcg 120
gaccccgaga gcggcg                                                 136

<210> SEQ ID NO 352
<211> LENGTH: 80
<212> TYPE: RNA
<213> ORGANISM: Homo sapiens

<400> SEQUENCE: 352
cugcagcgug cuucuccagg ccccgcgcgc ggacagacac acggacaagu cccgccaggg 60
gcugggcgcg cgccagccgg                                             80

<210> SEQ ID NO 353
<211> LENGTH: 47
<212> TYPE: RNA
<213> ORGANISM: Homo sapiens

<400> SEQUENCE: 353
cucggcgcgg ggcgcgggcu ccggguuggg gcgagccaac gccgggg               47

<210> SEQ ID NO 354
<211> LENGTH: 50
<212> TYPE: RNA
<213> ORGANISM: Homo sapiens

<400> SEQUENCE: 354
acccgggcgu ggugguggg gugggugccu guaauuccag cuaguuggga             50

<210> SEQ ID NO 355
<211> LENGTH: 67
<212> TYPE: RNA
<213> ORGANISM: Homo sapiens

<400> SEQUENCE: 355
gugaggaggg gcuggcaggg accccuccaa guuggggacg gcagccagcc ccugcucacc 60
ccucgcc                                                           67
```

<210> SEQ ID NO 356
<211> LENGTH: 106
<212> TYPE: RNA
<213> ORGANISM: Homo sapiens

<400> SEQUENCE: 356
agaagaaugc ccaaccagcc cucaguugcu acaguucccu guuguuucag cucgacaaca    60
acaggcggcu guagcaaugg ggggcuggau gggcaucuca augugc                  106

<210> SEQ ID NO 357
<211> LENGTH: 82
<212> TYPE: RNA
<213> ORGANISM: Homo sapiens

<400> SEQUENCE: 357
ugugggcagg gcccugggga gcugaggcuc uggggguggc cggggcugac ccugggccuc    60 ugcucccag ugucugaccg cg                                              82

<210> SEQ ID NO 358
<211> LENGTH: 69
<212> TYPE: RNA
<213> ORGANISM: Homo sapiens

<400> SEQUENCE: 358
cuuucggcca gcgggacggc auccgaggug ggcuaggcuc gggcccgugg cgggugcggg    60
gguggagg                                                             69

<210> SEQ ID NO 359
<211> LENGTH: 98
<212> TYPE: RNA
<213> ORGANISM: Homo sapiens

<400> SEQUENCE: 359
uugggcaagg ugcggggcua ggcuaacag cagucuuacu gaagguuucc uggaaaccac     60
gcacaugcug uugccacuaa ccucaaccuu acucgguc                            98

<210> SEQ ID NO 360
<211> LENGTH: 80
<212> TYPE: RNA
<213> ORGANISM: Homo sapiens

<400> SEQUENCE: 360
accugaggag ccagcccucc ucccgcaccc aaacuuggag cacuugaccu uuggcuguug    60 gaggggcag gcucgcgggu                                                 80

<210> SEQ ID NO 361
<211> LENGTH: 92
<212> TYPE: RNA
<213> ORGANISM: Homo sapiens

<400> SEQUENCE: 361 ccuguccuc cugcccugcg ccugcccagc ccuccugcuc uggugacuga ggaccgccag     60
gcaggggcug gugcugggcg gggggcggcg gg                                  92

<210> SEQ ID NO 362
<211> LENGTH: 79
<212> TYPE: RNA
<213> ORGANISM: Homo sapiens

<400> SEQUENCE: 362 gugaggugggg ggccagcagg gagugggcug ggcugggcug ggccaaggua caaggccuca    60
cccugcaucc cgcacccag                                                  79

<210> SEQ ID NO 363
<211> LENGTH: 84
<212> TYPE: RNA
<213> ORGANISM: Homo sapiens

<400> SEQUENCE: 363
ccgcagccgc cgcgccgggc ccggguuggc cgcugacccc cgcggggccc ccggcggccg    60
gggcgggggc gggggcugcc ccgg                                            84

<210> SEQ ID NO 364
<211> LENGTH: 65
<212> TYPE: RNA
<213> ORGANISM: Homo sapiens

<400> SEQUENCE: 364
agcccugggg guggucucua gccaaggcuc uggggucuca cccuuggcug gucucugcuc    60
cgcag                                                                 65

<210> SEQ ID NO 365
<211> LENGTH: 80
<212> TYPE: RNA
<213> ORGANISM: Homo sapiens

<400> SEQUENCE: 365
gguuccggag ccccggcgcg ggcgggguucu gggguguaga cgcugcuggc cagcccgccc    60
cagccgaggu ucucggcacc                                                 80

<210> SEQ ID NO 366
<211> LENGTH: 97
<212> TYPE: RNA
<213> ORGANISM: Homo sapiens

<400> SEQUENCE: 366
aucugaguug ggaggguccc ucuccaaaug ugucuugggg uggggauca agacacauuu      60 ggagagggaa ccucccaacu cggccucugc caucauu                              97

<210> SEQ ID NO 367
<211> LENGTH: 59
<212> TYPE: RNA
<213> ORGANISM: Homo sapiens

<400> SEQUENCE: 367
cuccagggag acagugugug aggccucuug ccauggccuc ccugcccgcc ucucugcag      59

<210> SEQ ID NO 368
<211> LENGTH: 67
<212> TYPE: RNA
<213> ORGANISM: Homo sapiens

<400> SEQUENCE: 368
gugggagggg agaggcagca agcacacagg gccugggacu agcaugcuga ccucccuccu    60
gccccag                                                               67

<210> SEQ ID NO 369
<211> LENGTH: 115
<212> TYPE: RNA

<213> ORGANISM: Homo sapiens

<400> SEQUENCE: 369
gagcaaaaac cagagaacaa caugggagcg uuccuaaccc cuaaggcaac uggaugggag    60
accugaccca uccaguucuc ugagggggcu cuugugucuu cuacaagguu guuca    115

<210> SEQ ID NO 370
<211> LENGTH: 86
<212> TYPE: RNA
<213> ORGANISM: Homo sapiens

<400> SEQUENCE: 370
uuugguacuu gaagagagga uacccuuugu auguucacuu gauuaauggc gaauauacag    60
ggggagacuc uuauuugcgu aucaaa    86

<210> SEQ ID NO 371
<211> LENGTH: 70
<212> TYPE: RNA
<213> ORGANISM: Homo sapiens

<400> SEQUENCE: 371
ugugcacuug ggcaggaggg acccuguaug ucccccgca gcaccgucau cgucccuc    60 uuguccacag    70

<210> SEQ ID NO 372
<211> LENGTH: 81
<212> TYPE: RNA
<213> ORGANISM: Homo sapiens

<400> SEQUENCE: 372
uacaggugca ggggaacugu agaugaaaag gcuuggcacu ugagggaaag ccucaguuca    60
uucucauuuu gcucaccugu u    81

<210> SEQ ID NO 373
<211> LENGTH: 63
<212> TYPE: RNA
<213> ORGANISM: Homo sapiens

<400> SEQUENCE: 373
gagucgagga cugguggaag ggccuuuccc cucagaccaa ggcccuggcc ccagcuucuu    60
cuc    63

<210> SEQ ID NO 374
<211> LENGTH: 103
<212> TYPE: RNA
<213> ORGANISM: Homo sapiens

<400> SEQUENCE: 374
gugucggcug uggcgugacu gucccucugu gucccccacu aggcccacug cucaguggag    60
cguggaggac gaggaggagg ccguccacga gcaaugccag cau    103

<210> SEQ ID NO 375
<211> LENGTH: 67
<212> TYPE: RNA
<213> ORGANISM: Homo sapiens

<400> SEQUENCE: 375
aauagauuau uggucaccac cuccaguuuc ugaauuugug agacuggggu ggggccugag    60
aauuugc    67

<210> SEQ ID NO 376
<211> LENGTH: 84
<212> TYPE: RNA
<213> ORGANISM: Homo sapiens

<400> SEQUENCE: 376
ugugcagugg aagggggggc cgauacacug uacgagagug aguagcaggu cucacaguga    60
accggucucu uucccuacug uguc                                          84

<210> SEQ ID NO 377
<211> LENGTH: 70
<212> TYPE: RNA
<213> ORGANISM: Homo sapiens

<400> SEQUENCE: 377
aggacccagc ggggcugggc gcgcggagca gcgcugggug cagcgccugc gccggcagcu    60
gcaagggccg                                                          70

<210> SEQ ID NO 378
<211> LENGTH: 64
<212> TYPE: RNA
<213> ORGANISM: Homo sapiens

<400> SEQUENCE: 378
ugcucuguag gcaugaggca gggcccaggu uccaugugau gcugaagcuc ugacauuccu    60
gcag                                                                64

<210> SEQ ID NO 379
<211> LENGTH: 72
<212> TYPE: RNA
<213> ORGANISM: Homo sapiens

<400> SEQUENCE: 379 cuggggagg aaggacaggc caucugcuau ucguccacca accugacuug auccucucuu    60
cccuccuccc ag                                                       72

<210> SEQ ID NO 380
<211> LENGTH: 69
<212> TYPE: RNA
<213> ORGANISM: Homo sapiens

<400> SEQUENCE: 380 uggguaggg gugggggaau ucaggggugu cgaacucaug gcugccaccu uuguccccc     60 auccugcag                                                           69

<210> SEQ ID NO 381
<211> LENGTH: 70
<212> TYPE: RNA
<213> ORGANISM: Homo sapiens

<400> SEQUENCE: 381
cucgggcccg accgcgccgg cccgcaccuc ccggcccgga gcugcgggcu gcggucaggg    60
cgaucccggg                                                          70

<210> SEQ ID NO 382
<211> LENGTH: 82
<212> TYPE: RNA
<213> ORGANISM: Homo sapiens

```
<400> SEQUENCE: 382
cugacuuuuu uaggagguag aagggugggg agcaugaaca auguuucuca cucccuaccc    60
cuccacuccc caaaaaaguc ag                                             82

<210> SEQ ID NO 383
<211> LENGTH: 79
<212> TYPE: RNA
<213> ORGANISM: Homo sapiens

<400> SEQUENCE: 383
gugcagaucc uugggagccc uguuagacuc uggauuuuac acuuggagug aacgggcgcc    60
aucccgaggc uuugcacag                                                 79

<210> SEQ ID NO 384
<211> LENGTH: 71
<212> TYPE: RNA
<213> ORGANISM: Homo sapiens

<400> SEQUENCE: 384
auggaggggg guguggagcc aggggggccca ggucuacagc uucuccccgc ucccugcccc   60
cauacuccca g                                                         71

<210> SEQ ID NO 385
<211> LENGTH: 92
<212> TYPE: RNA
<213> ORGANISM: Homo sapiens

<400> SEQUENCE: 385
cgcugcgcuu cugggcccgc ggcgggcgug gggcugcccg ggccggucga ccagcgcgcc    60
guagcucccg aggcccgagc cgcgacccgc gg                                  92

<210> SEQ ID NO 386
<211> LENGTH: 97
<212> TYPE: RNA
<213> ORGANISM: Homo sapiens

<400> SEQUENCE: 386
cucaggugcu cuggcugcuu ggguuccugg caugcugauu ugugacuuaa gauuaaaauc    60
acauugccag ggauuaccac gcaaccacga ccuuggc                             97

<210> SEQ ID NO 387
<211> LENGTH: 73
<212> TYPE: RNA
<213> ORGANISM: Homo sapiens

<400> SEQUENCE: 387
ggccggcugg gguuccuggg gaugggauuu gcuuccuguc acaaaucaca uugccaggga    60
uuuccaaccg acc                                                       73

<210> SEQ ID NO 388
<211> LENGTH: 85
<212> TYPE: RNA
<213> ORGANISM: Homo sapiens

<400> SEQUENCE: 388 agggauagagg gaugaggggg aaaguucuau aguccuguaa uuagaucuca ggacuauaga   60
acuuuccccc ucaucccucu gcccu                                          85
```

```
<210> SEQ ID NO 389
<211> LENGTH: 90
<212> TYPE: RNA
<213> ORGANISM: Homo sapiens

<400> SEQUENCE: 389
ucuaagaaac gcaguggucu cugaagccug caggggcagg ccagcccugc acugaacgcc      60
uguucuugcc agguggcaga agguugcugc                                      90

<210> SEQ ID NO 390
<211> LENGTH: 80
<212> TYPE: RNA
<213> ORGANISM: Homo sapiens

<400> SEQUENCE: 390
accucuaccu cccggcagag gaggcugcag aggcuggcuu ccaaaacuc ugcccccucc       60 gcugcugcca aguggcuggu                                                 80

<210> SEQ ID NO 391
<211> LENGTH: 75
<212> TYPE: RNA
<213> ORGANISM: Homo sapiens

<400> SEQUENCE: 391
ucaucccugg gugggauuu guugcauuac uuguguucua auaaaguau ugcacuuguc        60 ccggccugug gaaga                                                      75

<210> SEQ ID NO 392
<211> LENGTH: 109
<212> TYPE: RNA
<213> ORGANISM: Homo sapiens

<400> SEQUENCE: 392
ggucgggcuc accaugacac agugugagac cucgggcuac aacacaggac ccgggcgcug     60
cucugacccc ucgugucuug uguugcagcc ggagggacgc agguccgca                 109

<210> SEQ ID NO 393
<211> LENGTH: 89
<212> TYPE: RNA
<213> ORGANISM: Homo sapiens

<400> SEQUENCE: 393
gucagcagug ccuuagcagc acguaaauau uggcguuaag auucuaaaau uaucccagu      60 auuaacugug cugcugaagu aagguugac                                       89

<210> SEQ ID NO 394
<211> LENGTH: 81
<212> TYPE: RNA
<213> ORGANISM: Homo sapiens

<400> SEQUENCE: 394
guuccacucu agcagcacgu aaauauuggc guagugaaau auauauuaaa caccaauauu     60
acugugcugc uuuaguguga c                                               81

<210> SEQ ID NO 395
<211> LENGTH: 96
<212> TYPE: RNA
<213> ORGANISM: Homo sapiens

<400> SEQUENCE: 395
```

```
cgggccccgg gcgggcggga gggacgggac gcggugcagu guuguuuuuu cccccgccaa        60
uauugcacuc gucccggccu ccggcccccc cggccc                                 96
```

<210> SEQ ID NO 396
<211> LENGTH: 84
<212> TYPE: RNA
<213> ORGANISM: Homo sapiens

<400> SEQUENCE: 396

```
cuccccaugg cccugucucc caacccuugu accagugcug ggcucagacc cugguacagg        60 ccuggggac agggaccugg ggac                                                84
```

<210> SEQ ID NO 397
<211> LENGTH: 94
<212> TYPE: RNA
<213> ORGANISM: Homo sapiens

<400> SEQUENCE: 397

```
cgggcagcgg gugccaggca cggugucagc aggcaacaug gccgagaggc cggggccucc        60
gggcggcgcc guguccgcga ccgcguaccc ugac                                   94
```

<210> SEQ ID NO 398
<211> LENGTH: 86
<212> TYPE: RNA
<213> ORGANISM: Homo sapiens

<400> SEQUENCE: 398

```
ugccagucuc uaggucccug agacccuuua accugugagg acauccaggg ucacagguga        60
gguucuuggg agccuggcgu cuggcc                                            86
```

<210> SEQ ID NO 399
<211> LENGTH: 78
<212> TYPE: RNA
<213> ORGANISM: Homo sapiens

<400> SEQUENCE: 399

```
cuuucuacac agguugggau cgguugcaau gcuguguuuc uguaugguau ugcacuuguc        60
ccggccuguu gaguuugg                                                     78
```

<210> SEQ ID NO 400
<211> LENGTH: 93
<212> TYPE: RNA
<213> ORGANISM: Homo sapiens

<400> SEQUENCE: 400

```
ccuuccggcg ucccaggcgg ggcgccgcgg gaccgcccuc gugucugugg cgguggggauc       60 ccgcggccgu guuuuccugg uggcccggcc aug                                    93
```

<210> SEQ ID NO 401
<211> LENGTH: 83
<212> TYPE: RNA
<213> ORGANISM: Homo sapiens

<400> SEQUENCE: 401

```
gucuacuccc agggugccaa gcuguuucgu guucccuccc uaggggaucc caggugggg         60 cagcagagga ccugggccug gac                                               83
```

<210> SEQ ID NO 402
<211> LENGTH: 72

```
<212> TYPE: RNA
<213> ORGANISM: Homo sapiens

<400> SEQUENCE: 402
ugugggacug caaaugggag cucagcaccu gccugccacc cacgcagacc agccccugcu    60 cguucccac ag                                                        72

<210> SEQ ID NO 403
<211> LENGTH: 110
<212> TYPE: RNA
<213> ORGANISM: Homo sapiens

<400> SEQUENCE: 403
gucuaccagg ugugggccca gcuuuacaua guucaugcug aggccgggau uucaugcaga    60
aaacugguug caaaaggugc ugaaggggcu gggggagcac aagggagaag              110

<210> SEQ ID NO 404
<211> LENGTH: 89
<212> TYPE: RNA
<213> ORGANISM: Homo sapiens

<400> SEQUENCE: 404
agccuguggg aaagagaaga gcagggcagg gugaaggccc ggcggagaca cucugcccac    60
cccacacccu gccuaugggc cacacagcu                                     89

<210> SEQ ID NO 405
<211> LENGTH: 62
<212> TYPE: RNA
<213> ORGANISM: Homo sapiens

<400> SEQUENCE: 405
gaggugguug gaggaagagg gcagcuccca ugacugccug accgccuucu cuccuccccc    60
ag                                                                  62

<210> SEQ ID NO 406
<211> LENGTH: 75
<212> TYPE: RNA
<213> ORGANISM: Homo sapiens

<400> SEQUENCE: 406 uggaguggggg gggcaggagg ggcucaggga gaaagugcau acagccccug gcccucucug    60
cccuuccguc cccug                                                    75

<210> SEQ ID NO 407
<211> LENGTH: 72
<212> TYPE: RNA
<213> ORGANISM: Homo sapiens

<400> SEQUENCE: 407
ccaggcacac aggaaaagcg gggcccuggg uucggcugcu accccaaagg ccacauucuc    60
cugugcacac ag                                                       72

<210> SEQ ID NO 408
<211> LENGTH: 153
<212> TYPE: RNA
<213> ORGANISM: Homo sapiens

<400> SEQUENCE: 408
gcuccgcccc acgucgcaug cgccccggga acgcguggggg cggagcuucc ggaggccccg    60
```
cucugcugcc gacccugugg agcggagggu gaagccuccg gaugccaguc ccucaucgcu    120
ggccuggucg cgcuguggcg aaggggggcgg agc                                153

<210> SEQ ID NO 409
<211> LENGTH: 153
<212> TYPE: RNA
<213> ORGANISM: Homo sapiens

<400> SEQUENCE: 409
gcuccgcccc acgucgcaug cgccccggga acgcgugggg cggagcuucc ggaggccccg    60
cccugcugcc gacccugugg agcggagggu gaagccuccg gaugccaguc ccucaucgcu   120
ggcccggucg cgcuguggcg aaggggggcgg agc                                153

<210> SEQ ID NO 410
<211> LENGTH: 49
<212> TYPE: RNA
<213> ORGANISM: Homo sapiens

<400> SEQUENCE: 410
ggugaggcgg gggggcgagc ccugaggggc ucucgcuucu ggcgccaag               49

<210> SEQ ID NO 411
<211> LENGTH: 100
<212> TYPE: RNA
<213> ORGANISM: Homo sapiens

<400> SEQUENCE: 411
gaggugggag gauugcuuga gucagggugg uugaggcugc aguaaguugu gaucauacca    60
cugcacucca gccugaguga cagagcaaga ccuugucuca                         100

<210> SEQ ID NO 412
<211> LENGTH: 64
<212> TYPE: RNA
<213> ORGANISM: Homo sapiens

<400> SEQUENCE: 412 ggguggggc ggggcggcag gggccucccc cagugccagg ccccauucug cuucucuccc    60
agcu                                                                 64

<210> SEQ ID NO 413
<211> LENGTH: 74
<212> TYPE: RNA
<213> ORGANISM: Homo sapiens

<400> SEQUENCE: 413
ccugcaggag gcagugggcg agcaggcggg gcagcccaau gccaugggcc ugaucucacc    60
gcugccuccu uccc                                                      74

<210> SEQ ID NO 414
<211> LENGTH: 60
<212> TYPE: RNA
<213> ORGANISM: Homo sapiens

<400> SEQUENCE: 414
aggccuaggg gguggcaggc uggccaucag uguggggcuaa cccuguccuc ucccucccag   60

<210> SEQ ID NO 415
<211> LENGTH: 100
<212> TYPE: RNA
<213> ORGANISM: Homo sapiens

```
<400> SEQUENCE: 415
gugagcgggc gcggcaggga ucgcgggcgg guggcggccu agggcgcgga gggcggaccg      60
ggaauggcgc gccgugcgcc gccggcguaa cugcggcgcu                           100

<210> SEQ ID NO 416
<211> LENGTH: 56
<212> TYPE: RNA
<213> ORGANISM: Homo sapiens

<400> SEQUENCE: 416
guaggcaggg gcuggggtuu cagguucuca gucagaaccu uggcccucu ccccag           56

<210> SEQ ID NO 417
<211> LENGTH: 72
<212> TYPE: RNA
<213> ORGANISM: Homo sapiens

<400> SEQUENCE: 417
ucuccucgag gggucucugc cucuacccag gacucuuuca ugaccaggag gcugaggccc      60
cucacaggcg gc                                                         72

<210> SEQ ID NO 418
<211> LENGTH: 68
<212> TYPE: RNA
<213> ORGANISM: Homo sapiens

<400> SEQUENCE: 418
gcauccugua cugagcugcc ccgaggcccu ucaugcugcc cagcucgggg cagcucagua      60
caggauac                                                              68

<210> SEQ ID NO 419
<211> LENGTH: 64
<212> TYPE: RNA
<213> ORGANISM: Homo sapiens

<400> SEQUENCE: 419
uccuguacug agcugccccg agcugggcag caugaagggc cucggggcag cucaguacag      60
gaug                                                                  64

<210> SEQ ID NO 420
<211> LENGTH: 54
<212> TYPE: RNA
<213> ORGANISM: Homo sapiens

<400> SEQUENCE: 420
acgcgggugc gggccggcgg gguagaagcc acccggcccg gccggcccg gcga             54

<210> SEQ ID NO 421
<211> LENGTH: 89
<212> TYPE: RNA
<213> ORGANISM: Homo sapiens

<400> SEQUENCE: 421
accaugcugu agugugugua aacauccuac acucucagcu gugagcucaa gguggcuggg      60
agaggguugu uuacuccuuc ugccaugga                                       89

<210> SEQ ID NO 422
<211> LENGTH: 85
<212> TYPE: RNA
```

<213> ORGANISM: Homo sapiens

<400> SEQUENCE: 422
gugagcugcu ggggacgcgg gucgggucu gcagggcggu gcggcagccg ccaccugacg    60
ccgcgccuuu gucuguguccc cacag                                        85

<210> SEQ ID NO 423
<211> LENGTH: 71
<212> TYPE: RNA
<213> ORGANISM: Homo sapiens

<400> SEQUENCE: 423
ggguaaaggg gcagggacgg guggccccag gaagaagggc cgguggagc cgcucuucuc    60 ccugcccaca g                                                        71

<210> SEQ ID NO 424
<211> LENGTH: 73
<212> TYPE: RNA
<213> ORGANISM: Homo sapiens

<400> SEQUENCE: 424
ggggagguac cugggacagg aggaggaggc agccuugccu cagaaaccaa acugucaaaa    60
guguagguuc cac                                                      73

<210> SEQ ID NO 425
<211> LENGTH: 90
<212> TYPE: RNA
<213> ORGANISM: Homo sapiens

<400> SEQUENCE: 425
cgggcggggc ggguccggcc gccuccgagc ccggccggca gccccggcc uuaaagcgcg    60 ggcuguccgg aggggucggc uuucccaccg                                    90

<210> SEQ ID NO 426
<211> LENGTH: 83
<212> TYPE: RNA
<213> ORGANISM: Homo sapiens

<400> SEQUENCE: 426
acggcaucuu ugcacucagc aggcaggcug gugcagcccg uggugggga ccauccugcc    60 ugcugugggg uaaggacggc ugu                                           83

<210> SEQ ID NO 427
<211> LENGTH: 63
<212> TYPE: RNA
<213> ORGANISM: Homo sapiens

<400> SEQUENCE: 427
gagguguagg ggagguuggg ccagggaugc cuucacugug ucucucuggu cuugccaccc    60
cag                                                                 63

<210> SEQ ID NO 428
<211> LENGTH: 72
<212> TYPE: RNA
<213> ORGANISM: Homo sapiens

<400> SEQUENCE: 428
cugugcaccu gggggagugc agugauugug gaaugcaaag ucccacaauc acuguacucc    60
ccaggugcac ag                                                       72

```
<210> SEQ ID NO 429
<211> LENGTH: 67
<212> TYPE: RNA
<213> ORGANISM: Homo sapiens

<400> SEQUENCE: 429
guggcacuca acuguggggg gcacuuucug cucucuggug aaagugccgc caucuuuuga     60
guguuac                                                              67

<210> SEQ ID NO 430
<211> LENGTH: 62
<212> TYPE: RNA
<213> ORGANISM: Homo sapiens

<400> SEQUENCE: 430 gguaggggc gggcuccggc gcugggaccc cacuagggug gcgccuuggc cccgccccgc     60
cc                                                                   62

<210> SEQ ID NO 431
<211> LENGTH: 82
<212> TYPE: RNA
<213> ORGANISM: Homo sapiens

<400> SEQUENCE: 431
gugaguggga ggccagggca cggcaggggg agcugcaggg cuauggggagg ggccccagcg    60 ucugagcccu guccucccgc ag                                             82

<210> SEQ ID NO 432
<211> LENGTH: 82
<212> TYPE: RNA
<213> ORGANISM: Homo sapiens

<400> SEQUENCE: 432
gugaguggga ggccagggca cggcaggggg agcugcaggg cuauggggagg ggccccagcg    60 ucugagcccu guccucccgc ag                                             82

<210> SEQ ID NO 433
<211> LENGTH: 81
<212> TYPE: RNA
<213> ORGANISM: Homo sapiens

<400> SEQUENCE: 433
aguuggtggg ggagccauga gauaagagca ccuccuagag aauguugaac uaaaggugcc    60
cucucuggcu ccuccccaaa g                                              81

<210> SEQ ID NO 434
<211> LENGTH: 68
<212> TYPE: RNA
<213> ORGANISM: Homo sapiens

<400> SEQUENCE: 434
cuccggugcc uacugagcug auaucaguuc ucauuuuaca cacuggcuca guucagcagg    60
aacaggag                                                             68

<210> SEQ ID NO 435
<211> LENGTH: 73
<212> TYPE: RNA
<213> ORGANISM: Homo sapiens
```

<400> SEQUENCE: 435
cucugccucc cgugccuacu gagcugaaac acaguugguu uguguacacu ggcucaguuc    60
agcaggaaca ggg    73

<210> SEQ ID NO 436
<211> LENGTH: 83
<212> TYPE: RNA
<213> ORGANISM: Homo sapiens

<400> SEQUENCE: 436
gugaguggga gccccagugu gugguugggg ccauggcggg ugggcagccc agccucugag    60
ccuuccucgu cugucugccc cag    83

<210> SEQ ID NO 437
<211> LENGTH: 67
<212> TYPE: RNA
<213> ORGANISM: Homo sapiens

<400> SEQUENCE: 437
gcgcccuccc ucucuccccg gugugcaaau guguguguge gguguuaugc cggacaagag    60
ggaggug    67

<210> SEQ ID NO 438
<211> LENGTH: 58
<212> TYPE: RNA
<213> ORGANISM: Homo sapiens

<400> SEQUENCE: 438
gcugaagcuc uaagguuccg ccugcgggca ggaagcggag gaaccuugga gcuucggc    58

<210> SEQ ID NO 439
<211> LENGTH: 80
<212> TYPE: RNA
<213> ORGANISM: Homo sapiens

<400> SEQUENCE: 439
gagaggccaa gaccuuggga auggggguaa gggccuucug agcccagguc cgaacucucc    60
auuccucugc agagcgcucu    80

<210> SEQ ID NO 440
<211> LENGTH: 64
<212> TYPE: RNA
<213> ORGANISM: Homo sapiens

<400> SEQUENCE: 440
ccccgggccc ggcguucccu ccccuuccgu gcgccagugg aggccggggu ggggcggggc    60
gggg    64

<210> SEQ ID NO 441
<211> LENGTH: 64
<212> TYPE: RNA
<213> ORGANISM: Homo sapiens

<400> SEQUENCE: 441
ccccgggccc ggcguucccu ccccuuccgu gcgccagugg aggccggggu ggggcggggc    60
gggg    64

<210> SEQ ID NO 442
<211> LENGTH: 85

```
<212> TYPE: RNA
<213> ORGANISM: Homo sapiens

<400> SEQUENCE: 442
ggggagguag ggaaaaggaa gggggaggag aaggugagac caauguccug ggugccacuc    60
cugcccagug ccucccuucc ucguu                                         85

<210> SEQ ID NO 443
<211> LENGTH: 73
<212> TYPE: RNA
<213> ORGANISM: Homo sapiens

<400> SEQUENCE: 443
guucaagugg gaggacagga ggcaggugug guuggaggaa gcagccugaa ccugccuccc    60
ugacauucca cag                                                      73

<210> SEQ ID NO 444
<211> LENGTH: 98
<212> TYPE: RNA
<213> ORGANISM: Homo sapiens

<400> SEQUENCE: 444
agaaugggca aaugaacagu aaauuuggag gccuggggcc cucccugcug cuggagaagu    60
guuugcacgg gugggccuug ucuuugaaag gaggugga                           98

<210> SEQ ID NO 445
<211> LENGTH: 60
<212> TYPE: RNA
<213> ORGANISM: Homo sapiens

<400> SEQUENCE: 445
cgcugggucc gcgcgcccug ggccgggcga uguccgcuug ggggagcgag gggcggggcg    60

<210> SEQ ID NO 446
<211> LENGTH: 23
<212> TYPE: RNA
<213> ORGANISM: Homo sapiens

<400> SEQUENCE: 446
cuccuggggc ccgcacucuc gcu                                           23

<210> SEQ ID NO 447
<211> LENGTH: 18
<212> TYPE: RNA
<213> ORGANISM: Homo sapiens

<400> SEQUENCE: 447
cuccuggggc ccgcacuc                                                 18

<210> SEQ ID NO 448
<211> LENGTH: 21
<212> TYPE: RNA
<213> ORGANISM: Homo sapiens

<400> SEQUENCE: 448
caacucugau cucuucaucu a                                             21

<210> SEQ ID NO 449
<211> LENGTH: 20
<212> TYPE: RNA
<213> ORGANISM: Homo sapiens
```

```
<400> SEQUENCE: 449
ucucuucauc uacccccag                                               20

<210> SEQ ID NO 450
<211> LENGTH: 23
<212> TYPE: RNA
<213> ORGANISM: Homo sapiens

<400> SEQUENCE: 450
ggugggugag gucgggcccc aag                                          23

<210> SEQ ID NO 451
<211> LENGTH: 20
<212> TYPE: RNA
<213> ORGANISM: Homo sapiens

<400> SEQUENCE: 451
cggggugggu gaggucgggc                                              20

<210> SEQ ID NO 452
<211> LENGTH: 26
<212> TYPE: RNA
<213> ORGANISM: Homo sapiens

<400> SEQUENCE: 452
ccuucuggag aggcuuugug cggaua                                       26

<210> SEQ ID NO 453
<211> LENGTH: 15
<212> TYPE: RNA
<213> ORGANISM: Homo sapiens

<400> SEQUENCE: 453
ccuucuggag aggcu                                                   15

<210> SEQ ID NO 454
<211> LENGTH: 20
<212> TYPE: RNA
<213> ORGANISM: Homo sapiens

<400> SEQUENCE: 454
ggcuggucag augggagugg                                              20

<210> SEQ ID NO 455
<211> LENGTH: 20
<212> TYPE: RNA
<213> ORGANISM: Homo sapiens

<400> SEQUENCE: 455
ggcuggucag augggagugg                                              20

<210> SEQ ID NO 456
<211> LENGTH: 26
<212> TYPE: RNA
<213> ORGANISM: Homo sapiens

<400> SEQUENCE: 456
aggagggagg agaugggcca aguucc                                       26

<210> SEQ ID NO 457
<211> LENGTH: 15
<212> TYPE: RNA
<213> ORGANISM: Homo sapiens
```

```
<400> SEQUENCE: 457
gggaggaggg aggag                                              15

<210> SEQ ID NO 458
<211> LENGTH: 21
<212> TYPE: RNA
<213> ORGANISM: Homo sapiens

<400> SEQUENCE: 458 cuuccccca guaaucuuca u                                        21

<210> SEQ ID NO 459
<211> LENGTH: 21
<212> TYPE: RNA
<213> ORGANISM: Homo sapiens

<400> SEQUENCE: 459
cuucccccca guaaucuuca u                                       21

<210> SEQ ID NO 460
<211> LENGTH: 21
<212> TYPE: RNA
<213> ORGANISM: Homo sapiens

<400> SEQUENCE: 460
cggauccgag ucacggcacc a                                       21

<210> SEQ ID NO 461
<211> LENGTH: 15
<212> TYPE: RNA
<213> ORGANISM: Homo sapiens

<400> SEQUENCE: 461
ggauccgagu cacgg                                              15

<210> SEQ ID NO 462
<211> LENGTH: 21
<212> TYPE: RNA
<213> ORGANISM: Homo sapiens

<400> SEQUENCE: 462
cccaggcugg agcgagugca g                                       21

<210> SEQ ID NO 463
<211> LENGTH: 15
<212> TYPE: RNA
<213> ORGANISM: Homo sapiens

<400> SEQUENCE: 463
agcucacugc agccu                                              15

<210> SEQ ID NO 464
<211> LENGTH: 17
<212> TYPE: RNA
<213> ORGANISM: Homo sapiens

<400> SEQUENCE: 464
uccuagucac ggcacca                                            17

<210> SEQ ID NO 465
<211> LENGTH: 17
<212> TYPE: RNA
```

<213> ORGANISM: Homo sapiens

<400> SEQUENCE: 465
uccuagucac ggcacca                                                      17

<210> SEQ ID NO 466
<211> LENGTH: 24
<212> TYPE: RNA
<213> ORGANISM: Homo sapiens

<400> SEQUENCE: 466
gaggcuggga aggcaaaggg acgu                                              24

<210> SEQ ID NO 467
<211> LENGTH: 15
<212> TYPE: RNA
<213> ORGANISM: Homo sapiens

<400> SEQUENCE: 467
gaaggaggcu gggaa                                                        15

<210> SEQ ID NO 468
<211> LENGTH: 21
<212> TYPE: RNA
<213> ORGANISM: Homo sapiens

<400> SEQUENCE: 468
gaggcgaugu ggggauguag a                                                 21

<210> SEQ ID NO 469
<211> LENGTH: 20
<212> TYPE: RNA
<213> ORGANISM: Homo sapiens

<400> SEQUENCE: 469
cccagucuca uuuccucauc                                                   20

<210> SEQ ID NO 470
<211> LENGTH: 23
<212> TYPE: RNA
<213> ORGANISM: Homo sapiens

<400> SEQUENCE: 470
ggcccggccg ugccugaggu uuc                                               23

<210> SEQ ID NO 471
<211> LENGTH: 15
<212> TYPE: RNA
<213> ORGANISM: Homo sapiens

<400> SEQUENCE: 471
ggcgguggga ucccg                                                        15

<210> SEQ ID NO 472
<211> LENGTH: 16
<212> TYPE: RNA
<213> ORGANISM: Homo sapiens

<400> SEQUENCE: 472 cuggggqucc cccgac                                                       16

<210> SEQ ID NO 473
<211> LENGTH: 15

```
<212> TYPE: RNA
<213> ORGANISM: Homo sapiens

<400> SEQUENCE: 473
guguggagcu ggggc                                                   15

<210> SEQ ID NO 474
<211> LENGTH: 25
<212> TYPE: RNA
<213> ORGANISM: Homo sapiens

<400> SEQUENCE: 474
agcggggagg aagugggcgc ugcuu                                        25

<210> SEQ ID NO 475
<211> LENGTH: 21
<212> TYPE: RNA
<213> ORGANISM: Homo sapiens

<400> SEQUENCE: 475
agcggggagg aagugggcgc u                                            21

<210> SEQ ID NO 476
<211> LENGTH: 27
<212> TYPE: RNA
<213> ORGANISM: Homo sapiens

<400> SEQUENCE: 476
aaaccguuac cauuacugag uuuagua                                      27

<210> SEQ ID NO 477
<211> LENGTH: 15
<212> TYPE: RNA
<213> ORGANISM: Homo sapiens

<400> SEQUENCE: 477
gaaaccguua ccauu                                                   15

<210> SEQ ID NO 478
<211> LENGTH: 22
<212> TYPE: RNA
<213> ORGANISM: Homo sapiens

<400> SEQUENCE: 478
caggcacggg agcucaggug ag                                           22

<210> SEQ ID NO 479
<211> LENGTH: 17
<212> TYPE: RNA
<213> ORGANISM: Homo sapiens

<400> SEQUENCE: 479
caggcacggg agcucag                                                 17

<210> SEQ ID NO 480
<211> LENGTH: 23
<212> TYPE: RNA
<213> ORGANISM: Homo sapiens

<400> SEQUENCE: 480 ggggguccccc ggugcucgga ucu                                         23

<210> SEQ ID NO 481
```

```
<211> LENGTH: 16
<212> TYPE: RNA
<213> ORGANISM: Homo sapiens

<400> SEQUENCE: 481
ucgggagggg cgggag                                                        16

<210> SEQ ID NO 482
<211> LENGTH: 23
<212> TYPE: RNA
<213> ORGANISM: Homo sapiens

<400> SEQUENCE: 482
cggggccgua gcacugucug aga                                                23

<210> SEQ ID NO 483
<211> LENGTH: 20
<212> TYPE: RNA
<213> ORGANISM: Homo sapiens

<400> SEQUENCE: 483
cggggccgua gcacugucug                                                    20

<210> SEQ ID NO 484
<211> LENGTH: 20
<212> TYPE: RNA
<213> ORGANISM: Homo sapiens

<400> SEQUENCE: 484
aucccaccac ugccaccauu                                                    20

<210> SEQ ID NO 485
<211> LENGTH: 15
<212> TYPE: RNA
<213> ORGANISM: Homo sapiens

<400> SEQUENCE: 485
aucccaccac ugcca                                                         15

<210> SEQ ID NO 486
<211> LENGTH: 23
<212> TYPE: RNA
<213> ORGANISM: Homo sapiens

<400> SEQUENCE: 486
acaggagugg ggugggaca uaa                                                 23

<210> SEQ ID NO 487
<211> LENGTH: 20
<212> TYPE: RNA
<213> ORGANISM: Homo sapiens

<400> SEQUENCE: 487
acaggagugg ggugggaca                                                     20

<210> SEQ ID NO 488
<211> LENGTH: 23
<212> TYPE: RNA
<213> ORGANISM: Homo sapiens

<400> SEQUENCE: 488 cuggggacg cgugagcgcg agc                                                 23
```

```
<210> SEQ ID NO 489
<211> LENGTH: 21
<212> TYPE: RNA
<213> ORGANISM: Homo sapiens

<400> SEQUENCE: 489 cuggggacg cgugagcgcg a                                              21

<210> SEQ ID NO 490
<211> LENGTH: 22
<212> TYPE: RNA
<213> ORGANISM: Homo sapiens

<400> SEQUENCE: 490
cgcggcgggg acggcgauug gu                                            22

<210> SEQ ID NO 491
<211> LENGTH: 17
<212> TYPE: RNA
<213> ORGANISM: Homo sapiens

<400> SEQUENCE: 491
cggcggggac ggcgauu                                                  17

<210> SEQ ID NO 492
<211> LENGTH: 23
<212> TYPE: RNA
<213> ORGANISM: Homo sapiens

<400> SEQUENCE: 492
gagggccccc ccucaauccu guu                                           23

<210> SEQ ID NO 493
<211> LENGTH: 16
<212> TYPE: RNA
<213> ORGANISM: Homo sapiens

<400> SEQUENCE: 493 agggccccccc cucaau                                                  16

<210> SEQ ID NO 494
<211> LENGTH: 30
<212> TYPE: RNA
<213> ORGANISM: Homo sapiens

<400> SEQUENCE: 494
ugaggggcag agagcgagac uuuucuauuu                                    30

<210> SEQ ID NO 495
<211> LENGTH: 15
<212> TYPE: RNA
<213> ORGANISM: Homo sapiens

<400> SEQUENCE: 495
ugaggggcag agagc                                                    15

<210> SEQ ID NO 496
<211> LENGTH: 24
<212> TYPE: RNA
<213> ORGANISM: Homo sapiens

<400> SEQUENCE: 496
gugaguggga gccggugggg cugg                                          24
```

```
<210> SEQ ID NO 497
<211> LENGTH: 15
<212> TYPE: RNA
<213> ORGANISM: Homo sapiens

<400> SEQUENCE: 497
ggggcuggag uaagg                                                       15

<210> SEQ ID NO 498
<211> LENGTH: 23
<212> TYPE: RNA
<213> ORGANISM: Homo sapiens

<400> SEQUENCE: 498
ugaggauaug gcagggaagg gga                                              23

<210> SEQ ID NO 499
<211> LENGTH: 19
<212> TYPE: RNA
<213> ORGANISM: Homo sapiens

<400> SEQUENCE: 499
ugaggauaug gcagggaag                                                   19

<210> SEQ ID NO 500
<211> LENGTH: 23
<212> TYPE: RNA
<213> ORGANISM: Homo sapiens

<400> SEQUENCE: 500
cuaguggaag aagauggcgg aag                                              23

<210> SEQ ID NO 501
<211> LENGTH: 15
<212> TYPE: RNA
<213> ORGANISM: Homo sapiens

<400> SEQUENCE: 501
uaguggaaga agaug                                                       15

<210> SEQ ID NO 502
<211> LENGTH: 25
<212> TYPE: RNA
<213> ORGANISM: Homo sapiens

<400> SEQUENCE: 502
ugggcagggg cuuauuguag gaguc                                            25

<210> SEQ ID NO 503
<211> LENGTH: 19
<212> TYPE: RNA
<213> ORGANISM: Homo sapiens

<400> SEQUENCE: 503
ugggcagggg cuuauugua                                                   19

<210> SEQ ID NO 504
<211> LENGTH: 23
<212> TYPE: RNA
<213> ORGANISM: Homo sapiens

<400> SEQUENCE: 504
agaagaaggc ggucggucug cgg                                              23
```

<210> SEQ ID NO 505
<211> LENGTH: 21
<212> TYPE: RNA
<213> ORGANISM: Homo sapiens

<400> SEQUENCE: 505
aagaaggcgg ucggucugcg g                                        21

<210> SEQ ID NO 506
<211> LENGTH: 20
<212> TYPE: RNA
<213> ORGANISM: Homo sapiens

<400> SEQUENCE: 506
aucccaccuc ugccaccaaa                                          20

<210> SEQ ID NO 507
<211> LENGTH: 15
<212> TYPE: RNA
<213> ORGANISM: Homo sapiens

<400> SEQUENCE: 507
aucccaccuc ugcca                                               15

<210> SEQ ID NO 508
<211> LENGTH: 23
<212> TYPE: RNA
<213> ORGANISM: Homo sapiens

<400> SEQUENCE: 508
ggaggcgcag gcucggaaag gcg                                      23

<210> SEQ ID NO 509
<211> LENGTH: 15
<212> TYPE: RNA
<213> ORGANISM: Homo sapiens

<400> SEQUENCE: 509
gcaggcucgg aaagg                                               15

<210> SEQ ID NO 510
<211> LENGTH: 17
<212> TYPE: RNA
<213> ORGANISM: Homo sapiens

<400> SEQUENCE: 510
ccuccgggac ggcuggg                                             17

<210> SEQ ID NO 511
<211> LENGTH: 15
<212> TYPE: RNA
<213> ORGANISM: Homo sapiens

<400> SEQUENCE: 511
cuccgggacg gcugg                                               15

<210> SEQ ID NO 512
<211> LENGTH: 29
<212> TYPE: RNA
<213> ORGANISM: Homo sapiens

<400> SEQUENCE: 512

-continued

```
ggucaggcgg cucggacuga gcagguggg                             29

<210> SEQ ID NO 513
<211> LENGTH: 15
<212> TYPE: RNA
<213> ORGANISM: Homo sapiens

<400> SEQUENCE: 513
agaguguggu caggc                                            15

<210> SEQ ID NO 514
<211> LENGTH: 15
<212> TYPE: RNA
<213> ORGANISM: Homo sapiens

<400> SEQUENCE: 514
ggcgcgggga ggugc                                            15

<210> SEQ ID NO 515
<211> LENGTH: 15
<212> TYPE: RNA
<213> ORGANISM: Homo sapiens

<400> SEQUENCE: 515
ggcgcgggga ggugc                                            15

<210> SEQ ID NO 516
<211> LENGTH: 22
<212> TYPE: RNA
<213> ORGANISM: Homo sapiens

<400> SEQUENCE: 516
accccacucc ugguaccaua gu                                    22

<210> SEQ ID NO 517
<211> LENGTH: 15
<212> TYPE: RNA
<213> ORGANISM: Homo sapiens

<400> SEQUENCE: 517
accccacucc uggua                                            15

<210> SEQ ID NO 518
<211> LENGTH: 15
<212> TYPE: RNA
<213> ORGANISM: Homo sapiens

<400> SEQUENCE: 518
ugaagcgggg gggcg                                            15

<210> SEQ ID NO 519
<211> LENGTH: 15
<212> TYPE: RNA
<213> ORGANISM: Homo sapiens

<400> SEQUENCE: 519
ugaagcgggg gggcg                                            15

<210> SEQ ID NO 520
<211> LENGTH: 21
<212> TYPE: RNA
<213> ORGANISM: Homo sapiens

<400> SEQUENCE: 520
```
gaauggauuu uuggagcagg a                                              21

<210> SEQ ID NO 521
<211> LENGTH: 15
<212> TYPE: RNA
<213> ORGANISM: Homo sapiens

<400> SEQUENCE: 521
gaauggauuu uugga                                                     15

<210> SEQ ID NO 522
<211> LENGTH: 25
<212> TYPE: RNA
<213> ORGANISM: Homo sapiens

<400> SEQUENCE: 522
uggcggcggu aguuaugggc uucuc                                          25

<210> SEQ ID NO 523
<211> LENGTH: 25
<212> TYPE: RNA
<213> ORGANISM: Homo sapiens

<400> SEQUENCE: 523
uggcggcggu aguuaugggc uucuc                                          25

<210> SEQ ID NO 524
<211> LENGTH: 18
<212> TYPE: RNA
<213> ORGANISM: Homo sapiens

<400> SEQUENCE: 524
gaggcugaag gaagaugg                                                  18

<210> SEQ ID NO 525
<211> LENGTH: 15
<212> TYPE: RNA
<213> ORGANISM: Homo sapiens

<400> SEQUENCE: 525
gaggcugaag gaaga                                                     15

<210> SEQ ID NO 526
<211> LENGTH: 23
<212> TYPE: RNA
<213> ORGANISM: Homo sapiens

<400> SEQUENCE: 526 aggaggguc ccgcacuggg agg                                             23

<210> SEQ ID NO 527
<211> LENGTH: 15
<212> TYPE: RNA
<213> ORGANISM: Homo sapiens

<400> SEQUENCE: 527
ugggaggggc ccuca                                                     15

<210> SEQ ID NO 528
<211> LENGTH: 21
<212> TYPE: RNA
<213> ORGANISM: Homo sapiens

```
<400> SEQUENCE: 528
gagggcagcg ugggugcggc g                                              21

<210> SEQ ID NO 529
<211> LENGTH: 21
<212> TYPE: RNA
<213> ORGANISM: Homo sapiens

<400> SEQUENCE: 529
gagggcagcg ugggugcggc g                                              21

<210> SEQ ID NO 530
<211> LENGTH: 23
<212> TYPE: RNA
<213> ORGANISM: Homo sapiens

<400> SEQUENCE: 530
caccuugccu ugcugcccgg gcc                                            23

<210> SEQ ID NO 531
<211> LENGTH: 22
<212> TYPE: RNA
<213> ORGANISM: Homo sapiens

<400> SEQUENCE: 531
caccuugccu ugcugcccgg gc                                             22

<210> SEQ ID NO 532
<211> LENGTH: 19
<212> TYPE: RNA
<213> ORGANISM: Homo sapiens

<400> SEQUENCE: 532
guggguuggg gcgggcucu                                                 19

<210> SEQ ID NO 533
<211> LENGTH: 19
<212> TYPE: RNA
<213> ORGANISM: Homo sapiens

<400> SEQUENCE: 533
guggguuggg gcgggcucu                                                 19

<210> SEQ ID NO 534
<211> LENGTH: 24
<212> TYPE: RNA
<213> ORGANISM: Homo sapiens

<400> SEQUENCE: 534
auauacaggg ggagacucuc auuu                                           24

<210> SEQ ID NO 535
<211> LENGTH: 15
<212> TYPE: RNA
<213> ORGANISM: Homo sapiens

<400> SEQUENCE: 535
auauacaggg ggaga                                                     15

<210> SEQ ID NO 536
<211> LENGTH: 26
<212> TYPE: RNA
<213> ORGANISM: Homo sapiens
```

-continued

```
<400> SEQUENCE: 536
agggcuggac ucagcggcgg agcugg                                  26

<210> SEQ ID NO 537
<211> LENGTH: 17
<212> TYPE: RNA
<213> ORGANISM: Homo sapiens

<400> SEQUENCE: 537
gcggcggagc uggcugc                                            17

<210> SEQ ID NO 538
<211> LENGTH: 22
<212> TYPE: RNA
<213> ORGANISM: Homo sapiens

<400> SEQUENCE: 538
gugggcgggg gcaggugugu gg                                      22

<210> SEQ ID NO 539
<211> LENGTH: 15
<212> TYPE: RNA
<213> ORGANISM: Homo sapiens

<400> SEQUENCE: 539
cgggggcagg ugugu                                              15

<210> SEQ ID NO 540
<211> LENGTH: 16
<212> TYPE: RNA
<213> ORGANISM: Homo sapiens

<400> SEQUENCE: 540
ugcuggugau gcuuuc                                             16

<210> SEQ ID NO 541
<211> LENGTH: 16
<212> TYPE: RNA
<213> ORGANISM: Homo sapiens

<400> SEQUENCE: 541
ugcuggugau gcuuuc                                             16

<210> SEQ ID NO 542
<211> LENGTH: 22
<212> TYPE: RNA
<213> ORGANISM: Homo sapiens

<400> SEQUENCE: 542
acucggcugc gguggacaag uc                                      22

<210> SEQ ID NO 543
<211> LENGTH: 20
<212> TYPE: RNA
<213> ORGANISM: Homo sapiens

<400> SEQUENCE: 543
acucggcugc gguggacaag                                         20

<210> SEQ ID NO 544
<211> LENGTH: 18
<212> TYPE: RNA
```

```
<213> ORGANISM: Homo sapiens

<400> SEQUENCE: 544
ucuaggvggg gagacuga                                                    18

<210> SEQ ID NO 545
<211> LENGTH: 16
<212> TYPE: RNA
<213> ORGANISM: Homo sapiens

<400> SEQUENCE: 545
guggggagac ugacgg                                                      16

<210> SEQ ID NO 546
<211> LENGTH: 26
<212> TYPE: RNA
<213> ORGANISM: Homo sapiens

<400> SEQUENCE: 546
gucccggggc ugcgcgaggc acaggc                                           26

<210> SEQ ID NO 547
<211> LENGTH: 15
<212> TYPE: RNA
<213> ORGANISM: Homo sapiens

<400> SEQUENCE: 547
ggcccggggg gcggg                                                       15

<210> SEQ ID NO 548
<211> LENGTH: 23
<212> TYPE: RNA
<213> ORGANISM: Homo sapiens

<400> SEQUENCE: 548 guggggaga ggcugucuug ugu                                               23

<210> SEQ ID NO 549
<211> LENGTH: 15
<212> TYPE: RNA
<213> ORGANISM: Homo sapiens

<400> SEQUENCE: 549 gugugggga gaggc                                                        15

<210> SEQ ID NO 550
<211> LENGTH: 17
<212> TYPE: RNA
<213> ORGANISM: Homo sapiens

<400> SEQUENCE: 550
ggugagcgcu cgcuggc                                                     17

<210> SEQ ID NO 551
<211> LENGTH: 15
<212> TYPE: RNA
<213> ORGANISM: Homo sapiens

<400> SEQUENCE: 551
cggugagcgc ucgcu                                                       15

<210> SEQ ID NO 552
<211> LENGTH: 21
```

```
<212> TYPE: RNA
<213> ORGANISM: Homo sapiens

<400> SEQUENCE: 552
guuggaggcg uggguuuuag a                                              21

<210> SEQ ID NO 553
<211> LENGTH: 15
<212> TYPE: RNA
<213> ORGANISM: Homo sapiens

<400> SEQUENCE: 553
guuggaggcg ugggu                                                     15

<210> SEQ ID NO 554
<211> LENGTH: 25
<212> TYPE: RNA
<213> ORGANISM: Homo sapiens

<400> SEQUENCE: 554
caggaaggau uuagggacag gcuuu                                          25

<210> SEQ ID NO 555
<211> LENGTH: 19
<212> TYPE: RNA
<213> ORGANISM: Homo sapiens

<400> SEQUENCE: 555
caggaaggau uuagggaca                                                 19

<210> SEQ ID NO 556
<211> LENGTH: 15
<212> TYPE: RNA
<213> ORGANISM: Homo sapiens

<400> SEQUENCE: 556
ucugggcgag gggug                                                     15

<210> SEQ ID NO 557
<211> LENGTH: 15
<212> TYPE: RNA
<213> ORGANISM: Homo sapiens

<400> SEQUENCE: 557
ucugggcgag gggug                                                     15

<210> SEQ ID NO 558
<211> LENGTH: 23
<212> TYPE: RNA
<213> ORGANISM: Homo sapiens

<400> SEQUENCE: 558 gggggggaugu gcaugcuggu ugg                                           23

<210> SEQ ID NO 559
<211> LENGTH: 15
<212> TYPE: RNA
<213> ORGANISM: Homo sapiens

<400> SEQUENCE: 559
aucagcgugc acuuc                                                     15

<210> SEQ ID NO 560
```

```
<211> LENGTH: 20
<212> TYPE: RNA
<213> ORGANISM: Homo sapiens

<400> SEQUENCE: 560
ccccagggcg acgcggcggg                                              20

<210> SEQ ID NO 561
<211> LENGTH: 15
<212> TYPE: RNA
<213> ORGANISM: Homo sapiens

<400> SEQUENCE: 561
cgcggcgggg gcggc                                                   15

<210> SEQ ID NO 562
<211> LENGTH: 23
<212> TYPE: RNA
<213> ORGANISM: Homo sapiens

<400> SEQUENCE: 562
agggucgggg cagggagggc agg                                          23

<210> SEQ ID NO 563
<211> LENGTH: 15
<212> TYPE: RNA
<213> ORGANISM: Homo sapiens

<400> SEQUENCE: 563
gggagaaggg ucggg                                                   15

<210> SEQ ID NO 564
<211> LENGTH: 18
<212> TYPE: RNA
<213> ORGANISM: Homo sapiens

<400> SEQUENCE: 564
ggugggcuuc ccggaggg                                                18

<210> SEQ ID NO 565
<211> LENGTH: 15
<212> TYPE: RNA
<213> ORGANISM: Homo sapiens

<400> SEQUENCE: 565
ggugggcuuc ccgga                                                   15

<210> SEQ ID NO 566
<211> LENGTH: 20
<212> TYPE: RNA
<213> ORGANISM: Homo sapiens

<400> SEQUENCE: 566
aagacacauu uggagaggga                                              20

<210> SEQ ID NO 567
<211> LENGTH: 16
<212> TYPE: RNA
<213> ORGANISM: Homo sapiens

<400> SEQUENCE: 567
agacacauuu ggagag                                                  16
```

-continued

```
<210> SEQ ID NO 568
<211> LENGTH: 19
<212> TYPE: RNA
<213> ORGANISM: Homo sapiens

<400> SEQUENCE: 568
gagggcgggu ggaggagga                                                   19

<210> SEQ ID NO 569
<211> LENGTH: 15
<212> TYPE: RNA
<213> ORGANISM: Homo sapiens

<400> SEQUENCE: 569
gcggguggag gagga                                                       15

<210> SEQ ID NO 570
<211> LENGTH: 17
<212> TYPE: RNA
<213> ORGANISM: Homo sapiens

<400> SEQUENCE: 570
baucccagcg gugccuc                                                     17

<210> SEQ ID NO 571
<211> LENGTH: 15
<212> TYPE: RNA
<213> ORGANISM: Homo sapiens

<400> SEQUENCE: 571
gaucccagcg gugcc                                                       15

<210> SEQ ID NO 572
<211> LENGTH: 23
<212> TYPE: RNA
<213> ORGANISM: Homo sapiens

<400> SEQUENCE: 572
aagggaggag gagcggaggg gcc                                              23

<210> SEQ ID NO 573
<211> LENGTH: 15
<212> TYPE: RNA
<213> ORGANISM: Homo sapiens

<400> SEQUENCE: 573
gggaggagga gcgga                                                       15

<210> SEQ ID NO 574
<211> LENGTH: 23
<212> TYPE: RNA
<213> ORGANISM: Homo sapiens

<400> SEQUENCE: 574
ccaggaggcg gaggaggugg agg                                              23

<210> SEQ ID NO 575
<211> LENGTH: 15
<212> TYPE: RNA
<213> ORGANISM: Homo sapiens

<400> SEQUENCE: 575
acccaggagg cggag                                                       15
```

```
<210> SEQ ID NO 576
<211> LENGTH: 15
<212> TYPE: RNA
<213> ORGANISM: Homo sapiens

<400> SEQUENCE: 576
uggcagagcg cuguc                                                    15

<210> SEQ ID NO 577
<211> LENGTH: 15
<212> TYPE: RNA
<213> ORGANISM: Homo sapiens

<400> SEQUENCE: 577
uggcagagcg cuguc                                                    15

<210> SEQ ID NO 578
<211> LENGTH: 22
<212> TYPE: RNA
<213> ORGANISM: Homo sapiens

<400> SEQUENCE: 578
gaggguuggg uggaggcucu cc                                            22

<210> SEQ ID NO 579
<211> LENGTH: 15
<212> TYPE: RNA
<213> ORGANISM: Homo sapiens

<400> SEQUENCE: 579
gaggguuggg uggag                                                    15

<210> SEQ ID NO 580
<211> LENGTH: 21
<212> TYPE: RNA
<213> ORGANISM: Homo sapiens

<400> SEQUENCE: 580
cagcagggga gagagaggag u                                             21

<210> SEQ ID NO 581
<211> LENGTH: 20
<212> TYPE: RNA
<213> ORGANISM: Homo sapiens

<400> SEQUENCE: 581
cagcagggga gagagaggag                                               20

<210> SEQ ID NO 582
<211> LENGTH: 22
<212> TYPE: RNA
<213> ORGANISM: Homo sapiens

<400> SEQUENCE: 582
ccgggaacgu cgagacugga gc                                            22

<210> SEQ ID NO 583
<211> LENGTH: 15
<212> TYPE: RNA
<213> ORGANISM: Homo sapiens

<400> SEQUENCE: 583
cgggaacguc gagac                                                    15
```

```
<210> SEQ ID NO 584
<211> LENGTH: 17
<212> TYPE: RNA
<213> ORGANISM: Homo sapiens

<400> SEQUENCE: 584
aggggcuggg cgcgcgc                                                  17

<210> SEQ ID NO 585
<211> LENGTH: 15
<212> TYPE: RNA
<213> ORGANISM: Homo sapiens

<400> SEQUENCE: 585
caggggcugg gcgcg                                                    15

<210> SEQ ID NO 586
<211> LENGTH: 24
<212> TYPE: RNA
<213> ORGANISM: Homo sapiens

<400> SEQUENCE: 586
cgggcguggu ggugggggug ggug                                          24

<210> SEQ ID NO 587
<211> LENGTH: 15
<212> TYPE: RNA
<213> ORGANISM: Homo sapiens

<400> SEQUENCE: 587
cgggcguggu ggugg                                                    15

<210> SEQ ID NO 588
<211> LENGTH: 24
<212> TYPE: RNA
<213> ORGANISM: Homo sapiens

<400> SEQUENCE: 588
uggggagcug aggcucuggg ggug                                          24

<210> SEQ ID NO 589
<211> LENGTH: 15
<212> TYPE: RNA
<213> ORGANISM: Homo sapiens

<400> SEQUENCE: 589
ggcccugggg agcug                                                    15

<210> SEQ ID NO 590
<211> LENGTH: 19
<212> TYPE: RNA
<213> ORGANISM: Homo sapiens

<400> SEQUENCE: 590
uggcgggugc gggggtgggg                                               19

<210> SEQ ID NO 591
<211> LENGTH: 15
<212> TYPE: RNA
<213> ORGANISM: Homo sapiens

<400> SEQUENCE: 591
```

```
uggcgggugc ggggg                                                    15

<210> SEQ ID NO 592
<211> LENGTH: 25
<212> TYPE: RNA
<213> ORGANISM: Homo sapiens

<400> SEQUENCE: 592
ugcggggcua gggcuaacag caguc                                         25

<210> SEQ ID NO 593
<211> LENGTH: 15
<212> TYPE: RNA
<213> ORGANISM: Homo sapiens

<400> SEQUENCE: 593
ugcggggcua gggcu                                                    15

<210> SEQ ID NO 594
<211> LENGTH: 20
<212> TYPE: RNA
<213> ORGANISM: Homo sapiens

<400> SEQUENCE: 594
uggcuguugg aggggggcagg                                              20

<210> SEQ ID NO 595
<211> LENGTH: 15
<212> TYPE: RNA
<213> ORGANISM: Homo sapiens

<400> SEQUENCE: 595 ggaggggggca ggcuc                                                   15

<210> SEQ ID NO 596
<211> LENGTH: 24
<212> TYPE: RNA
<213> ORGANISM: Homo sapiens

<400> SEQUENCE: 596
aggcaggggc uggugcuggg cggg                                          24

<210> SEQ ID NO 597
<211> LENGTH: 15
<212> TYPE: RNA
<213> ORGANISM: Homo sapiens

<400> SEQUENCE: 597
gggcgggggg cggcg                                                    15

<210> SEQ ID NO 598
<211> LENGTH: 23
<212> TYPE: RNA
<213> ORGANISM: Homo sapiens

<400> SEQUENCE: 598
gugggcuggg cugggcuggg cca                                           23

<210> SEQ ID NO 599
<211> LENGTH: 15
<212> TYPE: RNA
<213> ORGANISM: Homo sapiens

<400> SEQUENCE: 599
```
gggcugggcu gggcu                                                      15

<210> SEQ ID NO 600
<211> LENGTH: 17
<212> TYPE: RNA
<213> ORGANISM: Homo sapiens

<400> SEQUENCE: 600
ggggcggggg cggggc                                                     17

<210> SEQ ID NO 601
<211> LENGTH: 15
<212> TYPE: RNA
<213> ORGANISM: Homo sapiens

<400> SEQUENCE: 601
cgcgccgggc ccggg                                                      15

<210> SEQ ID NO 602
<211> LENGTH: 23
<212> TYPE: RNA
<213> ORGANISM: Homo sapiens

<400> SEQUENCE: 602
gccccggcgc gggcggguuc ugg                                             23

<210> SEQ ID NO 603
<211> LENGTH: 16
<212> TYPE: RNA
<213> ORGANISM: Homo sapiens

<400> SEQUENCE: 603
ggagccccgg cgcggg                                                     16

<210> SEQ ID NO 604
<211> LENGTH: 24
<212> TYPE: RNA
<213> ORGANISM: Homo sapiens

<400> SEQUENCE: 604
agacacauuu ggagagggaa ccuc                                            24

<210> SEQ ID NO 605
<211> LENGTH: 16
<212> TYPE: RNA
<213> ORGANISM: Homo sapiens

<400> SEQUENCE: 605
agacacauuu ggagag                                                     16

<210> SEQ ID NO 606
<211> LENGTH: 22
<212> TYPE: RNA
<213> ORGANISM: Homo sapiens

<400> SEQUENCE: 606
ugggagggga gaggcagcaa gc                                              22

<210> SEQ ID NO 607
<211> LENGTH: 22
<212> TYPE: RNA
<213> ORGANISM: Homo sapiens -continued

<400> SEQUENCE: 607
ugggagggga gaggcagcaa gc					22

<210> SEQ ID NO 608
<211> LENGTH: 21
<212> TYPE: RNA
<213> ORGANISM: Homo sapiens

<400> SEQUENCE: 608
auccaguucu cugagggggc u						21

<210> SEQ ID NO 609
<211> LENGTH: 21
<212> TYPE: RNA
<213> ORGANISM: Homo sapiens

<400> SEQUENCE: 609
auccaguucu cugagggggc u						21

<210> SEQ ID NO 610
<211> LENGTH: 23
<212> TYPE: RNA
<213> ORGANISM: Homo sapiens

<400> SEQUENCE: 610
aauauacagg gggagacucu uau					23

<210> SEQ ID NO 611
<211> LENGTH: 15
<212> TYPE: RNA
<213> ORGANISM: Homo sapiens

<400> SEQUENCE: 611
auauacaggg ggaga						15

<210> SEQ ID NO 612
<211> LENGTH: 24
<212> TYPE: RNA
<213> ORGANISM: Homo sapiens

<400> SEQUENCE: 612
ucgaggacug guggaagggc cuuu					24

<210> SEQ ID NO 613
<211> LENGTH: 16
<212> TYPE: RNA
<213> ORGANISM: Homo sapiens

<400> SEQUENCE: 613
ucgaggacug guggaa						16

<210> SEQ ID NO 614
<211> LENGTH: 18
<212> TYPE: RNA
<213> ORGANISM: Homo sapiens

<400> SEQUENCE: 614
gagacugggg ugggggccu						18

<210> SEQ ID NO 615
<211> LENGTH: 16
<212> TYPE: RNA
<213> ORGANISM: Homo sapiens

```
<400> SEQUENCE: 615
agacuggggu ggggcc                                                   16

<210> SEQ ID NO 616
<211> LENGTH: 23
<212> TYPE: RNA
<213> ORGANISM: Homo sapiens

<400> SEQUENCE: 616
gggggccgau acacuguacg aga                                           23

<210> SEQ ID NO 617
<211> LENGTH: 20
<212> TYPE: RNA
<213> ORGANISM: Homo sapiens

<400> SEQUENCE: 617
gggggccgau acacuguacg                                               20

<210> SEQ ID NO 618
<211> LENGTH: 18
<212> TYPE: RNA
<213> ORGANISM: Homo sapiens

<400> SEQUENCE: 618
cagcggggcu gggcgcgc                                                 18

<210> SEQ ID NO 619
<211> LENGTH: 15
<212> TYPE: RNA
<213> ORGANISM: Homo sapiens

<400> SEQUENCE: 619
cagcggggcu gggcg                                                    15

<210> SEQ ID NO 620
<211> LENGTH: 24
<212> TYPE: RNA
<213> ORGANISM: Homo sapiens

<400> SEQUENCE: 620
gcugcgggcu gcggucaggg cgau                                          24

<210> SEQ ID NO 621
<211> LENGTH: 20
<212> TYPE: RNA
<213> ORGANISM: Homo sapiens

<400> SEQUENCE: 621
gcugcgggcu gcggucaggg                                               20

<210> SEQ ID NO 622
<211> LENGTH: 23
<212> TYPE: RNA
<213> ORGANISM: Homo sapiens

<400> SEQUENCE: 622
agggaguaga agggugggga gca                                           23

<210> SEQ ID NO 623
<211> LENGTH: 16
<212> TYPE: RNA
```

```
<213> ORGANISM: Homo sapiens

<400> SEQUENCE: 623
uagggaguag aagggu                                                    16

<210> SEQ ID NO 624
<211> LENGTH: 27
<212> TYPE: RNA
<213> ORGANISM: Homo sapiens

<400> SEQUENCE: 624
gugaacgggc gccaucccga ggcuuug                                        27

<210> SEQ ID NO 625
<211> LENGTH: 16
<212> TYPE: RNA
<213> ORGANISM: Homo sapiens

<400> SEQUENCE: 625
gugaacgggc gccauc                                                    16

<210> SEQ ID NO 626
<211> LENGTH: 25
<212> TYPE: RNA
<213> ORGANISM: Homo sapiens

<400> SEQUENCE: 626
uucugggccc gcggcgggcg ugggg                                          25

<210> SEQ ID NO 627
<211> LENGTH: 15
<212> TYPE: RNA
<213> ORGANISM: Homo sapiens

<400> SEQUENCE: 627
cgcggcgggc guggg                                                     15

<210> SEQ ID NO 628
<211> LENGTH: 26
<212> TYPE: RNA
<213> ORGANISM: Homo sapiens

<400> SEQUENCE: 628
aaaaucacau ugccagggau uaccac                                         26

<210> SEQ ID NO 629
<211> LENGTH: 15
<212> TYPE: RNA
<213> ORGANISM: Homo sapiens

<400> SEQUENCE: 629
aaucacauug ccagg                                                     15

<210> SEQ ID NO 630
<211> LENGTH: 27
<212> TYPE: RNA
<213> ORGANISM: Homo sapiens

<400> SEQUENCE: 630
aucacauugc cagggauuuc caaccga                                        27

<210> SEQ ID NO 631
<211> LENGTH: 15
```

<212> TYPE: RNA
<213> ORGANISM: Homo sapiens

<400> SEQUENCE: 631
aaucacauug ccagg                                             15

<210> SEQ ID NO 632
<211> LENGTH: 26
<212> TYPE: RNA
<213> ORGANISM: Homo sapiens

<400> SEQUENCE: 632
gacuauagaa cuucccccu cauccc                                  26

<210> SEQ ID NO 633
<211> LENGTH: 15
<212> TYPE: RNA
<213> ORGANISM: Homo sapiens

<400> SEQUENCE: 633
aacuuucccc cucau                                             15

<210> SEQ ID NO 634
<211> LENGTH: 22
<212> TYPE: RNA
<213> ORGANISM: Homo sapiens

<400> SEQUENCE: 634
ccucacaccu gccucgcccc cc                                     22

<210> SEQ ID NO 635
<211> LENGTH: 15
<212> TYPE: RNA
<213> ORGANISM: Homo sapiens

<400> SEQUENCE: 635
ucacaccugc cucgc                                             15

<210> SEQ ID NO 636
<211> LENGTH: 17
<212> TYPE: RNA
<213> ORGANISM: Homo sapiens

<400> SEQUENCE: 636
ugcaggggca ggccagc                                           17

<210> SEQ ID NO 637
<211> LENGTH: 17
<212> TYPE: RNA
<213> ORGANISM: Homo sapiens

<400> SEQUENCE: 637
ugcaggggca ggccagc                                           17

<210> SEQ ID NO 638
<211> LENGTH: 22
<212> TYPE: RNA
<213> ORGANISM: Homo sapiens

<400> SEQUENCE: 638
ccggcagagg aggcugcaga gg                                     22

<210> SEQ ID NO 639

```
<211> LENGTH: 19
<212> TYPE: RNA
<213> ORGANISM: Homo sapiens

<400> SEQUENCE: 639
ccggcagagg aggcugcag                                                    19

<210> SEQ ID NO 640
<211> LENGTH: 25
<212> TYPE: RNA
<213> ORGANISM: Homo sapiens

<400> SEQUENCE: 640
ggguggggau uguugcauu acuug                                              25

<210> SEQ ID NO 641
<211> LENGTH: 20
<212> TYPE: RNA
<213> ORGANISM: Homo sapiens

<400> SEQUENCE: 641
ggguggggau uguugcauu                                                    20

<210> SEQ ID NO 642
<211> LENGTH: 23
<212> TYPE: RNA
<213> ORGANISM: Homo sapiens

<400> SEQUENCE: 642
ggcuacaaca caggacccgg gcg                                               23

<210> SEQ ID NO 643
<211> LENGTH: 21
<212> TYPE: RNA
<213> ORGANISM: Homo sapiens

<400> SEQUENCE: 643
ggcuacaaca caggacccgg g                                                 21

<210> SEQ ID NO 644
<211> LENGTH: 27
<212> TYPE: RNA
<213> ORGANISM: Homo sapiens

<400> SEQUENCE: 644
uagcagcacg uaaauauugg cguuaag                                           27

<210> SEQ ID NO 645
<211> LENGTH: 15
<212> TYPE: RNA
<213> ORGANISM: Homo sapiens

<400> SEQUENCE: 645
uagcagcacg uaaau                                                        15

<210> SEQ ID NO 646
<211> LENGTH: 24
<212> TYPE: RNA
<213> ORGANISM: Homo sapiens

<400> SEQUENCE: 646
aauauugcac ucgucccggc cucc                                              24
```

```
<210> SEQ ID NO 647
<211> LENGTH: 15
<212> TYPE: RNA
<213> ORGANISM: Homo sapiens

<400> SEQUENCE: 647
uauugcacuc guccc                                                      15

<210> SEQ ID NO 648
<211> LENGTH: 24
<212> TYPE: RNA
<213> ORGANISM: Homo sapiens

<400> SEQUENCE: 648
cugguacagg ccuggggac aggg                                             24

<210> SEQ ID NO 649
<211> LENGTH: 18
<212> TYPE: RNA
<213> ORGANISM: Homo sapiens

<400> SEQUENCE: 649
cugguacagg ccuggggg                                                   18

<210> SEQ ID NO 650
<211> LENGTH: 18
<212> TYPE: RNA
<213> ORGANISM: Homo sapiens

<400> SEQUENCE: 650
cuccgggcgg cgccgugu                                                   18

<210> SEQ ID NO 651
<211> LENGTH: 18
<212> TYPE: RNA
<213> ORGANISM: Homo sapiens

<400> SEQUENCE: 651
cuccgggcgg cgccgugu                                                   18

<210> SEQ ID NO 652
<211> LENGTH: 23
<212> TYPE: RNA
<213> ORGANISM: Homo sapiens

<400> SEQUENCE: 652
cacaggugag guucuuggga gcc                                             23

<210> SEQ ID NO 653
<211> LENGTH: 15
<212> TYPE: RNA
<213> ORGANISM: Homo sapiens

<400> SEQUENCE: 653
acaggugagg uucuu                                                      15

<210> SEQ ID NO 654
<211> LENGTH: 26
<212> TYPE: RNA
<213> ORGANISM: Homo sapiens

<400> SEQUENCE: 654
agggacggga cgcggugcag uguugu                                          26
```

```
<210> SEQ ID NO 655
<211> LENGTH: 15
<212> TYPE: RNA
<213> ORGANISM: Homo sapiens

<400> SEQUENCE: 655
ggcgggcggg aggga                                                    15

<210> SEQ ID NO 656
<211> LENGTH: 28
<212> TYPE: RNA
<213> ORGANISM: Homo sapiens

<400> SEQUENCE: 656
guaugguauu gcacuugucc cggccugu                                      28

<210> SEQ ID NO 657
<211> LENGTH: 15
<212> TYPE: RNA
<213> ORGANISM: Homo sapiens

<400> SEQUENCE: 657
uauugcacuu guccc                                                    15

<210> SEQ ID NO 658
<211> LENGTH: 26
<212> TYPE: RNA
<213> ORGANISM: Homo sapiens

<400> SEQUENCE: 658 cgugggauc ccgcggccgu guuuuc                                         26

<210> SEQ ID NO 659
<211> LENGTH: 15
<212> TYPE: RNA
<213> ORGANISM: Homo sapiens

<400> SEQUENCE: 659
ggggcgccgc gggac                                                    15

<210> SEQ ID NO 660
<211> LENGTH: 23
<212> TYPE: RNA
<213> ORGANISM: Homo sapiens

<400> SEQUENCE: 660
uaggggcagc agaggaccug ggc                                           23

<210> SEQ ID NO 661
<211> LENGTH: 20
<212> TYPE: RNA
<213> ORGANISM: Homo sapiens

<400> SEQUENCE: 661
uaggggcagc agaggaccug                                               20

<210> SEQ ID NO 662
<211> LENGTH: 22
<212> TYPE: RNA
<213> ORGANISM: Homo sapiens

<400> SEQUENCE: 662
ugugggacug caaaugggag cu                                            22
```

<210> SEQ ID NO 663
<211> LENGTH: 22
<212> TYPE: RNA
<213> ORGANISM: Homo sapiens

<400> SEQUENCE: 663 uguggacug caaaugggag cu                                          22

<210> SEQ ID NO 664
<211> LENGTH: 16
<212> TYPE: RNA
<213> ORGANISM: Homo sapiens

<400> SEQUENCE: 664
gugaaggccc ggcgga                                                16

<210> SEQ ID NO 665
<211> LENGTH: 15
<212> TYPE: RNA
<213> ORGANISM: Homo sapiens

<400> SEQUENCE: 665
gugaaggccc ggcgg                                                 15

<210> SEQ ID NO 666
<211> LENGTH: 22
<212> TYPE: RNA
<213> ORGANISM: Homo sapiens

<400> SEQUENCE: 666 gggggcagg aggggcucag gg                                          22

<210> SEQ ID NO 667
<211> LENGTH: 16
<212> TYPE: RNA
<213> ORGANISM: Homo sapiens

<400> SEQUENCE: 667 guggggggc aggagg                                                 16

<210> SEQ ID NO 668
<211> LENGTH: 23
<212> TYPE: RNA
<213> ORGANISM: Homo sapiens

<400> SEQUENCE: 668 ugggggcggag cuuccggagg ccc                                       23

<210> SEQ ID NO 669
<211> LENGTH: 16
<212> TYPE: RNA
<213> ORGANISM: Homo sapiens

<400> SEQUENCE: 669
aucgcuggcc uggucg                                                16

<210> SEQ ID NO 670
<211> LENGTH: 26
<212> TYPE: RNA
<213> ORGANISM: Homo sapiens

<400> SEQUENCE: 670

```
gaggggcucu cgcuucuggc gccaag                                   26

<210> SEQ ID NO 671
<211> LENGTH: 15
<212> TYPE: RNA
<213> ORGANISM: Homo sapiens

<400> SEQUENCE: 671
ggugaggcgg ggggg                                               15

<210> SEQ ID NO 672
<211> LENGTH: 21
<212> TYPE: RNA
<213> ORGANISM: Homo sapiens

<400> SEQUENCE: 672
cagccugagu gacagagcaa g                                        21

<210> SEQ ID NO 673
<211> LENGTH: 15
<212> TYPE: RNA
<213> ORGANISM: Homo sapiens

<400> SEQUENCE: 673
acugcacucc agccu                                               15

<210> SEQ ID NO 674
<211> LENGTH: 17
<212> TYPE: RNA
<213> ORGANISM: Homo sapiens

<400> SEQUENCE: 674
gcggggcggc aggggcc                                             17

<210> SEQ ID NO 675
<211> LENGTH: 15
<212> TYPE: RNA
<213> ORGANISM: Homo sapiens

<400> SEQUENCE: 675
gggggcgggg cggca                                               15

<210> SEQ ID NO 676
<211> LENGTH: 21
<212> TYPE: RNA
<213> ORGANISM: Homo sapiens

<400> SEQUENCE: 676
aggaggcagu gggcgagcag g                                        21

<210> SEQ ID NO 677
<211> LENGTH: 21
<212> TYPE: RNA
<213> ORGANISM: Homo sapiens

<400> SEQUENCE: 677
aggaggcagu gggcgagcag g                                        21

<210> SEQ ID NO 678
<211> LENGTH: 16
<212> TYPE: RNA
<213> ORGANISM: Homo sapiens

<400> SEQUENCE: 678
```
ggcgcggagg gcggac                                        16

<210> SEQ ID NO 679
<211> LENGTH: 15
<212> TYPE: RNA
<213> ORGANISM: Homo sapiens

<400> SEQUENCE: 679
ggcgcggagg gcgga                                         15

<210> SEQ ID NO 680
<211> LENGTH: 22
<212> TYPE: RNA
<213> ORGANISM: Homo sapiens

<400> SEQUENCE: 680
accaggaggc ugaggccccu ca                                 22

<210> SEQ ID NO 681
<211> LENGTH: 15
<212> TYPE: RNA
<213> ORGANISM: Homo sapiens

<400> SEQUENCE: 681
accaggaggc ugagg                                         15

<210> SEQ ID NO 682
<211> LENGTH: 23
<212> TYPE: RNA
<213> ORGANISM: Homo sapiens

<400> SEQUENCE: 682
cggggcagcu caguacagga uac                                23

<210> SEQ ID NO 683
<211> LENGTH: 15
<212> TYPE: RNA
<213> ORGANISM: Homo sapiens

<400> SEQUENCE: 683
agcucaguac aggau                                         15

<210> SEQ ID NO 684
<211> LENGTH: 19
<212> TYPE: RNA
<213> ORGANISM: Homo sapiens

<400> SEQUENCE: 684
gggugcgggc cggcggggu                                     19

<210> SEQ ID NO 685
<211> LENGTH: 15
<212> TYPE: RNA
<213> ORGANISM: Homo sapiens

<400> SEQUENCE: 685
ugcgggccgg cgggg                                         15

<210> SEQ ID NO 686
<211> LENGTH: 27
<212> TYPE: RNA
<213> ORGANISM: Homo sapiens

```
<400> SEQUENCE: 686
caagguggcu gggagagggu uguuuac                                    27

<210> SEQ ID NO 687
<211> LENGTH: 15
<212> TYPE: RNA
<213> ORGANISM: Homo sapiens

<400> SEQUENCE: 687
gugagcucaa ggugg                                                 15

<210> SEQ ID NO 688
<211> LENGTH: 15
<212> TYPE: RNA
<213> ORGANISM: Homo sapiens

<400> SEQUENCE: 688
aggaggagga ggcag                                                 15

<210> SEQ ID NO 689
<211> LENGTH: 15
<212> TYPE: RNA
<213> ORGANISM: Homo sapiens

<400> SEQUENCE: 689
aggaggagga ggcag                                                 15

<210> SEQ ID NO 690
<211> LENGTH: 26
<212> TYPE: RNA
<213> ORGANISM: Homo sapiens

<400> SEQUENCE: 690
gcgggcuguc cggaggdguc ggcuuu                                     26

<210> SEQ ID NO 691
<211> LENGTH: 16
<212> TYPE: RNA
<213> ORGANISM: Homo sapiens

<400> SEQUENCE: 691
gcuguccgga gggguc                                                16

<210> SEQ ID NO 692
<211> LENGTH: 24
<212> TYPE: RNA
<213> ORGANISM: Homo sapiens

<400> SEQUENCE: 692 uggggagug cagugauugu ggaa                                        24

<210> SEQ ID NO 693
<211> LENGTH: 19
<212> TYPE: RNA
<213> ORGANISM: Homo sapiens

<400> SEQUENCE: 693 uggggagug cagugauug                                              19

<210> SEQ ID NO 694
<211> LENGTH: 22
<212> TYPE: RNA
<213> ORGANISM: Homo sapiens
```

-continued

```
<400> SEQUENCE: 694
acucaaacug uggggggcacu uu                                          22

<210> SEQ ID NO 695
<211> LENGTH: 19
<212> TYPE: RNA
<213> ORGANISM: Homo sapiens

<400> SEQUENCE: 695
acucaaacug uggggggcac                                              19

<210> SEQ ID NO 696
<211> LENGTH: 19
<212> TYPE: RNA
<213> ORGANISM: Homo sapiens

<400> SEQUENCE: 696 aggggggcggg cuccggcgc                                              19

<210> SEQ ID NO 697
<211> LENGTH: 15
<212> TYPE: RNA
<213> ORGANISM: Homo sapiens

<400> SEQUENCE: 697 guaggggggcg ggcuc                                                  15

<210> SEQ ID NO 698
<211> LENGTH: 19
<212> TYPE: RNA
<213> ORGANISM: Homo sapiens

<400> SEQUENCE: 698
agugggaggc cagggcacg                                               19

<210> SEQ ID NO 699
<211> LENGTH: 15
<212> TYPE: RNA
<213> ORGANISM: Homo sapiens

<400> SEQUENCE: 699 aggggggagcu gcagg                                                  15

<210> SEQ ID NO 700
<211> LENGTH: 25
<212> TYPE: RNA
<213> ORGANISM: Homo sapiens

<400> SEQUENCE: 700
gggggagcca ugagauaaga gcacc                                        25

<210> SEQ ID NO 701
<211> LENGTH: 20
<212> TYPE: RNA
<213> ORGANISM: Homo sapiens

<400> SEQUENCE: 701 uggggggagcc augagauaag                                             20

<210> SEQ ID NO 702
<211> LENGTH: 24
<212> TYPE: RNA
```

```
<213> ORGANISM: Homo sapiens

<400> SEQUENCE: 702
acuggcucag uucagcagga acag                                      24

<210> SEQ ID NO 703
<211> LENGTH: 15
<212> TYPE: RNA
<213> ORGANISM: Homo sapiens

<400> SEQUENCE: 703
uggcucaguu cagca                                                15

<210> SEQ ID NO 704
<211> LENGTH: 20
<212> TYPE: RNA
<213> ORGANISM: Homo sapiens

<400> SEQUENCE: 704
cuccccggug ugcaaaugug                                           20

<210> SEQ ID NO 705
<211> LENGTH: 15
<212> TYPE: RNA
<213> ORGANISM: Homo sapiens

<400> SEQUENCE: 705
gugugcggug uuaug                                                15

<210> SEQ ID NO 706
<211> LENGTH: 22
<212> TYPE: RNA
<213> ORGANISM: Homo sapiens

<400> SEQUENCE: 706
ggcaggaagc ggaggaaccu ug                                        22

<210> SEQ ID NO 707
<211> LENGTH: 17
<212> TYPE: RNA
<213> ORGANISM: Homo sapiens

<400> SEQUENCE: 707
ggaggaaccu uggagcu                                              17

<210> SEQ ID NO 708
<211> LENGTH: 21
<212> TYPE: RNA
<213> ORGANISM: Homo sapiens

<400> SEQUENCE: 708
ugggaauggg gguaagggcc u                                         21

<210> SEQ ID NO 709
<211> LENGTH: 15
<212> TYPE: RNA
<213> ORGANISM: Homo sapiens

<400> SEQUENCE: 709
cuucugagcc caggu                                                15

<210> SEQ ID NO 710
<211> LENGTH: 16
```

-continued

```
<212> TYPE: RNA
<213> ORGANISM: Homo sapiens

<400> SEQUENCE: 710
cgggcccggc guuccc                                                    16

<210> SEQ ID NO 711
<211> LENGTH: 15
<212> TYPE: RNA
<213> ORGANISM: Homo sapiens

<400> SEQUENCE: 711
ccgggcccgg cguuc                                                     15

<210> SEQ ID NO 712
<211> LENGTH: 18
<212> TYPE: RNA
<213> ORGANISM: Homo sapiens

<400> SEQUENCE: 712
aaaaggaagg gggaggag                                                  18

<210> SEQ ID NO 713
<211> LENGTH: 16
<212> TYPE: RNA
<213> ORGANISM: Homo sapiens

<400> SEQUENCE: 713
aaggaagggg gaggag                                                    16

<210> SEQ ID NO 714
<211> LENGTH: 22
<212> TYPE: RNA
<213> ORGANISM: Homo sapiens

<400> SEQUENCE: 714
uagggauggg aggccaggau ga                                             22

<210> SEQ ID NO 715
<211> LENGTH: 20
<212> TYPE: RNA
<213> ORGANISM: Homo sapiens

<400> SEQUENCE: 715
ggcuccuugg ucuaggggua                                                20

<210> SEQ ID NO 716
<211> LENGTH: 23
<212> TYPE: RNA
<213> ORGANISM: Homo sapiens

<400> SEQUENCE: 716
aggaagcccu ggaggggcug gag                                            23

<210> SEQ ID NO 717
<211> LENGTH: 17
<212> TYPE: RNA
<213> ORGANISM: Homo sapiens

<400> SEQUENCE: 717
ggggcgcggc cggaucg                                                   17

<210> SEQ ID NO 718
```

<210> SEQ ID NO 718
<211> LENGTH: 22
<212> TYPE: RNA
<213> ORGANISM: Homo sapiens

<400> SEQUENCE: 718 ugggggaaggc gucagugucg gg                                           22

<210> SEQ ID NO 719
<211> LENGTH: 21
<212> TYPE: RNA
<213> ORGANISM: Homo sapiens

<400> SEQUENCE: 719
aaggcagggc ccccgcuccc c                                             21

<210> SEQ ID NO 720
<211> LENGTH: 24
<212> TYPE: RNA
<213> ORGANISM: Homo sapiens

<400> SEQUENCE: 720
guaggggcgu cccgggcgcg cggg                                          24

<210> SEQ ID NO 721
<211> LENGTH: 20
<212> TYPE: RNA
<213> ORGANISM: Homo sapiens

<400> SEQUENCE: 721
aaaaggcggg agaagcccca                                               20

<210> SEQ ID NO 722
<211> LENGTH: 19
<212> TYPE: RNA
<213> ORGANISM: Homo sapiens

<400> SEQUENCE: 722
cggcgcgacc ggcccgggg                                                19

<210> SEQ ID NO 723
<211> LENGTH: 23
<212> TYPE: RNA
<213> ORGANISM: Homo sapiens

<400> SEQUENCE: 723 ugagugggc ucccgggacg gcg                                            23

<210> SEQ ID NO 724
<211> LENGTH: 23
<212> TYPE: RNA
<213> ORGANISM: Homo sapiens

<400> SEQUENCE: 724
cuggcggagc ccauuccaug cca                                           23

<210> SEQ ID NO 725
<211> LENGTH: 22
<212> TYPE: RNA
<213> ORGANISM: Homo sapiens

<400> SEQUENCE: 725 cuggggugg ggggcugggc gu                                             22

```
<210> SEQ ID NO 726
<211> LENGTH: 23
<212> TYPE: RNA
<213> ORGANISM: Homo sapiens

<400> SEQUENCE: 726 ccaggggau gggcgagcuu ggg                                              23

<210> SEQ ID NO 727
<211> LENGTH: 21
<212> TYPE: RNA
<213> ORGANISM: Homo sapiens

<400> SEQUENCE: 727
agccgcgggg aucgccgagg g                                               21

<210> SEQ ID NO 728
<211> LENGTH: 23
<212> TYPE: RNA
<213> ORGANISM: Homo sapiens

<400> SEQUENCE: 728
ccccgguguu ggggcgcguc ugc                                             23

<210> SEQ ID NO 729
<211> LENGTH: 21
<212> TYPE: RNA
<213> ORGANISM: Homo sapiens

<400> SEQUENCE: 729
augccucccc cggccccgca g                                               21

<210> SEQ ID NO 730
<211> LENGTH: 69
<212> TYPE: RNA
<213> ORGANISM: Homo sapiens

<400> SEQUENCE: 730
gggcuuaggg augggaggcc aggaugaaga uuaaucccua auccccaaca cuggccuugc     60
uauccccag                                                             69

<210> SEQ ID NO 731
<211> LENGTH: 86
<212> TYPE: RNA
<213> ORGANISM: Homo sapiens

<400> SEQUENCE: 731
aggagugacc aaaagacaag agugcgagcc uucuauuaug cccagacagg gccaccagag     60
ggcuccuugg ucuaggggua augcca                                          86

<210> SEQ ID NO 732
<211> LENGTH: 118
<212> TYPE: RNA
<213> ORGANISM: Homo sapiens

<400> SEQUENCE: 732
gcaggugaac uggcaggcca ggaagaggag gaagcccugg aggggcugga ggugauggau     60 guuuccucc gguucucagg gcuccaccuc uuucgggccg uagagccagg gcuggugc       118

<210> SEQ ID NO 733
<211> LENGTH: 84
<212> TYPE: RNA
```

<213> ORGANISM: Homo sapiens

<400> SEQUENCE: 733

| gaggcuggc ggggcgcggc cggaucgguc gagagcgucc uggcugauga cggucucccg | 60 |
| ugcccacgcc ccaaacgcag ucuc | 84 |

<210> SEQ ID NO 734
<211> LENGTH: 90
<212> TYPE: RNA
<213> ORGANISM: Homo sapiens

<400> SEQUENCE: 734

| gugucucucu ggagacccug cagccuuccc acccaccagg gagcuuucca ugggcugugg | 60 |
| ggaaggcguc agugucgggu gagggaacac | 90 |

<210> SEQ ID NO 735
<211> LENGTH: 94
<212> TYPE: RNA
<213> ORGANISM: Homo sapiens

<400> SEQUENCE: 735

| gugaggugug ggcccggccc caggagcggg gccugggcag ccccgugugu ugaggaagga | 60 |
| aggcagggcc cccgcucccc gggccugacc ccac | 94 |

<210> SEQ ID NO 736
<211> LENGTH: 98
<212> TYPE: RNA
<213> ORGANISM: Homo sapiens

<400> SEQUENCE: 736

| cgagguaggg gcgucccggg cgcgcgggcg gguccaggc ugggcccuc ggaggccggg | 60 |
| ugcucacugc cccgucccgg cgcccgoguc uccuccag | 98 |

<210> SEQ ID NO 737
<211> LENGTH: 83
<212> TYPE: RNA
<213> ORGANISM: Homo sapiens

<400> SEQUENCE: 737

| ggguuuccuc ugccuuuuuu uccaaugaaa auaacgaaac cuguuauuuc ccauugaggg | 60 |
| ggaaaaaggc gggagaagcc cca | 83 |

<210> SEQ ID NO 738
<211> LENGTH: 54
<212> TYPE: RNA
<213> ORGANISM: Homo sapiens

<400> SEQUENCE: 738

| ggacaagggc ggcgcgaccg gcccggggcu cuugggcggc cgcguuuccc cucc | 54 |

<210> SEQ ID NO 739
<211> LENGTH: 62
<212> TYPE: RNA
<213> ORGANISM: Homo sapiens

<400> SEQUENCE: 739

| gugagugggg cucccgggac ggcgcccgcc cuggcccugg cccggcgacg ucucacgguc | 60 |
| cc | 62 |

```
<210> SEQ ID NO 740
<211> LENGTH: 76
<212> TYPE: RNA
<213> ORGANISM: Homo sapiens

<400> SEQUENCE: 740
cgcaggccuc uggcggagcc cauuccaugc cagaugcuga gcgauggcug gugugugcug      60
cuccacaggc cuggug                                                     76

<210> SEQ ID NO 741
<211> LENGTH: 65
<212> TYPE: RNA
<213> ORGANISM: Homo sapiens

<400> SEQUENCE: 741
cucccucugg ggguggggggc ugggcguggu ggacagcgau gcaucccucg ccuucucacc    60
cucag                                                                 65

<210> SEQ ID NO 742
<211> LENGTH: 67
<212> TYPE: RNA
<213> ORGANISM: Homo sapiens

<400> SEQUENCE: 742
ggcagccagg gggaugggcg agcuugggcc cauuccuuuc cuuacccuac ccccauccc      60 ccuguag                                                               67

<210> SEQ ID NO 743
<211> LENGTH: 180
<212> TYPE: RNA
<213> ORGANISM: Homo sapiens

<400> SEQUENCE: 743
cgcgacugcg gcggcggugg uggggggagc cgcggggauc gccgagggcc ggucggccgc      60
cccgggugcc gcgcggugcc gccggcggcg gugaggcccc gcgcgugugu cccggcugcg     120
gucggccgcg cucgaggggu ccccguggcg uccccuuccc cgccggccgc cuuucucgcg    180

<210> SEQ ID NO 744
<211> LENGTH: 82
<212> TYPE: RNA
<213> ORGANISM: Homo sapiens

<400> SEQUENCE: 744
gggaaagcgg agggcgcgcc cagcucccgg gcugauugcg cuaacagugg ccccggguguu      60 ggggcgcguc ugccgcugcc cc                                              82

<210> SEQ ID NO 745
<211> LENGTH: 63
<212> TYPE: RNA
<213> ORGANISM: Homo sapiens

<400> SEQUENCE: 745
ggcuccgcag ggcccuggcg caggcaucca gacagcgggc gaaugccucc cccggccccg      60
cag                                                                   63

<210> SEQ ID NO 746
<211> LENGTH: 20
<212> TYPE: RNA
<213> ORGANISM: Homo sapiens
```

```
<400> SEQUENCE: 746
ggcuccuugg ucuaggggua                                              20

<210> SEQ ID NO 747
<211> LENGTH: 15
<212> TYPE: RNA
<213> ORGANISM: Homo sapiens

<400> SEQUENCE: 747
cuuggucuag gggua                                                   15

<210> SEQ ID NO 748
<211> LENGTH: 25
<212> TYPE: RNA
<213> ORGANISM: Homo sapiens

<400> SEQUENCE: 748
aggaagcccu ggaggggcug gaggu                                        25

<210> SEQ ID NO 749
<211> LENGTH: 15
<212> TYPE: RNA
<213> ORGANISM: Homo sapiens

<400> SEQUENCE: 749
aggaagagga ggaag                                                   15

<210> SEQ ID NO 750
<211> LENGTH: 24
<212> TYPE: RNA
<213> ORGANISM: Homo sapiens

<400> SEQUENCE: 750
gaucggucga gagcguccug gcug                                         24

<210> SEQ ID NO 751
<211> LENGTH: 15
<212> TYPE: RNA
<213> ORGANISM: Homo sapiens

<400> SEQUENCE: 751
gcugggcggg gcgcg                                                   15

<210> SEQ ID NO 752
<211> LENGTH: 23
<212> TYPE: RNA
<213> ORGANISM: Homo sapiens

<400> SEQUENCE: 752 ugggaaggc gucagugucg ggu                                           23

<210> SEQ ID NO 753
<211> LENGTH: 16
<212> TYPE: RNA
<213> ORGANISM: Homo sapiens

<400> SEQUENCE: 753 ugggaaggc gucagu                                                   16

<210> SEQ ID NO 754
<211> LENGTH: 23
<212> TYPE: RNA
<213> ORGANISM: Homo sapiens
```

-continued

<400> SEQUENCE: 754
aggaaggaag gcagggcccc cgc                                             23

<210> SEQ ID NO 755
<211> LENGTH: 15
<212> TYPE: RNA
<213> ORGANISM: Homo sapiens

<400> SEQUENCE: 755
gggcccccgc uccec                                                      15

<210> SEQ ID NO 756
<211> LENGTH: 20
<212> TYPE: RNA
<213> ORGANISM: Homo sapiens

<400> SEQUENCE: 756
ggaaaaaggc gggagaagcc                                                 20

<210> SEQ ID NO 757
<211> LENGTH: 15
<212> TYPE: RNA
<213> ORGANISM: Homo sapiens

<400> SEQUENCE: 757
ggcgggagaa gcccc                                                      15

<210> SEQ ID NO 758
<211> LENGTH: 20
<212> TYPE: RNA
<213> ORGANISM: Homo sapiens

<400> SEQUENCE: 758 ugagugggc ucccgggacg                                                  20

<210> SEQ ID NO 759
<211> LENGTH: 20
<212> TYPE: RNA
<213> ORGANISM: Homo sapiens

<400> SEQUENCE: 759
ugaguggggc ucccgggacg                                                 20

<210> SEQ ID NO 760
<211> LENGTH: 22
<212> TYPE: RNA
<213> ORGANISM: Homo sapiens

<400> SEQUENCE: 760
uggcggagcc cauuccaugc ca                                              22

<210> SEQ ID NO 761
<211> LENGTH: 21
<212> TYPE: RNA
<213> ORGANISM: Homo sapiens

<400> SEQUENCE: 761
cuggcggagc ccauuccaug c                                               21

<210> SEQ ID NO 762
<211> LENGTH: 29
<212> TYPE: RNA

```
<213> ORGANISM: Homo sapiens

<400> SEQUENCE: 762
gggagccgcg gggaucgccg agggccggu                                        29

<210> SEQ ID NO 763
<211> LENGTH: 15
<212> TYPE: RNA
<213> ORGANISM: Homo sapiens

<400> SEQUENCE: 763
ggcggcggug guggg                                                        15

<210> SEQ ID NO 764
<211> LENGTH: 22
<212> TYPE: RNA
<213> ORGANISM: Homo sapiens

<400> SEQUENCE: 764
ccccgguguu ggggcgcguc ug                                               22

<210> SEQ ID NO 765
<211> LENGTH: 21
<212> TYPE: RNA
<213> ORGANISM: Homo sapiens

<400> SEQUENCE: 765
cccgguguug gggcgcgucu g                                                21
```

LIVER CANCER DETECTION KIT OR DEVICE, AND DETECTION METHOD

TECHNICAL FIELD

The present invention relates to a kit or a device for the detection of liver cancer, comprising a nucleic acid capable of specifically binding to a particular miRNA, which is used for examining the presence or absence of liver cancer in a subject, and a method for detecting liver cancer, comprising measuring an expression level of the miRNA using the nucleic acid.

BACKGROUND ART

The liver is the largest organ in the body and is positioned in the upper right portion of the abdomen. Its main roles are the metabolism of nutrients and the detoxication and elimination of harmful substances. According to the 2011 statistics of cancer types in Japan disclosed by the Center for Cancer Control and Information Services, National Cancer Center, the number of individuals affected by liver cancer is 47,271 people. Namely, it is estimated that one out of every 35 Japanese individuals experience liver cancer. The number of individuals affected by liver cancer among other cancer types takes the 6th in place. Also, men are nearly twice as likely as women to develop liver cancer. The number of liver cancer deaths in men and women together climbed to 30,690 people and takes the 4th in place. An estimate of the number of American individuals affected by liver cancer in 2014 climbs to 33,190 people, among which approximately 23,000 people will die (Non-Patent Literature 1).

In general, primary liver cancer often refers to hepatocellular carcinoma which accounts for approximately 80% of primary liver cancer cases. However, there are other subtypes of primary liver cancer such as intrahepatic bile duct carcinoma which accounts for 10 to 20% of all primary liver cancer cases, and biliary cystadenocarcinoma which is a rarer cancer type.

The stages of liver cancer progression are specified separately for hepatocellular carcinoma and intrahepatic bile duct carcinoma in Non-Patent Literature 2. Herein, particularly, the hepatocellular carcinoma is classified into stage I (T1/N0/M0), stage II (T2/N0/M0), stage IIIA (T3a/NO/M0), stage IIIB (T3b/NO/M0), stage IIIC (T4/NO/M0), stage IVA (N1/M0), and stage IVB (M1) according to the degrees of tumor spread (T0 to T4), lymph node metastasis (N0 and N1), and distant metastasis (M0 and M1).

The 5-year relative survival rate of liver cancer differs depending on the stages of progression. According to Non-Patent Literature 1, the 5-year relative survival rate of liver cancer is reportedly 28% for tumors localized within liver (stage 1, stage 2 and some cases of stage 3), 7% for tumors found to have metastasized to a surrounding area of liver (stage IIIC and stage IVA), and 2% for tumors found to have metastasized distantly (stage IVB). Thus, the detection and treatment of liver cancer at an early stage before metastasis makes a significant contribution to improvement in the survival rate.

The treatment of liver cancer is performed mainly by 3 procedures: surgical therapy mainly involving resection and/or liver transplantation; local therapy which involves injecting a drug through centesis or performing cauterization to kill cancer; and hepatic arterial embolization. These procedures are used in combination with drug therapy or radiotherapy. Particularly, early liver cancer which is found not to metastasize to a blood vessel or an adjacent site is often cured by the partial resection of the liver (Non-Patent Literature 1). On the other hand, even if cancer is localized, liver transplantation is desirable for the cases where such resection is impossible on the ground that the tumors have a large size or are placed in proximity to a blood vessel, for example. If metastasis is found, systemic drug therapy or radiotherapy is performed (Non-Patent Literature 1).

As described in Non-Patent Literature 1, primary tests of liver cancer are inspection and palpation as well as imaging tests such as ultrasonography, CT scan, MRI scan, and angiography. For example, AFP (alpha fetoprotein) and PIVKA-II are known as tumor markers for the detection of liver cancer. The tests using these tumor markers are often performed in combination with ultrasonography. When there are findings that suspect liver cancer by these primary tests, pathological examination which involves inserting a needle into a lesion and collecting cells or tissues, which are then examined under a microscope is carried out as a secondary test.

Meanwhile, it is known that the most important leading cause of liver cancer is prolonged infection with hepatitis B or C virus. Therefore, subjects suspected of having liver cancer may be subjected to a hepatitis virus test in addition to the primary tests described above.

As shown in Patent Literatures 1 to 5, there are reports, albeit at a research stage, on methods for detecting liver cancer using the expression levels of microRNAs (miRNAs) in biological samples including blood and hepatic tissues.

Patent Literature 1 discloses a method for detecting leukemia, breast cancer, and liver cancer using miRNAs: hsa-miR-92a-3p, hsa-miR-92b-3p, hsa-miR-92a-2-5p, and hsa-miR-92b-5p in tissues as markers.

Patent Literature 2 has reported a method for diagnosing various cancers using, as markers, miRNAs such as hsa-miR-23a-3p, hsa-miR-23b-3p, hsa-miR-24-3p, hsa-miR-557, hsa-miR-564, hsa-miR-614, hsa-miR-150-3p, and hsa-miR-486-3p contained in vesicles circulating in body fluids.

Patent Literature 3 discloses a method for detecting various diseases including liver cancer using miRNAs such as hsa-miR-23b-3p, hsa-miR-30c-1-3p, hsa-miR-125a-3p, and hsa-miR-486-3p in tissues or body fluids as markers.

Patent Literature 4 discloses a method for detecting various pathological conditions including liver cancer using, as markers, miRNAs such as hsa-miR-16-5p, hsa-miR-92a-3p, hsa-miR-663a, hsa-miR-1913, and hsa-miR-625-3p, or proteins contained in vesicles circulating in body fluids.

Patent Literature 5 discloses that hsa-miR-187-5p, hsa-miR-92a-3p, hsa-miR-16-5p, and hsa-miR-30c-1-3p in plasma are markers for colorectal cancer, liver cancer, and lung cancer.

CITATION LIST

Patent Literature

Patent Literature 1: International Publication No. WO 2010/123043
Patent Literature 2: U.S. Patent Application Publication No. 2011/003704
Patent Literature 3: International Publication No. WO 2010/054386
Patent Literature 4: International Publication No. WO 2012/174282
Patent Literature 5: International Publication No. WO 2011/076142

Non-Patent Literature

Non-Patent Literature 1: American Cancer Society, "Liver Cancer", 2013, p. 5 to 8, 14 to 15, 17 to 23, and 27 to 41

Non-Patent Literature 2: Sobin, L. et al., "TNM Classification of Malignant Tumours, the 7th edition", 2010, p. 104-107

Non-Patent Literature 3: NCCN Guidelines, "Hepatobiliary Cancers, the 2nd edition", 2014, MS-4

Non-Patent Literature 4: Zhang, B and Yang, B., 1999, Journal of Medical Screening, Vol. 6 (2), p. 108-110

Non-Patent Literature 5: Takahashi, A. et al., 2008, World Journal of Gastroenterology, Vol. 14 (1), p. 129-31

SUMMARY OF INVENTION

Problem to be Solved by Invention

An object of the present invention is to find a novel tumor marker for liver cancer and to provide a method that can effectively detect liver cancer using a nucleic acid capable of specifically binding to the marker.

Liver cancer progresses without particular symptoms and is therefore difficult to detect early. Since the most part of the liver is housed in the right rib, liver cancer is difficult to detect by palpation. An effective method for liver cancer screening has not yet been established for ordinary people lacking a risk of liver cancer such as hepatitis virus infection or liver cirrhosis (Non-Patent Literature 1). Ultrasonography is a widely prevalent method for liver cancer screening because this method places less burden on patients and is convenient. Nonetheless, liver cancer may be difficult to detect depending on its site of occurrence by ultrasonography. In addition, examination results of ultrasonography largely depend on the skill of technicians. Therefore, it is considered to be desirable that ultrasonography should be used in combination with a tumor marker (Non-Patent Literature 3). Although AFP is known as a tumor marker for the detection of liver cancer, liver cancer found to have an elevated level of AFP is already at an advanced stage and is impossible to resect or has metastasized to an area outside the liver in many cases (Non-Patent Literature 1). It has been reported that some liver cancers do not produce AFP. Meanwhile, AFP is known to also elevate in cancers other than liver cancer, for example, testicular cancer or ovary cancer, and further to elevate in non-cancer liver diseases, for example, sustained hepatitis virus infection, and is therefore regarded as a low specific marker (Non-Patent Literature 1). For example, false diagnosis of other cancers as liver cancer wastes appropriate therapeutic opportunity or places unnecessary economical and physical burdens on patients due to the application of wrong medicine. According to results of large-scale screening research targeting hepatitis B-infected people and prolonged hepatitis patients (Non-Patent Literature 4), the AFP test has liver cancer detection sensitivity as low as 69% and thus has insufficient examination performance for use as a liver cancer screening test. Furthermore, CT scan or MRI scan can detect liver cancer with high performance, but is not suitable as a widely prevalent primary test because these tests require a specific apparatus and high examination cost.

As described below, there are reports, albeit at a research stage, on the determination of liver cancer using the expression levels of microRNAs (miRNAs) in biological samples including blood, none of which, however, have yet been brought into practical use.

Patent Literature 1 discloses a method for detecting leukemia, breast cancer, and liver cancer using miRNAs hsa-miR-92a-3p, hsa-miR-92b-3p, hsa-miR-92a-2-5p, and hsa-miR-92b-5p in blood cells or tissues as markers. This detection method, however, inevitably requires tissue resection by surgical operation for obtaining samples, and this step places a heavy physical burden on patients. Therefore, this method is not favorable as an examination method. In addition, Patent Literature 1 does not describe specific detection performance such as accuracy, sensitivity, or specificity for determining liver cancer as to this detection method, which is thus industrially less practical.

Patent Literature 2 has reported a method for diagnosing various cancers using, as markers, miRNAs such as hsa-miR-23a-3p, hsa-miR-23b-3p, hsa-miR-24-3p, hsa-miR-557, hsa-miR-564, hsa-miR-614, hsa-miR-150-3p, and hsa-miR-486-3p contained in vesicles circulating in body fluids. Patent Literature 2, however, neither describes a specific method for diagnosing liver cancer by use of this detection method nor describes detection performance such as accuracy, sensitivity, or specificity for determining liver cancer. Therefore, this detection method is industrially less practical.

Patent Literature 3 discloses a method for detecting various diseases including liver cancer using miRNAs such as hsa-miR-23b-3p, hsa-miR-30c-1-3p, hsa-miR-125a-3p, and hsa-miR-486-3p in tissues or body fluids as markers. This detection method, however, is based on results of experiments using mouse models, and the detection of liver cancer in humans is unknown about the method. In addition, Patent Literature 3 does not describe detection performance such as accuracy, sensitivity, or specificity for determining liver cancer. Therefore, this detection method is industrially less practical.

Patent Literature 4 discloses a method for detecting various pathological conditions including liver cancer using, as markers, miRNAs such as hsa-miR-16-5p, hsa-miR-92a-3p, hsa-miR-663a, hsa-miR-1913, and hsa-miR-625-3p, or proteins contained in vesicles circulating in body fluids. Patent Literature 4, however, neither describes a specific method for diagnosing liver cancer by use of this detection method nor validated these miRNA markers in an independent sample group. Therefore, this detection method is less reliable.

Patent Literature 5 discloses that hsa-miR-187-5p, hsa-miR-92a-3p, hsa-miR-16-5p, and hsa-miR-30c-1-3p in plasma are markers for colorectal cancer, liver cancer, and lung cancer. These markers, however, are markers for discriminating a group of colorectal cancers from a group of liver cancers, lung cancers, and healthy subjects and is not a marker for detecting liver cancer.

As mentioned above, the existing tumor markers exhibit low performance in the detection of liver cancer, and neither performance nor detection methods are specifically shown as to the markers at a research stage. Therefore, use of these markers might lead to carrying out needless extra examination due to the false detection of healthy subjects as being liver cancer patients, or might waste therapeutic opportunity because of overlooking liver cancer patients. In addition, the measurement of several dozens to several hundreds of miRNAs increases examination cost and is therefore difficult to use in large-scale screening such as medical checkup. Furthermore, the collection of liver tissues for measuring the tumor markers is highly invasive to patients and is not favorable. Hence, there is a demand for a highly accurate liver cancer marker that is detectable from blood, which can be collected with limited invasiveness, and is capable of correctly determining a liver cancer patient as a liver cancer patient and a healthy subject as a healthy subject. Particularly, the early detection and treatment of liver cancer can improve the survival rates. In addition, such liver cancer is often cured by the partial resection of the liver. Therefore, a highly sensitive liver cancer marker capable of detecting liver cancer even at an early stage of progression is desired.

Means for Solution of Problem

The present inventors have conducted diligent studies to attain the object and consequently completed the present invention by finding multiple genes usable as markers for the detection of liver cancer from blood, which can be collected with limited invasiveness, and finding that liver cancer can be significantly detected by using nucleic acid(s) capable of specifically binding to any of these markers.

SUMMARY OF INVENTION

Specifically, the present invention has the following features:

(1) A kit for the detection of liver cancer, comprising nucleic acid(s) capable of specifically binding to at least one or more polynucleotide(s) selected from the group consisting of liver cancer markers: miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p.

(2) The kit according to (1), wherein miR-1343-3p is hsa-miR-1343-3p, miR-6726-5p is hsa-miR-6726-5p, miR-6515-3p is hsa-miR-6515-3p, miR-4651 is hsa-miR-4651, miR-4257 is hsa-miR-4257, miR-3188 is hsa-miR-3188, miR-6131 is hsa-miR-6131, miR-6766-3p is hsa-miR-6766-3p, miR-7641 is hsa-miR-7641, miR-1249 is hsa-miR-1249, miR-3679-3p is hsa-miR-3679-3p, miR-6787-5p is hsa-miR-6787-5p, miR-4454 is hsa-miR-4454, miR-3135b is hsa-miR-3135b, miR-6765-3p is hsa-miR-6765-3p, miR-7975 is hsa-miR-7975, miR-204-3p is hsa-miR-204-3p, miR-7977 is hsa-miR-7977, miR-7110-5p is hsa-miR-7110-5p, miR-6717-5p is hsa-miR-6717-5p, miR-6870-5p is hsa-miR-6870-5p, miR-663b is hsa-miR-663b, miR-6875-5p is hsa-miR-6875-5p, miR-8072 is hsa-miR-8072, miR-6816-5p is hsa-miR-6816-5p, miR-4281 is hsa-miR-4281, miR-6729-5p is hsa-miR-6729-5p, miR-8069 is hsa-miR-8069, miR-4706 is hsa-miR-4706, miR-7108-5p is hsa-miR-7108-5p, miR-4433b-3p is hsa-miR-4433b-3p, miR-6893-5p is hsa-miR-6893-5p, miR-6857-5p is hsa-miR-6857-5p, miR-1227-5p is hsa-miR-1227-5p, miR-6741-5p is hsa-miR-6741-5p, miR-451a is hsa-miR-451a, miR-8063 is hsa-miR-8063, miR-3622a-5p is hsa-miR-3622a-5p, miR-615-5p is hsa-miR-615-5p, miR-128-1-5p is hsa-miR-128-1-5p, miR-6825-5p is hsa-miR-6825-5p, miR-1260b is hsa-miR-1260b, miR-4433-3p is hsa-miR-4433-3p, miR-4665-5p is hsa-miR-4665-5p, miR-7845-5p is hsa-miR-7845-5p, miR-1908-5p is hsa-miR-1908-5p, miR-6840-3p is hsa-miR-6840-3p, miR-6765-5p is hsa-miR-6765-5p, miR-296-5p is hsa-miR-296-5p, miR-3675-3p is hsa-miR-3675-3p, miR-6781-5p is hsa-miR-6781-5p, miR-423-5p is hsa-miR-423-5p, miR-3663-3p is hsa-miR-3663-3p, miR-6784-5p is hsa-miR-6784-5p, miR-6749-5p is hsa-miR-6749-5p, miR-1231 is hsa-miR-1231, miR-4746-3p is hsa-miR-4746-3p, miR-6780b-5p is hsa-miR-6780b-5p, miR-4758-5p is hsa-miR-4758-5p, miR-3679-5p is hsa-miR-3679-5p, miR-3184-5p is hsa-miR-3184-5p, miR-6125 is hsa-miR-6125, miR-6721-5p is hsa-miR-6721-5p, miR-6791-5p is hsa-miR-6791-5p, miR-3185 is hsa-miR-3185, miR-1260a is hsa-miR-1260a, miR-3197 is hsa-miR-3197, miR-6845-5p is hsa-miR-6845-5p, miR-6887-5p is hsa-miR-6887-5p, miR-6738-5p is hsa-miR-6738-5p, miR-6872-3p is hsa-miR-6872-3p, miR-4497 is hsa-miR-4497, miR-1229-5p is hsa-miR-1229-5p, miR-6820-5p is hsa-miR-6820-5p, miR-6777-5p is hsa-miR-6777-5p, miR-3917 is hsa-miR-3917, miR-5787 is hsa-miR-5787, miR-4286 is hsa-miR-4286, miR-6877-5p is hsa-miR-6877-5p, miR-1225-3p is hsa-miR-1225-3p, miR-6088 is hsa-miR-6088, miR-6800-5p is hsa-miR-6800-5p, miR-1246 is hsa-miR-1246, miR-4467 is hsa-miR-4467, miR-4419b is hsa-miR-4419b, miR-1914-3p is hsa-miR-1914-3p, miR-4632-5p is hsa-miR-4632-5p, miR-1915-5p is hsa-miR-1915-5p, miR-3940-5p is hsa-miR-3940-5p, miR-1185-2-3p is hsa-miR-1185-2-3p, miR-6746-5p is hsa-miR-6746-5p, miR-5001-5p is hsa-miR-5001-5p, miR-1228-5p is hsa-miR-1228-5p, miR-5572 is hsa-miR-5572, miR-4327 is hsa-miR-4327, miR-4638-5p is hsa-miR-4638-5p, miR-6799-5p is hsa-miR-6799-5p, miR-6861-5p is hsa-miR-6861-5p, miR-6727-5p is hsa-miR-6727-5p, miR-4513 is hsa-miR-4513, miR-6805-3p is hsa-miR-6805-3p, miR-6808-5p is hsa-miR-6808-5p, miR-4449 is hsa-miR-4449, miR-1199-5p is hsa-miR-1199-5p, miR-1275 is hsa-miR-1275, miR-4792 is hsa-miR-4792, miR-4443 is hsa-miR-4443, miR-6891-5p is hsa-miR-6891-5p, miR-6826-5p is hsa-miR-6826-5p, miR-6807-5p is hsa-miR-6807-5p, miR-7150 is hsa-miR-7150, miR-4534 is hsa-miR-4534, miR-4476 is hsa-miR-4476, miR-4649-5p is hsa-miR-4649-5p, miR-4525 is hsa-miR-4525, miR-1915-3p is hsa-miR-1915-3p, miR-4516 is hsa-miR-4516, miR-4417 is hsa-miR-4417, miR-642b-3p is hsa-miR-642b-3p, miR-3141 is hsa-miR-3141, miR-5100 is hsa-miR-5100, miR-6848-5p is hsa-miR-6848-5p, miR-4739 is hsa-miR-4739, miR-4459 is hsa-miR- 4459, miR-1237-5p is hsa-miR-1237-5p, miR-296-3p is hsa-miR-296-3p, miR-4665-3p is hsa-miR-4665-3p, miR-6786-5p is hsa-miR-6786-5p, miR-4258 is hsa-miR-4258, miR-6510-5p is hsa-miR-6510-5p, miR-1343-5p is hsa-miR-1343-5p, miR-1247-3p is hsa-miR-1247-3p, miR-6805-5p is hsa-miR-6805-5p, miR-4492 is hsa-miR-4492, miR-1469 is hsa-miR-1469, miR-1268b is hsa-miR-1268b, miR-6858-5p is hsa-miR-6858-5p, miR-3937 is hsa-miR-3937, miR-939-5p is hsa-miR-939-5p, miR-3656 is hsa-miR-3656, miR-744-5p is hsa-miR-744-5p, miR-4687-3p is hsa-miR-4687-3p, miR-4763-3p is hsa-miR-4763-3p, miR-3620-5p is hsa-miR-3620-5p, miR-3195 is hsa-miR-3195, miR-6842-5p is hsa-miR-6842-5p, miR-4707-5p is hsa-miR-4707-5p, miR-642a-3p is hsa-miR-642a-3p, miR-7113-3p is hsa-miR-7113-3p, miR-4728-5p is hsa-miR-4728-5p, miR-5195-3p is hsa-miR-5195-3p, miR-1185-1-3p is hsa-miR-1185-1-3p, miR-6774-5p is hsa-miR-6774-5p, miR-8059 is hsa-miR-8059, miR-3131 is hsa-miR-3131, miR-7847-3p is hsa-miR-7847-3p, miR-4463 is hsa-miR-4463, miR-128-2-5p is hsa-miR-128-2-5p, miR-4508 is hsa-miR-4508, miR-6806-5p is hsa-miR-6806-5p, miR-7111-5p is hsa-miR-7111-5p, miR-6782-5p is hsa-miR-6782-5p, miR-4734 is hsa-miR-4734, miR-3162-5p is hsa-miR-3162-5p, miR-887-3p is hsa-miR-887-3p, miR-6752-5p is hsa-miR-6752-5p, miR-6724-5p is hsa-miR-6724-5p, miR-6757-5p is hsa-miR-6757-5p, miR-4448 is hsa-miR-4448, miR-671-5p is hsa-miR-671-5p, miR-3178 is hsa-miR-3178, miR-4725-3p is hsa-miR-4725-3p, miR-940 is hsa-miR-940, miR-6789-5p is hsa-miR-6789-5p, miR-4484 is hsa-miR-4484, miR-4634 is hsa-miR-4634, miR-4745-5p is hsa-miR-4745-5p, miR-4730 is hsa-miR-4730, miR-6803-5p is hsa-miR-6803-5p, miR-6798-5p is hsa-miR-6798-5p, miR-3648 is hsa-miR-3648, miR-4783-3p is hsa-miR-4783-3p, and miR-6836-3p is hsa-miR-6836-3p.

(3) The kit according to (1) or (2), wherein the nucleic acid is a polynucleotide selected from the group consisting of the following polynucleotides (a) to (e):
(a) a polynucleotide consisting of a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 167 and 714 to 729,
(c) a polynucleotide consisting of a nucleotide sequence complementary to a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 167 and 714 to 729 or a nucleotide sequence derived from the nucleotide sequence by the replacement of u with t, and
(e) a polynucleotide hybridizing under stringent conditions to any of the polynucleotides (a) to (d).

(4) The kit according to any of (1) to (3), wherein the kit further comprises nucleic acid(s) capable of specifically binding to at least one or more polynucleotide(s) selected from the group consisting of other liver cancer markers: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a.

(5) The kit according to (4), wherein miR-23b-3p is hsa-miR-23b-3p, miR-23a-3p is hsa-miR-23a-3p, miR-625-3p is hsa-miR-625-3p, miR-1228-3p is hsa-miR-1228-3p, miR-614 is hsa-miR-614, miR-1913 is hsa-miR-1913, miR-92a-2-5p is hsa-miR-92a-2-5p, miR-187-5p is hsa-miR-187-5p, miR-16-5p is hsa-miR-16-5p, miR-92b-3p is hsa-miR-92b-3p, miR-150-3p is hsa-miR-150-3p, miR-564 is hsa-miR-564, miR-125a-3p is hsa-miR-125a-3p, miR-92b-5p is hsa-miR-92b-5p, miR-92a-3p is hsa-miR-92a-3p, and miR-663a is hsa-miR-663a.

(6) The kit according to (4) or (5), wherein the nucleic acid is a polynucleotide selected from the group consisting of the following polynucleotides (f) to (j):
(f) a polynucleotide consisting of a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 168 to 183,
(h) a polynucleotide consisting of a nucleotide sequence complementary to a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 168 to 183 or a nucleotide sequence derived from the nucleotide sequence by the replacement of u with t, and
(j) a polynucleotide hybridizing under stringent conditions to any of the polynucleotides (f) to (i).

(7) The kit according to any of (1) to (6), wherein the kit further comprises nucleic acid(s) capable of specifically binding to at least one or more polynucleotide(s) selected from the group consisting of other liver cancer markers: miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090.

(8) The kit according to (7), wherein miR-4688 is hsa-miR-4688, miR-4648 is hsa-miR-4648, miR-6085 is hsa-miR-6085, miR-6126 is hsa-miR-6126, miR-6880-5p is hsa-miR-6880-5p, miR-328-5p is hsa-miR-328-5p, miR-6768-5p is hsa-miR-6768-5p, miR-3180 is hsa-miR-3180, miR-6087 is hsa-miR-6087, miR-1273g-3p is hsa-miR-1273g-3p, miR-1225-5p is hsa-miR-1225-5p, miR-3196 is hsa-miR-3196, miR-4695-5p is hsa-miR-4695-5p, miR-6732-5p is hsa-miR-6732-5p, miR-638 is hsa-miR-638, miR-6813-5p is hsa-miR-6813-5p, miR-665 is hsa-miR-665, miR-486-3p is hsa-miR-486-3p, miR-4466 is hsa-miR-4466, miR-30c-1-3p is hsa-miR-30c-1-3p, miR-3621 is hsa-miR-3621, miR-6743-5p is hsa-miR-6743-5p, miR-4298 is hsa-miR-4298, miR-4741 is hsa-miR-4741, miR-3619-3p is hsa-miR-3619-3p, miR-6824-5p is hsa-miR-6824-5p, miR-5698 is hsa-miR-5698, miR-371a-5p is hsa-miR-371a-5p, miR-4488 is hsa-miR-4488, miR-1233-5p is hsa-miR-1233-5p, miR-4723-5p is hsa-miR-4723-5p, miR-24-3p is hsa-miR-24-3p, miR-1238-5p is hsa-miR-1238-5p, miR-4442 is hsa-miR-4442, miR-3928-3p is hsa-miR-3928-3p, miR- 6716-5p is hsa-miR-6716-5p, miR-6089 is hsa-miR-6089, miR-6124 is hsa-miR-6124, miR-6778-5p is hsa-miR-6778-5p, miR-557 is hsa-miR-557, and miR-6090 is hsa-miR-6090.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 184 to 224, (m) a polynucleotide consisting of a nucleotide sequence complementary to a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 184 to 224 or a nucleotide sequence derived from the nucleotide sequence by the replacement of u with t, and (o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from all of the liver cancer markers according to (1) or (2).

(11) A device for the detection of liver cancer, comprising nucleic acid(s) capable of specifically binding to at least one or more polynucleotide(s) selected from the group consisting of liver cancer markers: miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p.

(12) The device according to (11), wherein miR-1343-3p is hsa-miR-1343-3p, miR-6726-5p is hsa-miR-6726-5p, miR-6515-3p is hsa-miR-6515-3p, miR-4651 is hsa-miR-4651, miR-4257 is hsa-miR-4257, miR-3188 is hsa-miR-3188, miR-6131 is hsa-miR-6131, miR-6766-3p is hsa-miR-6766-3p, miR-7641 is hsa-miR-7641, miR-1249 is hsa-miR-1249, miR-3679-3p is hsa-miR-3679-3p, miR-6787-5p is hsa-miR-6787-5p, miR-4454 is hsa-miR-4454, miR-3135b is hsa-miR-3135b, miR-6765-3p is hsa-miR-6765-3p, miR-7975 is hsa-miR-7975, miR-204-3p is hsa-miR-204-3p, miR-7977 is hsa-miR-7977, miR-7110-5p is hsa-miR-7110-5p, miR-6717-5p is hsa-miR-6717-5p, miR-6870-5p is hsa-miR-6870-5p, miR-663b is hsa-miR-663b, miR-6875-5p is hsa-miR-6875-5p, miR-8072 is hsa-miR-8072, miR-6816-5p is hsa-miR-6816-5p, miR-4281 is hsa-miR-4281, miR-6729-5p is hsa-miR-6729-5p, miR-8069 is hsa-miR-8069, miR-4706 is hsa-miR-4706, miR-7108-5p is hsa-miR-7108-5p, miR-4433b-3p is hsa-miR-4433b-3p, miR-6893-5p is hsa-miR-6893-5p, miR-6857-5p is hsa-miR-6857-5p, miR-1227-5p is hsa-miR-1227-5p, miR-6741-5p is hsa-miR-6741-5p, miR-451a is hsa-miR-451a, miR-8063 is hsa-miR-8063, miR-3622a-5p is hsa-miR-3622a-5p, miR-615-5p is hsa-miR-615-5p, miR-128-1-5p is hsa-miR-128-1-5p, miR-6825-5p is hsa-miR-6825-5p, miR-1260b is hsa-miR-1260b, miR-4433-3p is hsa-miR-4433-3p, miR-4665-5p is hsa-miR-4665-5p, miR-7845-5p is hsa-miR-7845-5p, miR-1908-5p is hsa-miR-1908-5p, miR-6840-3p is hsa-miR-6840-3p, miR-6765-5p is hsa-miR-6765-5p, miR-296-5p is hsa-miR-296-5p, miR-3675-3p is hsa-miR-3675-3p, miR-6781-5p is hsa-miR-6781-5p, miR-423-5p is hsa-miR-423-5p, miR-3663-3p is hsa-miR-3663-3p, miR-6784-5p is hsa-miR-6784-5p, miR-6749-5p is hsa-miR-6749-5p, miR-1231 is hsa-miR-1231, miR-4746-3p is hsa-miR-4746-3p, miR-6780b-5p is hsa-miR-6780b-5p, miR-4758-5p is hsa-miR-4758-5p, miR-3679-5p is hsa-miR-3679-5p, miR-3184-5p is hsa-miR-3184-5p, miR-6125 is hsa-miR-6125, miR-6721-5p is hsa-miR-6721-5p, miR-6791-5p is hsa-miR-6791-5p, miR-3185 is hsa-miR-3185, miR-1260a is hsa-miR-1260a, miR-3197 is hsa-miR-3197, miR-6845-5p is hsa-miR-6845-5p, miR-6887-5p is hsa-miR-6887-5p, miR-6738-5p is hsa-miR-6738-5p, miR-6872-3p is hsa-miR-6872-3p, miR-4497 is hsa-miR-4497, miR-1229-5p is hsa-miR-1229-5p, miR-6820-5p is hsa-miR-6820-5p, miR-6777-5p is hsa-miR-6777-5p, miR-3917 is hsa-miR-3917, miR-5787 is hsa-miR-5787, miR-4286 is hsa-miR-4286, miR-6877-5p is hsa-miR-6877-5p, miR-1225-3p is hsa-miR-1225-3p, miR-6088 is hsa-miR-6088, miR-6800-5p is hsa-miR-6800-5p, miR-1246 is hsa-miR-1246, miR-4467 is hsa-miR-4467, miR-4419b is hsa-miR-4419b, miR-1914-3p is hsa-miR-1914-3p, miR-4632-5p is hsa-miR-4632-5p, miR-1915-5p is hsa-miR-1915-5p, miR-3940-5p is hsa-miR-3940-5p, miR-1185-2-3p is hsa-miR-1185-2-3p, miR-6746-5p is hsa-miR-6746-5p, miR-5001-5p is hsa-miR-5001-5p, miR-1228-5p is hsa-miR-1228-5p, miR-5572 is hsa-miR-5572, miR-4327 is hsa-miR-4327, miR-4638-5p is hsa-miR-4638-5p, miR-6799-5p is hsa-miR-6799-5p, miR-6861-5p is hsa-miR-6861-5p, miR-6727-5p is hsa-miR-6727-5p, miR-4513 is hsa-miR-4513, miR-6805-3p is hsa-miR-6805-3p, miR-6808-5p is hsa-miR-6808-5p, miR-4449 is hsa-miR-4449, miR-1199-5p is hsa-miR-1199-5p, miR-1275 is hsa-miR-1275, miR-4792 is hsa-miR-4792, miR-4443 is hsa-miR-4443, miR-6891-5p is hsa-miR-6891-5p, miR-6826-5p is hsa-miR-6826-5p, miR-6807-5p is hsa-miR-6807-5p, miR-7150 is hsa-miR-7150, miR-4534 is hsa-miR-4534, miR-4476 is hsa-miR-4476, miR-4649-5p is hsa-miR-4649-5p, miR-4525 is hsa-miR-4525, miR-1915-3p is hsa-miR-1915-3p, miR-4516 is hsa-miR-4516, miR-4417 is hsa-miR-4417, miR-642b-3p is hsa-miR-642b-3p, miR-3141 is hsa-miR-3141, miR-5100 is hsa-miR-5100, miR-6848-5p is hsa-miR-6848-5p, miR-4739 is hsa-miR-4739, miR-4459 is hsa-miR-4459, miR-1237-5p is hsa-miR-1237-5p, miR-296-3p is hsa-miR-296-3p, miR-4665-3p is hsa-miR-4665-3p, miR-6786-5p is hsa-miR-6786-5p, miR-4258 is hsa-miR-4258, miR-6510-5p is hsa-miR-6510-5p, miR-1343-5p is hsa-miR-1343-5p, miR-1247-3p is hsa-miR-1247-3p, miR-6805-5p is hsa-miR-6805-5p, miR-4492 is hsa-miR-4492, miR-1469 is hsa-miR-1469, miR-1268b is hsa-miR-1268b, miR-6858-5p is hsa-miR-6858-5p, miR-3937 is hsa-miR-3937, miR-939-5p is hsa-miR-939-5p, miR-3656 is hsa-miR-3656, miR-744-5p is hsa-miR-744-5p, miR-4687-3p is hsa-miR-4687-3p, miR-4763-3p is hsa-miR-4763-3p, miR-3620-5p is hsa-miR-3620-5p, miR-3195 is hsa-miR-3195, miR-6842-5p is hsa-miR-6842-5p, miR-4707-5p is hsa-miR-4707-5p, miR-642a-3p is hsa-miR-642a-3p, miR-7113-3p is hsa-miR-7113-3p, miR-4728-5p is hsa-miR-4728-5p, miR-5195-3p is hsa-miR-5195-3p, miR-1185-1-3p is hsa-miR-1185-1-3p, miR-6774-5p is hsa-miR-6774-5p, miR-8059 is hsa-miR-8059, miR-3131 is hsa-miR-3131, miR-7847-3p is hsa-miR-7847-3p, miR-4463 is hsa-miR-4463, miR-128-2-5p is hsa-miR-128-2-5p, miR-4508 is hsa-miR-4508, miR-6806-5p is hsa-miR-6806-5p, miR-7111-5p is hsa-miR-7111-5p, miR-6782-5p is hsa-miR-6782-5p, miR-4734 is hsa-miR-4734, miR-3162-5p is hsa-miR-3162-5p, miR-887-3p is hsa-miR-887-3p, miR-6752-5p is hsa-miR-6752-5p, miR-6724-5p is hsa-miR-6724-5p, miR-6757-5p is hsa-miR-6757-5p, miR-4448 is hsa-miR-4448, miR-671-5p is hsa-miR-671-5p, miR-3178 is hsa-miR-3178, miR-4725-3p is hsa-miR-4725-3p, miR-940 is hsa-miR-940, miR-6789-5p is hsa-miR-6789-5p, miR-4484 is hsa-miR-4484, miR-4634 is hsa-miR-4634, miR-4745-5p is hsa-miR-4745-5p, miR-4730 is hsa-miR-4730, miR-6803-5p is hsa-miR-6803-5p, miR-6798-5p is hsa-miR-6798-5p, miR-3648 is hsa-miR-3648, miR-4783-3p is hsa-miR-4783-3p, and miR-6836-3p is hsa-miR-6836-3p.

(13) The device according to (11) or (12), wherein the nucleic acid is a polynucleotide selected from the group consisting of the following polynucleotides (a) to (e):
(a) a polynucleotide consisting of a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 167 and 714 to 729,
(c) a polynucleotide consisting of a nucleotide sequence complementary to a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 167 and 714 to 729 or a nucleotide sequence derived from the nucleotide sequence by the replacement of u with t, and
(e) a polynucleotide hybridizing under stringent conditions to any of the polynucleotides (a) to (d).

(14) The device according to any of (11) to (13), wherein the device further comprises nucleic acid(s) capable of specifically binding to at least one or more polynucleotide(s) selected from the group consisting of other liver cancer markers: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a.

(15) The device according to (14), wherein miR-23b-3p is hsa-miR-23b-3p, miR-23a-3p is hsa-miR-23a-3p, miR-625-3p is hsa-miR-625-3p, miR-1228-3p is hsa-miR-1228-3p, miR-614 is hsa-miR-614, miR-1913 is hsa-miR-1913, miR-92a-2-5p is hsa-miR-92a-2-5p, miR-187-5p is hsa-miR-187-5p, miR-16-5p is hsa-miR-16-5p, miR-92b-3p is hsa-miR-92b-3p, miR-150-3p is hsa-miR-150-3p, miR-564 is hsa-miR-564, miR-125a-3p is hsa-miR-125a-3p, miR-92b-5p is hsa-miR-92b-5p, miR-92a-3p is hsa-miR-92a-3p, and miR-663a is hsa-miR-663a.

(16) The device according to (14) or (15), wherein the nucleic acid is a polynucleotide selected from the group consisting of the following polynucleotides (f) to (j):
(f) a polynucleotide consisting of a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 168 to 183,
(h) a polynucleotide consisting of a nucleotide sequence complementary to a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 168 to 183 or a nucleotide sequence derived from the nucleotide sequence by the replacement of u with t, and
(j) a polynucleotide hybridizing under stringent conditions to any of the polynucleotides (f) to (i).

(17) The device according to any of (11) to (16), wherein the device further comprises nucleic acid(s) capable of specifically binding to at least one or more polynucleotide(s) selected from the group consisting of other liver cancer markers: miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090.

(18) The device according to (17), wherein miR-4688 is hsa-miR-4688, miR-4648 is hsa-miR-4648, miR-6085 is hsa-miR-6085, miR-6126 is hsa-miR-6126, miR-6880-5p is hsa-miR-6880-5p, miR-328-5p is hsa-miR-328-5p, miR-6768-5p is hsa-miR-6768-5p, miR-3180 is hsa-miR-3180, miR-6087 is hsa-miR-6087, miR-1273g-3p is hsa-miR-1273g-3p, miR-1225-5p is hsa-miR-1225-5p, miR-3196 is hsa-miR-3196, miR-4695-5p is hsa-miR-4695-5p, miR-6732-5p is hsa-miR-6732-5p, miR-638 is hsa-miR-638, miR-6813-5p is hsa-miR-6813-5p, miR-665 is hsa-miR-665, miR-486-3p is hsa-miR-486-3p, miR-4466 is hsa-miR-4466, miR-30c-1-3p is hsa-miR-30c-1-3p, miR-3621 is hsa-miR-3621, miR-6743-5p is hsa-miR-6743-5p, miR-4298 is hsa-miR-4298, miR-4741 is hsa-miR-4741, miR-3619-3p is hsa-miR-3619-3p, miR-6824-5p is hsa-miR-6824-5p, miR-5698 is hsa-miR-5698, miR-371a-5p is hsa-miR-371a-5p, miR-4488 is hsa-miR-4488, miR-1233-5p is hsa-miR-1233-5p, miR-4723-5p is hsa-miR-4723-5p, miR-24-3p is hsa-miR-24-3p, miR-1238-5p is hsa-miR-1238-5p, miR-4442 is hsa-miR-4442, miR-3928-3p is hsa-miR-3928-3p, miR-6716-5p is hsa-miR-6716-5p, miR-6089 is hsa-miR-6089, miR-6124 is hsa-miR-6124, miR-6778-5p is hsa-miR-6778-5p, miR-557 is hsa-miR-557, and miR-6090 is hsa-miR-6090.

(19) The device according to (17) or (18), wherein the nucleic acid is a polynucleotide selected from the group consisting of the following polynucleotides (k) to (o):
(k) a polynucleotide consisting of a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 184 to 224,
(m) a polynucleotide consisting of a nucleotide sequence complementary to a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 184 to 224 or a nucleotide sequence derived from the nucleotide sequence by the replacement of u with t, and
(o) a polynucleotide hybridizing under stringent conditions to any of the polynucleotides (k) to (n).

(20) The device according to any one of (11) to (19), wherein the device is a device for measurement by a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the liver cancer markers according to (11) or (12).

(23) A method for detecting liver cancer, comprising measuring an expression level of a target nucleic acid in a sample of a subject using the kit according to any one of (1) to (10) or the device according to any one of (11) to (22); and evaluating in vitro whether or not the subject has liver cancer using the measured expression level and a control expression level for a healthy subject measured in the same way.

(24) The method according to (23), wherein the subject is a human.

(25) The method according to (23) or (24), wherein the sample is blood, serum, or plasma.

DEFINITION OF TERM

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid, including any of RNA, DNA, and RNA/DNA (chimera). The DNA includes any of cDNA, genomic DNA, and synthetic DNA. The RNA includes all of total RNA, mRNA, rRNA, miRNA, siRNA, snoRNA, snRNA, non-coding RNA and synthetic RNA. The "synthetic DNA" and the "synthetic RNA" used herein refer to DNA and RNA artificially prepared using, for example, an automated nucleic acid synthesizer, on the basis of predetermined nucleotide sequences (which may be any of natural and non-natural sequences). The "non-natural sequence" used herein is intended to be used in a broad sense and includes, for example, a sequence containing substitution, deletion, insertion, and/or addition of one or more nucleotide(s) (i.e., a variant sequence) and a sequence containing one or more modified nucleotide(s) (i.e., a modified sequence), which are different from the natural sequence. As used herein, the term "polynucleotide" is used interchangeably with the term "nucleic acid."

The term "fragment" used herein is a polynucleotide having a nucleotide sequence having a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus strand (or a sense strand) or a complementary strand (or an antisense strand) constituting the duplex. The gene is not particularly limited by its length.

Thus, the "gene" used herein includes all of double-stranded DNA including human genomic DNA, single-stranded DNA (plus strand), single-stranded DNA having a sequence complementary to the plus strand (complementary strand) including cDNA, microRNA (miRNA), and their fragments, and transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 765 or a nucleotide sequence derived from the nucleotide sequence by the replacement of u with t. The "gene" is not particularly limited by its functional region and can contain, for example, an expression regulatory region, a coding region, an exon, or an intron. The "gene" may be contained in a cell or may exist alone after being released into the outside of a cell. Alternatively, the "gene" may be in a state enclosed in a vesicle called exosome.

The term "exosome" used herein is a vesicle that is delimited by a lipid bilayer and secreted from a cell. The exosome is derived from a multivesicular endosome and may incorporate biomaterials such as "gene(s)" (e.g., RNA or DNA) or protein(s) when released into an extracellular environment. The exosome is known to be contained in a body fluid such as blood, serum, plasma, serum, or lymph.

The term "transcript" used herein refers to RNA synthesized from the DNA sequence of a gene as a template. RNA polymerase binds to a site called a promoter located upstream of the gene and adds ribonucleotides complementary to the nucleotide sequence of the DNA to the 3' end to synthesize RNA. This RNA contains not only the gene itself but also the whole sequence from a transcription initiation site to the end of a polyA sequence, including an expression regulatory region, a coding region, an exon, or an intron.

The term "microRNA (miRNA)" used herein is intended to mean a 15- to 25-nucleotide non-coding RNA that is transcribed as an RNA precursor having a hairpin-like structure, cleaved by a dsRNA-cleaving enzyme which has RNase III cleavage activity, and integrated into a protein complex called RISC, and involved in the suppression of translation of mRNA, unless otherwise specified. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 765. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto.

In this context, the complementary polynucleotide (complementary strand or reverse strand) means a polynucleotide in a complementary relationship of A:T (U) and G:C base pairs with the full-length sequence of a polynucleotide consisting of a nucleotide sequence defined by any of SEQ ID NOs: 1 to 765 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence that is 100% complementary to the nucleic acid probe can be identified by controlling the stringency of hybridization and/or washing conditions. Specific examples of the "stringent conditions" is mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 765 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

As used herein, the "nucleic acid" capable of specifically binding to a polynucleotide selected from the group of the miRNAs described above which are the liver cancer markers is a synthesized or prepared nucleic acid and specifically includes a "nucleic acid probe" or a "primer". The "nucleic acid" is utilized directly or indirectly for detecting the presence or absence of liver cancer in a subject, for diagnosing the presence or absence of liver cancer, the severity of liver cancer, the presence or absence of amelioration or the degree of amelioration of liver cancer, or the therapeutic sensitivity of liver cancer, or for screening for a candidate substance useful in the prevention, amelioration, or treatment of liver cancer. The "nucleic acid" includes a nucleotide, an oligonucleotide, and a polynucleotide capable of specifically recognizing and binding to a transcript represented by any of SEQ ID NOs: 1 to 765 or a synthetic cDNA nucleic acid thereof in vivo, particularly, in a sample such as a body fluid (e.g., blood or urine), in relation to the development of liver cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection" or "decision support". The term "evaluation" used herein is meant to include diagnosis or evaluation support on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "liver cancer" used herein means "primary liver cancer", which develops primarily in the liver. The liver cancer includes, for example, "hepatocellular carcinoma" and "combined hepatocellular and cholangiocellular carcinoma" caused by the malignant transformation of cells of the liver.

The term "P" or "P value" used herein refers to a probability at which a more extreme statistic than that actually calculated from data under null hypothesis is observed in a statistical test. Thus, smaller "P" or "P value" is regarded as being more significant difference between subjects to be compared.

The term "sensitivity" used herein means a value of (the number of true positives)/(the number of true positives+the number of false negatives). High sensitivity allows liver cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being liver cancer patients, leading to reduction in burden on patients and reduction in medical expense.

The term "accuracy" used herein means a value of (the number of true positives+the number of true negatives)/(the total number of cases). The accuracy indicates the ratio of samples that are correctly identified in the discriminant results to all samples, and serves as a primary index for evaluating detection performance.

As used herein, the "sample" that is subjected to determination, detection, or diagnosis refers to a tissue and a biological material in which the expression of the gene of the present invention varies as liver cancer develops, as liver cancer progresses, or as therapeutic effects on liver cancer are exerted. Specifically, the "sample" refers to a hepatic tissue, a perihepatic vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-1343-3p gene" or "hsa-miR-1343-3p" used herein includes the hsa-miR-1343-3p gene (miRBase Accession No. MIMAT0019776) described in SEQ ID NO: 1, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 225) having a hairpin-like structure is known as a precursor of "hsa-miR-1343-3p".

The term "hsa-miR-6726-5p gene" or "hsa-miR-6726-5p" used herein includes the hsa-miR-6726-5p gene (miRBase Accession No. MIMAT0027353) described in SEQ ID NO: 2, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 226) having a hairpin-like structure is known as a precursor of "hsa-miR-6726-5p".

The term "hsa-miR-6515-3p gene" or "hsa-miR-6515-3p" used herein includes the hsa-miR-6515-3p gene (miRBase Accession No. MIMAT0025487) described in SEQ ID NO: 3, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 227) having a hairpin-like structure is known as a precursor of "hsa-miR-6515-3p".

The term "hsa-miR-4651 gene" or "hsa-miR-4651" used herein includes the hsa-miR-4651 gene (miRBase Accession No. MIMAT0019715) described in SEQ ID NO: 4, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 228) having a hairpin-like structure is known as a precursor of "hsa-miR-4651".

The term "hsa-miR-4257 gene" or "hsa-miR-4257" used herein includes the hsa-miR-4257 gene (miRBase Accession No. MIMAT0016878) described in SEQ ID NO: 5, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 229) having a hairpin-like structure is known as a precursor of "hsa-miR-4257".

The term "hsa-miR-3188 gene" or "hsa-miR-3188" used herein includes the hsa-miR-3188 gene (miRBase Accession No. MIMAT0015070) described in SEQ ID NO: 6, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 230) having a hairpin-like structure is known as a precursor of "hsa-miR-3188".

The term "hsa-miR-6131 gene" or "hsa-miR-6131" used herein includes the hsa-miR-6131 gene (miRBase Accession No. MIMAT0024615) described in SEQ ID NO: 7, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 231) having a hairpin-like structure is known as a precursor of "hsa-miR-6131".

The term "hsa-miR-6766-3p gene" or "hsa-miR-6766-3p" used herein includes the hsa-miR-6766-3p gene (miRBase Accession No. MIMAT0027433) described in SEQ ID NO: 8, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611, SEQ ID NO: 232) having a hairpin-like structure is known as a precursor of "hsa-miR-6766-3p".

The term "hsa-miR-7641 gene" or "hsa-miR-7641" used herein includes the hsa-miR-7641 gene (miRBase Accession No. MIMAT0029782) described in SEQ ID NO: 9, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1" and "hsa-mir-7641-2" (miRBase Accession Nos. MI0024975 and MI0024976, SEQ ID NOs: 233 and 234) having a hairpin-like structure are known as precursors of "hsa-miR-7641".

The term "hsa-miR-1249 gene" or "hsa-miR-1249" used herein includes the hsa-miR-1249 gene (miRBase Accession No. MIMAT0005901) described in SEQ ID NO: 10, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 235) having a hairpin-like structure is known as a precursor of "hsa-miR-1249".

The term "hsa-miR-3679-3p gene" or "hsa-miR-3679-3p" used herein includes the hsa-miR-3679-3p gene (miRBase Accession No. MIMAT0018105) described in SEQ ID NO: 11, a homolog or an ortholog of a different organism species, and the like. The hsa-miR-3679-3p gene can be obtained by a method described in Creighton C J et al., 2010, PLoS One, Vol. 5, e9637. Also, "hsa-mir-3679" (miRBase Accession No. MI0016080, SEQ ID NO: 236) having a hairpin-like structure is known as a precursor of "hsa-miR-3679-3p".

The term "hsa-miR-6787-5p gene" or "hsa-miR-6787-5p" used herein includes the hsa-miR-6787-5p gene (miRBase Accession No. MIMAT0027474) described in SEQ ID NO: 12, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 237) having a hairpin-like structure is known as a precursor of "hsa-miR-6787-5p".

The term "hsa-miR-4454 gene" or "hsa-miR-4454" used herein includes the hsa-miR-4454 gene (miRBase Accession No. MIMAT0018976) described in SEQ ID NO: 13, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 238) having a hairpin-like structure is known as a precursor of "hsa-miR-4454".

The term "hsa-miR-3135b gene" or "hsa-miR-3135b" used herein includes the hsa-miR-3135b gene (miRBase Accession No. MIMAT0018985) described in SEQ ID NO: 14, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 239) having a hairpin-like structure is known as a precursor of "hsa-miR-3135b".

The term "hsa-miR-6765-3p gene" or "hsa-miR-6765-3p" used herein includes the hsa-miR-6765-3p gene (miRBase Accession No. MIMAT0027431) described in SEQ ID NO: 15, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 240) having a hairpin-like structure is known as a precursor of "hsa-miR-6765-3p".

The term "hsa-miR-7975 gene" or "hsa-miR-7975" used herein includes the hsa-miR-7975 gene (miRBase Accession No. MIMAT0031178) described in SEQ ID NO: 16, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 241) having a hairpin-like structure is known as a precursor of "hsa-miR-7975".

The term "hsa-miR-204-3p gene" or "hsa-miR-204-3p" used herein includes the hsa-miR-204-3p gene (miRBase Accession No. MIMAT0022693) described in SEQ ID NO: 17, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 242) having a hairpin-like structure is known as a precursor of "hsa-miR-204-3p".

The term "hsa-miR-7977 gene" or "hsa-miR-7977" used herein includes the hsa-miR-7977 gene (miRBase Accession No. MIMAT0031180) described in SEQ ID NO: 18, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 243) having a hairpin-like structure is known as a precursor of "hsa-miR-7977".

The term "hsa-miR-7110-5p gene" or "hsa-miR-7110-5p" used herein includes the hsa-miR-7110-5p gene (miRBase Accession No. MIMAT0028117) described in SEQ ID NO: 19, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 244) having a hairpin-like structure is known as a precursor of "hsa-miR-7110-5p".

The term "hsa-miR-6717-5p gene" or "hsa-miR-6717-5p" used herein includes the hsa-miR-6717-5p gene (miRBase Accession No. MIMAT0025846) described in SEQ ID NO: 20, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 245) having a hairpin-like structure is known as a precursor of "hsa-miR-6717-5p".

The term "hsa-miR-6870-5p gene" or "hsa-miR-6870-5p" used herein includes the hsa-miR-6870-5p gene (miRBase Accession No. MIMAT0027640) described in SEQ ID NO: 21, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 246) having a hairpin-like structure is known as a precursor of "hsa-miR-6870-5p".

The term "hsa-miR-663b gene" or "hsa-miR-663b" used herein includes the hsa-miR-663b gene (miRBase Accession No. MIMAT0005867) described in SEQ ID NO: 22, a homolog or an ortholog of a different organism species, and the like. The hsa-miR-663b gene can be obtained by a method described in Takada S et al., 2008, Leukemia, Vol.

22, p. 1274-1278. Also, "hsa-mir-663b" (miRBase Accession No. MI0006336, SEQ ID NO: 247) having a hairpin-like structure is known as a precursor of "hsa-miR-663b".

The term "hsa-miR-6875-5p gene" or "hsa-miR-6875-5p" used herein includes the hsa-miR-6875-5p gene (miRBase Accession No. MIMAT0027650) described in SEQ ID NO: 23, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 248) having a hairpin-like structure is known as a precursor of "hsa-miR-6875-5p".

The term "hsa-miR-8072 gene" or "hsa-miR-8072" used herein includes the hsa-miR-8072 gene (miRBase Accession No. MIMAT0030999) described in SEQ ID NO: 24, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 249) having a hairpin-like structure is known as a precursor of "hsa-miR-8072".

The term "hsa-miR-6816-5p gene" or "hsa-miR-6816-5p" used herein includes the hsa-miR-6816-5p gene (miRBase Accession No. MIMAT0027532) described in SEQ ID NO: 25, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 250) having a hairpin-like structure is known as a precursor of "hsa-miR-6816-5p".

The term "hsa-miR-4281 gene" or "hsa-miR-4281" used herein includes the hsa-miR-4281 gene (miRBase Accession No. MIMAT0016907) described in SEQ ID NO: 26, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 251) having a hairpin-like structure is known as a precursor of "hsa-miR-4281".

The term "hsa-miR-6729-5p gene" or "hsa-miR-6729-5p" used herein includes the hsa-miR-6729-5p gene (miRBase Accession No. MIMAT0027359) described in SEQ ID NO: 27, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 252) having a hairpin-like structure is known as a precursor of "hsa-miR-6729-5p".

The term "hsa-miR-8069 gene" or "hsa-miR-8069" used herein includes the hsa-miR-8069 gene (miRBase Accession No. MIMAT0030996) described in SEQ ID NO: 28, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 253) having a hairpin-like structure is known as a precursor of "hsa-miR-8069".

The term "hsa-miR-4706 gene" or "hsa-miR-4706" used herein includes the hsa-miR-4706 gene (miRBase Accession No. MIMAT0019806) described in SEQ ID NO: 29, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 254) having a hairpin-like structure is known as a precursor of "hsa-miR-4706".

The term "hsa-miR-7108-5p gene" or "hsa-miR-7108-5p" used herein includes the hsa-miR-7108-5p gene (miRBase Accession No. MIMAT0028113) described in SEQ ID NO: 30, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 255) having a hairpin-like structure is known as a precursor of "hsa-miR-7108-5p".

The term "hsa-miR-4433b-3p gene" or "hsa-miR-4433b-3p" used herein includes the hsa-miR-4433b-3p gene (miRBase Accession No. MIMAT0030414) described in SEQ ID NO: 31, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 256) having a hairpin-like structure is known as a precursor of "hsa-miR-4433b-3p".

The term "hsa-miR-6893-5p gene" or "hsa-miR-6893-5p" used herein includes the hsa-miR-6893-5p gene (miRBase Accession No. MIMAT0027686) described in SEQ ID NO: 32, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 257) having a hairpin-like structure is known as a precursor of "hsa-miR-6893-5p".

The term "hsa-miR-6857-5p gene" or "hsa-miR-6857-5p" used herein includes the hsa-miR-6857-5p gene (miRBase Accession No. MIMAT0027614) described in SEQ ID NO: 33, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 258) having a hairpin-like structure is known as a precursor of "hsa-miR-6857-5p".

The term "hsa-miR-1227-5p gene" or "hsa-miR-1227-5p" used herein includes the hsa-miR-1227-5p gene (miRBase Accession No. MIMAT0022941) described in SEQ ID NO: 34, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 259) having a hairpin-like structure is known as a precursor of "hsa-miR-1227-5p".

The term "hsa-miR-6741-5p gene" or "hsa-miR-6741-5p" used herein includes the hsa-miR-6741-5p gene (miRBase Accession No. MIMAT0027383) described in SEQ ID NO: 35, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 260) having a hairpin-like structure is known as a precursor of "hsa-miR-6741-5p".

The term "hsa-miR-451a gene" or "hsa-miR-451a" used herein includes the hsa-miR-451a gene (miRBase Accession No. MIMAT0001631) described in SEQ ID NO: 36, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 261) having a hairpin-like structure is known as a precursor of "hsa-miR-451a".

The term "hsa-miR-8063 gene" or "hsa-miR-8063" used herein includes the hsa-miR-8063 gene (miRBase Accession No. MIMAT0030990) described in SEQ ID NO: 37, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 262) having a hairpin-like structure is known as a precursor of "hsa-miR-8063".

The term "hsa-miR-3622a-5p gene" or "hsa-miR-3622a-5p" used herein includes the hsa-miR-3622a-5p gene (miRBase Accession No. MIMAT0018003) described in SEQ ID NO: 38, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 263) having a hairpin-like structure is known as a precursor of "hsa-miR-3622a-5p".

The term "hsa-miR-615-5p gene" or "hsa-miR-615-5p" used herein includes the hsa-miR-615-5p gene (miRBase Accession No. MIMAT0004804) described in SEQ ID NO: 39, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 264) having a hairpin-like structure is known as a precursor of "hsa-miR-615-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 40, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 265) having a hairpin-like structure is known as a precursor of "hsa-miR-128-1-5p".

The term "hsa-miR-6825-5p gene" or "hsa-miR-6825-5p" used herein includes the hsa-miR-6825-5p gene (miRBase Accession No. MIMAT0027550) described in SEQ ID NO: 41, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 266) having a hairpin-like structure is known as a precursor of "hsa-miR-6825-5p".

The term "hsa-miR-1260b gene" or "hsa-miR-1260b" used herein includes the hsa-miR-1260b gene (miRBase Accession No. MIMAT0015041) described in SEQ ID NO: 42, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 267) having a hairpin-like structure is known as a precursor of "hsa-miR-1260b".

The term "hsa-miR-4433-3p gene" or "hsa-miR-4433-3p" used herein includes the hsa-miR-4433-3p gene (miRBase Accession No. MIMAT0018949) described in SEQ ID NO: 43, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 268) having a hairpin-like structure is known as a precursor of "hsa-miR-4433-3p".

The term "hsa-miR-4665-5p gene" or "hsa-miR-4665-5p" used herein includes the hsa-miR-4665-5p gene (miRBase Accession No. MIMAT0019739) described in SEQ ID NO: 44, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 269) having a hairpin-like structure is known as a precursor of "hsa-miR-4665-5p".

The term "hsa-miR-7845-5p gene" or "hsa-miR-7845-5p" used herein includes the hsa-miR-7845-5p gene (miRBase Accession No. MIMAT0030420) described in SEQ ID NO: 45, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 270) having a hairpin-like structure is known as a precursor of "hsa-miR-7845-5p".

The term "hsa-miR-1908-5p gene" or "hsa-miR-1908-5p" used herein includes the hsa-miR-1908-5p gene (miRBase Accession No. MIMAT0007881) described in SEQ ID NO: 46, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 271) having a hairpin-like structure is known as a precursor of "hsa-miR-1908-5p".

The term "hsa-miR-6840-3p gene" or "hsa-miR-6840-3p" used herein includes the hsa-miR-6840-3p gene (miRBase Accession No. MIMAT0027583) described in SEQ ID NO: 47, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 272) having a hairpin-like structure is known as a precursor of "hsa-miR-6840-3p".

The term "hsa-miR-6765-5p gene" or "hsa-miR-6765-5p" used herein includes the hsa-miR-6765-5p gene (miRBase Accession No. MIMAT0027430) described in SEQ ID NO: 48, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 240) having a hairpin-like structure is known as a precursor of "hsa-miR-6765-5p".

The term "hsa-miR-296-5p gene" or "hsa-miR-296-5p" used herein includes the hsa-miR-296-5p gene (miRBase Accession No. MIMAT0000690) described in SEQ ID NO: 49, a homolog or an ortholog of a different organism species, and the like. The hsa-miR-296-5p gene can be obtained by a method described in Houbaviy H B et al., 2003, Dev Cell, Vol. 5, p. 351-358. Also, "hsa-mir-296" (miRBase Accession No. MI0000747, SEQ ID NO: 273) having a hairpin-like structure is known as a precursor of "hsa-miR-296-5p".

The term "hsa-miR-3675-3p gene" or "hsa-miR-3675-3p" used herein includes the hsa-miR-3675-3p gene (miRBase Accession No. MIMAT0018099) described in SEQ ID NO: 50, a homolog or an ortholog of a different organism species, and the like. The hsa-miR-3675-3p gene can be obtained by a method described in Vaz C et al., 2010, BMC Genomics, Vol. 11, p. 288. Also, "hsa-mir-3675" (miRBase Accession No. MI0016076, SEQ ID NO: 274) having a hairpin-like structure is known as a precursor of "hsa-miR-3675-3p".

The term "hsa-miR-6781-5p gene" or "hsa-miR-6781-5p" used herein includes the hsa-miR-6781-5p gene (miRBase Accession No. MIMAT0027462) described in SEQ ID NO: 51, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 275) having a hairpin-like structure is known as a precursor of "hsa-miR-6781-5p".

The term "hsa-miR-423-5p gene" or "hsa-miR-423-5p" used herein includes the hsa-miR-423-5p gene (miRBase Accession No. MIMAT0004748) described in SEQ ID NO: 52, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 276) having a hairpin-like structure is known as a precursor of "hsa-miR-423-5p".

The term "hsa-miR-3663-3p gene" or "hsa-miR-3663-3p" used herein includes the hsa-miR-3663-3p gene (miRBase Accession No. MIMAT0018085) described in SEQ ID NO: 53, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 277) having a hairpin-like structure is known as a precursor of "hsa-miR-3663-3p".

The term "hsa-miR-6784-5p gene" or "hsa-miR-6784-5p" used herein includes the hsa-miR-6784-5p gene (miRBase Accession No. MIMAT0027468) described in SEQ ID NO: 54, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 278) having a hairpin-like structure is known as a precursor of "hsa-miR-6784-5p".

The term "hsa-miR-6749-5p gene" or "hsa-miR-6749-5p" used herein includes the hsa-miR-6749-5p gene (miRBase Accession No. MIMAT0027398) described in SEQ ID NO: 55, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 279) having a hairpin-like structure is known as a precursor of "hsa-miR-6749-5p".

The term "hsa-miR-1231 gene" or "hsa-miR-1231" used herein includes the hsa-miR-1231 gene (miRBase Accession No. MIMAT0005586) described in SEQ ID NO: 56, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 280) having a hairpin-like structure is known as a precursor of "hsa-miR-1231".

The term "hsa-miR-4746-3p gene" or "hsa-miR-4746-3p" used herein includes the hsa-miR-4746-3p gene (miRBase Accession No. MIMAT0019881) described in SEQ ID NO: 57, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 281) having a hairpin-like structure is known as a precursor of "hsa-miR-4746-3p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 58, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 282) having a hairpin-like structure is known as a precursor of "hsa-miR-6780b-5p".

The term "hsa-miR-4758-5p gene" or "hsa-miR-4758-5p" used herein includes the hsa-miR-4758-5p gene (miRBase Accession No. MIMAT0019903) described in SEQ ID NO: 59, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 283) having a hairpin-like structure is known as a precursor of "hsa-miR-4758-5p".

The term "hsa-miR-3679-5p gene" or "hsa-miR-3679-5p" used herein includes the hsa-miR-3679-5p gene (miRBase Accession No. MIMAT0018104) described in SEQ ID NO: 60, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 236) having a hairpin-like structure is known as a precursor of "hsa-miR-3679-5p".

The term "hsa-miR-3184-5p gene" or "hsa-miR-3184-5p" used herein includes the hsa-miR-3184-5p gene (miRBase Accession No. MIMAT0015064) described in SEQ ID NO: 61, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 284) having a hairpin-like structure is known as a precursor of "hsa-miR-3184-5p".

The term "hsa-miR-6125 gene" or "hsa-miR-6125" used herein includes the hsa-miR-6125 gene (miRBase Accession No. MIMAT0024598) described in SEQ ID NO: 62, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 285) having a hairpin-like structure is known as a precursor of "hsa-miR-6125".

The term "hsa-miR-6721-5p gene" or "hsa-miR-6721-5p" used herein includes the hsa-miR-6721-5p gene (miRBase Accession No. MIMAT0025852) described in SEQ ID NO: 63, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 286) having a hairpin-like structure is known as a precursor of "hsa-miR-6721-5p".

The term "hsa-miR-6791-5p gene" or "hsa-miR-6791-5p" used herein includes the hsa-miR-6791-5p gene (miRBase Accession No. MIMAT0027482) described in SEQ ID NO: 64, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 287) having a hairpin-like structure is known as a precursor of "hsa-miR-6791-5p".

The term "hsa-miR-3185 gene" or "hsa-miR-3185" used herein includes the hsa-miR-3185 gene (miRBase Accession No. MIMAT0015065) described in SEQ ID NO: 65, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 288) having a hairpin-like structure is known as a precursor of "hsa-miR-3185".

The term "hsa-miR-1260a gene" or "hsa-miR-1260a" used herein includes the hsa-miR-1260a gene (miRBase Accession No. MIMAT0005911) described in SEQ ID NO: 66, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 289) having a hairpin-like structure is known as a precursor of "hsa-miR-1260a".

The term "hsa-miR-3197 gene" or "hsa-miR-3197" used herein includes the hsa-miR-3197 gene (miRBase Accession No. MIMAT0015082) described in SEQ ID NO: 67, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 290) having a hairpin-like structure is known as a precursor of "hsa-miR-3197".

The term "hsa-miR-6845-5p gene" or "hsa-miR-6845-5p" used herein includes the hsa-miR-6845-5p gene (miRBase Accession No. MIMAT0027590) described in SEQ ID NO: 68, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 291) having a hairpin-like structure is known as a precursor of "hsa-miR-6845-5p".

The term "hsa-miR-6887-5p gene" or "hsa-miR-6887-5p" used herein includes the hsa-miR-6887-5p gene (miRBase Accession No. MIMAT0027674) described in SEQ ID NO: 69, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 292) having a hairpin-like structure is known as a precursor of "hsa-miR-6887-5p".

The term "hsa-miR-6738-5p gene" or "hsa-miR-6738-5p" used herein includes the hsa-miR-6738-5p gene (miRBase Accession No. MIMAT0027377) described in SEQ ID NO: 70, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 293) having a hairpin-like structure is known as a precursor of "hsa-miR-6738-5p".

The term "hsa-miR-6872-3p gene" or "hsa-miR-6872-3p" used herein includes the hsa-miR-6872-3p gene (miRBase Accession No. MIMAT0027645) described in SEQ ID NO: 71, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. MI0022719, SEQ ID NO: 294) having a hairpin-like structure is known as a precursor of "hsa-miR-6872-3p".

The term "hsa-miR-4497 gene" or "hsa-miR-4497" used herein includes the hsa-miR-4497 gene (miRBase Accession No. MIMAT0019032) described in SEQ ID NO: 72, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 295) having a hairpin-like structure is known as a precursor of "hsa-miR-4497".

The term "hsa-miR-1229-5p gene" or "hsa-miR-1229-5p" used herein includes the hsa-miR-1229-5p gene (miRBase Accession No. MIMAT0022942) described in SEQ ID NO: 73, a homolog or an ortholog of a different organism species, and the like. The hsa-miR-1229-5p gene can be obtained by a method described in Berezikov E et al., 2007, Mol Cell, Vol. 28, p. 328-336. Also, "hsa-mir-1229" (miRBase Accession No. MI0006319, SEQ ID NO: 296) having a hairpin-like structure is known as a precursor of "hsa-miR-1229-5p".

The term "hsa-miR-6820-5p gene" or "hsa-miR-6820-5p" used herein includes the hsa-miR-6820-5p gene (miRBase Accession No. MIMAT0027540) described in SEQ ID NO: 74, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 297) having a hairpin-like structure is known as a precursor of "hsa-miR-6820-5p".

The term "hsa-miR-6777-5p gene" or "hsa-miR-6777-5p" used herein includes the hsa-miR-6777-5p gene (miRBase Accession No. MIMAT0027454) described in SEQ ID NO: 75, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 298) having a hairpin-like structure is known as a precursor of "hsa-miR-6777-5p".

The term "hsa-miR-3917 gene" or "hsa-miR-3917" used herein includes the hsa-miR-3917 gene (miRBase Accession No. MIMAT0018191) described in SEQ ID NO: 76, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423, SEQ ID NO: 299) having a hairpin-like structure is known as a precursor of "hsa-miR-3917".

The term "hsa-miR-5787 gene" or "hsa-miR-5787" used herein includes the hsa-miR-5787 gene (miRBase Accession No. MIMAT0023252) described in SEQ ID NO: 77, a homolog or an ortholog of a different organism species, and the like. The hsa-miR-5787 gene can be obtained by a method described in Yoo H et al., 2011, Biochem Biophys Res Commun, Vol. 415, p. 567-572. Also, "hsa-mir-5787" (miRBase Accession No. MI0019797, SEQ ID NO: 300) having a hairpin-like structure is known as a precursor of "hsa-miR-5787".

The term "hsa-miR-4286 gene" or "hsa-miR-4286" used herein includes the hsa-miR-4286 gene (miRBase Accession No. MIMAT0016916) described in SEQ ID NO: 78, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 301) having a hairpin-like structure is known as a precursor of "hsa-miR-4286".

The term "hsa-miR-6877-5p gene" or "hsa-miR-6877-5p" used herein includes the hsa-miR-6877-5p gene (miRBase Accession No. MIMAT0027654) described in SEQ ID NO: 79, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI0022724, SEQ ID NO: 302) having a hairpin-like structure is known as a precursor of "hsa-miR-6877-5p".

The term "hsa-miR-1225-3p gene" or "hsa-miR-1225-3p" used herein includes the hsa-miR-1225-3p gene (miRBase Accession No. MIMAT0005573) described in SEQ ID NO: 80, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 303) having a hairpin-like structure is known as a precursor of "hsa-miR-1225-3p".

The term "hsa-miR-6088 gene" or "hsa-miR-6088" used herein includes the hsa-miR-6088 gene (miRBase Accession No. MIMAT0023713) described in SEQ ID NO: 81, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 304) having a hairpin-like structure is known as a precursor of "hsa-miR-6088".

The term "hsa-miR-6800-5p gene" or "hsa-miR-6800-5p" used herein includes the hsa-miR-6800-5p gene (miRBase Accession No. MIMAT0027500) described in SEQ ID NO: 82, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 305) having a hairpin-like structure is known as a precursor of "hsa-miR-6800-5p".

The term "hsa-miR-1246 gene" or "hsa-miR-1246" used herein includes the hsa-miR-1246 gene (miRBase Accession No. MIMAT0005898) described in SEQ ID NO: 83, a homolog or an ortholog of a different organism species, and the like. The hsa-miR-1246 gene can be obtained by a method described in Morin R D et al., 2008, Genome Res, Vol. 18, p. 610-621. Also, "hsa-mir-1246" (miRBase Accession No. MI0006381, SEQ ID NO: 306) having a hairpin-like structure is known as a precursor of "hsa-miR-1246".

The term "hsa-miR-4467 gene" or "hsa-miR-4467" used herein includes the hsa-miR-4467 gene (miRBase Accession No. MIMAT0018994) described in SEQ ID NO: 84, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 307) having a hairpin-like structure is known as a precursor of "hsa-miR-4467".

The term "hsa-miR-4419b gene" or "hsa-miR-4419b" used herein includes the hsa-miR-4419b gene (miRBase Accession No. MIMAT0019034) described in SEQ ID NO: 85, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 308) having a hairpin-like structure is known as a precursor of "hsa-miR-4419b".

The term "hsa-miR-1914-3p gene" or "hsa-miR-1914-3p" used herein includes the hsa-miR-1914-3p gene (miRBase Accession No. MIMAT0007890) described in SEQ ID NO: 86, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 309) having a hairpin-like structure is known as a precursor of "hsa-miR-1914-3p".

The term "hsa-miR-4632-5p gene" or "hsa-miR-4632-5p" used herein includes the hsa-miR-4632-5p gene (miRBase Accession No. MIMAT0022977) described in SEQ ID NO: 87, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 310) having a hairpin-like structure is known as a precursor of "hsa-miR-4632-5p".

The term "hsa-miR-1915-5p gene" or "hsa-miR-1915-5p" used herein includes the hsa-miR-1915-5p gene (miRBase Accession No. MIMAT0007891) described in SEQ ID NO: 88, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 311) having a hairpin-like structure is known as a precursor of "hsa-miR-1915-5p".

The term "hsa-miR-3940-5p gene" or "hsa-miR-3940-5p" used herein includes the hsa-miR-3940-5p gene (miRBase Accession No. MIMAT0019229) described in SEQ ID NO: 89, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 312) having a hairpin-like structure is known as a precursor of "hsa-miR-3940-5p".

The term "hsa-miR-1185-2-3p gene" or "hsa-miR-1185-2-3p" used herein includes the hsa-miR-1185-2-3p gene (miRBase Accession No. MIMAT0022713) described in SEQ ID NO: 90, a homolog or an ortholog of a different organism species, and the like. The hsa-miR-1185-2-3p gene can be obtained by a method described in Berezikov E et al., 2006, Genome Res, Vol. 16, p. 1289-1298. Also, "hsa-mir-1185-2" (miRBase Accession No. MI0003821, SEQ ID NO: 313) having a hairpin-like structure is known as a precursor of "hsa-miR-1185-2-3p".

The term "hsa-miR-6746-5p gene" or "hsa-miR-6746-5p" used herein includes the hsa-miR-6746-5p gene (miRBase Accession No. MIMAT0027392) described in SEQ ID NO: 91, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 314) having a hairpin-like structure is known as a precursor of "hsa-miR-6746-5p".

The term "hsa-miR-5001-5p gene" or "hsa-miR-5001-5p" used herein includes the hsa-miR-5001-5p gene (miRBase Accession No. MIMAT0021021) described in SEQ ID NO: 92, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 315) having a hairpin-like structure is known as a precursor of "hsa-miR-5001-5p".

The term "hsa-miR-1228-5p gene" or "hsa-miR-1228-5p" used herein includes the hsa-miR-1228-5p gene (miRBase Accession No. MIMAT0005582) described in SEQ ID NO: 93, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 316) having a hairpin-like structure is known as a precursor of "hsa-miR-1228-5p".

The term "hsa-miR-5572 gene" or "hsa-miR-5572" used herein includes the hsa-miR-5572 gene (miRBase Accession No. MIMAT0022260) described in SEQ ID NO: 94, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 317) having a hairpin-like structure is known as a precursor of "hsa-miR-5572".

The term "hsa-miR-4327 gene" or "hsa-miR-4327" used herein includes the hsa-miR-4327 gene (miRBase Accession No. MIMAT0016889) described in SEQ ID NO: 95, a homolog or an ortholog of a different organism species, and the like. The hsa-miR-4327 gene can be obtained by a method described in Goff L A et al., 2009, PLoS One, Vol. 4, e7192. Also, "hsa-mir-4327" (miRBase Accession No. MI0015867, SEQ ID NO: 318) having a hairpin-like structure is known as a precursor of "hsa-miR-4327".

The term "hsa-miR-4638-5p gene" or "hsa-miR-4638-5p" used herein includes the hsa-miR-4638-5p gene (miRBase Accession No. MIMAT0019695) described in SEQ ID NO: 96, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 319) having a hairpin-like structure is known as a precursor of "hsa-miR-4638-5p".

The term "hsa-miR-6799-5p gene" or "hsa-miR-6799-5p" used herein includes the hsa-miR-6799-5p gene (miRBase Accession No. MIMAT0027498) described in SEQ ID NO: 97, a homolog or an ortholog of a different organism species, and the like. The hsa-miR-6799-5p gene can be obtained by a method described in Ladewig E et al., 2012, Genome Res, Vol. 22, p. 1634-1645. Also, "hsa-mir-6799" (miRBase Accession No. MI0022644, SEQ ID NO: 320) having a hairpin-like structure is known as a precursor of "hsa-miR-6799-5p".

The term "hsa-miR-6861-5p gene" or "hsa-miR-6861-5p" used herein includes the hsa-miR-6861-5p gene (miRBase Accession No. MIMAT0027623) described in SEQ ID NO: 98, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 321) having a hairpin-like structure is known as a precursor of "hsa-miR-6861-5p".

The term "hsa-miR-6727-5p gene" or "hsa-miR-6727-5p" used herein includes the hsa-miR-6727-5p gene (miRBase Accession No. MIMAT0027355) described in SEQ ID NO: 99, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 322) having a hairpin-like structure is known as a precursor of "hsa-miR-6727-5p".

The term "hsa-miR-4513 gene" or "hsa-miR-4513" used herein includes the hsa-miR-4513 gene (miRBase Accession No. MIMAT0019050) described in SEQ ID NO: 100, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 323) having a hairpin-like structure is known as a precursor of "hsa-miR-4513".

The term "hsa-miR-6805-3p gene" or "hsa-miR-6805-3p" used herein includes the hsa-miR-6805-3p gene (miRBase Accession No. MIMAT0027511) described in SEQ ID NO: 101, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 324) having a hairpin-like structure is known as a precursor of "hsa-miR-6805-3p".

The term "hsa-miR-6808-5p gene" or "hsa-miR-6808-5p" used herein includes the hsa-miR-6808-5p gene (miRBase Accession No. MIMAT0027516) described in SEQ ID NO: 102, a homolog or an ortholog of a different organism species, and the like. The hsa-miR-6808-5p gene can be obtained by a method described in Ladewig E et al., 2012, Genome Res, Vol. 22, p. 1634-1645. Also, "hsa-mir-6808" (miRBase Accession No. MI0022653, SEQ ID NO: 325) having a hairpin-like structure is known as a precursor of "hsa-miR-6808-5p".

The term "hsa-miR-4449 gene" or "hsa-miR-4449" used herein includes the hsa-miR-4449 gene (miRBase Accession No. MIMAT0018968) described in SEQ ID NO: 103, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 326) having a hairpin-like structure is known as a precursor of "hsa-miR-4449".

The term "hsa-miR-1199-5p gene" or "hsa-miR-1199-5p" used herein includes the hsa-miR-1199-5p gene (miRBase Accession No. MIMAT0031119) described in SEQ ID NO: 104, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 327) having a hairpin-like structure is known as a precursor of "hsa-miR-1199-5p".

The term "hsa-miR-1275 gene" or "hsa-miR-1275" used herein includes the hsa-miR-1275 gene (miRBase Accession No. MIMAT0005929) described in SEQ ID NO: 105, a homolog or an ortholog of a different organism species, and the like. The hsa-miR-1275 gene can be obtained by a method described in Morin R D et al., 2008, Genome Res, Vol. 18, p. 610-621. Also, "hsa-mir-1275" (miRBase Accession No. MI0006415, SEQ ID NO: 328) having a hairpin-like structure is known as a precursor of "hsa-miR-1275".

The term "hsa-miR-4792 gene" or "hsa-miR-4792" used herein includes the hsa-miR-4792 gene (miRBase Accession No. MIMAT0019964) described in SEQ ID NO: 106, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 329) having a hairpin-like structure is known as a precursor of "hsa-miR-4792".

The term "hsa-miR-4443 gene" or "hsa-miR-4443" used herein includes the hsa-miR-4443 gene (miRBase Accession No. MIMAT0018961) described in SEQ ID NO: 107, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 330) having a hairpin-like structure is known as a precursor of "hsa-miR-4443".

The term "hsa-miR-6891-5p gene" or "hsa-miR-6891-5p" used herein includes the hsa-miR-6891-5p gene (miRBase Accession No. MIMAT0027682) described in SEQ ID NO: 108, a homolog or an ortholog of a different organism species, and the like. The hsa-miR-6891-5p gene can be obtained by a method described in Ladewig E et al., 2012, Genome Res, Vol. 22, p. 1634-1645. Also, "hsa-mir-6891" (miRBase Accession No. MI0022738, SEQ ID NO: 331) having a hairpin-like structure is known as a precursor of "hsa-miR-6891-5p".

The term "hsa-miR-6826-5p gene" or "hsa-miR-6826-5p" used herein includes the hsa-miR-6826-5p gene (miRBase Accession No. MIMAT0027552) described in SEQ ID NO: 109, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 332) having a hairpin-like structure is known as a precursor of "hsa-miR-6826-5p".

The term "hsa-miR-6807-5p gene" or "hsa-miR-6807-5p" used herein includes the hsa-miR-6807-5p gene (miRBase Accession No. MIMAT0027514) described in SEQ ID NO: 110, a homolog or an ortholog of a different organism species, and the like. The hsa-miR-6807-5p gene can be obtained by a method described in Ladewig E et al., 2012, Genome Res, Vol. 22, p. 1634-1645. Also, "hsa-mir-6807" (miRBase Accession No. MI0022652, SEQ ID NO: 333) having a hairpin-like structure is known as a precursor of "hsa-miR-6807-5p".

The term "hsa-miR-7150 gene" or "hsa-miR-7150" used herein includes the hsa-miR-7150 gene (miRBase Accession No. MIMAT0028211) described in SEQ ID NO: 111, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 334) having a hairpin-like structure is known as a precursor of "hsa-miR-7150".

The term "hsa-miR-4534 gene" or "hsa-miR-4534" used herein includes the hsa-miR-4534 gene (miRBase Accession No. MIMAT0019073) described in SEQ ID NO: 112, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 335) having a hairpin-like structure is known as a precursor of "hsa-miR-4534".

The term "hsa-miR-4476 gene" or "hsa-miR-4476" used herein includes the hsa-miR-4476 gene (miRBase Accession No. MIMAT0019003) described in SEQ ID NO: 113, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 336) having a hairpin-like structure is known as a precursor of "hsa-miR-4476".

The term "hsa-miR-4649-5p gene" or "hsa-miR-4649-5p" used herein includes the hsa-miR-4649-5p gene (miRBase Accession No. MIMAT0019711) described in SEQ ID NO: 114, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 337) having a hairpin-like structure is known as a precursor of "hsa-miR-4649-5p".

The term "hsa-miR-4525 gene" or "hsa-miR-4525" used herein includes the hsa-miR-4525 gene (miRBase Accession No. MIMAT0019064) described in SEQ ID NO: 115, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 338) having a hairpin-like structure is known as a precursor of "hsa-miR-4525".

The term "hsa-miR-1915-3p gene" or "hsa-miR-1915-3p" used herein includes the hsa-miR-1915-3p gene (miRBase Accession No. MIMAT0007892) described in SEQ ID NO: 116, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 311) having a hairpin-like structure is known as a precursor of "hsa-miR-1915-3p".

The term "hsa-miR-4516 gene" or "hsa-miR-4516" used herein includes the hsa-miR-4516 gene (miRBase Accession No. MIMAT0019053) described in SEQ ID NO: 117, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 339) having a hairpin-like structure is known as a precursor of "hsa-miR-4516".

The term "hsa-miR-4417 gene" or "hsa-miR-4417" used herein includes the hsa-miR-4417 gene (miRBase Accession No. MIMAT0018929) described in SEQ ID NO: 118, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 340) having a hairpin-like structure is known as a precursor of "hsa-miR-4417".

The term "hsa-miR-642b-3p gene" or "hsa-miR-642b-3p" used herein includes the hsa-miR-642b-3p gene (miRBase Accession No. MIMAT0018444) described in SEQ ID NO: 119, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 341) having a hairpin-like structure is known as a precursor of "hsa-miR-642b-3p".

The term "hsa-miR-3141 gene" or "hsa-miR-3141" used herein includes the hsa-miR-3141 gene (miRBase Accession No. MIMAT0015010) described in SEQ ID NO: 120, a homolog or an ortholog of a different organism species, and the like. The hsa-miR-3141 gene can be obtained by a method described in Stark M S et al., 2010, PLoS One, Vol.

5, e9685. Also, "hsa-mir-3141" (miRBase Accession No. MI0014165, SEQ ID NO: 342) having a hairpin-like structure is known as a precursor of "hsa-miR-3141".

The term "hsa-miR-5100 gene" or "hsa-miR-5100" used herein includes the hsa-miR-5100 gene (miRBase Accession No. MIMAT0022259) described in SEQ ID NO: 121, a homolog or an ortholog of a different organism species, and the like. The hsa-miR-5100 gene can be obtained by a method described in Tandon M et al., 2012, Oral Dis, Vol. 18, p. 127-131. Also, "hsa-mir-5100" (miRBase Accession No. MI0019116, SEQ ID NO: 343) having a hairpin-like structure is known as a precursor of "hsa-miR-5100".

The term "hsa-miR-6848-5p gene" or "hsa-miR-6848-5p" used herein includes the hsa-miR-6848-5p gene (miRBase Accession No. MIMAT0027596) described in SEQ ID NO: 122, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 344) having a hairpin-like structure is known as a precursor of "hsa-miR-6848-5p".

The term "hsa-miR-4739 gene" or "hsa-miR-4739" used herein includes the hsa-miR-4739 gene (miRBase Accession No. MIMAT0019868) described in SEQ ID NO: 123, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 345) having a hairpin-like structure is known as a precursor of "hsa-miR-4739".

The term "hsa-miR-4459 gene" or "hsa-miR-4459" used herein includes the hsa-miR-4459 gene (miRBase Accession No. MIMAT0018981) described in SEQ ID NO: 124, a homolog or an ortholog of a different organism species, and the like. The hsa-miR-4459 gene can be obtained by a method described in Jima D D et al., 2010, Blood, Vol. 116, e118-e127. Also, "hsa-mir-4459" (miRBase Accession No. MI0016805, SEQ ID NO: 346) having a hairpin-like structure is known as a precursor of "hsa-miR-4459".

The term "hsa-miR-1237-5p gene" or "hsa-miR-1237-5p" used herein includes the hsa-miR-1237-5p gene (miRBase Accession No. MIMAT0022946) described in SEQ ID NO: 125, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 347) having a hairpin-like structure is known as a precursor of "hsa-miR-1237-5p".

The term "hsa-miR-296-3p gene" or "hsa-miR-296-3p" used herein includes the hsa-miR-296-3p gene (miRBase Accession No. MIMAT0004679) described in SEQ ID NO: 126, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 273) having a hairpin-like structure is known as a precursor of "hsa-miR-296-3p".

The term "hsa-miR-4665-3p gene" or "hsa-miR-4665-3p" used herein includes the hsa-miR-4665-3p gene (miRBase Accession No. MIMAT0019740) described in SEQ ID NO: 127, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 269) having a hairpin-like structure is known as a precursor of "hsa-miR-4665-3p".

The term "hsa-miR-6786-5p gene" or "hsa-miR-6786-5p" used herein includes the hsa-miR-6786-5p gene (miRBase Accession No. MIMAT0027472) described in SEQ ID NO: 128, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786" (miRBase Accession No. MI0022631, SEQ ID NO: 348) having a hairpin-like structure is known as a precursor of "hsa-miR-6786-5p".

The term "hsa-miR-4258 gene" or "hsa-miR-4258" used herein includes the hsa-miR-4258 gene (miRBase Accession No. MIMAT0016879) described in SEQ ID NO: 129, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 349) having a hairpin-like structure is known as a precursor of "hsa-miR-4258".

The term "hsa-miR-6510-5p gene" or "hsa-miR-6510-5p" used herein includes the hsa-miR-6510-5p gene (miRBase Accession No. MIMAT0025476) described in SEQ ID NO: 130, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 350) having a hairpin-like structure is known as a precursor of "hsa-miR-6510-5p".

The term "hsa-miR-1343-5p gene" or "hsa-miR-1343-5p" used herein includes the hsa-miR-1343-5p gene (miRBase Accession No. MIMAT0027038) described in SEQ ID NO: 131, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 225) having a hairpin-like structure is known as a precursor of "hsa-miR-1343-5p".

The term "hsa-miR-1247-3p gene" or "hsa-miR-1247-3p" used herein includes the hsa-miR-1247-3p gene (miRBase Accession No. MIMAT0022721) described in SEQ ID NO: 132, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 351) having a hairpin-like structure is known as a precursor of "hsa-miR-1247-3p".

The term "hsa-miR-6805-5p gene" or "hsa-miR-6805-5p" used herein includes the hsa-miR-6805-5p gene (miRBase Accession No. MIMAT0027510) described in SEQ ID NO: 133, a homolog or an ortholog of a different organism species, and the like. The hsa-miR-6805-5p gene can be obtained by a method described in Ladewig E et al., 2012, Genome Res, Vol. 22, p. 1634-1645. Also, "hsa-mir-6805" (miRBase Accession No. MI0022650, SEQ ID NO: 324) having a hairpin-like structure is known as a precursor of "hsa-miR-6805-5p".

The term "hsa-miR-4492 gene" or "hsa-miR-4492" used herein includes the hsa-miR-4492 gene (miRBase Accession No. MIMAT0019027) described in SEQ ID NO: 134, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 352) having a hairpin-like structure is known as a precursor of "hsa-miR-4492".

The term "hsa-miR-1469 gene" or "hsa-miR-1469" used herein includes the hsa-miR-1469 gene (miRBase Accession No. MIMAT0007347) described in SEQ ID NO: 135, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 353) having a hairpin-like structure is known as a precursor of "hsa-miR-1469".

The term "hsa-miR-1268b gene" or "hsa-miR-1268b" used herein includes the hsa-miR-1268b gene (miRBase Accession No. MIMAT0018925) described in SEQ ID NO: 136, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 354) having a hairpin-like structure is known as a precursor of "hsa-miR-1268b".

The term "hsa-miR-6858-5p gene" or "hsa-miR-6858-5p" used herein includes the hsa-miR-6858-5p gene (miRBase Accession No. MIMAT0027616) described in SEQ ID NO: 137, a homolog or an ortholog of a different organism species, and the like. The hsa-miR-6858-5p gene can be obtained by a method described in Ladewig E et al., 2012, Genome Res, Vol. 22, p. 1634-1645. Also, "hsa-mir-6858" (miRBase Accession No. MI0022704, SEQ ID NO: 355) having a hairpin-like structure is known as a precursor of "hsa-miR-6858-5p".

The term "hsa-miR-3937 gene" or "hsa-miR-3937" used herein includes the hsa-miR-3937 gene (miRBase Accession No. MIMAT0018352) described in SEQ ID NO: 138, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 356) having a hairpin-like structure is known as a precursor of "hsa-miR-3937".

The term "hsa-miR-939-5p gene" or "hsa-miR-939-5p" used herein includes the hsa-miR-939-5p gene (miRBase Accession No. MIMAT0004982) described in SEQ ID NO: 139, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 357) having a hairpin-like structure is known as a precursor of "hsa-miR-939-5p".

The term "hsa-miR-3656 gene" or "hsa-miR-3656" used herein includes the hsa-miR-3656 gene (miRBase Accession No. MIMAT0018076) described in SEQ ID NO: 140, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 358) having a hairpin-like structure is known as a precursor of "hsa-miR-3656".

The term "hsa-miR-744-5p gene" or "hsa-miR-744-5p" used herein includes the hsa-miR-744-5p gene (miRBase Accession No. MIMAT0004945) described in SEQ ID NO: 141, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 359) having a hairpin-like structure is known as a precursor of "hsa-miR-744-5p".

The term "hsa-miR-4687-3p gene" or "hsa-miR-4687-3p" used herein includes the hsa-miR-4687-3p gene (miRBase Accession No. MIMAT0019775) described in SEQ ID NO: 142, a homolog or an ortholog of a different organism species, and the like. The hsa-miR-4687-3p gene can be obtained by a method described in Persson H et al., 2011, Cancer Res, Vol. 71, p. 78-86. Also, "hsa-mir-4687" (miRBase Accession No. MI0017319, SEQ ID NO: 360) having a hairpin-like structure is known as a precursor of "hsa-miR-4687-3p".

The term "hsa-miR-4763-3p gene" or "hsa-miR-4763-3p" used herein includes the hsa-miR-4763-3p gene (miRBase Accession No. MIMAT0019913) described in SEQ ID NO: 143, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 361) having a hairpin-like structure is known as a precursor of "hsa-miR-4763-3p".

The term "hsa-miR-3620-5p gene" or "hsa-miR-3620-5p" used herein includes the hsa-miR-3620-5p gene (miRBase Accession No. MIMAT0022967) described in SEQ ID NO: 144, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 362) having a hairpin-like structure is known as a precursor of "hsa-miR-3620-5p".

The term "hsa-miR-3195 gene" or "hsa-miR-3195" used herein includes the hsa-miR-3195 gene (miRBase Accession No. MIMAT0015079) described in SEQ ID NO: 145, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 363) having a hairpin-like structure is known as a precursor of "hsa-miR-3195".

The term "hsa-miR-6842-5p gene" or "hsa-miR-6842-5p" used herein includes the hsa-miR-6842-5p gene (miRBase Accession No. MIMAT0027586) described in SEQ ID NO: 146, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 364) having a hairpin-like structure is known as a precursor of "hsa-miR-6842-5p".

The term "hsa-miR-4707-5p gene" or "hsa-miR-4707-5p" used herein includes the hsa-miR-4707-5p gene (miRBase Accession No. MIMAT0019807) described in SEQ ID NO: 147, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 365) having a hairpin-like structure is known as a precursor of "hsa-miR-4707-5p".

The term "hsa-miR-642a-3p gene" or "hsa-miR-642a-3p" used herein includes the hsa-miR-642a-3p gene (miRBase Accession No. MIMAT0020924) described in SEQ ID NO:

148, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 366) having a hairpin-like structure is known as a precursor of "hsa-miR-642a-3p".

The term "hsa-miR-7113-3p gene" or "hsa-miR-7113-3p" used herein includes the hsa-miR-7113-3p gene (miRBase Accession No. MIMAT0028124) described in SEQ ID NO: 149, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 367) having a hairpin-like structure is known as a precursor of "hsa-miR-7113-3p".

The term "hsa-miR-4728-5p gene" or "hsa-miR-4728-5p" used herein includes the hsa-miR-4728-5p gene (miRBase Accession No. MIMAT0019849) described in SEQ ID NO: 150, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 368) having a hairpin-like structure is known as a precursor of "hsa-miR-4728-5p".

The term "hsa-miR-5195-3p gene" or "hsa-miR-5195-3p" used herein includes the hsa-miR-5195-3p gene (miRBase Accession No. MIMAT0021127) described in SEQ ID NO: 151, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 369) having a hairpin-like structure is known as a precursor of "hsa-miR-5195-3p".

The term "hsa-miR-1185-1-3p gene" or "hsa-miR-1185-1-3p" used herein includes the hsa-miR-1185-1-3p gene (miRBase Accession No. MIMAT0022838) described in SEQ ID NO: 152, a homolog or an ortholog of a different organism species, and the like. The hsa-miR-1185-1-3p gene can be obtained by a method described in Berezikov E et al., 2006, Genome Res, Vol. 16, p. 1289-1298. Also, "hsa-mir-1185-1" (miRBase Accession No. MI0003844, SEQ ID NO: 370) having a hairpin-like structure is known as a precursor of "hsa-miR-1185-1-3p".

The term "hsa-miR-6774-5p gene" or "hsa-miR-6774-5p" used herein includes the hsa-miR-6774-5p gene (miRBase Accession No. MIMAT0027448) described in SEQ ID NO: 153, a homolog or an ortholog of a different organism species, and the like. The hsa-miR-6774-5p gene can be obtained by a method described in Ladewig E et al., 2012, Genome Res, Vol. 22, p. 1634-1645. Also, "hsa-mir-6774" (miRBase Accession No. MI0022619, SEQ ID NO: 371) having a hairpin-like structure is known as a precursor of "hsa-miR-6774-5p".

The term "hsa-miR-8059 gene" or "hsa-miR-8059" used herein includes the hsa-miR-8059 gene (miRBase Accession No. MIMAT0030986) described in SEQ ID NO: 154, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 372) having a hairpin-like structure is known as a precursor of "hsa-miR-8059".

The term "hsa-miR-3131 gene" or "hsa-miR-3131" used herein includes the hsa-miR-3131 gene (miRBase Accession No. MIMAT0014996) described in SEQ ID NO: 155, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 373) having a hairpin-like structure is known as a precursor of "hsa-miR-3131".

The term "hsa-miR-7847-3p gene" or "hsa-miR-7847-3p" used herein includes the hsa-miR-7847-3p gene (miRBase Accession No. MIMAT0030422) described in SEQ ID NO: 156, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 374) having a hairpin-like structure is known as a precursor of "hsa-miR-7847-3p".

The term "hsa-miR-4463 gene" or "hsa-miR-4463" used herein includes the hsa-miR-4463 gene (miRBase Accession No. MIMAT0018987) described in SEQ ID NO: 157, a homolog or an ortholog of a different organism species, and the like. The hsa-miR-4463 gene can be obtained by a method described in Jima D D et al., 2010, Blood, Vol. 116, e118-e127. Also, "hsa-mir-4463" (miRBase Accession No. MI0016811, SEQ ID NO: 375) having a hairpin-like structure is known as a precursor of "hsa-miR-4463".

The term "hsa-miR-128-2-5p gene" or "hsa-miR-128-2-5p" used herein includes the hsa-miR-128-2-5p gene (miRBase Accession No. MIMAT0031095) described in SEQ ID NO: 158, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 376) having a hairpin-like structure is known as a precursor of "hsa-miR-128-2-5p".

The term "hsa-miR-4508 gene" or "hsa-miR-4508" used herein includes the hsa-miR-4508 gene (miRBase Accession No. MIMAT0019045) described in SEQ ID NO: 159, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 377) having a hairpin-like structure is known as a precursor of "hsa-miR-4508".

The term "hsa-miR-6806-5p gene" or "hsa-miR-6806-5p" used herein includes the hsa-miR-6806-5p gene (miRBase Accession No. MIMAT0027512) described in SEQ ID NO: 160, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 378) having a hairpin-like structure is known as a precursor of "hsa-miR-6806-5p".

The term "hsa-miR-7111-5p gene" or "hsa-miR-7111-5p" used herein includes the hsa-miR-7111-5p gene (miRBase Accession No. MIMAT0028119) described in SEQ ID NO: 161, a homolog or an ortholog of a different organism species, and the like. The hsa-miR-7111-5p gene can be obtained by a method described in Ladewig E et al., 2012, Genome Res, Vol. 22, p. 1634-1645. Also, "hsa-mir-7111" (miRBase Accession No. MI0022962, SEQ ID NO: 379) having a hairpin-like structure is known as a precursor of "hsa-miR-7111-5p".

The term "hsa-miR-6782-5p gene" or "hsa-miR-6782-5p" used herein includes the hsa-miR-6782-5p gene (miRBase Accession No. MIMAT0027464) described in SEQ ID NO: 162, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 380) having a hairpin-like structure is known as a precursor of "hsa-miR-6782-5p".

The term "hsa-miR-4734 gene" or "hsa-miR-4734" used herein includes the hsa-miR-4734 gene (miRBase Accession No. MIMAT0019859) described in SEQ ID NO: 163, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 381) having a hairpin-like structure is known as a precursor of "hsa-miR-4734".

The term "hsa-miR-3162-5p gene" or "hsa-miR-3162-5p" used herein includes the hsa-miR-3162-5p gene (miRBase Accession No. MIMAT0015036) described in SEQ ID NO: 164, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 382) having a hairpin-like structure is known as a precursor of "hsa-miR-3162-5p".

The term "hsa-miR-887-3p gene" or "hsa-miR-887-3p" used herein includes the hsa-miR-887-3p gene (miRBase Accession No. MIMAT0004951) described in SEQ ID NO: 165, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 383) having a hairpin-like structure is known as a precursor of "hsa-miR-887-3p".

The term "hsa-miR-6752-5p gene" or "hsa-miR-6752-5p" used herein includes the hsa-miR-6752-5p gene (miRBase Accession No. MIMAT0027404) described in SEQ ID NO: 166, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 384) having a hairpin-like structure is known as a precursor of "hsa-miR-6752-5p".

The term "hsa-miR-6724-5p gene" or "hsa-miR-6724-5p" used herein includes the hsa-miR-6724-5p gene (miRBase Accession No. MIMAT0025856) described in SEQ ID NO: 167, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 385) having a hairpin-like structure is known as a precursor of "hsa-miR-6724-5p".

The term "hsa-miR-23b-3p gene" or "hsa-miR-23b-3p" used herein includes the hsa-miR-23b-3p gene (miRBase Accession No. MIMAT0000418) described in SEQ ID NO: 168, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 386) having a hairpin-like structure is known as a precursor of "hsa-miR-23b-3p".

The term "hsa-miR-23a-3p gene" or "hsa-miR-23a-3p" used herein includes the hsa-miR-23a-3p gene (miRBase Accession No. MIMAT0000078) described in SEQ ID NO: 169, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 387) having a hairpin-like structure is known as a precursor of "hsa-miR-23a-3p".

The term "hsa-miR-625-3p gene" or "hsa-miR-625-3p" used herein includes the hsa-miR-625-3p gene (miRBase Accession No. MIMAT0004808) described in SEQ ID NO: 170, a homolog or an ortholog of a different organism species, and the like. The hsa-miR-625-3p gene can be obtained by a method described in Cummins J M et al., 2006, Proc Natl Acad Sci U.S.A., Vol. 103, p. 3687-3692. Also, "hsa-mir-625" (miRBase Accession No. MI0003639, SEQ ID NO: 388) having a hairpin-like structure is known as a precursor of "hsa-miR-625-3p".

The term "hsa-miR-1228-3p gene" or "hsa-miR-1228-3p" used herein includes the hsa-miR-1228-3p gene (miRBase Accession No. MIMAT0005583) described in SEQ ID NO: 171, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 316) having a hairpin-like structure is known as a precursor of "hsa-miR-1228-3p".

The term "hsa-miR-614 gene" or "hsa-miR-614" used herein includes the hsa-miR-614 gene (miRBase Accession No. MIMAT0003282) described in SEQ ID NO: 172, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 389) having a hairpin-like structure is known as a precursor of "hsa-miR-614".

The term "hsa-miR-1913 gene" or "hsa-miR-1913" used herein includes the hsa-miR-1913 gene (miRBase Accession No. MIMAT0007888) described in SEQ ID NO: 173, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 390) having a hairpin-like structure is known as a precursor of "hsa-miR-1913".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 174, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 391) having a hairpin-like structure is known as a precursor of "hsa-miR-92a-2-5p".

The term "hsa-miR-187-5p gene" or "hsa-miR-187-5p" used herein includes the hsa-miR-187-5p gene (miRBase Accession No. MIMAT0004561) described in SEQ ID NO: 175, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 392) having a hairpin-like structure is known as a precursor of "hsa-miR-187-5p".

The term "hsa-miR-16-5p gene" or "hsa-miR-16-5p" used herein includes the hsa-miR-16-5p gene (miRBase Accession No. MIMAT0000069) described in SEQ ID NO: 176, a homolog or an ortholog of a different organism species, and the like. The hsa-miR-16-5p gene can be obtained by a method described in Lagos-Quintana M et al., 2001, Science, Vol. 294, p. 853-858. Also, "hsa-mir-16-1" and "hsa-mir-16-2" (miRBase Accession Nos. MI0000070 and MI0000115, SEQ ID NOs: 393 and 394) having a hairpin-like structure are known as precursors of "hsa-miR-16-5p".

The term "hsa-miR-92b-3p gene" or "hsa-miR-92b-3p" used herein includes the hsa-miR-92b-3p gene (miRBase Accession No. MIMAT0003218) described in SEQ ID NO: 177, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 395) having a hairpin-like structure is known as a precursor of "hsa-miR-92b-3p".

The term "hsa-miR-150-3p gene" or "hsa-miR-150-3p" used herein includes the hsa-miR-150-3p gene (miRBase Accession No. MIMAT0004610) described in SEQ ID NO: 178, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 396) having a hairpin-like structure is known as a precursor of "hsa-miR-150-3p".

The term "hsa-miR-564 gene" or "hsa-miR-564" used herein includes the hsa-miR-564 gene (miRBase Accession No. MIMAT0003228) described in SEQ ID NO: 179, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 397) having a hairpin-like structure is known as a precursor of "hsa-miR-564".

The term "hsa-miR-125a-3p gene" or "hsa-miR-125a-3p" used herein includes the hsa-miR-125a-3p gene (miRBase Accession No. MIMAT0004602) described in SEQ ID NO: 180, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 398) having a hairpin-like structure is known as a precursor of "hsa-miR-125a-3p".

The term "hsa-miR-92b-5p gene" or "hsa-miR-92b-5p" used herein includes the hsa-miR-92b-5p gene (miRBase Accession No. MIMAT0004792) described in SEQ ID NO: 181, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 395) having a hairpin-like structure is known as a precursor of "hsa-miR-92b-5p".

The term "hsa-miR-92a-3p gene" or "hsa-miR-92a-3p" used herein includes the hsa-miR-92a-3p gene (miRBase Accession No. MIMAT0000092) described in SEQ ID NO: 182, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1" and "hsa-mir-92a-2" (miRBase Accession Nos. MI0000093 and MI0000094, SEQ ID NOs: 399 and 391) having a hairpin-like structure are known as precursors of "hsa-miR-92a-3p".

The term "hsa-miR-663a gene" or "hsa-miR-663a" used herein includes the hsa-miR-663a gene (miRBase Accession No. MIMAT0003326) described in SEQ ID NO: 183, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 400) having a hairpin-like structure is known as a precursor of "hsa-miR-663a".

The term "hsa-miR-4688 gene" or "hsa-miR-4688" used herein includes the hsa-miR-4688 gene (miRBase Accession No. MIMAT0019777) described in SEQ ID NO: 184, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 401) having a hairpin-like structure is known as a precursor of "hsa-miR-4688".

The term "hsa-miR-4648 gene" or "hsa-miR-4648" used herein includes the hsa-miR-4648 gene (miRBase Accession No. MIMAT0019710) described in SEQ ID NO: 185, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 402) having a hairpin-like structure is known as a precursor of "hsa-miR-4648".

The term "hsa-miR-6085 gene" or "hsa-miR-6085" used herein includes the hsa-miR-6085 gene (miRBase Accession No. MIMAT0023710) described in SEQ ID NO: 186, a homolog or an ortholog of a different organism species, and the like. The hsa-miR-6085 gene can be obtained by a method described in Voellenkle C et al., 2012, RNA, Vol. 18, p. 472-484. Also, "hsa-mir-6085" (miRBase Accession No. MI0020362, SEQ ID NO: 403) having a hairpin-like structure is known as a precursor of "hsa-miR-6085".

The term "hsa-miR-6126 gene" or "hsa-miR-6126" used herein includes the hsa-miR-6126 gene (miRBase Accession No. MIMAT0024599) described in SEQ ID NO: 187, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 404) having a hairpin-like structure is known as a precursor of "hsa-miR-6126".

The term "hsa-miR-6880-5p gene" or "hsa-miR-6880-5p" used herein includes the hsa-miR-6880-5p gene (miRBase Accession No. MIMAT0027660) described in SEQ ID NO: 188, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 405) having a hairpin-like structure is known as a precursor of "hsa-miR-6880-5p".

The term "hsa-miR-328-5p gene" or "hsa-miR-328-5p" used herein includes the hsa-miR-328-5p gene (miRBase Accession No. MIMAT0026486) described in SEQ ID NO: 189, a homolog or an ortholog of a different organism species, and the like. The hsa-miR-328-5p gene can be obtained by a method described in Kim J et al., 2004, Proc Natl Acad Sci USA, Vol. 101, p. 360-365. Also, "hsa-mir-328" (miRBase Accession No. MI0000804, SEQ ID NO: 406) having a hairpin-like structure is known as a precursor of "hsa-miR-328-5p".

The term "hsa-miR-6768-5p gene" or "hsa-miR-6768-5p" used herein includes the hsa-miR-6768-5p gene (miRBase Accession No. MIMAT0027436) described in SEQ ID NO: 190, a homolog or an ortholog of a different organism species, and the like. The hsa-miR-6768-5p gene can be obtained by a method described in Ladewig E et al., 2012, Genome Res, Vol. 22, p. 1634-1645. Also, "hsa-mir-6768" (miRBase Accession No. MI0022613, SEQ ID NO: 407) having a hairpin-like structure is known as a precursor of "hsa-miR-6768-5p".

The term "hsa-miR-3180 gene" or "hsa-miR-3180" used herein includes the hsa-miR-3180 gene (miRBase Accession No. MIMAT0018178) described in SEQ ID NO: 191, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4" and "hsa-mir-3180-5" (miRBase Accession Nos. MI0016408 and MI0016409, SEQ ID NOs: 408 and 409) having a hairpin-like structure are known as precursors of "hsa-miR-3180".

The term "hsa-miR-6087 gene" or "hsa-miR-6087" used herein includes the hsa-miR-6087 gene (miRBase Accession No. MIMAT0023712) described in SEQ ID NO: 192, a homolog or an ortholog of a different organism species, and the like. The hsa-miR-6087 gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 410) having a hairpin-like structure is known as a precursor of "hsa-miR-6087".

The term "hsa-miR-1273g-3p gene" or "hsa-miR-1273g-3p" used herein includes the hsa-miR-1273g-3p gene (miRBase Accession No. MIMAT0022742) described in SEQ ID NO: 193, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 411) having a hairpin-like structure is known as a precursor of "hsa-miR-1273g-3p".

The term "hsa-miR-1225-5p gene" or "hsa-miR-1225-5p" used herein includes the hsa-miR-1225-5p gene (miRBase Accession No. MIMAT0005572) described in SEQ ID NO: 194, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 303) having a hairpin-like structure is known as a precursor of "hsa-miR-1225-5p".

The term "hsa-miR-3196 gene" or "hsa-miR-3196" used herein includes the hsa-miR-3196 gene (miRBase Accession No. MIMAT0015080) described in SEQ ID NO: 195, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 412) having a hairpin-like structure is known as a precursor of "hsa-miR-3196".

The term "hsa-miR-4695-5p gene" or "hsa-miR-4695-5p" used herein includes the hsa-miR-4695-5p gene (miRBase Accession No. MIMAT0019788) described in SEQ ID NO: 196, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 413) having a hairpin-like structure is known as a precursor of "hsa-miR-4695-5p".

The term "hsa-miR-6732-5p gene" or "hsa-miR-6732-5p" used herein includes the hsa-miR-6732-5p gene (miRBase Accession No. MIMAT0027365) described in SEQ ID NO: 197, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 414) having a hairpin-like structure is known as a precursor of "hsa-miR-6732-5p".

The term "hsa-miR-638 gene" or "hsa-miR-638" used herein includes the hsa-miR-638 gene (miRBase Accession No. MIMAT0003308) described in SEQ ID NO: 198, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 415) having a hairpin-like structure is known as a precursor of "hsa-miR-638".

The term "hsa-miR-6813-5p gene" or "hsa-miR-6813-5p" used herein includes the hsa-miR-6813-5p gene (miRBase Accession No. MIMAT0027526) described in SEQ ID NO: 199, a homolog or an ortholog of a different organism species, and the like. The hsa-miR-6813-5p gene can be obtained by a method described in Ladewig E et al., 2012, Genome Res, Vol. 22, p. 1634-1645. Also, "hsa-mir-6813" (miRBase Accession No. MI0022658, SEQ ID NO: 416) having a hairpin-like structure is known as a precursor of "hsa-miR-6813-5p".

The term "hsa-miR-665 gene" or "hsa-miR-665" used herein includes the hsa-miR-665 gene (miRBase Accession No. MIMAT0004952) described in SEQ ID NO: 200, a homolog or an ortholog of a different organism species, and the like. The hsa-miR-665 gene can be obtained by a method described in Berezikov E et al., 2006, Genome Res, Vol. 16, p. 1289-1298. Also, "hsa-mir-665" (miRBase Accession No. MI0005563, SEQ ID NO: 417) having a hairpin-like structure is known as a precursor of "hsa-miR-665".

The term "hsa-miR-486-3p gene" or "hsa-miR-486-3p" used herein includes the hsa-miR-486-3p gene (miRBase Accession No. MIMAT0004762) described in SEQ ID NO: 201, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486" and "hsa-mir-486-2" (miRBase Accession Nos. MI0002470 and MI0023622, SEQ ID NOs: 418 and 419) having a hairpin-like structure are known as precursors of "hsa-miR-486-3p".

The term "hsa-miR-4466 gene" or "hsa-miR-4466" used herein includes the hsa-miR-4466 gene (miRBase Accession No. MIMAT0018993) described in SEQ ID NO: 202, a homolog or an ortholog of a different organism species, and the like. The hsa-miR-4466 gene can be obtained by a method described in Jima D D et al., 2010, Blood, Vol. 116, e118-e127. Also, "hsa-mir-4466" (miRBase Accession No. MI0016817, SEQ ID NO: 420) having a hairpin-like structure is known as a precursor of "hsa-miR-4466".

The term "hsa-miR-30c-1-3p gene" or "hsa-miR-30c-1-3p" used herein includes the hsa-miR-30c-1-3p gene (miRBase Accession No. MIMAT0004674) described in SEQ ID NO: 203, a homolog or an ortholog of a different organism species, and the like. The hsa-miR-30c-1-3p gene can be obtained by a method described in Lagos-Quintana M et al., 2002, Curr Biol, Vol. 12, p. 735-739. Also, "hsa-mir-30c-1" (miRBase Accession No. MI0000736, SEQ ID NO: 421) having a hairpin-like structure is known as a precursor of "hsa-miR-30c-1-3p".

The term "hsa-miR-3621 gene" or "hsa-miR-3621" used herein includes the hsa-miR-3621 gene (miRBase Accession No. MIMAT0018002) described in SEQ ID NO: 204, a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 422) having a hairpin-like structure is known as a precursor of "hsa-miR-3621".

The term "hsa-miR-6743-5p gene" or "hsa-miR-6743-5p" used herein includes the hsa-miR-6743-5p gene (miRBase Accession No. MIMAT0027387) described in SEQ ID NO: 205, a homolog or an ortholog of a different organism species, and the like. The hsa-miR-6743-5p gene can be obtained by a method described in Ladewig E et al., 2012, Genome Res, Vol. 22, p. 1634-1645. Also, "hsa-mir-6743" (miRBase Accession No. MI0022588, SEQ ID NO: 423) having a hairpin-like structure is known as a precursor of "hsa-miR-6743-5p".

The term "hsa-miR-4298 gene" or "hsa-miR-4298" used herein includes the hsa-miR-4298 gene (miRBase Accession No. MIMAT0016852) described in SEQ ID NO: 206, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 424) having a hairpin-like structure is known as a precursor of "hsa-miR-4298".

The term "hsa-miR-4741 gene" or "hsa-miR-4741" used herein includes the hsa-miR-4741 gene (miRBase Accession No. MIMAT0019871) described in SEQ ID NO: 207, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 425) having a hairpin-like structure is known as a precursor of "hsa-miR-4741".

The term "hsa-miR-3619-3p gene" or "hsa-miR-3619-3p" used herein includes the hsa-miR-3619-3p gene (miRBase Accession No. MIMAT0019219) described in SEQ ID NO: 208, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 426) having a hairpin-like structure is known as a precursor of "hsa-miR-3619-3p".

The term "hsa-miR-6824-5p gene" or "hsa-miR-6824-5p" used herein includes the hsa-miR-6824-5p gene (miRBase Accession No. MIMAT0027548) described in SEQ ID NO: 209, a homolog or an ortholog of a different organism species, and the like. The hsa-miR-6824-5p gene can be obtained by a method described in Ladewig E et al., 2012, Genome Res, Vol. 22, p. 1634-1645. Also, "hsa-mir-6824" (miRBase Accession No. MI0022669, SEQ ID NO: 427) having a hairpin-like structure is known as a precursor of "hsa-miR-6824-5p".

The term "hsa-miR-5698 gene" or "hsa-miR-5698" used herein includes the hsa-miR-5698 gene (miRBase Accession No. MIMAT0022491) described in SEQ ID NO: 210, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 428) having a hairpin-like structure is known as a precursor of "hsa-miR-5698".

The term "hsa-miR-371a-5p gene" or "hsa-miR-371a-5p" used herein includes the hsa-miR-371a-5p gene (miRBase Accession No. MIMAT0004687) described in SEQ ID NO: 211, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 429) having a hairpin-like structure is known as a precursor of "hsa-miR-371a-5p".

The term "hsa-miR-4488 gene" or "hsa-miR-4488" used herein includes the hsa-miR-4488 gene (miRBase Accession No. MIMAT0019022) described in SEQ ID NO: 212, a homolog or an ortholog of a different organism species, and the like. The hsa-miR-4488 gene can be obtained by a method described in Jima D D et al., 2010, Blood, Vol. 116, e118-e127. Also, "hsa-mir-4488" (miRBase Accession No. MI0016849, SEQ ID NO: 430) having a hairpin-like structure is known as a precursor of "hsa-miR-4488".

The term "hsa-miR-1233-5p gene" or "hsa-miR-1233-5p" used herein includes the hsa-miR-1233-5p gene (miRBase Accession No. MIMAT0022943) described in SEQ ID NO: 213, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1" and "hsa-mir-1233-2" (miRBase Accession Nos. MI0006323 and MI0015973, SEQ ID NOs: 431 and 432) having a hairpin-like structure are known as precursors of "hsa-miR-1233-5p".

The term "hsa-miR-4723-5p gene" or "hsa-miR-4723-5p" used herein includes the hsa-miR-4723-5p gene (miRBase Accession No. MIMAT0019838) described in SEQ ID NO: 214, a homolog or an ortholog of a different organism species, and the like. The hsa-miR-4723-5p gene can be obtained by a method described in Persson H et al., 2011, Cancer Res, Vol. 71, p. 78-86. Also, "hsa-miR-4723" (miRBase Accession No. MI0017359, SEQ ID NO: 433) having a hairpin-like structure is known as a precursor of "hsa-miR-4723-5p".

The term "hsa-miR-24-3p gene" or "hsa-miR-24-3p" used herein includes the hsa-miR-24-3p gene (miRBase Accession No. MIMAT0000080) described in SEQ ID NO: 215, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1" and "hsa-mir-24-2" (miRBase Accession Nos. MI0000080 and MI0000081, SEQ ID NOs: 434 and 435) having a hairpin-like structure are known as precursors of "hsa-miR-24-3p".

The term "hsa-miR-1238-5p gene" or "hsa-miR-1238-5p" used herein includes the hsa-miR-1238-5p gene (miRBase Accession No. MIMAT0022947) described in SEQ ID NO: 216, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 436) having a hairpin-like structure is known as a precursor of "hsa-miR-1238-5p".

The term "hsa-miR-4442 gene" or "hsa-miR-4442" used herein includes the hsa-miR-4442 gene (miRBase Accession No. MIMAT0018960) described in SEQ ID NO: 217, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 437) having a hairpin-like structure is known as a precursor of "hsa-miR-4442".

The term "hsa-miR-3928-3p gene" or "hsa-miR-3928-3p" used herein includes the hsa-miR-3928-3p gene (miRBase Accession No. MIMAT0018205) described in SEQ ID NO: 218, a homolog or an ortholog of a different organism species, and the like. The hsa-miR-3928-3p gene can be obtained by a method described in Creighton C J et al., 2010, PLoS One, Vol. 5, e9637. Also, "hsa-mir-3928" (miRBase Accession No. MI0016438, SEQ ID NO: 438) having a hairpin-like structure is known as a precursor of "hsa-miR-3928-3p".

The term "hsa-miR-6716-5p gene" or "hsa-miR-6716-5p" used herein includes the hsa-miR-6716-5p gene (miRBase Accession No. MIMAT0025844) described in SEQ ID NO: 219, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 439) having a hairpin-like structure is known as a precursor of "hsa-miR-6716-5p".

The term "hsa-miR-6089 gene" or "hsa-miR-6089" used herein includes the hsa-miR-6089 gene (miRBase Accession No. MIMAT0023714) described in SEQ ID NO: 220, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1" and "hsa-mir-6089-2" (miRBase Accession Nos. MI0020366 and MI0023563, SEQ ID NOs: 440 and 441) having a hairpin-like structure are known as precursors of "hsa-miR-6089".

The term "hsa-miR-6124 gene" or "hsa-miR-6124" used herein includes the hsa-miR-6124 gene (miRBase Accession No. MIMAT0024597) described in SEQ ID NO: 221, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 442) having a hairpin-like structure is known as a precursor of "hsa-miR-6124".

The term "hsa-miR-6778-5p gene" or "hsa-miR-6778-5p" used herein includes the hsa-miR-6778-5p gene (miRBase Accession No. MIMAT0027456) described in SEQ ID NO: 222, a homolog or an ortholog of a different organism species, and the like. The hsa-miR-6778-5p gene can be obtained by a method described in Ladewig E et al., 2012, Genome Res, Vol. 22, p. 1634-1645. Also, "hsa-mir-6778" (miRBase Accession No. MI0022623, SEQ ID NO: 443) having a hairpin-like structure is known as a precursor of "hsa-miR-6778-5p".

The term "hsa-miR-557 gene" or "hsa-miR-557" used herein includes the hsa-miR-557 gene (miRBase Accession No. MIMAT0003221) described in SEQ ID NO: 223, a homolog or an ortholog of a different organism species, and the like. The hsa-miR-557 gene can be obtained by a method described in Cummins J M et al., 2006, Proc Natl Acad Sci USA, Vol. 103, p. 3687-3692. Also, "hsa-mir-557" (miRBase Accession No. MI0003563, SEQ ID NO: 444) having a hairpin-like structure is known as a precursor of "hsa-miR-557".

The term "hsa-miR-6090 gene" or "hsa-miR-6090" used herein includes the hsa-miR-6090 gene (miRBase Accession No. MIMAT0023715) described in SEQ ID NO: 224, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 445) having a hairpin-like structure is known as a precursor of "hsa-miR-6090".

The term "hsa-miR-6757-5p gene" or "hsa-miR-6757-5p" used herein includes the hsa-miR-6757-5p gene (miRBase Accession No. MIMAT0027414) described in SEQ ID NO: 714, a homolog or an ortholog of a different organism species, and the like. The hsa-miR-6757-5p gene can be obtained by a method described in Ladewig E et al., 2012, Genome Res., Vol. 22, p. 1634-1645. Also, "hsa-mir-6757" (miRBase Accession No. MI0022602, SEQ ID NO: 730) having a hairpin-like structure is known as a precursor of "hsa-miR-6757-5p".

The term "hsa-miR-4448 gene" or "hsa-miR-4448" used herein includes the hsa-miR-4448 gene (miRBase Accession No. MIMAT0018967) described in SEQ ID NO: 715, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No. MI0016791, SEQ ID NO: 731) having a hairpin-like structure is known as a precursor of "hsa-miR-4448".

The term "hsa-miR-671-5p gene" or "hsa-miR-671-5p" used herein includes the hsa-miR-671-5p gene (miRBase Accession No. MIMAT0003880) described in SEQ ID NO: 716, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 732) having a hairpin-like structure is known as a precursor of "hsa-miR-671-5p".

The term "hsa-miR-3178 gene" or "hsa-miR-3178" used herein includes the hsa-miR-3178 gene (miRBase Accession No. MIMAT0015055) described in SEQ ID NO: 717, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 733) having a hairpin-like structure is known as a precursor of "hsa-miR-3178".

The term "hsa-miR-4725-3p gene" or "hsa-miR-4725-3p" used herein includes the hsa-miR-4725-3p gene (miRBase Accession No. MIMAT0019844) described in SEQ ID NO: 718, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 734) having a hairpin-like structure is known as a precursor of "hsa-miR-4725-3p".

The term "hsa-miR-940 gene" or "hsa-miR-940" used herein includes the hsa-miR-940 gene (miRBase Accession No. MIMAT0004983) described in SEQ ID NO: 719, a homolog or an ortholog of a different organism species, and the like. The hsa-miR-940 gene can be obtained by a method described in Lui W O et al., 2007, A Cancer Res., Vol. 67, p. 6031-6043. Also, "hsa-mir-940" (miRBase Accession No. MI0005762, SEQ ID NO: 735) having a hairpin-like structure is known as a precursor of "hsa-miR-940".

The term "hsa-miR-6789-5p gene" or "hsa-miR-6789-5p" used herein includes the hsa-miR-6789-5p gene (miRBase Accession No. MIMAT0027478) described in SEQ ID NO: 720, a homolog or an ortholog of a different organism species, and the like. The hsa-miR-6789-5p gene can be obtained by a method described in Ladewig E et al., 2012, Genome Res., Vol. 22, p. 1634-1645. Also, "hsa-mir-6789" (miRBase Accession No. MI0022634, SEQ ID NO: 736) having a hairpin-like structure is known as a precursor of "hsa-miR-6789-5p".

The term "hsa-miR-4484 gene" or "hsa-miR-4484" used herein includes the hsa-miR-4484 gene (miRBase Accession No. MIMAT0019018) described in SEQ ID NO: 721, a homolog or an ortholog of a different organism species, and the like. The hsa-miR-4484 gene can be obtained by a method described in Jima D D et al., 2010, Blood., Vol. 116, e118-e127. Also, "hsa-mir-4484" (miRBase Accession No. MI0016845, SEQ ID NO: 737) having a hairpin-like structure is known as a precursor of "hsa-miR-4484".

The term "hsa-miR-4634 gene" or "hsa-miR-4634" used herein includes the hsa-miR-4634 gene (miRBase Accession No. MIMAT0019691) described in SEQ ID NO: 722, a homolog or an ortholog of a different organism species, and the like. The hsa-miR-4634 gene can be obtained by a method described in Persson H et al., 2011, Cancer Res., Vol. 71, p. 78-86. Also, "hsa-mir-4634" (miRBase Accession No. MI0017261, SEQ ID NO: 738) having a hairpin-like structure is known as a precursor of "hsa-miR-4634".

The term "hsa-miR-4745-5p gene" or "hsa-miR-4745-5p" used herein includes the hsa-miR-4745-5p gene (miRBase Accession No. MIMAT0019878) described in SEQ ID NO: 723, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 739) having a hairpin-like structure is known as a precursor of "hsa-miR-4745-5p".

The term "hsa-miR-4730 gene" or "hsa-miR-4730" used herein includes the hsa-miR-4730 gene (miRBase Accession No. MIMAT0019852) described in SEQ ID NO: 724, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 740) having a hairpin-like structure is known as a precursor of "hsa-miR-4730".

The term "hsa-miR-6803-5p gene" or "hsa-miR-6803-5p" used herein includes the hsa-miR-6803-5p gene (miRBase Accession No. MIMAT0027506) described in SEQ ID NO: 725, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 741) having a hairpin-like structure is known as a precursor of "hsa-miR-6803-5p".

The term "hsa-miR-6798-5p gene" or "hsa-miR-6798-5p" used herein includes the hsa-miR-6798-5p gene (miRBase Accession No. MIMAT0027496) described in SEQ ID NO: 726, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 742) having a hairpin-like structure is known as a precursor of "hsa-miR-6798-5p".

The term "hsa-miR-3648 gene" or "hsa-miR-3648" used herein includes the hsa-miR-3648 gene (miRBase Accession No. MIMAT0018068) described in SEQ ID NO: 727, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 743) having a hairpin-like structure is known as a precursor of "hsa-miR-3648".

The term "hsa-miR-4783-3p gene" or "hsa-miR-4783-3p" used herein includes the hsa-miR-4783-3p gene (miRBase Accession No. MIMAT0019947) described in SEQ ID NO: 728, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 744) having a hairpin-like structure is known as a precursor of "hsa-miR-4783-3p".

The term "hsa-miR-6836-3p gene" or "hsa-miR-6836-3p" used herein includes the hsa-miR-6836-3p gene (miRBase Accession No. MIMAT0027575) described in SEQ ID NO: 729, a homolog or an ortholog of a different organism species, and the like. The hsa-miR-6836-3p gene can be obtained by a method described in Ladewig E et al., 2012, Genome Res., Vol. 22, p. 1634-1645. Also, "hsa-mir-6836" (miRBase Accession No. MI0022682, SEQ ID NO: 745) having a hairpin-like structure is known as a precursor of "hsa-miR-6836-3p".

A mature miRNA may become a variant due to the sequence cleaved shorter or longer by one to several flanking nucleotides, or nucleotide substitution, when cleaved as the mature miRNA from its RNA precursor having a hairpin-like structure. This variant is called isomiR (Morin R D. et al., 2008, Genome Res., Vol. 18, p. 610-621). miRBase Release 20 shows the nucleotide sequences represented by SEQ ID NOs: 1 to 224 and 714 to 729 as well as a large number of the nucleotide sequence variants and fragments represented by SEQ ID NOs: 446 to 713 and 746 to 765, called isomiRs. These variants can also be obtained as miRNAs having a nucleotide sequence represented by any of SEQ ID NOs: 1 to 224 and 714 to 729.

Specifically, among the variants of polynucleotides consisting of a nucleotide sequence represented by any of SEQ ID NOs: 1, 3, 4, 6, 7, 10, 11, 13, 14, 16, 17, 20, 22, 26, 29, 36, 38, 39, 40, 42, 43, 44, 46, 49, 52, 59, 60, 62, 63, 65, 66, 67, 72, 76, 77, 78, 81, 83, 84, 85, 86, 87, 88, 89, 90, 92, 93, 94, 96, 100, 103, 105, 106, 107, 113, 114, 115, 116, 117, 118, 119, 120, 121, 123, 124, 125, 126, 130, 132, 134, 136, 139, 140, 141, 142, 143, 144, 145, 147, 148, 150, 151, 152, 155, 157, 158, 159, 163, 164, 165, 167, 168, 169, 170, 171, 172, 173, 174, 175, 176, 177, 178, 179, 180, 181, 182, 183, 184, 185, 187, 189, 191, 192, 193, 195, 196, 198, 200, 201, 202, 203, 206, 207, 210, 211, 212, 213, 214, 215, 217, 218, 219, 220, 221, 715, 716, 717, 718, 719, 721, 723, 724, 727 and 728 or a nucleotide sequence derived from the nucleotide sequence by the replacement of u with t according to the present invention, examples of the longest variants registered in miRBase Release 20 include polynucleotides represented by SEQ ID NOs: 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 746, 748, 750, 752, 754, 756, 758, 760, 762 and 764, respectively.

Also, among the variants of polynucleotides consisting of a nucleotide sequence represented by any of SEQ ID NOs: 1, 3, 4, 6, 7, 10, 11, 13, 14, 16, 17, 20, 22, 26, 29, 36, 38, 39, 40, 42, 43, 44, 46, 49, 52, 59, 60, 62, 63, 65, 66, 67, 72, 76, 77, 78, 81, 83, 84, 85, 86, 87, 88, 89, 90, 92, 93, 94, 96, 100, 103, 105, 106, 107, 113, 114, 115, 116, 117, 118, 119, 120, 121, 123, 124, 125, 126, 130, 132, 134, 136, 139, 140, 141, 142, 143, 144, 145, 147, 148, 150, 151, 152, 155, 157, 158, 159, 163, 164, 165, 167, 168, 169, 170, 171, 172, 173, 174, 175, 176, 177, 178, 179, 180, 181, 182, 183, 184, 185, 187, 189, 191, 192, 193, 195, 196, 198, 200, 201, 202, 203, 206, 207, 210, 211, 212, 213, 214, 215, 217, 218, 219, 220, 221, 715, 716, 717, 718, 719, 721, 723, 724, 727 and 728 or a nucleotide sequence derived from the nucleotide sequence by the replacement of u with t according to the present invention, examples of the shortest variants registered in miRBase Release 20 include polynucleotides having sequences represented by SEQ ID NOs: 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 747, 749, 751, 753, 755, 757, 759, 761, 763 and 765, respectively.

In addition to these variants and fragments, examples thereof include a large number of isomiR polynucleotides of SEQ ID NOs: 1 to 224 and 714 to 729 registered in miRBase. Examples of the polynucleotide comprising a nucleotide sequence represented by any of SEQ ID NOs: 1 to 224 and 714 to 729 include a polynucleotide represented by any of SEQ ID NOs: 225 to 445 and 730 to 745, which are their respective precursors.

The names and miRBase Accession Nos. (registration numbers) of the genes represented by SEQ ID NOs: 1 to 765 are shown in Table 1.

As used herein, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-1343-3p | MIMAT0019776 |
| 2 | hsa-miR-6726-5p | MIMAT0027353 |
| 3 | hsa-miR-6515-3p | MIMAT0025487 |

TABLE 1-continued

| SEQ ID NO: | Gene name | miRBase registration No. |
|---|---|---|
| 4 | hsa-miR-4651 | MIMAT0019715 |
| 5 | hsa-miR-4257 | MIMAT0016878 |
| 6 | hsa-miR-3188 | MIMAT0015070 |
| 7 | hsa-miR-6131 | MIMAT0024615 |
| 8 | hsa-miR-6766-3p | MIMAT0027433 |
| 9 | hsa-miR-7641 | MIMAT0029782 |
| 10 | hsa-miR-1249 | MIMAT0005901 |
| 11 | hsa-miR-3679-3p | MIMAT0018105 |
| 12 | hsa-miR-6787-5p | MIMAT0027474 |
| 13 | hsa-miR-4454 | MIMAT0018976 |
| 14 | hsa-miR-3135b | MIMAT0018985 |
| 15 | hsa-miR-6765-3p | MIMAT0027431 |
| 16 | hsa-miR-7975 | MIMAT0031178 |
| 17 | hsa-miR-204-3p | MIMAT0022693 |
| 18 | hsa-miR-7977 | MIMAT0031180 |
| 19 | hsa-miR-7110-5p | MIMAT0028117 |
| 20 | hsa-miR-6717-5p | MIMAT0025846 |
| 21 | hsa-miR-6870-5p | MIMAT0027640 |
| 22 | hsa-miR-663b | MIMAT0005867 |
| 23 | hsa-miR-6875-5p | MIMAT0027650 |
| 24 | hsa-miR-8072 | MIMAT0030999 |
| 25 | hsa-miR-6816-5p | MIMAT0027532 |
| 26 | hsa-miR-4281 | MIMAT0016907 |
| 27 | hsa-miR-6729-5p | MIMAT0027359 |
| 28 | hsa-miR-8069 | MIMAT0030996 |
| 29 | hsa-miR-4706 | MIMAT0019806 |
| 30 | hsa-miR-7108-5p | MIMAT0028113 |
| 31 | hsa-miR-4433b-3p | MIMAT0030414 |
| 32 | hsa-miR-6893-5p | MIMAT0027686 |
| 33 | hsa-miR-6857-5p | MIMAT0027614 |
| 34 | hsa-miR-1227-5p | MIMAT0022941 |
| 35 | hsa-miR-6741-5p | MIMAT0027383 |
| 36 | hsa-miR-451a | MIMAT0001631 |
| 37 | hsa-miR-8063 | MIMAT0030990 |
| 38 | hsa-miR-3622a-5p | MIMAT0018003 |
| 39 | hsa-miR-615-5p | MIMAT0004804 |
| 40 | hsa-miR-128-1-5p | MIMAT0026477 |
| 41 | hsa-miR-6825-5p | MIMAT0027550 |
| 42 | hsa-miR-1260b | MIMAT0015041 |
| 43 | hsa-miR-4433-3p | MIMAT0018949 |
| 44 | hsa-miR-4665-5p | MIMAT0019739 |
| 45 | hsa-miR-7845-5p | MIMAT0030420 |
| 46 | hsa-miR-1908-5p | MIMAT0007881 |
| 47 | hsa-miR-6840-3p | MIMAT0027583 |
| 48 | hsa-miR-6765-5p | MIMAT0027430 |
| 49 | hsa-miR-296-5p | MIMAT0000690 |
| 50 | hsa-miR-3675-3p | MIMAT0018099 |
| 51 | hsa-miR-6781-5p | MIMAT0027462 |
| 52 | hsa-miR-423-5p | MIMAT0004748 |
| 53 | hsa-miR-3663-3p | MIMAT0018085 |
| 54 | hsa-miR-6784-5p | MIMAT0027468 |
| 55 | hsa-miR-6749-5p | MIMAT0027398 |
| 56 | hsa-miR-1231 | MIMAT0005586 |
| 57 | hsa-miR-4746-3p | MIMAT0019881 |
| 58 | hsa-miR-6780b-5p | MIMAT0027572 |
| 59 | hsa-miR-4758-5p | MIMAT0019903 |
| 60 | hsa-miR-3679-5p | MIMAT0018104 |
| 61 | hsa-miR-3184-5p | MIMAT0015064 |
| 62 | hsa-miR-6125 | MIMAT0024598 |
| 63 | hsa-miR-6721-5p | MIMAT0025852 |
| 64 | hsa-miR-6791-5p | MIMAT0027482 |
| 65 | hsa-miR-3185 | MIMAT0015065 |
| 66 | hsa-miR-1260a | MIMAT0005911 |
| 67 | hsa-miR-3197 | MIMAT0015082 |
| 68 | hsa-miR-6845-5p | MIMAT0027590 |
| 69 | hsa-miR-6887-5p | MIMAT0027674 |
| 70 | hsa-miR-6738-5p | MIMAT0027377 |
| 71 | hsa-miR-6872-3p | MIMAT0027645 |
| 72 | hsa-miR-4497 | MIMAT0019032 |
| 73 | hsa-miR-1229-5p | MIMAT0022942 |
| 74 | hsa-miR-6820-5p | MIMAT0027540 |
| 75 | hsa-miR-6777-5p | MIMAT0027454 |
| 76 | hsa-miR-3917 | MIMAT0018191 |
| 77 | hsa-miR-5787 | MIMAT0023252 |
| 78 | hsa-miR-4286 | MIMAT0016916 |
| 79 | hsa-miR-6877-5p | MIMAT0027654 |
| 80 | hsa-miR-1225-3p | MIMAT0005573 |

TABLE 1-continued

| SEQ ID NO: | Gene name | miRBase registration No. |
|---|---|---|
| 81 | hsa-miR-6088 | MIMAT0023713 |
| 82 | hsa-miR-6800-5p | MIMAT0027500 |
| 83 | hsa-miR-1246 | MIMAT0005898 |
| 84 | hsa-miR-4467 | MIMAT0018994 |
| 85 | hsa-miR-4419b | MIMAT0019034 |
| 86 | hsa-miR-1914-3p | MIMAT0007890 |
| 87 | hsa-miR-4632-5p | MIMAT0022977 |
| 88 | hsa-miR-1915-5p | MIMAT0007891 |
| 89 | hsa-miR-3940-5p | MIMAT0019229 |
| 90 | hsa-miR-1185-2-3p | MIMAT0022713 |
| 91 | hsa-miR-6746-5p | MIMAT0027392 |
| 92 | hsa-miR-5001-5p | MIMAT0021021 |
| 93 | hsa-miR-1228-5p | MIMAT0005582 |
| 94 | hsa-miR-5572 | MIMAT0022260 |
| 95 | hsa-miR-4327 | MIMAT0016889 |
| 96 | hsa-miR-4638-5p | MIMAT0019695 |
| 97 | hsa-miR-6799-5p | MIMAT0027498 |
| 98 | hsa-miR-6861-5p | MIMAT0027623 |
| 99 | hsa-miR-6727-5p | MIMAT0027355 |
| 100 | hsa-miR-4513 | MIMAT0019050 |
| 101 | hsa-miR-6805-3p | MIMAT0027511 |
| 102 | hsa-miR-6808-5p | MIMAT0027516 |
| 103 | hsa-miR-4449 | MIMAT0018968 |
| 104 | hsa-miR-1199-5p | MIMAT0031119 |
| 105 | hsa-miR-1275 | MIMAT0005929 |
| 106 | hsa-miR-4792 | MIMAT0019964 |
| 107 | hsa-miR-4443 | MIMAT0018961 |
| 108 | hsa-miR-6891-5p | MIMAT0027682 |
| 109 | hsa-miR-6826-5p | MIMAT0027552 |
| 110 | hsa-miR-6807-5p | MIMAT0027514 |
| 111 | hsa-miR-7150 | MIMAT0028211 |
| 112 | hsa-miR-4534 | MIMAT0019073 |
| 113 | hsa-miR-4476 | MIMAT0019003 |
| 114 | hsa-miR-4649-5p | MIMAT0019711 |
| 115 | hsa-miR-4525 | MIMAT0019064 |
| 116 | hsa-miR-1915-3p | MIMAT0007892 |
| 117 | hsa-miR-4516 | MIMAT0019053 |
| 118 | hsa-miR-4417 | MIMAT0018929 |
| 119 | hsa-miR-642b-3p | MIMAT0018444 |
| 120 | hsa-miR-3141 | MIMAT0015010 |
| 121 | hsa-miR-5100 | MIMAT0022259 |
| 122 | hsa-miR-6848-5p | MIMAT0027596 |
| 123 | hsa-miR-4739 | MIMAT0019868 |
| 124 | hsa-miR-4459 | MIMAT0018981 |
| 125 | hsa-miR-1237-5p | MIMAT0022946 |
| 126 | hsa-miR-296-3p | MIMAT0004679 |
| 127 | hsa-miR-4665-3p | MIMAT0019740 |
| 128 | hsa-miR-6786-5p | MIMAT0027472 |
| 129 | hsa-miR-4258 | MIMAT0016879 |
| 130 | hsa-miR-6510-5p | MIMAT0025476 |
| 131 | hsa-miR-1343-5p | MIMAT0027038 |
| 132 | hsa-miR-1247-3p | MIMAT0022721 |
| 133 | hsa-miR-6805-5p | MIMAT0027510 |
| 134 | hsa-miR-4492 | MIMAT0019027 |
| 135 | hsa-miR-1469 | MIMAT0007347 |
| 136 | hsa-miR-1268b | MIMAT0018925 |
| 137 | hsa-miR-6858-5p | MIMAT0027616 |
| 138 | hsa-miR-3937 | MIMAT0018352 |
| 139 | hsa-miR-939-5p | MIMAT0004982 |
| 140 | hsa-miR-3656 | MIMAT0018076 |
| 141 | hsa-miR-744-5p | MIMAT0004945 |
| 142 | hsa-miR-4687-3p | MIMAT0019775 |
| 143 | hsa-miR-4763-3p | MIMAT0019913 |
| 144 | hsa-miR-3620-5p | MIMAT0022967 |
| 145 | hsa-miR-3195 | MIMAT0015079 |
| 146 | hsa-miR-6842-5p | MIMAT0027586 |
| 147 | hsa-miR-4707-5p | MIMAT0019807 |
| 148 | hsa-miR-642a-3p | MIMAT0020924 |
| 149 | hsa-miR-7113-3p | MIMAT0028124 |
| 150 | hsa-miR-4728-5p | MIMAT0019849 |
| 151 | hsa-miR-5195-3p | MIMAT0021127 |
| 152 | hsa-miR-1185-1-3p | MIMAT0022838 |
| 153 | hsa-miR-6774-5p | MIMAT0027448 |
| 154 | hsa-miR-8059 | MIMAT0030986 |
| 155 | hsa-miR-3131 | MIMAT0014996 |
| 156 | hsa-miR-7847-3p | MIMAT0030422 |
| 157 | hsa-miR-4463 | MIMAT0018987 |
| 158 | hsa-miR-128-2-5p | MIMAT0031095 |
| 159 | hsa-miR-4508 | MIMAT0019045 |
| 160 | hsa-miR-6806-5p | MIMAT0027512 |
| 161 | hsa-miR-7111-5p | MIMAT0028119 |
| 162 | hsa-miR-6782-5p | MIMAT0027464 |
| 163 | hsa-miR-4734 | MIMAT0019859 |
| 164 | hsa-miR-3162-5p | MIMAT0015036 |
| 165 | hsa-miR-887-3p | MIMAT0004951 |
| 166 | hsa-miR-6752-5p | MIMAT0027404 |
| 167 | hsa-miR-6724-5p | MIMAT0025856 |
| 168 | hsa-miR-23b-3p | MIMAT0000418 |
| 169 | hsa-miR-23a-3p | MIMAT0000078 |
| 170 | hsa-miR-625-3p | MIMAT0004808 |
| 171 | hsa-miR-1228-3p | MIMAT0005583 |
| 172 | hsa-miR-614 | MIMAT0003282 |
| 173 | hsa-miR-1913 | MIMAT0007888 |
| 174 | hsa-miR-92a-2-5p | MIMAT0004508 |
| 175 | hsa-miR-187-5p | MIMAT0004561 |
| 176 | hsa-miR-16-5p | MIMAT0000069 |
| 177 | hsa-miR-92b-3p | MIMAT0003218 |
| 178 | hsa-miR-150-3p | MIMAT0004610 |
| 179 | hsa-miR-564 | MIMAT0003228 |
| 180 | hsa-miR-125a-3p | MIMAT0004602 |
| 181 | hsa-miR-92b-5p | MIMAT0004792 |
| 182 | hsa-miR-92a-3p | MIMAT0000092 |
| 183 | hsa-miR-663a | MIMAT0003326 |
| 184 | hsa-miR-4688 | MIMAT0019777 |
| 185 | hsa-miR-4648 | MIMAT0019710 |
| 186 | hsa-miR-6085 | MIMAT0023710 |
| 187 | hsa-miR-6126 | MIMAT0024599 |
| 188 | hsa-miR-6880-5p | MIMAT0027660 |
| 189 | hsa-miR-328-5p | MIMAT0026486 |
| 190 | hsa-miR-6768-5p | MIMAT0027436 |
| 191 | hsa-miR-3180 | MIMAT0018178 |
| 192 | hsa-miR-6087 | MIMAT0023712 |
| 193 | hsa-miR-1273g-3p | MIMAT0022742 |
| 194 | hsa-miR-1225-5p | MIMAT0005572 |
| 195 | hsa-miR-3196 | MIMAT0015080 |
| 196 | hsa-miR-4695-5p | MIMAT0019788 |
| 197 | hsa-miR-6732-5p | MIMAT0027365 |
| 198 | hsa-miR-638 | MIMAT0003308 |
| 199 | hsa-miR-6813-5p | MIMAT0027526 |
| 200 | hsa-miR-665 | MIMAT0004952 |
| 201 | hsa-miR-486-3p | MIMAT0004762 |
| 202 | hsa-miR-4466 | MIMAT0018993 |
| 203 | hsa-miR-30c-1-3p | MIMAT0004674 |
| 204 | hsa-miR-3621 | MIMAT0018002 |
| 205 | hsa-miR-6743-5p | MIMAT0027387 |
| 206 | hsa-miR-4298 | MIMAT0016852 |
| 207 | hsa-miR-4741 | MIMAT0019871 |
| 208 | hsa-miR-3619-3p | MIMAT0019219 |
| 209 | hsa-miR-6824-5p | MIMAT0027548 |
| 210 | hsa-miR-5698 | MIMAT0022491 |
| 211 | hsa-miR-371a-5p | MIMAT0004687 |
| 212 | hsa-miR-4488 | MIMAT0019022 |
| 213 | hsa-miR-1233-5p | MIMAT0022943 |
| 214 | hsa-miR-4723-5p | MIMAT0019838 |
| 215 | hsa-miR-24-3p | MIMAT0000080 |
| 216 | hsa-miR-1238-5p | MIMAT0022947 |
| 217 | hsa-miR-4442 | MIMAT0018960 |
| 218 | hsa-miR-3928-3p | MIMAT0018205 |
| 219 | hsa-miR-6716-5p | MIMAT0025844 |
| 220 | hsa-miR-6089 | MIMAT0023714 |
| 221 | hsa-miR-6124 | MIMAT0024597 |
| 222 | hsa-miR-6778-5p | MIMAT0027456 |
| 223 | hsa-miR-557 | MIMAT0003221 |
| 224 | hsa-miR-6090 | MIMAT0023715 |
| 225 | hsa-mir-1343 | MI0017320 |
| 226 | hsa-mir-6726 | MI0022571 |
| 227 | hsa-mir-6515 | MI0022227 |
| 228 | hsa-mir-4651 | MI0017279 |
| 229 | hsa-mir-4257 | MI0015856 |
| 230 | hsa-mir-3188 | MI0014232 |
| 231 | hsa-mir-6131 | MI0021276 |
| 232 | hsa-mir-6766 | MI0022611 |
| 233 | hsa-mir-7641-1 | MI0024975 |
| 234 | hsa-mir-7641-2 | MI0024976 |

TABLE 1-continued

| SEQ ID NO: | Gene name | miRBase registration No. |
|---|---|---|
| 235 | hsa-mir-1249 | MI0006384 |
| 236 | hsa-mir-3679 | MI0016080 |
| 237 | hsa-mir-6787 | MI0022632 |
| 238 | hsa-mir-4454 | MI0016800 |
| 239 | hsa-mir-3135b | MI0016809 |
| 240 | hsa-mir-6765 | MI0022610 |
| 241 | hsa-mir-7975 | MI0025751 |
| 242 | hsa-mir-204 | MI0000284 |
| 243 | hsa-mir-7977 | MI0025753 |
| 244 | hsa-mir-7110 | MI0022961 |
| 245 | hsa-mir-6717 | MI0022551 |
| 246 | hsa-mir-6870 | MI0022717 |
| 247 | hsa-mir-663b | MI0006336 |
| 248 | hsa-mir-6875 | MI0022722 |
| 249 | hsa-mir-8072 | MI0025908 |
| 250 | hsa-mir-6816 | MI0022661 |
| 251 | hsa-mir-4281 | MI0015885 |
| 252 | hsa-mir-6729 | MI0022574 |
| 253 | hsa-mir-8069 | MI0025905 |
| 254 | hsa-mir-4706 | MI0017339 |
| 255 | hsa-mir-7108 | MI0022959 |
| 256 | hsa-mir-4433b | MI0025511 |
| 257 | hsa-mir-6893 | MI0022740 |
| 258 | hsa-mir-6857 | MI0022703 |
| 259 | hsa-mir-1227 | MI0006316 |
| 260 | hsa-mir-6741 | MI0022586 |
| 261 | hsa-mir-451a | MI0001729 |
| 262 | hsa-mir-8063 | MI0025899 |
| 263 | hsa-mir-3622a | MI0016013 |
| 264 | hsa-mir-615 | MI0003628 |
| 265 | hsa-mir-128-1 | MI0000447 |
| 266 | hsa-mir-6825 | MI0022670 |
| 267 | hsa-mir-1260b | MI0014197 |
| 268 | hsa-mir-4433 | MI0016773 |
| 269 | hsa-mir-4665 | MI0017295 |
| 270 | hsa-mir-7845 | MI0025515 |
| 271 | hsa-mir-1908 | MI0008329 |
| 272 | hsa-mir-6840 | MI0022686 |
| 240 | hsa-mir-6765 | MI0022610 |
| 273 | hsa-mir-296 | MI0000747 |
| 274 | hsa-mir-3675 | MI0016076 |
| 275 | hsa-mir-6781 | MI0022626 |
| 276 | hsa-mir-423 | MI0001445 |
| 277 | hsa-mir-3663 | MI0016064 |
| 278 | hsa-mir-6784 | MI0022629 |
| 279 | hsa-mir-6749 | MI0022594 |
| 280 | hsa-mir-1231 | MI0006321 |
| 281 | hsa-mir-4746 | MI0017385 |
| 282 | hsa-mir-6780b | MI0022681 |
| 283 | hsa-mir-4758 | MI0017399 |
| 236 | hsa-mir-3679 | MI0016080 |
| 284 | hsa-mir-3184 | MI0014226 |
| 285 | hsa-mir-6125 | MI0021259 |
| 286 | hsa-mir-6721 | MI0022556 |
| 287 | hsa-mir-6791 | MI0022636 |
| 288 | hsa-mir-3185 | MI0014227 |
| 289 | hsa-mir-1260a | MI0006394 |
| 290 | hsa-mir-3197 | MI0014245 |
| 291 | hsa-mir-6845 | MI0022691 |
| 292 | hsa-mir-6887 | MI0022734 |
| 293 | hsa-mir-6738 | MI0022583 |
| 294 | hsa-mir-6872 | MI0022719 |
| 295 | hsa-mir-4497 | MI0016859 |
| 296 | hsa-mir-1229 | MI0006319 |
| 297 | hsa-mir-6820 | MI0022665 |
| 298 | hsa-mir-6777 | MI0022622 |
| 299 | hsa-mir-3917 | MI0016423 |
| 300 | hsa-mir-5787 | MI0019797 |
| 301 | hsa-mir-4286 | MI0015894 |
| 302 | hsa-mir-6877 | MI0022724 |
| 303 | hsa-mir-1225 | MI0006311 |
| 304 | hsa-mir-6088 | MI0020365 |
| 305 | hsa-mir-6800 | MI0022645 |
| 306 | hsa-mir-1246 | MI0006381 |
| 307 | hsa-mir-4467 | MI0016818 |
| 308 | hsa-mir-4419b | MI0016861 |
| 309 | hsa-mir-1914 | MI0008335 |
| 310 | hsa-mir-4632 | MI0017259 |
| 311 | hsa-mir-1915 | MI0008336 |
| 312 | hsa-mir-3940 | MI0016597 |
| 313 | hsa-mir-1185-2 | MI0003821 |
| 314 | hsa-mir-6746 | MI0022591 |
| 315 | hsa-mir-5001 | MI0017867 |
| 316 | hsa-mir-1228 | MI0006318 |
| 317 | hsa-mir-5572 | MI0019117 |
| 318 | hsa-mir-4327 | MI0015867 |
| 319 | hsa-mir-4638 | MI0017265 |
| 320 | hsa-mir-6799 | MI0022644 |
| 321 | hsa-mir-6861 | MI0022708 |
| 322 | hsa-mir-6727 | MI0022572 |
| 323 | hsa-mir-4513 | MI0016879 |
| 324 | hsa-mir-6805 | MI0022650 |
| 325 | hsa-mir-6808 | MI0022653 |
| 326 | hsa-mir-4449 | MI0016792 |
| 327 | hsa-mir-1199 | MI0020340 |
| 328 | hsa-mir-1275 | MI0006415 |
| 329 | hsa-mir-4792 | MI0017439 |
| 330 | hsa-mir-4443 | MI0016786 |
| 331 | hsa-mir-6891 | MI0022738 |
| 332 | hsa-mir-6826 | MI0022671 |
| 333 | hsa-mir-6807 | MI0022652 |
| 334 | hsa-mir-7150 | MI0023610 |
| 335 | hsa-mir-4534 | MI0016901 |
| 336 | hsa-mir-4476 | MI0016828 |
| 337 | hsa-mir-4649 | MI0017276 |
| 338 | hsa-mir-4525 | MI0016892 |
| 311 | hsa-mir-1915 | MI0008336 |
| 339 | hsa-mir-4516 | MI0016882 |
| 340 | hsa-mir-4417 | MI0016753 |
| 341 | hsa-mir-642b | MI0016685 |
| 342 | hsa-mir-3141 | MI0014165 |
| 343 | hsa-mir-5100 | MI0019116 |
| 344 | hsa-mir-6848 | MI0022694 |
| 345 | hsa-mir-4739 | MI0017377 |
| 346 | hsa-mir-4459 | MI0016805 |
| 347 | hsa-mir-1237 | MI0006327 |
| 273 | hsa-mir-296 | MI0000747 |
| 269 | hsa-mir-4665 | MI0017295 |
| 348 | hsa-mir-6786 | MI0022631 |
| 349 | hsa-mir-4258 | MI0015857 |
| 350 | hsa-mir-6510 | MI0022222 |
| 225 | hsa-mir-1343 | MI0017320 |
| 351 | hsa-mir-1247 | MI0006382 |
| 324 | hsa-mir-6805 | MI0022650 |
| 352 | hsa-mir-4492 | MI0016854 |
| 353 | hsa-mir-1469 | MI0007074 |
| 354 | hsa-mir-1268b | MI0016748 |
| 355 | hsa-mir-6858 | MI0022704 |
| 356 | hsa-mir-3937 | MI0016593 |
| 357 | hsa-mir-939 | MI0005761 |
| 358 | hsa-mir-3656 | MI0016056 |
| 359 | hsa-mir-744 | MI0005559 |
| 360 | hsa-mir-4687 | MI0017319 |
| 361 | hsa-mir-4763 | MI0017404 |
| 362 | hsa-mir-3620 | MI0016011 |
| 363 | hsa-mir-3195 | MI0014240 |
| 364 | hsa-mir-6842 | MI0022688 |
| 365 | hsa-mir-4707 | MI0017340 |
| 366 | hsa-mir-642a | MI0003657 |
| 367 | hsa-mir-7113 | MI0022964 |
| 368 | hsa-mir-4728 | MI0017365 |
| 369 | hsa-mir-5195 | MI0018174 |
| 370 | hsa-mir-1185-1 | MI0003844 |
| 371 | hsa-mir-6774 | MI0022619 |
| 372 | hsa-mir-8059 | MI0025895 |
| 373 | hsa-mir-3131 | MI0014151 |
| 374 | hsa-mir-7847 | MI0025517 |
| 375 | hsa-mir-4463 | MI0016811 |
| 376 | hsa-mir-128-2 | MI0000727 |
| 377 | hsa-mir-4508 | MI0016872 |
| 378 | hsa-mir-6806 | MI0022651 |
| 379 | hsa-mir-7111 | MI0022962 |
| 380 | hsa-mir-6782 | MI0022627 |
| 381 | hsa-mir-4734 | MI0017371 |

TABLE 1-continued

| SEQ ID NO: | Gene name | miRBase registration No. |
|---|---|---|
| 382 | hsa-mir-3162 | MI0014192 |
| 383 | hsa-mir-887 | MI0005562 |
| 384 | hsa-mir-6752 | MI0022597 |
| 385 | hsa-mir-6724 | MI0022559 |
| 386 | hsa-mir-23b | MI0000439 |
| 387 | hsa-mir-23a | MI0000079 |
| 388 | hsa-mir-625 | MI0003639 |
| 316 | hsa-mir-1228 | MI0006318 |
| 389 | hsa-mir-614 | MI0003627 |
| 390 | hsa-mir-1913 | MI0008334 |
| 391 | hsa-mir-92a-2 | MI0000094 |
| 392 | hsa-mir-187 | MI0000274 |
| 393 | hsa-mir-16-1 | MI0000070 |
| 394 | hsa-mir-16-2 | MI0000115 |
| 395 | hsa-mir-92b | MI0003560 |
| 396 | hsa-mir-150 | MI0000479 |
| 397 | hsa-mir-564 | MI0003570 |
| 398 | hsa-mir-125a | MI0000469 |
| 395 | hsa-mir-92b | MI0003560 |
| 399 | hsa-mir-92a-1 | MI0000093 |
| 391 | hsa-mir-92a-2 | MI0000094 |
| 400 | hsa-mir-663a | MI0003672 |
| 401 | hsa-mir-4688 | MI0017321 |
| 402 | hsa-mir-4648 | MI0017275 |
| 403 | hsa-mir-6085 | MI0020362 |
| 404 | hsa-mir-6126 | MI0021260 |
| 405 | hsa-mir-6880 | MI0022727 |
| 406 | hsa-mir-328 | MI0000804 |
| 407 | hsa-mir-6768 | MI0022613 |
| 408 | hsa-mir-3180-4 | MI0016408 |
| 409 | hsa-mir-3180-5 | MI0016409 |
| 410 | hsa-mir-6087 | MI0020364 |
| 411 | hsa-mir-1273g | MI0018003 |
| 303 | hsa-mir-1225 | MI0006311 |
| 412 | hsa-mir-3196 | MI0014241 |
| 413 | hsa-mir-4695 | MI0017328 |
| 414 | hsa-mir-6732 | MI0022577 |
| 415 | hsa-mir-638 | MI0003653 |
| 416 | hsa-mir-6813 | MI0022658 |
| 417 | hsa-mir-665 | MI0005563 |
| 418 | hsa-mir-486 | MI0002470 |
| 419 | hsa-mir-486-2 | MI0023622 |
| 420 | hsa-mir-4466 | MI0016817 |
| 421 | hsa-mir-30c-1 | MI0000736 |
| 422 | hsa-mir-3621 | MI0016012 |
| 423 | hsa-mir-6743 | MI0022588 |
| 424 | hsa-mir-4298 | MI0015830 |
| 425 | hsa-mir-4741 | MI0017379 |
| 426 | hsa-mir-3619 | MI0016009 |
| 427 | hsa-mir-6824 | MI0022669 |
| 428 | hsa-mir-5698 | MI0019305 |
| 429 | hsa-mir-371a | MI0000779 |
| 430 | hsa-mir-4488 | MI0016849 |
| 431 | hsa-mir-1233-1 | MI0006323 |
| 432 | hsa-mir-1233-2 | MI0015973 |
| 433 | hsa-mir-4723 | MI0017359 |
| 434 | hsa-mir-24-1 | MI0000080 |
| 435 | hsa-mir-24-2 | MI0000081 |
| 436 | hsa-mir-1238 | MI0006328 |
| 437 | hsa-mir-4442 | MI0016785 |
| 438 | hsa-mir-3928 | MI0016438 |
| 439 | hsa-mir-6716 | MI0022550 |
| 440 | hsa-mir-6089-1 | MI0020366 |
| 441 | hsa-mir-6089-2 | MI0023563 |
| 442 | hsa-mir-6124 | MI0021258 |
| 443 | hsa-mir-6778 | MI0022623 |
| 444 | hsa-mir-557 | MI0003563 |
| 445 | hsa-mir-6090 | MI0020367 |
| 446 | isomiR example 1 of SEQ ID NO: 1 | — |
| 447 | isomiR example 2 of SEQ ID NO: 1 | — |
| 448 | isomiR example 1 of SEQ ID NO: 3 | — |
| 449 | isomiR example 2 of SEQ ID NO: 3 | — |
| 450 | isomiR example 1 of SEQ ID NO: 4 | — |
| 451 | isomiR example 2 of SEQ ID NO: 4 | — |
| 452 | isomiR example 1 of SEQ ID NO: 6 | — |
| 453 | isomiR example 2 of SEQ ID NO: 6 | — |
| 454 | isomiR example 1 of SEQ ID NO: 7 | — |
| 455 | isomiR example 2 of SEQ ID NO: 7 | — |
| 456 | isomiR example 1 of SEQ ID NO: 10 | — |
| 457 | isomiR example 2 of SEQ ID NO: 10 | — |
| 458 | isomiR example 1 of SEQ ID NO: 11 | — |
| 459 | isomiR example 2 of SEQ ID NO: 11 | — |
| 460 | isomiR example 1 of SEQ ID NO: 13 | — |
| 461 | isomiR example 2 of SEQ ID NO: 13 | — |
| 462 | isomiR example 1 of SEQ ID NO: 14 | — |
| 463 | isomiR example 2 of SEQ ID NO: 14 | — |
| 464 | isomiR example 1 of SEQ ID NO: 16 | — |
| 465 | isomiR example 2 of SEQ ID NO: 16 | — |
| 466 | isomiR example 1 of SEQ ID NO: 17 | — |
| 467 | isomiR example 2 of SEQ ID NO: 17 | — |
| 468 | isomiR example 1 of SEQ ID NO: 20 | — |
| 469 | isomiR example 2 of SEQ ID NO: 20 | — |
| 470 | isomiR example 1 of SEQ ID NO: 22 | — |
| 471 | isomiR example 2 of SEQ ID NO: 22 | — |
| 472 | isomiR example 1 of SEQ ID NO: 26 | — |
| 473 | isomiR example 2 of SEQ ID NO: 26 | — |
| 474 | isomiR example 1 of SEQ ID NO: 29 | — |
| 475 | isomiR example 2 of SEQ ID NO: 29 | — |
| 476 | isomiR example 1 of SEQ ID NO: 36 | — |
| 477 | isomiR example 2 of SEQ ID NO: 36 | — |
| 478 | isomiR example 1 of SEQ ID NO: 38 | — |
| 479 | isomiR example 2 of SEQ ID NO: 38 | — |
| 480 | isomiR example 1 of SEQ ID NO: 39 | — |
| 481 | isomiR example 2 of SEQ ID NO: 39 | — |
| 482 | isomiR example 1 of SEQ ID NO: 40 | — |
| 483 | isomiR example 2 of SEQ ID NO: 40 | — |
| 484 | isomiR example 1 of SEQ ID NO: 42 | — |
| 485 | isomiR example 2 of SEQ ID NO: 42 | — |
| 486 | isomiR example 1 of SEQ ID NO: 43 | — |
| 487 | isomiR example 2 of SEQ ID NO: 43 | — |
| 488 | isomiR example 1 of SEQ ID NO: 44 | — |
| 489 | isomiR example 2 of SEQ ID NO: 44 | — |
| 490 | isomiR example 1 of SEQ ID NO: 46 | — |
| 491 | isomiR example 2 of SEQ ID NO: 46 | — |
| 492 | isomiR example 1 of SEQ ID NO: 49 | — |
| 493 | isomiR example 2 of SEQ ID NO: 49 | — |
| 494 | isomiR example 1 of SEQ ID NO: 52 | — |
| 495 | isomiR example 2 of SEQ ID NO: 52 | — |
| 496 | isomiR example 1 of SEQ ID NO: 59 | — |
| 497 | isomiR example 2 of SEQ ID NO: 59 | — |
| 498 | isomiR example 1 of SEQ ID NO: 60 | — |
| 499 | isomiR example 2 of SEQ ID NO: 60 | — |
| 500 | isomiR example 1 of SEQ ID NO: 62 | — |
| 501 | isomiR example 2 of SEQ ID NO: 62 | — |
| 502 | isomiR example 1 of SEQ ID NO: 63 | — |
| 503 | isomiR example 2 of SEQ ID NO: 63 | — |
| 504 | isomiR example 1 of SEQ ID NO: 65 | — |
| 505 | isomiR example 2 of SEQ ID NO: 65 | — |
| 506 | isomiR example 1 of SEQ ID NO: 66 | — |
| 507 | isomiR example 2 of SEQ ID NO: 66 | — |
| 508 | isomiR example 1 of SEQ ID NO: 67 | — |
| 509 | isomiR example 2 of SEQ ID NO: 67 | — |
| 510 | isomiR example 1 of SEQ ID NO: 72 | — |
| 511 | isomiR example 2 of SEQ ID NO: 72 | — |
| 512 | isomiR example 1 of SEQ ID NO: 76 | — |
| 513 | isomiR example 2 of SEQ ID NO: 76 | — |
| 514 | isomiR example 1 of SEQ ID NO: 77 | — |
| 515 | isomiR example 2 of SEQ ID NO: 77 | — |
| 516 | isomiR example 1 of SEQ ID NO: 78 | — |
| 517 | isomiR example 2 of SEQ ID NO: 78 | — |
| 518 | isomiR example 1 of SEQ ID NO: 81 | — |
| 519 | isomiR example 2 of SEQ ID NO: 81 | — |
| 520 | isomiR example 1 of SEQ ID NO: 83 | — |
| 521 | isomiR example 2 of SEQ ID NO: 83 | — |
| 522 | isomiR example 1 of SEQ ID NO: 84 | — |
| 523 | isomiR example 2 of SEQ ID NO: 84 | — |
| 524 | isomiR example 1 of SEQ ID NO: 85 | — |
| 525 | isomiR example 2 of SEQ ID NO: 85 | — |
| 526 | isomiR example 1 of SEQ ID NO: 86 | — |
| 527 | isomiR example 2 of SEQ ID NO: 86 | — |
| 528 | isomiR example 1 of SEQ ID NO: 87 | — |
| 529 | isomiR example 2 of SEQ ID NO: 87 | — |
| 530 | isomiR example 1 of SEQ ID NO: 88 | — |
| 531 | isomiR example 2 of SEQ ID NO: 88 | — |

TABLE 1-continued

| SEQ ID NO: | Gene name | miRBase registration No. |
|---|---|---|
| 532 | isomiR example 1 of SEQ ID NO: 89 | — |
| 533 | isomiR example 2 of SEQ ID NO: 89 | — |
| 534 | isomiR example 1 of SEQ ID NO: 90 | — |
| 535 | isomiR example 2 of SEQ ID NO: 90 | — |
| 536 | isomiR example 1 of SEQ ID NO: 92 | — |
| 537 | isomiR example 2 of SEQ ID NO: 92 | — |
| 538 | isomiR example 1 of SEQ ID NO: 93 | — |
| 539 | isomiR example 2 of SEQ ID NO: 93 | — |
| 540 | isomiR example 1 of SEQ ID NO: 94 | — |
| 541 | isomiR example 2 of SEQ ID NO: 94 | — |
| 542 | isomiR example 1 of SEQ ID NO: 96 | — |
| 543 | isomiR example 2 of SEQ ID NO: 96 | — |
| 544 | isomiR example 1 of SEQ ID NO: 100 | — |
| 545 | isomiR example 2 of SEQ ID NO: 100 | — |
| 546 | isomiR example 1 of SEQ ID NO: 103 | — |
| 547 | isomiR example 2 of SEQ ID NO: 103 | — |
| 548 | isomiR example 1 of SEQ ID NO: 105 | — |
| 549 | isomiR example 2 of SEQ ID NO: 105 | — |
| 550 | isomiR example 1 of SEQ ID NO: 106 | — |
| 551 | isomiR example 2 of SEQ ID NO: 106 | — |
| 552 | isomiR example 1 of SEQ ID NO: 107 | — |
| 553 | isomiR example 2 of SEQ ID NO: 107 | — |
| 554 | isomiR example 1 of SEQ ID NO: 113 | — |
| 555 | isomiR example 2 of SEQ ID NO: 113 | — |
| 556 | isomiR example 1 of SEQ ID NO: 114 | — |
| 557 | isomiR example 2 of SEQ ID NO: 114 | — |
| 558 | isomiR example 1 of SEQ ID NO: 115 | — |
| 559 | isomiR example 2 of SEQ ID NO: 115 | — |
| 560 | isomiR example 1 of SEQ ID NO: 116 | — |
| 561 | isomiR example 2 of SEQ ID NO: 116 | — |
| 562 | isomiR example 1 of SEQ ID NO: 117 | — |
| 563 | isomiR example 2 of SEQ ID NO: 117 | — |
| 564 | isomiR example 1 of SEQ ID NO: 118 | — |
| 565 | isomiR example 2 of SEQ ID NO: 118 | — |
| 566 | isomiR example 1 of SEQ ID NO: 119 | — |
| 567 | isomiR example 2 of SEQ ID NO: 119 | — |
| 568 | isomiR example 1 of SEQ ID NO: 120 | — |
| 569 | isomiR example 2 of SEQ ID NO: 120 | — |
| 570 | isomiR example 1 of SEQ ID NO: 121 | — |
| 571 | isomiR example 2 of SEQ ID NO: 121 | — |
| 572 | isomiR example 1 of SEQ ID NO: 123 | — |
| 573 | isomiR example 2 of SEQ ID NO: 123 | — |
| 574 | isomiR example 1 of SEQ ID NO: 124 | — |
| 575 | isomiR example 2 of SEQ ID NO: 124 | — |
| 576 | isomiR example 1 of SEQ ID NO: 125 | — |
| 577 | isomiR example 2 of SEQ ID NO: 125 | — |
| 578 | isomiR example 1 of SEQ ID NO: 126 | — |
| 579 | isomiR example 2 of SEQ ID NO: 126 | — |
| 580 | isomiR example 1 of SEQ ID NO: 130 | — |
| 581 | isomiR example 2 of SEQ ID NO: 130 | — |
| 582 | isomiR example 1 of SEQ ID NO: 132 | — |
| 583 | isomiR example 2 of SEQ ID NO: 132 | — |
| 584 | isomiR example 1 of SEQ ID NO: 134 | — |
| 585 | isomiR example 2 of SEQ ID NO: 134 | — |
| 586 | isomiR example 1 of SEQ ID NO: 136 | — |
| 587 | isomiR example 2 of SEQ ID NO: 136 | — |
| 588 | isomiR example 1 of SEQ ID NO: 139 | — |
| 589 | isomiR example 2 of SEQ ID NO: 139 | — |
| 590 | isomiR example 1 of SEQ ID NO: 140 | — |
| 591 | isomiR example 2 of SEQ ID NO: 140 | — |
| 592 | isomiR example 1 of SEQ ID NO: 141 | — |
| 593 | isomiR example 2 of SEQ ID NO: 141 | — |
| 594 | isomiR example 1 of SEQ ID NO: 142 | — |
| 595 | isomiR example 2 of SEQ ID NO: 142 | — |
| 596 | isomiR example 1 of SEQ ID NO: 143 | — |
| 597 | isomiR example 2 of SEQ ID NO: 143 | — |
| 598 | isomiR example 1 of SEQ ID NO: 144 | — |
| 599 | isomiR example 2 of SEQ ID NO: 144 | — |
| 600 | isomiR example 1 of SEQ ID NO: 145 | — |
| 601 | isomiR example 2 of SEQ ID NO: 145 | — |
| 602 | isomiR example 1 of SEQ ID NO: 147 | — |
| 603 | isomiR example 2 of SEQ ID NO: 147 | — |
| 604 | isomiR example 1 of SEQ ID NO: 148 | — |
| 605 | isomiR example 2 of SEQ ID NO: 148 | — |
| 606 | isomiR example 1 of SEQ ID NO: 150 | — |
| 607 | isomiR example 2 of SEQ ID NO: 150 | — |
| 608 | isomiR example 1 of SEQ ID NO: 151 | — |
| 609 | isomiR example 2 of SEQ ID NO: 151 | — |
| 610 | isomiR example 1 of SEQ ID NO: 152 | — |
| 611 | isomiR example 2 of SEQ ID NO: 152 | — |
| 612 | isomiR example 1 of SEQ ID NO: 155 | — |
| 613 | isomiR example 2 of SEQ ID NO: 155 | — |
| 614 | isomiR example 1 of SEQ ID NO: 157 | — |
| 615 | isomiR example 2 of SEQ ID NO: 157 | — |
| 616 | isomiR example 1 of SEQ ID NO: 158 | — |
| 617 | isomiR example 2 of SEQ ID NO: 158 | — |
| 618 | isomiR example 1 of SEQ ID NO: 159 | — |
| 619 | isomiR example 2 of SEQ ID NO: 159 | — |
| 620 | isomiR example 1 of SEQ ID NO: 163 | — |
| 621 | isomiR example 2 of SEQ ID NO: 163 | — |
| 622 | isomiR example 1 of SEQ ID NO: 164 | — |
| 623 | isomiR example 2 of SEQ ID NO: 164 | — |
| 624 | isomiR example 1 of SEQ ID NO: 165 | — |
| 625 | isomiR example 2 of SEQ ID NO: 165 | — |
| 626 | isomiR example 1 of SEQ ID NO: 167 | — |
| 627 | isomiR example 2 of SEQ ID NO: 167 | — |
| 628 | isomiR example 1 of SEQ ID NO: 168 | — |
| 629 | isomiR example 2 of SEQ ID NO: 168 | — |
| 630 | isomiR example 1 of SEQ ID NO: 169 | — |
| 631 | isomiR example 2 of SEQ ID NO: 169 | — |
| 632 | isomiR example 1 of SEQ ID NO: 170 | — |
| 633 | isomiR example 2 of SEQ ID NO: 170 | — |
| 634 | isomiR example 1 of SEQ ID NO: 171 | — |
| 635 | isomiR example 2 of SEQ ID NO: 171 | — |
| 636 | isomiR example 1 of SEQ ID NO: 172 | — |
| 637 | isomiR example 2 of SEQ ID NO: 172 | — |
| 638 | isomiR example 1 of SEQ ID NO: 173 | — |
| 639 | isomiR example 2 of SEQ ID NO: 173 | — |
| 640 | isomiR example 1 of SEQ ID NO: 174 | — |
| 641 | isomiR example 2 of SEQ ID NO: 174 | — |
| 642 | isomiR example 1 of SEQ ID NO: 175 | — |
| 643 | isomiR example 2 of SEQ ID NO: 175 | — |
| 644 | isomiR example 1 of SEQ ID NO: 176 | — |
| 645 | isomiR example 2 of SEQ ID NO: 176 | — |
| 646 | isomiR example 1 of SEQ ID NO: 177 | — |
| 647 | isomiR example 2 of SEQ ID NO: 177 | — |
| 648 | isomiR example 1 of SEQ ID NO: 178 | — |
| 649 | isomiR example 2 of SEQ ID NO: 178 | — |
| 650 | isomiR example 1 of SEQ ID NO: 179 | — |
| 651 | isomiR example 2 of SEQ ID NO: 179 | — |
| 652 | isomiR example 1 of SEQ ID NO: 180 | — |
| 653 | isomiR example 2 of SEQ ID NO: 180 | — |
| 654 | isomiR example 1 of SEQ ID NO: 181 | — |
| 655 | isomiR example 2 of SEQ ID NO: 181 | — |
| 656 | isomiR example 1 of SEQ ID NO: 182 | — |
| 657 | isomiR example 2 of SEQ ID NO: 182 | — |
| 658 | isomiR example 1 of SEQ ID NO: 183 | — |
| 659 | isomiR example 2 of SEQ ID NO: 183 | — |
| 660 | isomiR example 1 of SEQ ID NO: 184 | — |
| 661 | isomiR example 2 of SEQ ID NO: 184 | — |
| 662 | isomiR example 1 of SEQ ID NO: 185 | — |
| 663 | isomiR example 2 of SEQ ID NO: 185 | — |
| 664 | isomiR example 1 of SEQ ID NO: 187 | — |
| 665 | isomiR example 2 of SEQ ID NO: 187 | — |
| 666 | isomiR example 1 of SEQ ID NO: 189 | — |
| 667 | isomiR example 2 of SEQ ID NO: 189 | — |
| 668 | isomiR example 1 of SEQ ID NO: 191 | — |
| 669 | isomiR example 2 of SEQ ID NO: 191 | — |
| 670 | isomiR example 1 of SEQ ID NO: 192 | — |
| 671 | isomiR example 2 of SEQ ID NO: 192 | — |
| 672 | isomiR example 1 of SEQ ID NO: 193 | — |
| 673 | isomiR example 2 of SEQ ID NO: 193 | — |
| 674 | isomiR example 1 of SEQ ID NO: 195 | — |
| 675 | isomiR example 2 of SEQ ID NO: 195 | — |
| 676 | isomiR example 1 of SEQ ID NO: 196 | — |
| 677 | isomiR example 2 of SEQ ID NO: 196 | — |
| 678 | isomiR example 1 of SEQ ID NO: 198 | — |
| 679 | isomiR example 2 of SEQ ID NO: 198 | — |
| 680 | isomiR example 1 of SEQ ID NO: 200 | — |
| 681 | isomiR example 2 of SEQ ID NO: 200 | — |
| 682 | isomiR example 1 of SEQ ID NO: 201 | — |
| 683 | isomiR example 2 of SEQ ID NO: 201 | — |
| 684 | isomiR example 1 of SEQ ID NO: 202 | — |
| 685 | isomiR example 2 of SEQ ID NO: 202 | — |

TABLE 1-continued

| SEQ ID NO: | Gene name | miRBase registration No. |
|---|---|---|
| 686 | isomiR example 1 of SEQ ID NO: 203 | — |
| 687 | isomiR example 2 of SEQ ID NO: 203 | — |
| 688 | isomiR example 1 of SEQ ID NO: 206 | — |
| 689 | isomiR example 2 of SEQ ID NO: 206 | — |
| 690 | isomiR example 1 of SEQ ID NO: 207 | — |
| 691 | isomiR example 2 of SEQ ID NO: 207 | — |
| 692 | isomiR example 1 of SEQ ID NO: 210 | — |
| 693 | isomiR example 2 of SEQ ID NO: 210 | — |
| 694 | isomiR example 1 of SEQ ID NO: 211 | — |
| 695 | isomiR example 2 of SEQ ID NO: 211 | — |
| 696 | isomiR example 1 of SEQ ID NO: 212 | — |
| 697 | isomiR example 2 of SEQ ID NO: 212 | — |
| 698 | isomiR example 1 of SEQ ID NO: 213 | — |
| 699 | isomiR example 2 of SEQ ID NO: 213 | — |
| 700 | isomiR example 1 of SEQ ID NO: 214 | — |
| 701 | isomiR example 2 of SEQ ID NO: 214 | — |
| 702 | isomiR example 1 of SEQ ID NO: 215 | — |
| 703 | isomiR example 2 of SEQ ID NO: 215 | — |
| 704 | isomiR example 1 of SEQ ID NO: 217 | — |
| 705 | isomiR example 2 of SEQ ID NO: 217 | — |
| 706 | isomiR example 1 of SEQ ID NO: 218 | — |
| 707 | isomiR example 2 of SEQ ID NO: 218 | — |
| 708 | isomiR example 1 of SEQ ID NO: 219 | — |
| 709 | isomiR example 2 of SEQ ID NO: 219 | — |
| 710 | isomiR example 1 of SEQ ID NO: 220 | — |
| 711 | isomiR example 2 of SEQ ID NO: 220 | — |
| 712 | isomiR example 1 of SEQ ID NO: 221 | — |
| 713 | isomiR example 2 of SEQ ID NO: 221 | — |
| 714 | hsa-miR-6757-5p | MIMAT0027414 |
| 715 | hsa-miR-4448 | MIMAT0018967 |
| 716 | hsa-miR-671-5p | MIMAT0003880 |
| 717 | hsa-miR-3178 | MIMAT0015055 |
| 718 | hsa-miR-4725-3p | MIMAT0019844 |
| 719 | hsa-miR-940 | MIMAT0004983 |
| 720 | hsa-miR-6789-5p | MIMAT0027478 |
| 721 | hsa-miR-4484 | MIMAT0019018 |
| 722 | hsa-miR-4634 | MIMAT0019691 |
| 723 | hsa-miR-4745-5p | MIMAT0019878 |
| 724 | hsa-miR-4730 | MIMAT0019852 |
| 725 | hsa-miR-6803-5p | MIMAT0027506 |
| 726 | hsa-miR-6798-5p | MIMAT0027496 |
| 727 | hsa-miR-3648 | MIMAT0018068 |
| 728 | hsa-miR-4783-3p | MIMAT0019947 |
| 729 | hsa-miR-6836-3p | MIMAT0027575 |
| 730 | hsa-mir-6757 | MI0022602 |
| 731 | hsa-mir-4448 | MI0016791 |
| 732 | hsa-mir-671 | MI0003760 |
| 733 | hsa-mir-3178 | MI0014212 |
| 734 | hsa-mir-4725 | MI0017362 |
| 735 | hsa-mir-940 | MI0005762 |
| 736 | hsa-mir-6789 | MI0022634 |
| 737 | hsa-mir-4484 | MI0016845 |
| 738 | hsa-mir-4634 | MI0017261 |
| 739 | hsa-mir-4745 | MI0017384 |
| 740 | hsa-mir-4730 | MI0017367 |
| 741 | hsa-mir-6803 | MI0022648 |
| 742 | hsa-mir-6798 | MI0022643 |
| 743 | hsa-mir-3648 | MI0016048 |
| 744 | hsa-mir-4783 | MI0017428 |
| 745 | hsa-mir-6836 | MI0022682 |
| 746 | isomiR example 1 of SEQ ID NO: 715 | — |
| 747 | isomiR example 2 of SEQ ID NO: 715 | — |
| 748 | isomiR example 1 of SEQ ID NO: 716 | — |
| 749 | isomiR example 2 of SEQ ID NO: 716 | — |
| 750 | isomiR example 1 of SEQ ID NO: 717 | — |
| 751 | isomiR example 2 of SEQ ID NO: 717 | — |
| 752 | isomiR example 1 of SEQ ID NO: 718 | — |
| 753 | isomiR example 2 of SEQ ID NO: 718 | — |
| 754 | isomiR example 1 of SEQ ID NO: 719 | — |
| 755 | isomiR example 2 of SEQ ID NO: 719 | — |
| 756 | isomiR example 1 of SEQ ID NO: 721 | — |
| 757 | isomiR example 2 of SEQ ID NO: 721 | — |
| 758 | isomiR example 1 of SEQ ID NO: 723 | — |
| 759 | isomiR example 2 of SEQ ID NO: 723 | — |
| 760 | isomiR example 1 of SEQ ID NO: 724 | — |
| 761 | isomiR example 2 of SEQ ID NO: 724 | — |
| 762 | isomiR example 1 of SEQ ID NO: 727 | — |
| 763 | isomiR example 2 of SEQ ID NO: 727 | — |
| 764 | isomiR example 1 of SEQ ID NO: 728 | — |
| 765 | isomiR example 2 of SEQ ID NO: 728 | — |

The present specification encompasses the contents described in the specifications and drawings of Japanese Patent Application Nos. 2014-124880 on which the priority of the present application is based.

Advantageous Effects of Invention

According to the present invention, liver cancer can be detected easily and highly accurately. For example, the presence or absence of liver cancer in a patient can be easily detected by using, as an indicator, the measurement values of several miRNAs in blood, serum, and/or plasma of the patient, which can be collected with limited invasiveness.

DESCRIPTION OF EMBODIMENTS

Figure 1:
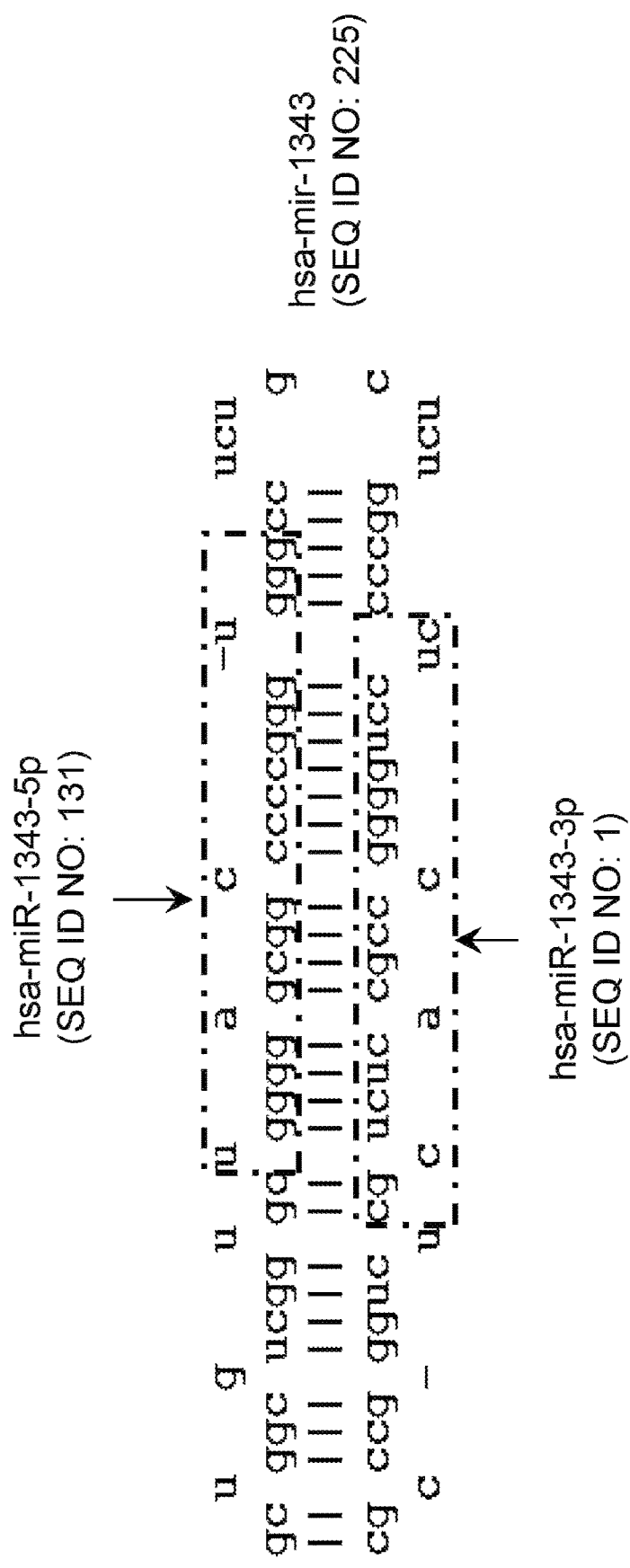
FIG. 1 This figure shows the relationship between the nucleotide sequences of hsa-miR-1343-5p represented by SEQ ID NO: 131 and hsa-miR-1343-3p represented by SEQ ID NO: 1, which are produced from a precursor hsa-mir-1343 represented by SEQ ID NO: 225.

Hereinafter, the present invention will be further described specifically.

1. Target Nucleic Acid for Liver Cancer

As a primary target nucleic acid as a liver cancer marker for detecting the presence and/or absence of liver cancer or liver cancer cells using the nucleic acid probe or the primer for the detection of liver cancer defined above according to the present invention, at least one or more miRNA(s) selected from the group consisting of hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-6757-5p, hsa-miR-4448, hsa-miR-671-5p, hsa-miR-3178, hsa-miR-4725-3p, hsa-miR-940, hsa-miR-6789-5p, hsa-miR-4484, hsa-miR-4634, hsa-miR-4745-5p, hsa-miR-4730, hsa-miR-6803-5p, hsa-miR-6798-5p, hsa-miR-3648, hsa-miR-4783-3p and hsa-miR-6836-3p can be used. Furthermore, at least one or more miRNA(s) selected from the group consisting of other liver cancer markers that can be combined with these miRNAs, i.e., hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p and hsa-miR-663a can also be preferably used as a target nucleic acid. Moreover, at least one or more miRNA(s) selected from the group consisting of other liver cancer markers that can be combined with these miRNAs, i.e., hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557 and hsa-miR-6090 can also be preferably used as a target nucleic acid.

These miRNAs include, for example, a human gene comprising a nucleotide sequence represented by any of SEQ ID NOs: 1 to 224 and 714 to 729 (i.e., hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR- 3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-6757-5p, hsa-miR-4448, hsa-miR-671-5p, hsa-miR-3178, hsa-miR-4725-3p, hsa-miR-940, hsa-miR-6789-5p, hsa-miR-4484, hsa-miR-4634, hsa-miR-4745-5p, hsa-miR-4730, hsa-miR-6803-5p, hsa-miR-6798-5p, hsa-miR-3648, hsa-miR-4783-3p, hsa-miR-6836-3p, hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p, hsa-miR-663a, hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557 and hsa-miR-6090, respectively), a congener thereof, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 765 or a transcript thereof, more preferably the transcript, i.e., a miRNA or its precursor RNA (pri-miRNA or pre-miRNA).

The first target gene is the hsa-miR-1343-3p gene, a congener thereof, a transcript thereof, or a variant or a derivative thereof. None of the previously known reports show that change in the expression of the gene or the transcript thereof can serve as a marker for liver cancer.

The second target gene is the hsa-miR-6726-5p gene, a congener thereof, a transcript thereof, or a variant or a derivative thereof. None of the previously known reports show that change in the expression of the gene or the transcript thereof can serve as a marker for liver cancer.

The third target gene is the hsa-miR-6515-3p gene, a congener thereof, a transcript thereof, or a variant or a derivative thereof. None of the previously known reports show that change in the expression of the gene or the transcript thereof can serve as a marker for liver cancer.

The fourth target gene is the hsa-miR-4651 gene, a congener thereof, a transcript thereof, or a variant or a derivative thereof. None of the previously known reports show that change in the expression of the gene or the transcript thereof can serve as a marker for liver cancer.

The fifth target gene is the hsa-miR-4257 gene, a congener thereof, a transcript thereof, or a variant or a derivative thereof. None of the previously known reports show that change in the expression of the gene or the transcript thereof can serve as a marker for liver cancer.

The sixth target gene is the hsa-miR-3188 gene, a congener thereof, a transcript thereof, or a variant or a derivative thereof. None of the previously known reports show that change in the expression of the gene or the transcript thereof can serve as a marker for liver cancer.

The seventh target gene is the hsa-miR-6131 gene, a congener thereof, a transcript thereof, or a variant or a derivative thereof. None of the previously known reports show that change in the expression of the gene or the transcript thereof can serve as a marker for liver cancer.

The eighth target gene is the hsa-miR-6766-3p gene, a congener thereof, a transcript thereof, or a variant or a derivative thereof. None of the previously known reports show that change in the expression of the gene or the transcript thereof can serve as a marker for liver cancer.

The ninth target gene is the hsa-miR-7641 gene, a congener thereof, a transcript thereof, or a variant or a derivative thereof. None of the previously known reports show that change in the expression of the gene or the transcript thereof can serve as a marker for liver cancer.

The 10th target gene is the hsa-miR-1249 gene, a congener thereof, a transcript thereof, or a variant or a derivative thereof. None of the previously known reports show that change in the expression of the gene or the transcript thereof can serve as a marker for liver cancer.

The 11th target gene is the hsa-miR-3679-3p gene, a congener thereof, a transcript thereof, or a variant or a derivative thereof. None of the previously known reports show that change in the expression of the gene or the transcript thereof can serve as a marker for liver cancer.

The 12th target gene is the hsa-miR-6787-5p gene, a congener thereof, a transcript thereof, or a variant or a derivative thereof. None of the previously known reports show that change in the expression of the gene or the transcript thereof can serve as a marker for liver cancer.

The 13th target gene is the hsa-miR-4454 gene, a congener thereof, a transcript thereof, or a variant or a derivative thereof. None of the previously known reports show that change in the expression of the gene or the transcript thereof can serve as a marker for liver cancer.

The 14th target gene is the hsa-miR-3135b gene, a congener thereof, a transcript thereof, or a variant or a derivative thereof. None of the previously known reports show that change in the expression of the gene or the transcript thereof can serve as a marker for liver cancer.

The 15th target gene is the hsa-miR-6765-3p gene, a congener thereof, a transcript thereof, or a variant or a derivative thereof. None of the previously known reports show that change in the expression of the gene or the transcript thereof can serve as a marker for liver cancer.

The 16th target gene is the hsa-miR-7975 gene, a congener thereof, a transcript thereof, or a variant or a derivative thereof. None of the previously known reports show that change in the expression of the gene or the transcript thereof can serve as a marker for liver cancer.

The 17th target gene is the hsa-miR-204-3p gene, a congener thereof, a transcript thereof, or a variant or a derivative thereof. None of the previously known reports show that change in the expression of the gene or the transcript thereof can serve as a marker for liver cancer.

The 18th target gene is the hsa-miR-7977 gene, a congener thereof, a transcript thereof, or a variant or a derivative thereof. None of the previously known reports show that change in the expression of the gene or the transcript thereof can serve as a marker for liver cancer.

The 19th target gene is the hsa-miR-7110-5p gene, a congener thereof, a transcript thereof, or a variant or a derivative thereof. None of the previously known reports show that change in the expression of the gene or the transcript thereof can serve as a marker for liver cancer.

The 20th target gene is the hsa-miR-6717-5p gene, a congener thereof, a transcript thereof, or a variant or a derivative thereof. None of the previously known reports show that change in the expression of the gene or the transcript thereof can serve as a marker for liver cancer.

The 21st target gene is the hsa-miR-6870-5p gene, a congener thereof, a transcript thereof, or a variant or a derivative thereof. None of the previously known reports show that change in the expression of the gene or the transcript thereof can serve as a marker for liver cancer.

The 22nd target gene is the hsa-miR-663b gene, a congener thereof, a transcript thereof, or a variant or a derivative thereof. None of the previously known reports show that change in the expression of the gene or the transcript thereof can serve as a marker for liver cancer.

The 23rd target gene is the hsa-miR-6875-5p gene, a congener thereof, a transcript thereof, or a variant or a derivative thereof. None of the previously known reports show that change in the expression of the gene or the transcript thereof can serve as a marker for liver cancer.

The 24th target gene is the hsa-miR-8072 gene, a congener thereof, a transcript thereof, or a variant or a derivative thereof. None of the previously known reports show that change in the expression of the gene or the transcript thereof can serve as a marker for liver cancer.

The 25th target gene is the hsa-miR-6816-5p gene, a congener thereof, a transcript thereof, or a variant or a derivative thereof. None of the previously known reports show that change in the expression of the gene or the transcript thereof can serve as a marker for liver cancer.

The 26th target gene is the hsa-miR-4281 gene, a congener thereof, a transcript thereof, or a variant or a derivative thereof. None of the previously known reports show that change in the expression of the gene or the transcript thereof can serve as a marker for liver cancer.

The 27th target gene is the hsa-miR-6729-5p gene, a congener thereof, a transcript thereof, or a variant or a derivative thereof. None of the previously known reports show that change in the expression of the gene or the transcript thereof can serve as a marker for liver cancer.

The 28th target gene is the hsa-miR-8069 gene, a congener thereof, a transcript thereof, or a variant or a derivative thereof. None of the previously known reports show that change in the expression of the gene or the transcript thereof can serve as a marker for liver cancer.

The 29th target gene is the hsa-miR-4706 gene, a congener thereof, a transcript thereof, or a variant or a derivative thereof. None of the previously known reports show that change in the expression of the gene or the transcript thereof can serve as a marker for liver cancer.

The 30th target gene is the hsa-miR-7108-5p gene, a congener thereof, a transcript thereof, or a variant or a derivative thereof. None of the previously known reports show that change in the expression of the gene or the transcript thereof can serve as a marker for liver cancer.

The 31st target gene is the hsa-miR-4433b-3p gene, a congener thereof, a transcript thereof, or a variant or a derivative thereof. None of the previously known reports show that change in the expression of the gene or the transcript thereof can serve as a marker for liver cancer.

The 32nd target gene is the hsa-miR-6893-5p gene, a congener thereof, a transcript thereof, or a variant or a derivative thereof. None of the previously known reports show that change in the expression of the gene or the transcript thereof can serve as a marker for liver cancer.

The 33rd target gene is the hsa-miR-6857-5p gene, a congener thereof, a transcript thereof, or a variant or a derivative thereof. None of the previously known reports show that change in the expression of the gene or the transcript thereof can serve as a marker for liver cancer.

The 34th target gene is the hsa-miR-1227-5p gene, a congener thereof, a transcript thereof, or a variant or a derivative thereof. None of the previously known reports show that change in the expression of the gene or the transcript thereof can serve as a marker for liver cancer.

The 35th target gene is the hsa-miR-6741-5p gene, a congener thereof, a transcript thereof, or a variant or a derivative thereof. None of the previously known reports show that change in the expression of the gene or the transcript thereof can serve as a marker for liver cancer.

The 36th target gene is the hsa-miR-451a gene, a congener thereof, a transcript thereof, or a variant or a derivative thereof. None of the previously known reports show that change in the expression of the gene or the transcript thereof can serve as a marker for liver cancer.

The 37th target gene is the hsa-miR-8063 gene, a congener thereof, a transcript thereof, or a variant or a derivative thereof. None of the previously known reports show that change in the expression of the gene or the transcript thereof can serve as a marker for liver cancer.

The 38th target gene is the hsa-miR-3622a-5p gene, a congener thereof, a transcript thereof, or a variant or a derivative thereof. None of the previously known reports show that change in the expression of the gene or the transcript thereof can serve as a marker for liver cancer.

The 39th target gene is the hsa-miR-615-5p gene, a congener thereof, a transcript thereof, or a variant or a derivative thereof. None of the previously known reports show that change in the expression of the gene or the transcript thereof can serve as a marker for liver cancer.

The 40th target gene is the hsa-miR-128-1-5p gene, a congener thereof, a transcript thereof, or a variant or a derivative thereof. None of the previously known reports show that change in the expression of the gene or the transcript thereof can serve as a marker for liver cancer.

The 41st target gene is the hsa-miR-6825-5p gene, a congener thereof, a transcript thereof, or a variant or a derivative thereof. None of the previously known reports show that change in the expression of the gene or the transcript thereof can serve as a marker for liver cancer.

The 42nd target gene is the hsa-miR-1260b gene, a congener thereof, a transcript thereof, or a variant or a derivative thereof. None of the previously known reports show that change in the expression of the gene or the transcript thereof can serve as a marker for liver cancer.

The 43rd target gene is the hsa-miR-4433-3p gene, a congener thereof, a transcript thereof, or a variant or a derivative thereof. None of the previously known reports show that change in the expression of the gene or the transcript thereof can serve as a marker for liver cancer.

The 44th target gene is the hsa-miR-4665-5p gene, a congener thereof, a transcript thereof, or a variant or a derivative thereof. None of the previously known reports show that change in the expression of the gene or the transcript thereof can serve as a marker for liver cancer.

The 45th target gene is the hsa-miR-7845-5p gene, a congener thereof, a transcript thereof, or a variant or a derivative thereof. None of the previously known reports show that change in the expression of the gene or the transcript thereof can serve as a marker for liver cancer.

The 46th target gene is the hsa-miR-1908-5p gene, a congener thereof, a transcript thereof, or a variant or a derivative thereof. None of the previously known reports show that change in the expression of the gene or the transcript thereof can serve as a marker for liver cancer.

The 47th target gene is the hsa-miR-6840-3p gene, a congener thereof, a transcript thereof, or a variant or a derivative thereof. None of the previously known reports show that change in the expression of the gene or the transcript thereof can serve as a marker for liver cancer.

The 48th target gene is the hsa-miR-6765-5p gene, a congener thereof, a transcript thereof, or a variant or a derivative thereof. None of the previously known reports show that change in the expression of the gene or the transcript thereof can serve as a marker for liver cancer.

The 49th target gene is the hsa-miR-296-5p gene, a congener thereof, a transcript thereof, or a variant or a derivative thereof. None of the previously known reports show that change in the expression of the gene or the transcript thereof can serve as a marker for liver cancer.

The 50th target gene is the hsa-miR-3675-3p gene, a congener thereof, a transcript thereof, or a variant or a derivative thereof. None of the previously known reports show that change in the expression of the gene or the transcript thereof can serve as a marker for liver cancer.

The 51st target gene is the hsa-miR-6781-5p gene, a congener thereof, a transcript thereof, or a variant or a derivative thereof. None of the previously known reports show that change in the expression of the gene or the transcript thereof can serve as a marker for liver cancer.

The 52nd target gene is the hsa-miR-423-5p gene, a congener thereof, a transcript thereof, or a variant or a derivative thereof. None of the previously known reports show that change in the expression of the gene or the transcript thereof can serve as a marker for liver cancer.

The 53rd target gene is the hsa-miR-3663-3p gene, a congener thereof, a transcript thereof, or a variant or a derivative thereof. None of the previously known reports show that change in the expression of the gene or the transcript thereof can serve as a marker for liver cancer.

The 54th target gene is the hsa-miR-6784-5p gene, a congener thereof, a transcript thereof, or a variant or a derivative thereof. None of the previously known reports show that change in the expression of the gene or the transcript thereof can serve as a marker for liver cancer.

The 55th target gene is the hsa-miR-6749-5p gene, a congener thereof, a transcript thereof, or a variant or a derivative thereof. None of the previously known reports show that change in the expression of the gene or the transcript thereof can serve as a marker for liver cancer.

The 56th target gene is the hsa-miR-1231 gene, a congener thereof, a transcript thereof, or a variant or a derivative thereof. None of the previously known reports show that change in the expression of the gene or the transcript thereof can serve as a marker for liver cancer.

The 57th target gene is the hsa-miR-4746-3p gene, a congener thereof, a transcript thereof, or a variant or a derivative thereof. None of the previously known reports show that change in the expression of the gene or the transcript thereof can serve as a marker for liver cancer.

The 58th target gene is the hsa-miR-6780b-5p gene, a congener thereof, a transcript thereof, or a variant or a derivative thereof. None of the previously known reports show that change in the expression of the gene or the transcript thereof can serve as a marker for liver cancer.

The 59th target gene is the hsa-miR-4758-5p gene, a congener thereof, a transcript thereof, or a variant or a derivative thereof. None of the previously known reports show that change in the expression of the gene or the transcript thereof can serve as a marker for liver cancer.

The 60th target gene is the hsa-miR-3679-5p gene, a congener thereof, a transcript thereof, or a variant or a derivative thereof. None of the previously known reports show that change in the expression of the gene or the transcript thereof can serve as a marker for liver cancer.

The 61st target gene is the hsa-miR-3184-5p gene, a congener thereof, a transcript thereof, or a variant or a derivative thereof. None of the previously known reports show that change in the expression of the gene or the transcript thereof can serve as a marker for liver cancer.

The 62nd target gene is the hsa-miR-6125 gene, a congener thereof, a transcript thereof, or a variant or a derivative thereof. None of the previously known reports show that change in the expression of the gene or the transcript thereof can serve as a marker for liver cancer.

The 63rd target gene is the hsa-miR-6721-5p gene, a congener thereof, a transcript thereof, or a variant or a derivative thereof. None of the previously known reports show that change in the expression of the gene or the transcript thereof can serve as a marker for liver cancer.

The 64th target gene is the hsa-miR-6791-5p gene, a congener thereof, a transcript thereof, or a variant or a derivative thereof. None of the previously known reports show that change in the expression of the gene or the transcript thereof can serve as a marker for liver cancer.

The 65th target gene is the hsa-miR-3185 gene, a congener thereof, a transcript thereof, or a variant or a derivative thereof. None of the previously known reports show that change in the expression of the gene or the transcript thereof can serve as a marker for liver cancer.

The 66th target gene is the hsa-miR-1260a gene, a congener thereof, a transcript thereof, or a variant or a derivative thereof. None of the previously known reports show that change in the expression of the gene or the transcript thereof can serve as a marker for liver cancer.

The 67th target gene is the hsa-miR-3197 gene, a congener thereof, a transcript thereof, or a variant or a derivative thereof. None of the previously known reports show that change in the expression of the gene or the transcript thereof can serve as a marker for liver cancer.

The 68th target gene is the hsa-miR-6845-5p gene, a congener thereof, a transcript thereof, or a variant or a derivative thereof. None of the previously known reports show that change in the expression of the gene or the transcript thereof can serve as a marker for liver cancer.

The 69th target gene is the hsa-miR-6887-5p gene, a congener thereof, a transcript thereof, or a variant or a derivative thereof. None of the previously known reports show that change in the expression of the gene or the transcript thereof can serve as a marker for liver cancer.

The 70th target gene is the hsa-miR-6738-5p gene, a congener thereof, a transcript thereof, or a variant or a derivative thereof. None of the previously known reports show that change in the expression of the gene or the transcript thereof can serve as a marker for liver cancer.

The 71st target gene is the hsa-miR-6872-3p gene, a congener thereof, a transcript thereof, or a variant or a derivative thereof. None of the previously known reports show that change in the expression of the gene or the transcript thereof can serve as a marker for liver cancer.

The 72nd target gene is the hsa-miR-4497 gene, a congener thereof, a transcript thereof, or a variant or a derivative thereof. None of the previously known reports show that change in the expression of the gene or the transcript thereof can serve as a marker for liver cancer.

The 73rd target gene is the hsa-miR-1229-5p gene, a congener thereof, a transcript thereof, or a variant or a derivative thereof. None of the previously known reports show that change in the expression of the gene or the transcript thereof can serve as a marker for liver cancer.

The 74th target gene is the hsa-miR-6820-5p gene, a congener thereof, a transcript thereof, or a variant or a derivative thereof. None of the previously known reports show that change in the expression of the gene or the transcript thereof can serve as a marker for liver cancer.

The 75th target gene is the hsa-miR-6777-5p gene, a congener thereof, a transcript thereof, or a variant or a derivative thereof. None of the previously known reports show that change in the expression of the gene or the transcript thereof can serve as a marker for liver cancer.

The 76th target gene is the hsa-miR-3917 gene, a congener thereof, a transcript thereof, or a variant or a derivative thereof. None of the previously known reports show that change in the expression of the gene or the transcript thereof can serve as a marker for liver cancer.

The 77th target gene is the hsa-miR-5787 gene, a congener thereof, a transcript thereof, or a variant or a derivative thereof. None of the previously known reports show that change in the expression of the gene or the transcript thereof can serve as a marker for liver cancer.

The 78th target gene is the hsa-miR-4286 gene, a congener thereof, a transcript thereof, or a variant or a derivative thereof. None of the previously known reports show that change in the expression of the gene or the transcript thereof can serve as a marker for liver cancer.

The 79th target gene is the hsa-miR-6877-5p gene, a congener thereof, a transcript thereof, or a variant or a derivative thereof. None of the previously known reports show that change in the expression of the gene or the transcript thereof can serve as a marker for liver cancer.

The 80th target gene is the hsa-miR-1225-3p gene, a congener thereof, a transcript thereof, or a variant or a derivative thereof. None of the previously known reports show that change in the expression of the gene or the transcript thereof can serve as a marker for liver cancer.

The 81st target gene is the hsa-miR-6088 gene, a congener thereof, a transcript thereof, or a variant or a derivative thereof. None of the previously known reports show that change in the expression of the gene or the transcript thereof can serve as a marker for liver cancer.

The 82nd target gene is the hsa-miR-6800-5p gene, a congener thereof, a transcript thereof, or a variant or a derivative thereof. None of the previously known reports show that change in the expression of the gene or the transcript thereof can serve as a marker for liver cancer.

The 83rd target gene is the hsa-miR-1246 gene, a congener thereof, a transcript thereof, or a variant or a derivative thereof. None of the previously known reports show that change in the expression of the gene or the transcript thereof can serve as a marker for liver cancer.

The 84th target gene is the hsa-miR-4467 gene, a congener thereof, a transcript thereof, or a variant or a derivative thereof. None of the previously known reports show that change in the expression of the gene or the transcript thereof can serve as a marker for liver cancer.

The 85th target gene is the hsa-miR-4419b gene, a congener thereof, a transcript thereof, or a variant or a derivative thereof. None of the previously known reports show that change in the expression of the gene or the transcript thereof can serve as a marker for liver cancer.

The 86th target gene is the hsa-miR-1914-3p gene, a congener thereof, a transcript thereof, or a variant or a derivative thereof. None of the previously known reports show that change in the expression of the gene or the transcript thereof can serve as a marker for liver cancer.

The 87th target gene is the hsa-miR-4632-5p gene, a congener thereof, a transcript thereof, or a variant or a derivative thereof. None of the previously known reports show that change in the expression of the gene or the transcript thereof can serve as a marker for liver cancer.

The 88th target gene is the hsa-miR-1915-5p gene, a congener thereof, a transcript thereof, or a variant or a derivative thereof. None of the previously known reports show that change in the expression of the gene or the transcript thereof can serve as a marker for liver cancer.

The 89th target gene is the hsa-miR-3940-5p gene, a congener thereof, a transcript thereof, or a variant or a derivative thereof. None of the previously known reports show that change in the expression of the gene or the transcript thereof can serve as a marker for liver cancer.

The 90th target gene is the hsa-miR-1185-2-3p gene, a congener thereof, a transcript thereof, or a variant or a derivative thereof. None of the previously known reports show that change in the expression of the gene or the transcript thereof can serve as a marker for liver cancer.

The 91st target gene is the hsa-miR-6746-5p gene, a congener thereof, a transcript thereof, or a variant or a derivative thereof. None of the previously known reports show that change in the expression of the gene or the transcript thereof can serve as a marker for liver cancer.

The 92nd target gene is the hsa-miR-5001-5p gene, a congener thereof, a transcript thereof, or a variant or a derivative thereof. None of the previously known reports show that change in the expression of the gene or the transcript thereof can serve as a marker for liver cancer.

The 93rd target gene is the hsa-miR-1228-5p gene, a congener thereof, a transcript thereof, or a variant or a derivative thereof. None of the previously known reports show that change in the expression of the gene or the transcript thereof can serve as a marker for liver cancer.

The 94th target gene is the hsa-miR-5572 gene, a congener thereof, a transcript thereof, or a variant or a derivative The 95th target gene is the hsa-miR-4327 gene, a congener thereof, a transcript thereof, or a variant or a derivative thereof. None of the previously known reports show that change in the expression of the gene or the transcript thereof can serve as a marker for liver cancer.

The 96th target gene is the hsa-miR-4638-5p gene, a congener thereof, a transcript thereof, or a variant or a derivative thereof. None of the previously known reports show that change in the expression of the gene or the transcript thereof can serve as a marker for liver cancer.

The 97th target gene is the hsa-miR-6799-5p gene, a congener thereof, a transcript thereof, or a variant or a derivative thereof. None of the previously known reports show that change in the expression of the gene or the transcript thereof can serve as a marker for liver cancer.

The 98th target gene is the hsa-miR-6861-5p gene, a congener thereof, a transcript thereof, or a variant or a derivative thereof. None of the previously known reports show that change in the expression of the gene or the transcript thereof can serve as a marker for liver cancer.

The 99th target gene is the hsa-miR-6727-5p gene, a congener thereof, a transcript thereof, or a variant or a derivative thereof. None of the previously known reports show that change in the expression of the gene or the transcript thereof can serve as a marker for liver cancer.

The 100th target gene is the hsa-miR-4513 gene, a congener thereof, a transcript thereof, or a variant or a derivative thereof. None of the previously known reports show that change in the expression of the gene or the transcript thereof can serve as a marker for liver cancer.

The 101st target gene is the hsa-miR-6805-3p gene, a congener thereof, a transcript thereof, or a variant or a derivative thereof. None of the previously known reports show that change in the expression of the gene or the transcript thereof can serve as a marker for liver cancer.

The 102nd target gene is the hsa-miR-6808-5p gene, a congener thereof, a transcript thereof, or a variant or a derivative thereof. None of the previously known reports show that change in the expression of the gene or the transcript thereof can serve as a marker for liver cancer.

The 103rd target gene is the hsa-miR-4449 gene, a congener thereof, a transcript thereof, or a variant or a derivative thereof. None of the previously known reports show that change in the expression of the gene or the transcript thereof can serve as a marker for liver cancer.

The 104th target gene is the hsa-miR-1199-5p gene, a congener thereof, a transcript thereof, or a variant or a derivative thereof. None of the previously known reports show that change in the expression of the gene or the transcript thereof can serve as a marker for liver cancer.

The 105th target gene is the hsa-miR-1275 gene, a congener thereof, a transcript thereof, or a variant or a derivative thereof. None of the previously known reports show that change in the expression of the gene or the transcript thereof can serve as a marker for liver cancer.

The 106th target gene is the hsa-miR-4792 gene, a congener thereof, a transcript thereof, or a variant or a derivative thereof. None of the previously known reports show that change in the expression of the gene or the transcript thereof can serve as a marker for liver cancer.

The 107th target gene is the hsa-miR-4443 gene, a congener thereof, a transcript thereof, or a variant or a derivative thereof. None of the previously known reports show that change in the expression of the gene or the transcript thereof can serve as a marker for liver cancer.

The 108th target gene is the hsa-miR-6891-5p gene, a congener thereof, a transcript thereof, or a variant or a derivative thereof. None of the previously known reports show that change in the expression of the gene or the transcript thereof can serve as a marker for liver cancer.

The 109th target gene is the hsa-miR-6826-5p gene, a congener thereof, a transcript thereof, or a variant or a derivative thereof. None of the previously known reports show that change in the expression of the gene or the transcript thereof can serve as a marker for liver cancer.

The 110th target gene is the hsa-miR-6807-5p gene, a congener thereof, a transcript thereof, or a variant or a derivative thereof. None of the previously known reports show that change in the expression of the gene or the transcript thereof can serve as a marker for liver cancer.

The 111th target gene is the hsa-miR-7150 gene, a congener thereof, a transcript thereof, or a variant or a derivative thereof. None of the previously known reports show that change in the expression of the gene or the transcript thereof can serve as a marker for liver cancer.

The 112th target gene is the hsa-miR-4534 gene, a congener thereof, a transcript thereof, or a variant or a derivative thereof. None of the previously known reports show that change in the expression of the gene or the transcript thereof can serve as a marker for liver cancer.

The 113th target gene is the hsa-miR-4476 gene, a congener thereof, a transcript thereof, or a variant or a derivative thereof. None of the previously known reports show that change in the expression of the gene or the transcript thereof can serve as a marker for liver cancer.

The 114th target gene is the hsa-miR-4649-5p gene, a congener thereof, a transcript thereof, or a variant or a derivative thereof. None of the previously known reports show that change in the expression of the gene or the transcript thereof can serve as a marker for liver cancer.

The 115th target gene is the hsa-miR-4525 gene, a congener thereof, a transcript thereof, or a variant or a derivative thereof. None of the previously known reports show that change in the expression of the gene or the transcript thereof can serve as a marker for liver cancer.

The 116th target gene is the hsa-miR-1915-3p gene, a congener thereof, a transcript thereof, or a variant or a derivative thereof. None of the previously known reports show that change in the expression of the gene or the transcript thereof can serve as a marker for liver cancer.

The 117th target gene is the hsa-miR-4516 gene, a congener thereof, a transcript thereof, or a variant or a derivative thereof. None of the previously known reports show that change in the expression of the gene or the transcript thereof can serve as a marker for liver cancer.

The 118th target gene is the hsa-miR-4417 gene, a congener thereof, a transcript thereof, or a variant or a derivative thereof. None of the previously known reports show that change in the expression of the gene or the transcript thereof can serve as a marker for liver cancer.

The 119th target gene is the hsa-miR-642b-3p gene, a congener thereof, a transcript thereof, or a variant or a derivative thereof. None of the previously known reports show that change in the expression of the gene or the transcript thereof can serve as a marker for liver cancer.

The 120th target gene is the hsa-miR-3141 gene, a congener thereof, a transcript thereof, or a variant or a derivative thereof. None of the previously known reports show that change in the expression of the gene or the transcript thereof can serve as a marker for liver cancer.

The 121st target gene is the hsa-miR-5100 gene, a congener thereof, a transcript thereof, or a variant or a derivative thereof. None of the previously known reports show that change in the expression of the gene or the transcript thereof can serve as a marker for liver cancer.

The 122nd target gene is the hsa-miR-6848-5p gene, a congener thereof, a transcript thereof, or a variant or a derivative thereof. None of the previously known reports show that change in the expression of the gene or the transcript thereof can serve as a marker for liver cancer.

The 123rd target gene is the hsa-miR-4739 gene, a congener thereof, a transcript thereof, or a variant or a derivative thereof. None of the previously known reports show that change in the expression of the gene or the transcript thereof can serve as a marker for liver cancer.

The 124th target gene is the hsa-miR-4459 gene, a congener thereof, a transcript thereof, or a variant or a derivative thereof. None of the previously known reports show that change in the expression of the gene or the transcript thereof can serve as a marker for liver cancer.

The 125th target gene is the hsa-miR-1237-5p gene, a congener thereof, a transcript thereof, or a variant or a derivative thereof. None of the previously known reports show that change in the expression of the gene or the transcript thereof can serve as a marker for liver cancer.

The 126th target gene is the hsa-miR-296-3p gene, a congener thereof, a transcript thereof, or a variant or a derivative thereof. None of the previously known reports show that change in the expression of the gene or the transcript thereof can serve as a marker for liver cancer.

The 127th target gene is the hsa-miR-4665-3p gene, a congener thereof, a transcript thereof, or a variant or a derivative thereof. None of the previously known reports show that change in the expression of the gene or the transcript thereof can serve as a marker for liver cancer.

The 128th target gene is the hsa-miR-6786-5p gene, a congener thereof, a transcript thereof, or a variant or a derivative thereof. None of the previously known reports show that change in the expression of the gene or the transcript thereof can serve as a marker for liver cancer.

The 129th target gene is the hsa-miR-4258 gene, a congener thereof, a transcript thereof, or a variant or a derivative thereof. None of the previously known reports show that change in the expression of the gene or the transcript thereof can serve as a marker for liver cancer.

The 130th target gene is the hsa-miR-6510-5p gene, a congener thereof, a transcript thereof, or a variant or a derivative thereof. None of the previously known reports show that change in the expression of the gene or the transcript thereof can serve as a marker for liver cancer.

The 131st target gene is the hsa-miR-1343-5p gene, a congener thereof, a transcript thereof, or a variant or a derivative thereof. None of the previously known reports show that change in the expression of the gene or the transcript thereof can serve as a marker for liver cancer.

The 132nd target gene is the hsa-miR-1247-3p gene, a congener thereof, a transcript thereof, or a variant or a derivative thereof. None of the previously known reports show that change in the expression of the gene or the transcript thereof can serve as a marker for liver cancer.

The 133rd target gene is the hsa-miR-6805-5p gene, a congener thereof, a transcript thereof, or a variant or a derivative thereof. None of the previously known reports show that change in the expression of the gene or the transcript thereof can serve as a marker for liver cancer.

The 134th target gene is the hsa-miR-4492 gene, a congener thereof, a transcript thereof, or a variant or a derivative thereof. None of the previously known reports show that change in the expression of the gene or the transcript thereof can serve as a marker for liver cancer.

The 135th target gene is the hsa-miR-1469 gene, a congener thereof, a transcript thereof, or a variant or a derivative thereof. None of the previously known reports show that change in the expression of the gene or the transcript thereof can serve as a marker for liver cancer.

The 136th target gene is the hsa-miR-1268b gene, a congener thereof, a transcript thereof, or a variant or a derivative thereof. None of the previously known reports show that change in the expression of the gene or the transcript thereof can serve as a marker for liver cancer.

The 137th target gene is the hsa-miR-6858-5p gene, a congener thereof, a transcript thereof, or a variant or a derivative thereof. None of the previously known reports show that change in the expression of the gene or the transcript thereof can serve as a marker for liver cancer.

The 138th target gene is the hsa-miR-3937 gene, a congener thereof, a transcript thereof, or a variant or a derivative thereof. None of the previously known reports show that change in the expression of the gene or the transcript thereof can serve as a marker for liver cancer.

The 139th target gene is the hsa-miR-939-5p gene, a congener thereof, a transcript thereof, or a variant or a derivative thereof. None of the previously known reports show that change in the expression of the gene or the transcript thereof can serve as a marker for liver cancer.

The 140th target gene is the hsa-miR-3656 gene, a congener thereof, a transcript thereof, or a variant or a derivative thereof. None of the previously known reports show that change in the expression of the gene or the transcript thereof can serve as a marker for liver cancer.

The 141st target gene is the hsa-miR-744-5p gene, a congener thereof, a transcript thereof, or a variant or a derivative thereof. None of the previously known reports show that change in the expression of the gene or the transcript thereof can serve as a marker for liver cancer.

The 142nd target gene is the hsa-miR-4687-3p gene, a congener thereof, a transcript thereof, or a variant or a derivative thereof. None of the previously known reports show that change in the expression of the gene or the transcript thereof can serve as a marker for liver cancer.

The 143rd target gene is the hsa-miR-4763-3p gene, a congener thereof, a transcript thereof, or a variant or a derivative thereof. None of the previously known reports show that change in the expression of the gene or the transcript thereof can serve as a marker for liver cancer.

The 144th target gene is the hsa-miR-3620-5p gene, a congener thereof, a transcript thereof, or a variant or a derivative thereof. None of the previously known reports show that change in the expression of the gene or the transcript thereof can serve as a marker for liver cancer.

The 145th target gene is the hsa-miR-3195 gene, a congener thereof, a transcript thereof, or a variant or a derivative thereof. None of the previously known reports show that change in the expression of the gene or the transcript thereof can serve as a marker for liver cancer.

The 146th target gene is the hsa-miR-6842-5p gene, a congener thereof, a transcript thereof, or a variant or a derivative thereof. None of the previously known reports show that change in the expression of the gene or the transcript thereof can serve as a marker for liver cancer.

The 147th target gene is the hsa-miR-4707-5p gene, a congener thereof, a transcript thereof, or a variant or a derivative thereof. None of the previously known reports show that change in the expression of the gene or the transcript thereof can serve as a marker for liver cancer.

The 148th target gene is the hsa-miR-642a-3p gene, a congener thereof, a transcript thereof, or a variant or a derivative thereof. None of the previously known reports show that change in the expression of the gene or the transcript thereof can serve as a marker for liver cancer.

The 149th target gene is the hsa-miR-7113-3p gene, a congener thereof, a transcript thereof, or a variant or a derivative thereof. None of the previously known reports show that change in the expression of the gene or the transcript thereof can serve as a marker for liver cancer.

The 150th target gene is the hsa-miR-4728-5p gene, a congener thereof, a transcript thereof, or a variant or a derivative thereof. None of the previously known reports show that change in the expression of the gene or the transcript thereof can serve as a marker for liver cancer.

The 151st target gene is the hsa-miR-5195-3p gene, a congener thereof, a transcript thereof, or a variant or a derivative thereof. None of the previously known reports show that change in the expression of the gene or the transcript thereof can serve as a marker for liver cancer.

The 152nd target gene is the hsa-miR-1185-1-3p gene, a congener thereof, a transcript thereof, or a variant or a derivative thereof. None of the previously known reports show that change in the expression of the gene or the transcript thereof can serve as a marker for liver cancer.

The 153rd target gene is the hsa-miR-6774-5p gene, a congener thereof, a transcript thereof, or a variant or a derivative thereof. None of the previously known reports show that change in the expression of the gene or the transcript thereof can serve as a marker for liver cancer.

The 154th target gene is the hsa-miR-8059 gene, a congener thereof, a transcript thereof, or a variant or a derivative thereof. None of the previously known reports show that change in the expression of the gene or the transcript thereof can serve as a marker for liver cancer.

The 155th target gene is the hsa-miR-3131 gene, a congener thereof, a transcript thereof, or a variant or a derivative thereof. None of the previously known reports show that change in the expression of the gene or the transcript thereof can serve as a marker for liver cancer.

The 156th target gene is the hsa-miR-7847-3p gene, a congener thereof, a transcript thereof, or a variant or a derivative thereof. None of the previously known reports show that change in the expression of the gene or the transcript thereof can serve as a marker for liver cancer.

The 157th target gene is the hsa-miR-4463 gene, a congener thereof, a transcript thereof, or a variant or a derivative thereof. None of the previously known reports show that change in the expression of the gene or the transcript thereof can serve as a marker for liver cancer.

The 158th target gene is the hsa-miR-128-2-5p gene, a congener thereof, a transcript thereof, or a variant or a derivative thereof. None of the previously known reports show that change in the expression of the gene or the transcript thereof can serve as a marker for liver cancer.

The 159th target gene is the hsa-miR-4508 gene, a congener thereof, a transcript thereof, or a variant or a derivative thereof. None of the previously known reports show that change in the expression of the gene or the transcript thereof can serve as a marker for liver cancer.

The 160th target gene is the hsa-miR-6806-5p gene, a congener thereof, a transcript thereof, or a variant or a derivative thereof. None of the previously known reports show that change in the expression of the gene or the transcript thereof can serve as a marker for liver cancer.

The 161st target gene is the hsa-miR-7111-5p gene, a congener thereof, a transcript thereof, or a variant or a derivative thereof. None of the previously known reports show that change in the expression of the gene or the transcript thereof can serve as a marker for liver cancer.

The 162nd target gene is the hsa-miR-6782-5p gene, a congener thereof, a transcript thereof, or a variant or a derivative thereof. None of the previously known reports show that change in the expression of the gene or the transcript thereof can serve as a marker for liver cancer.

The 163rd target gene is the hsa-miR-4734 gene, a congener thereof, a transcript thereof, or a variant or a derivative thereof. None of the previously known reports show that change in the expression of the gene or the transcript thereof can serve as a marker for liver cancer.

The 164th target gene is the hsa-miR-3162-5p gene, a congener thereof, a transcript thereof, or a variant or a derivative thereof. None of the previously known reports show that change in the expression of the gene or the transcript thereof can serve as a marker for liver cancer.

The 165th target gene is the hsa-miR-887-3p gene, a congener thereof, a transcript thereof, or a variant or a derivative thereof. None of the previously known reports show that change in the expression of the gene or the transcript thereof can serve as a marker for liver cancer.

The 166th target gene is the hsa-miR-6752-5p gene, a congener thereof, a transcript thereof, or a variant or a derivative thereof. None of the previously known reports show that change in the expression of the gene or the transcript thereof can serve as a marker for liver cancer.

The 167th target gene is the hsa-miR-6724-5p gene, a congener thereof, a transcript thereof, or a variant or a derivative thereof. None of the previously known reports show that change in the expression of the gene or the transcript thereof can serve as a marker for liver cancer.

The 168th target gene is the hsa-miR-23b-3p gene, a congener thereof, a transcript thereof, or a variant or a derivative thereof. The previously known reports show that change in the expression of the gene or the transcript thereof can serve as a marker for liver cancer (Patent Literatures 2 and 3).

The 169th target gene is the hsa-miR-23a-3p gene, a congener thereof, a transcript thereof, or a variant or a derivative thereof. The previously known report shows that change in the expression of the gene or the transcript thereof can serve as a marker for liver cancer (Patent Literature 2).

The 170th target gene is the hsa-miR-625-3p gene, a congener thereof, a transcript thereof, or a variant or a derivative thereof. The previously known report shows that change in the expression of the gene or the transcript thereof can serve as a marker for liver cancer (Patent Literature 4).

The 171st target gene is the hsa-miR-1228-3p gene, a congener thereof, a transcript thereof, or a variant or a derivative thereof. None of the previously known reports show that change in the expression of the gene or the transcript thereof can serve as a marker for liver cancer.

The 172nd target gene is the hsa-miR-614 gene, a congener thereof, a transcript thereof, or a variant or a derivative thereof. The previously known report shows that change in the expression of the gene or the transcript thereof can serve as a marker for liver cancer (Patent Literature 2).

The 173rd target gene is the hsa-miR-1913 gene, a congener thereof, a transcript thereof, or a variant or a derivative thereof. The previously known report shows that change in the expression of the gene or the transcript thereof can serve as a marker for liver cancer (Patent Literature 4).

The 174th target gene is the hsa-miR-92a-2-5p gene, a congener thereof, a transcript thereof, or a variant or a derivative thereof. The previously known report shows that change in the expression of the gene or the transcript thereof can serve as a marker for liver cancer (Patent Literature 1).

The 175th target gene is the hsa-miR-187-5p gene, a congener thereof, a transcript thereof, or a variant or a derivative thereof. The previously known report shows that change in the expression of the gene or the transcript thereof can serve as a marker for liver cancer (Patent Literature 5).

The 176th target gene is the hsa-miR-16-5p gene, a congener thereof, a transcript thereof, or a variant or a derivative thereof. The previously known report shows that change in the expression of the gene or the transcript thereof can serve as a marker for liver cancer (Patent Literatures 4 and 5).

The 177th target gene is the hsa-miR-92b-3p gene, a congener thereof, a transcript thereof, or a variant or a derivative thereof. The previously known report shows that change in the expression of the gene or the transcript thereof can serve as a marker for liver cancer (Patent Literature 1).

The 178th target gene is the hsa-miR-150-3p gene, a congener thereof, a transcript thereof, or a variant or a derivative thereof. The previously known report shows that change in the expression of the gene or the transcript thereof can serve as a marker for liver cancer (Patent Literature 2).

The 179th target gene is the hsa-miR-564 gene, a congener thereof, a transcript thereof, or a variant or a derivative thereof. The previously known report shows that change in the expression of the gene or the transcript thereof can serve as a marker for liver cancer (Patent Literature 2).

The 180th target gene is the hsa-miR-125a-3p gene, a congener thereof, a transcript thereof, or a variant or a derivative thereof. The previously known report shows that change in the expression of the gene or the transcript thereof can serve as a marker for liver cancer (Patent Literature 3).

The 181st target gene is the hsa-miR-92b-5p gene, a congener thereof, a transcript thereof, or a variant or a derivative thereof. The previously known report shows that change in the expression of the gene or the transcript thereof can serve as a marker for liver cancer (Patent Literature 1).

The 182nd target gene is the hsa-miR-92a-3p gene, a congener thereof, a transcript thereof, or a variant or a derivative thereof. The previously known report shows that change in the expression of the gene or the transcript thereof can serve as a marker for liver cancer (Patent Literatures 1, 4, and 5).

The 183rd target gene is the hsa-miR-663a gene, a congener thereof, a transcript thereof, or a variant or a derivative thereof. The previously known report shows that change in the expression of the gene or the transcript thereof can serve as a marker for liver cancer (Patent Literature 4).

The 184th target gene is the hsa-miR-4688 gene, a congener thereof, a transcript thereof, or a variant or a derivative thereof. None of the previously known reports show that change in the expression of the gene or the transcript thereof can serve as a marker for liver cancer.

The 185th target gene is the hsa-miR-4648 gene, a congener thereof, a transcript thereof, or a variant or a derivative thereof. None of the previously known reports show that change in the expression of the gene or the transcript thereof can serve as a marker for liver cancer.

The 186th target gene is the hsa-miR-6085 gene, a congener thereof, a transcript thereof, or a variant or a derivative thereof. None of the previously known reports show that change in the expression of the gene or the transcript thereof can serve as a marker for liver cancer.

The 187th target gene is the hsa-miR-6126 gene, a congener thereof, a transcript thereof, or a variant or a derivative thereof. None of the previously known reports show that change in the expression of the gene or the transcript thereof can serve as a marker for liver cancer.

The 188th target gene is the hsa-miR-6880-5p gene, a congener thereof, a transcript thereof, or a variant or a derivative thereof. None of the previously known reports show that change in the expression of the gene or the transcript thereof can serve as a marker for liver cancer.

The 189th target gene is the hsa-miR-328-5p gene, a congener thereof, a transcript thereof, or a variant or a derivative thereof. None of the previously known reports show that change in the expression of the gene or the transcript thereof can serve as a marker for liver cancer.

The 190th target gene is the hsa-miR-6768-5p gene, a congener thereof, a transcript thereof, or a variant or a derivative thereof. None of the previously known reports show that change in the expression of the gene or the transcript thereof can serve as a marker for liver cancer.

The 191st target gene is the hsa-miR-3180 gene, a congener thereof, a transcript thereof, or a variant or a derivative thereof. None of the previously known reports show that change in the expression of the gene or the transcript thereof can serve as a marker for liver cancer.

The 192nd target gene is the hsa-miR-6087 gene, a congener thereof, a transcript thereof, or a variant or a derivative thereof. None of the previously known reports show that change in the expression of the gene or the transcript thereof can serve as a marker for liver cancer.

The 193rd target gene is the hsa-miR-1273g-3p gene, a congener thereof, a transcript thereof, or a variant or a derivative thereof. None of the previously known reports show that change in the expression of the gene or the transcript thereof can serve as a marker for liver cancer.

The 194th target gene is the hsa-miR-1225-5p gene, a congener thereof, a transcript thereof, or a variant or a derivative thereof. None of the previously known reports show that change in the expression of the gene or the transcript thereof can serve as a marker for liver cancer.

The 195th target gene is the hsa-miR-3196 gene, a congener thereof, a transcript thereof, or a variant or a derivative thereof. None of the previously known reports show that change in the expression of the gene or the transcript thereof can serve as a marker for liver cancer.

The 196th target gene is the hsa-miR-4695-5p gene, a congener thereof, a transcript thereof, or a variant or a derivative thereof. None of the previously known reports show that change in the expression of the gene or the transcript thereof can serve as a marker for liver cancer.

The 197th target gene is the hsa-miR-6732-5p gene, a congener thereof, a transcript thereof, or a variant or a derivative thereof. None of the previously known reports show that change in the expression of the gene or the transcript thereof can serve as a marker for liver cancer.

The 198th target gene is the hsa-miR-638 gene, a congener thereof, a transcript thereof, or a variant or a derivative thereof. None of the previously known reports show that change in the expression of the gene or the transcript thereof can serve as a marker for liver cancer.

The 199th target gene is the hsa-miR-6813-5p gene, a congener thereof, a transcript thereof, or a variant or a derivative thereof. None of the previously known reports show that change in the expression of the gene or the transcript thereof can serve as a marker for liver cancer.

The 200th target gene is the hsa-miR-665 gene, a congener thereof, a transcript thereof, or a variant or a derivative thereof. None of the previously known reports show that change in the expression of the gene or the transcript thereof can serve as a marker for liver cancer.

The 201st target gene is the hsa-miR-486-3p gene, a congener thereof, a transcript thereof, or a variant or a derivative thereof. The previously known report shows that change in the expression of the gene or the transcript thereof can serve as a marker for liver cancer (Patent Literatures 2 and 3).

The 202nd target gene is the hsa-miR-4466 gene, a congener thereof, a transcript thereof, or a variant or a derivative thereof. None of the previously known reports show that change in the expression of the gene or the transcript thereof can serve as a marker for liver cancer.

The 203rd target gene is the hsa-miR-30c-1-3p gene, a congener thereof, a transcript thereof, or a variant or a derivative thereof. The previously known report shows that change in the expression of the gene or the transcript thereof can serve as a marker for liver cancer (Patent Literatures 3 and 5).

The 204th target gene is the hsa-miR-3621 gene, a congener thereof, a transcript thereof, or a variant or a derivative thereof. None of the previously known reports show that change in the expression of the gene or the transcript thereof can serve as a marker for liver cancer.

The 205th target gene is the hsa-miR-6743-5p gene, a congener thereof, a transcript thereof, or a variant or a derivative thereof. None of the previously known reports show that change in the expression of the gene or the transcript thereof can serve as a marker for liver cancer.

The 206th target gene is the hsa-miR-4298 gene, a congener thereof, a transcript thereof, or a variant or a derivative thereof. None of the previously known reports show that change in the expression of the gene or the transcript thereof can serve as a marker for liver cancer.

The 207th target gene is the hsa-miR-4741 gene, a congener thereof, a transcript thereof, or a variant or a derivative thereof. None of the previously known reports show that change in the expression of the gene or the transcript thereof can serve as a marker for liver cancer.

The 208th target gene is the hsa-miR-3619-3p gene, a congener thereof, a transcript thereof, or a variant or a derivative thereof. None of the previously known reports show that change in the expression of the gene or the transcript thereof can serve as a marker for liver cancer.

The 209th target gene is the hsa-miR-6824-5p gene, a congener thereof, a transcript thereof, or a variant or a derivative thereof. None of the previously known reports show that change in the expression of the gene or the transcript thereof can serve as a marker for liver cancer.

The 210th target gene is the hsa-miR-5698 gene, a congener thereof, a transcript thereof, or a variant or a derivative thereof. None of the previously known reports show that change in the expression of the gene or the transcript thereof can serve as a marker for liver cancer.

The 211th target gene is the hsa-miR-371a-5p gene, a congener thereof, a transcript thereof, or a variant or a derivative thereof. None of the previously known reports show that change in the expression of the gene or the transcript thereof can serve as a marker for liver cancer.

The 212th target gene is the hsa-miR-4488 gene, a congener thereof, a transcript thereof, or a variant or a derivative thereof. None of the previously known reports show that change in the expression of the gene or the transcript thereof can serve as a marker for liver cancer.

The 213th target gene is the hsa-miR-1233-5p gene, a congener thereof, a transcript thereof, or a variant or a derivative thereof. None of the previously known reports show that change in the expression of the gene or the transcript thereof can serve as a marker for liver cancer.

The 214th target gene is the hsa-miR-4723-5p gene, a congener thereof, a transcript thereof, or a variant or a derivative thereof. None of the previously known reports show that change in the expression of the gene or the transcript thereof can serve as a marker for liver cancer.

The 215th target gene is the hsa-miR-24-3p gene, a congener thereof, a transcript thereof, or a variant or a derivative thereof. The previously known report shows that change in the expression of the gene or the transcript thereof can serve as a marker for liver cancer (Patent Literature 2).

The 216th target gene is the hsa-miR-1238-5p gene, a congener thereof, a transcript thereof, or a variant or a derivative thereof. None of the previously known reports show that change in the expression of the gene or the transcript thereof can serve as a marker for liver cancer.

The 217th target gene is the hsa-miR-4442 gene, a congener thereof, a transcript thereof, or a variant or a derivative thereof. None of the previously known reports show that change in the expression of the gene or the transcript thereof can serve as a marker for liver cancer.

The 218th target gene is the hsa-miR-3928-3p gene, a congener thereof, a transcript thereof, or a variant or a derivative thereof. None of the previously known reports show that change in the expression of the gene or the transcript thereof can serve as a marker for liver cancer.

The 219th target gene is the hsa-miR-6716-5p gene, a congener thereof, a transcript thereof, or a variant or a derivative thereof. None of the previously known reports show that change in the expression of the gene or the transcript thereof can serve as a marker for liver cancer.

The 220th target gene is the hsa-miR-6089 gene, a congener thereof, a transcript thereof, or a variant or a derivative thereof. None of the previously known reports show that change in the expression of the gene or the transcript thereof can serve as a marker for liver cancer.

The 221st target gene is the hsa-miR-6124 gene, a congener thereof, a transcript thereof, or a variant or a derivative thereof. None of the previously known reports show that change in the expression of the gene or the transcript thereof can serve as a marker for liver cancer.

The 222nd target gene is the hsa-miR-6778-5p gene, a congener thereof, a transcript thereof, or a variant or a derivative thereof. None of the previously known reports show that change in the expression of the gene or the transcript thereof can serve as a marker for liver cancer.

The 223rd target gene is the hsa-miR-557 gene, a congener thereof, a transcript thereof, or a variant or a derivative thereof. The previously known report shows that change in the expression of the gene or the transcript thereof can serve as a marker for liver cancer (Patent Literature 2).

The 224th target gene is the hsa-miR-6090 gene, a congener thereof, a transcript thereof, or a variant or a derivative thereof. None of the previously known reports show that change in the expression of the gene or the transcript thereof can serve as a marker for liver cancer.

The 225th target gene is the hsa-miR-6757-5p gene, a congener thereof, a transcript thereof, or a variant or a derivative thereof. None of the previously known reports show that change in the expression of the gene or the transcript thereof can serve as a marker for liver cancer.

The 226th target gene is the hsa-miR-4448 gene, a congener thereof, a transcript thereof, or a variant or a derivative thereof. None of the previously known reports show that change in the expression of the gene or the transcript thereof can serve as a marker for liver cancer.

The 227th target gene is the hsa-miR-671-5p gene, a congener thereof, a transcript thereof, or a variant or a derivative thereof. None of the previously known reports show that change in the expression of the gene or the transcript thereof can serve as a marker for liver cancer.

The 228th target gene is the hsa-miR-3178 gene, a congener thereof, a transcript thereof, or a variant or a derivative thereof. None of the previously known reports show that change in the expression of the gene or the transcript thereof can serve as a marker for liver cancer.

The 229th target gene is the hsa-miR-4725-3p gene, a congener thereof, a transcript thereof, or a variant or a derivative thereof. None of the previously known reports show that change in the expression of the gene or the transcript thereof can serve as a marker for liver cancer.

The 230th target gene is the hsa-miR-940 gene, a congener thereof, a transcript thereof, or a variant or a derivative thereof. None of the previously known reports show that change in the expression of the gene or the transcript thereof can serve as a marker for liver cancer.

The 231st target gene is the hsa-miR-6789-5p gene, a congener thereof, a transcript thereof, or a variant or a derivative thereof. None of the previously known reports show that change in the expression of the gene or the transcript thereof can serve as a marker for liver cancer.

The 232nd target gene is the hsa-miR-4484 gene, a congener thereof, a transcript thereof, or a variant or a derivative thereof. None of the previously known reports show that change in the expression of the gene or the transcript thereof can serve as a marker for liver cancer.

The 233rd target gene is the hsa-miR-4634 gene, a congener thereof, a transcript thereof, or a variant or a derivative thereof. None of the previously known reports show that change in the expression of the gene or the transcript thereof can serve as a marker for liver cancer.

The 234th target gene is the hsa-miR-4745-5p gene, a congener thereof, a transcript thereof, or a variant or a derivative thereof. None of the previously known reports show that change in the expression of the gene or the transcript thereof can serve as a marker for liver cancer.

The 235th target gene is the hsa-miR-4730 gene, a congener thereof, a transcript thereof, or a variant or a derivative thereof. None of the previously known reports show that change in the expression of the gene or the transcript thereof can serve as a marker for liver cancer.

The 236th target gene is the hsa-miR-6803-5p gene, a congener thereof, a transcript thereof, or a variant or a derivative thereof. None of the previously known reports show that change in the expression of the gene or the transcript thereof can serve as a marker for liver cancer.

The 237th target gene is the hsa-miR-6798-5p gene, a congener thereof, a transcript thereof, or a variant or a derivative thereof. None of the previously known reports show that change in the expression of the gene or the transcript thereof can serve as a marker for liver cancer.

The 238th target gene is the hsa-miR-3648 gene, a congener thereof, a transcript thereof, or a variant or a derivative thereof. None of the previously known reports show that change in the expression of the gene or the transcript thereof can serve as a marker for liver cancer.

The 239th target gene is the hsa-miR-4783-3p gene, a congener thereof, a transcript thereof, or a variant or a derivative thereof. None of the previously known reports show that change in the expression of the gene or the transcript thereof can serve as a marker for liver cancer.

The 240th target gene is the hsa-miR-6836-3p gene, a congener thereof, a transcript thereof, or a variant or a derivative thereof. None of the previously known reports show that change in the expression of the gene or the transcript thereof can serve as a marker for liver cancer.

2. Nucleic Acid Probe or Primer for Detection of Liver Cancer

In the present invention, a nucleic acid capable of specifically binding to any of the target nucleic acids as the liver cancer markers described above can be used as a nucleic acid, for example, a nucleic acid probe or a primer, for the detection or diagnosis of liver cancer.

In the present invention, the nucleic acid probe or the primer that can be used for detecting liver cancer or for diagnosing liver cancer enables qualitative and/or quantitative measurement of the presence, expression level, or abundance of a target nucleic acid as the liver cancer marker described above, for example, human-derived hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-6757-5p, hsa-miR-4448, hsa-miR-671-5p, hsa-miR-3178, hsa-miR-4725-3p, hsa-miR-940, hsa-miR-6789-5p, hsa-miR-4484, hsa-miR-4634, hsa-miR-4745-5p, hsa-miR-4730, hsa-miR-6803-5p, hsa-miR-6798-5p, hsa-miR-3648, hsa-miR-4783-3p, or hsa-miR-6836-3p, or a combination thereof, or a congener thereof, a transcript thereof, or a variant or derivative thereof; and, optionally in combination therewith, hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p, or hsa-miR-663a, or a combination thereof, a congener thereof, a transcript thereof, or a variant or derivative thereof; and optionally in combination therewith, hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557, and hsa-miR-6090, or a combination thereof, a congener thereof, a transcript thereof, or a variant or derivative thereof.

The expression level of each target nucleic acid described above is increased or decreased (hereinafter, referred to as "increased/decreased") depending on the type of the target nucleic acid in a subject having liver cancer as compared with a healthy subject. Hence, the nucleic acid of the present invention can be effectively used for measuring the expression level of the target nucleic acid described above in a body fluid derived from a subject (e.g., a human) suspected of having liver cancer and a body fluid derived from a healthy subject and comparing them to detect liver cancer.

The nucleic acid probe or the primer that can be used in the present invention is a nucleic acid probe capable of specifically binding to a polynucleotide consisting of a nucleotide sequence represented by at least one of SEQ ID NOs: 1 to 167 and 714 to 729, or a primer for amplifying a polynucleotide consisting of a nucleotide sequence represented by at least one of SEQ ID NOs: 1 to 167 and 714 to 729.

The nucleic acid probe or the primer that can be further used in the present invention may comprise a nucleic acid probe capable of specifically binding to a polynucleotide consisting of a nucleotide sequence represented by at least one of SEQ ID NOs: 168 to 183, or a primer for amplifying a polynucleotide consisting of a nucleotide sequence represented by at least one of SEQ ID NOs: 168 to 183.

The nucleic acid probe or the primer that can be further used in the present invention may comprise a nucleic acid probe capable of specifically binding to a polynucleotide consisting of a nucleotide sequence represented by at least one of SEQ ID NOs: 184 to 224, or a primer for amplifying a polynucleotide consisting of a nucleotide sequence represented by at least one of SEQ ID NOs: 184 to 224.

Specifically, these nucleic acid probes or primers comprise a combination of one or more polynucleotides selected from a group of polynucleotides comprising nucleotide sequences represented by any of SEQ ID NOs: 1 to 765 or nucleotide sequences derived from the nucleotide sequences by the replacement of u with t, and a group of complementary polynucleotides thereof, a group of polynucleotides respectively hybridizing under stringent conditions (mentioned later) to DNAs consisting of nucleotide sequences complementary to these nucleotide sequences, and a group of complementary polynucleotides thereof, and a group of polynucleotides comprising 15 or more, preferably 17 or more consecutive nucleotides in the nucleotide sequences of these polynucleotide groups. These polynucleotides can be used as nucleic acid probes and primers for detecting the liver cancer markers as target nucleic acids.

More specifically, examples of the nucleic acid probe or the primer that can be used in the present invention include one or more polynucleotide(s) selected from the group consisting of the following polynucleotides (a) to (e):

(a) a polynucleotide consisting of a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 167 and 714 to 729, (c) a polynucleotide consisting of a nucleotide sequence complementary to a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 167 and 714 to 729 or a nucleotide sequence derived from the nucleotide sequence by the replacement of u with t, and (e) a polynucleotide hybridizing under stringent conditions to any of the polynucleotides (a) to (d).

In addition to at least one or more polynucleotide(s) selected from the group consisting of the polynucleotides (a) to (e), the nucleic acid probe or the primer that can be further used in the present invention may comprise a polynucleotide selected from the group consisting of the following polynucleotides (f) to (j):

(f) a polynucleotide consisting of a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 168 to 183, (h) a polynucleotide consisting of a nucleotide sequence complementary to a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 168 to 183 or a nucleotide sequence derived from the nucleotide sequence by the replacement of u with t, and (j) a polynucleotide hybridizing under stringent conditions to any of the polynucleotides (f) to (i).

In addition to at least one or more polynucleotide(s) selected from the group consisting of the polynucleotides (a)

to (j), the nucleic acid probe or the primer that can be further used in the present invention may comprise a polynucleotide selected from the group consisting of the following polynucleotides (k) to (o):

(k) a polynucleotide consisting of a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 184 to 224, (m) a polynucleotide consisting of a nucleotide sequence complementary to a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 184 to 224 or a nucleotide sequence derived from the nucleotide sequence by the replacement of u with t, and (o) a polynucleotide hybridizing under stringent conditions to any of the polynucleotides (k) to (n).

For these polynucleotides, the "fragment thereof comprising 15 or more consecutive nucleotides" can comprise the number of nucleotides in the range from, for example, 15 consecutive nucleotides to less than the total number of nucleotides of the sequence, 17 consecutive nucleotides to less than the total number of nucleotides of the sequence, or 19 consecutive nucleotides to less than the total number of nucleotides of the sequence, in the nucleotide sequence of each polynucleotide, though the fragment is not limited thereto.

These polynucleotides or fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-6757-5p, hsa-miR-4448, hsa-miR-671-5p, hsa-miR-3178, hsa-miR-4725-3p, hsa-miR-940, hsa-miR-6789-5p, hsa-miR-4484, hsa-miR-4634, hsa-miR-4745-5p, hsa-miR-4730, hsa-miR-6803-5p, hsa-miR-6798-5p, hsa-miR-3648, hsa-miR-4783-3p, hsa-miR-6836-3p, hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p, hsa-miR-663a, hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557 and hsa-miR-6090 represented by SEQ ID NOs: 1 to 224 and 714 to 729 are known in the art, and their obtainment methods are also known as mentioned above. Therefore, each polynucleotide that can be used as a nucleic acid probe or a primer in the present invention can be prepared by cloning the gene.

Such a nucleic acid probe or a primer can be chemically synthesized using an automated DNA synthesizer. In general, a phosphoramidite method is used in this synthesis, and single-stranded DNA up to approximately 100 nucleotides can be automatically synthesized by this method. The automated DNA synthesizer is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probe and the primer for detecting the polynucleotide consisting of a nucleotide sequence represented by any of SEQ ID NOs: 1 to 224 and 714 to 729 do not exist as miRNAs or precursors thereof in vivo. For example, the nucleotide sequences represented by SEQ ID NO: 1 and SEQ ID NO: 131 are produced from the precursor represented by SEQ ID NO: 225. This precursor has a hairpin-like structure as shown in FIG. 1, and the nucleotide sequences represented by SEQ ID NO: 1 and SEQ ID NO: 131 have mismatch sequences with each other. Therefore, a nucleotide sequence completely complementary to the nucleotide sequence represented by SEQ ID NO: 1 or SEQ ID NO: 131 is not naturally produced in vivo. Likewise, the nucleic acid probe and the primer for detecting the nucleotide sequence represented by any of SEQ ID NOs: 1 to 224 and 714 to 729 each have an artificial nucleotide sequence that does not exist in vivo.

3. Kit or Device for Detection of Liver Cancer

The present invention also provides a kit or a device for the detection of liver cancer, comprising one or more polynucleotide(s) (which may include a variant, a fragment, or a derivative thereof; hereinafter, also referred to as a polynucleotide for detection) that can be used as a nucleic acid probe or a primer in the present invention for measuring a target nucleic acid as a liver cancer marker.

The target nucleic acid as a liver cancer marker according to the present invention is preferably selected from the following group 1:

miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-5p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p.

An additional target nucleic acid that may be optionally used in the measurement is preferably selected from the following group 2: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a.

An additional target nucleic acid that can be optionally further used in the measurement is preferably selected from the following group 3: miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090.

The kit or the device of the present invention comprises a nucleic acid capable of specifically binding to any of the target nucleic acids as the liver cancer markers described above, preferably one or more polynucleotide(s) selected from the nucleic acid probes or the primers described in Section 2 above, specifically, the polynucleotides described in Section 2 above, or variant(s) thereof.

Specifically, the kit or the device of the present invention may comprise at least one or more polynucleotide(s) comprising (or consisting of) a nucleotide sequence represented by any of SEQ ID NOs: 1 to 167 and 714 to 729 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention may further comprise one or more polynucleotide(s) comprising (or consisting of) a nucleotide sequence represented by any of SEQ ID NOs: 168 to 183 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention may further comprise one or more polynucleotide(s) comprising (or consisting of) a nucleotide sequence represented by any of SEQ ID NOs: 184 to 224 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that may be contained in the kit or the device of the present invention is, for example, one or more, preferably two or more polynucleotides selected from the group consisting of the following polynucleotides (1) to (3):
(1) a polynucleotide comprising 15 or more consecutive nucleotides in a nucleotide sequence derived from a nucleotide sequence represented by any of SEQ ID NOs: 1 to 167 and 714 to 729 by the replacement of u with t, or a complementary sequence thereof;
(2) a polynucleotide comprising 15 or more consecutive nucleotides in a nucleotide sequence derived from a nucleotide sequence represented by any of SEQ ID NOs: 168 to 183 by the replacement of u with t, or a complementary sequence thereof; and
(3) a polynucleotide comprising 15 or more consecutive nucleotides in a nucleotide sequence derived from a nucleotide sequence represented by any of SEQ ID NOs: 184 to 224 by the replacement of u with t, or a complementary sequence thereof.

In a preferred embodiment, the polynucleotide is a polynucleotide consisting of a nucleotide sequence represented by any of SEQ ID NOs: 1 to 167 and 714 to 729 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 168 to 183 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 184 to 224 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment may be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, 17 consecutive nucleotides to less than the total number of nucleotides of the sequence, or 19 consecutive nucleotides to less than the total number of nucleotides of the sequence, in the nucleotide sequence of each polynucleotide.

Specific examples of the aforementioned polynucleotide combination constituting the kit or the device of the present invention can include any combination of the polynucleotides consisting of nucleotide sequences represented by SEQ ID NOs shown in Table 1 (SEQ ID NOs: 1 to 224 and 714 to 729 corresponding to the miRNA markers in Table 1) or complementary sequences thereof. However, these are given merely for illustrative purposes, and all of various other possible combinations are included in the present invention.

The aforementioned combination constituting the kit or the device for discriminating a liver cancer patient from a healthy subject according to the present invention is desirably, for example, a combination of two or more of the aforementioned polynucleotides consisting of nucleotide sequences represented by SEQ ID NOs shown in Table 1. Usually, a combination of two of these polynucleotides can produce adequate performance.

The combination of two polynucleotides consisting of the nucleotide sequences or the complementary sequences thereof for specifically discriminating a liver cancer patient from a healthy subject is preferably a combination comprising at least one or more of newly found polynucleotides consisting of the nucleotide sequences represented by SEQ ID NOs: 1 to 167 and 714 to 729, among the combinations of two selected from the polynucleotides consisting of the nucleotide sequences represented by SEQ ID NOs: 1 to 224 and 714 to 729.

The combination of polynucleotides with cancer type specificity capable of discriminating a liver cancer patient not only from a healthy subject but also from other cancer patients is preferably, for example, a combination of a plurality of polynucleotides comprising at least one polynucleotide selected from the group consisting of polynucleotides consisting of the nucleotide sequences represented by SEQ ID NOs: 1, 2, 3, 5, 7, 9, 12, 17, 20, 22, 27, 28, 29, 38, 39, 44, 46, 48, 51, 54, 61, 76, 89, 93, 101, 109, 116, 123, 132, 134, 136, 148, 150, 151, 155, 157, 164, 166, 167, 172, 180, 186, 188, 189, 197, 198, 214, 216, 714, 715, 716, 717, 718, 719, 720, 721, 722, 723, 724, 725, 726, 727, 728 and 729 or complementary sequences thereof (hereinafter, this group is referred to as "cancer type-specific polynucleotide group 1"), with any of the polynucleotides of the other SEQ ID NOs.

The combination of polynucleotides with cancer type specificity capable of discriminating a liver cancer patient not only from a healthy subject but also from other cancer patients is more preferably a combination of a plurality of polynucleotides selected from cancer type-specific polynucleotide group 1.

The combination of polynucleotides with cancer type specificity capable of discriminating a liver cancer patient not only from a healthy subject but also from other cancer patients is more preferably a combination comprising at least one or more polynucleotide(s) selected from the group consisting of polynucleotides consisting of the nucleotide sequences represented by SEQ ID NOs: 1, 3, 7, 9, 22, 38, 44, 134, 148, 155, 157, 164, 167, 172, 214, 714, 715, 716 and 717 or complementary sequences thereof (hereinafter, this group is referred to as "cancer type-specific polynucleotide group 2") included in the cancer type-specific polynucleotide group 1, among the combinations of a plurality of polynucleotides selected from the cancer type-specific polynucleotide group 1.

The number of the polynucleotides with cancer type specificity in the combination described above can be 1, 2, 3, 4, 5, 6, 7, 8, 9, 10 or more in the combination and is more preferably 4 or more in the combination. Usually, the combination of 4 of the polynucleotides can produce adequate performance.

Non-limiting examples of the combination of the polynucleotide consisting of the nucleotide sequence represented by SEQ ID NO: 1 or a complementary sequence thereof with polynucleotides consisting of nucleotide sequences represented by SEQ ID NOs of three polynucleotides selected from the cancer type-specific polynucleotide group 1 or complementary sequences thereof are listed below.

(1) a combination of SEQ ID NOs: 1, 7, 9, and 148 (markers: hsa-miR-1343-3p, hsa-miR-6131, hsa-miR-7641, and hsa-miR-642a-3p);

(2) a combination of SEQ ID NOs: 1, 9, 155, and 172 (markers: hsa-miR-1343-3p, hsa-miR-7641, hsa-miR-3131, and hsa-miR-614);

(3) a combination of SEQ ID NOs: 1, 9, 148, and 155 (markers: hsa-miR-1343-3p, hsa-miR-7641, hsa-miR-642a-3p, and hsa-miR-3131);

(4) a combination of SEQ ID NOs: 1, 155, 172, and 715 (markers: hsa-miR-1343-3p, hsa-miR-3131, hsa-miR-614, and hsa-miR-4448); and (5) a combination of SEQ ID NOs: 1, 155, 164, and 715 (markers: hsa-miR-1343-3p, hsa-miR-3131, hsa-miR-3162-5p, and hsa-miR-4448).

Non-limiting examples of the combination of the polynucleotide consisting of the nucleotide sequence represented by SEQ ID NO: 3 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 3, 7, 9, and 148 (markers: hsa-miR-6515-3p, hsa-miR-6131, hsa-miR-7641, and hsa-miR-642a-3p);

(2) a combination of SEQ ID NOs: 3, 22, 27, and 46 (markers: hsa-miR-6515-3p, hsa-miR-663b, hsa-miR-6729-5p, and hsa-miR-1908-5p);

(3) a combination of SEQ ID NOs: 1, 3, 29, and 155 (markers: hsa-miR-1343-3p, hsa-miR-6515-3p, hsa-miR-4706, and hsa-miR-3131);

(4) a combination of SEQ ID NOs: 1, 3, 151, and 155 (markers: hsa-miR-1343-3p, hsa-miR-6515-3p, hsa-miR-5195-3p, and hsa-miR-3131); and (5) a combination of SEQ ID NOs: 3, 7, 148, and 715 (markers: hsa-miR-6515-3p, hsa-miR-6131, hsa-miR-642a-3p, and hsa-miR-4448).

Non-limiting examples of the combination of the polynucleotide consisting of the nucleotide sequence represented by SEQ ID NO: 7 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 28, 148, and 717 (markers: hsa-miR-6131, hsa-miR-8069, hsa-miR-642a-3p, and hsa-miR-3178);

(2) a combination of SEQ ID NOs: 7, 9, 148, and 186 (markers: hsa-miR-6131, hsa-miR-7641, hsa-miR-642a-3p, and hsa-miR-6085);

(3) a combination of SEQ ID NOs: 7, 148, 172, and 715 (markers: hsa-miR-6131, hsa-miR-642a-3p, hsa-miR-614, and hsa-miR-4448);

(4) a combination of SEQ ID NOs: 7, 9, 148, and 723 (markers: hsa-miR-6131, hsa-miR-7641, hsa-miR-642a-3p, and hsa-miR-4745-5p); and (5) a combination of SEQ ID NOs: 7, 9, 28, and 148 (markers: hsa-miR-6131, hsa-miR-7641, hsa-miR-8069, and hsa-miR-642a-3p).

Non-limiting examples of the combination of the polynucleotide consisting of the nucleotide sequence represented by SEQ ID NO: 9 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 157 (markers: hsa-miR-6131, hsa-miR-7641, hsa-miR-642a-3p, and hsa-miR-4463);

(2) a combination of SEQ ID NOs: 7, 9, 148, and 722 (markers: hsa-miR-6131, hsa-miR-7641, hsa-miR-642a-3p, and hsa-miR-4634);

(3) a combination of SEQ ID NOs: 7, 9, 27, and 148 (markers: hsa-miR-6131, hsa-miR-7641, hsa-miR-6729-5p, and hsa-miR-642a-3p);

(4) a combination of SEQ ID NOs: 7, 9, 148, and 725 (markers: hsa-miR-6131, hsa-miR-7641, hsa-miR-642a-3p, and hsa-miR-6803-5p); and (5) a combination of SEQ ID NOs: 7, 9, 148, and 729 (markers: hsa-miR-6131, hsa-miR-7641, hsa-miR-642a-3p, and hsa-miR-6836-3p).

Non-limiting examples of the combination of the polynucleotide consisting of the nucleotide sequence represented by SEQ ID NO: 22 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 22, and 148 (markers: hsa-miR-6131, hsa-miR-7641, hsa-miR-663b, and hsa-miR-642a-3p);

(2) a combination of SEQ ID NOs: 7, 22, 28, and 148 (markers: hsa-miR-6131, hsa-miR-663b, hsa-miR-8069, and hsa-miR-642a-3p);

(3) a combination of SEQ ID NOs: 7, 22, 148, and 189 (markers: hsa-miR-6131, hsa-miR-663b, hsa-miR-642a-3p, and hsa-miR-328-5p);

(4) a combination of SEQ ID NOs: 2, 7, 22, and 148 (markers: hsa-miR-6726-5p, hsa-miR-6131, hsa-miR-663b, and hsa-miR-642a-3p); and (5) a combination of SEQ ID NOs: 7, 22, 148, and 720 (markers: hsa-miR-6131, hsa-miR-663b, hsa-miR-642a-3p, and hsa-miR-6789-5p).

Non-limiting examples of the combination of the polynucleotide consisting of the nucleotide sequence represented by SEQ ID NO: 38 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 38, and 148 (markers: hsa-miR-6131, hsa-miR-7641, hsa-miR-3622a-5p, and hsa-miR-642a-3p);

(2) a combination of SEQ ID NOs: 7, 38, 51, and 148 (markers: hsa-miR-6131, hsa-miR-3622a-5p, hsa-miR-6781-5p, and hsa-miR-642a-3p);

(3) a combination of SEQ ID NOs: 7, 38, 148, and 718 (markers: hsa-miR-6131, hsa-miR-3622a-5p, hsa-miR-642a-3p, and hsa-miR-4725-3p);

(4) a combination of SEQ ID NOs: 7, 38, 148, and 216 (markers: hsa-miR-6131, hsa-miR-3622a-5p, hsa-miR-642a-3p, and hsa-miR-1238-5p); and (5) a combination of SEQ ID NOs: 7, 38, 148, and 728 (markers: hsa-miR-6131, hsa-miR-3622a-5p, hsa-miR-642a-3p, and hsa-miR-4783-3p).

Non-limiting examples of the combination of the polynucleotide consisting of the nucleotide sequence represented by SEQ ID NO: 44 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 44, and 148 (markers: hsa-miR-6131, hsa-miR-7641, hsa-miR-4665-5p, and hsa-miR-642a-3p);

(2) a combination of SEQ ID NOs: 7, 44, 123, and 148 (markers: hsa-miR-6131, hsa-miR-4665-5p, hsa-miR-4739, and hsa-miR-642a-3p);

(3) a combination of SEQ ID NOs: 7, 38, 44, and 148 (markers: hsa-miR-6131, hsa-miR-3622a-5p, hsa-miR-4665-5p, and hsa-miR-642a-3p);

(4) a combination of SEQ ID NOs: 7, 44, 148, and 723 (markers: hsa-miR-6131, hsa-miR-4665-5p, hsa-miR-642a-3p, and hsa-miR-4745-5p); and (5) a combination of SEQ ID NOs: 7, 44, 48, and 148 (markers: hsa-miR-6131, hsa-miR-4665-5p, hsa-miR-6765-5p, and hsa-miR-642a-3p).

Non-limiting examples of the combination of the polynucleotide consisting of the nucleotide sequence represented by SEQ ID NO: 134 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 134, and 148 (markers: hsa-miR-6131, hsa-miR-7641, hsa-miR-4492, and hsa-miR-642a-3p);

(2) a combination of SEQ ID NOs: 7, 134, 148, and 724 (markers: hsa-miR-6131, hsa-miR-4492, hsa-miR-642a-3p, and hsa-miR-4730);

(3) a combination of SEQ ID NOs: 7, 22, 134, and 148 (markers: hsa-miR-6131, hsa-miR-663b, hsa-miR-4492, and hsa-miR-642a-3p);

(4) a combination of SEQ ID NOs: 7, 134, 148, and 189 (markers: hsa-miR-6131, hsa-miR-4492, hsa-miR-642a-3p, and hsa-miR-328-5p); and (5) a combination of SEQ ID NOs: 7, 134, 148, and 714 (markers: hsa-miR-6131, hsa-miR-4492, hsa-miR-642a-3p, and hsa-miR-6757-5p).

Non-limiting examples of the combination of the polynucleotide consisting of the nucleotide sequence represented by SEQ ID NO: 148 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 726 (markers: hsa-miR-6131, hsa-miR-7641, hsa-miR-642a-3p, and hsa-miR-6798-5p);

(2) a combination of SEQ ID NOs: 7, 9, 148, and 151 (markers: hsa-miR-6131, hsa-miR-7641, hsa-miR-642a-3p, and hsa-miR-5195-3p);

(3) a combination of SEQ ID NOs: 7, 9, 109, and 148 (markers: hsa-miR-6131, hsa-miR-7641, hsa-miR-6826-5p, and hsa-miR-642a-3p);

(4) a combination of SEQ ID NOs: 5, 7, 9, and 148 (markers: hsa-miR-4257, hsa-miR-6131, hsa-miR-7641, and hsa-miR-642a-3p); and (5) a combination of SEQ ID NOs: 7, 9, 76, and 148 (markers: hsa-miR-6131, hsa-miR-7641, hsa-miR-3917, and hsa-miR-642a-3p).

Non-limiting examples of the combination of the polynucleotide consisting of the nucleotide sequence represented by SEQ ID NO: 155 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 155 (markers: hsa-miR-6131, hsa-miR-7641, hsa-miR-642a-3p, and hsa-miR-3131);

(2) a combination of SEQ ID NOs: 7, 38, 148, and 155 (markers: hsa-miR-6131, hsa-miR-3622a-5p, hsa-miR-642a-3p, and hsa-miR-3131);

(3) a combination of SEQ ID NOs: 1, 9, 155, and 167 (markers: hsa-miR-1343-3p, hsa-miR-7641, hsa-miR-3131, and hsa-miR-6724-5p);

(4) a combination of SEQ ID NOs: 1, 3, 155, and 715 (markers: hsa-miR-1343-3p, hsa-miR-6515-3p, hsa-miR-3131, and hsa-miR-4448); and (5) a combination of SEQ ID NOs: 1, 3, 38, and 155 (markers: hsa-miR-1343-3p, hsa-miR-6515-3p, hsa-miR-3622a-5p, and hsa-miR-3131).

Non-limiting examples of the combination of the polynucleotide consisting of the nucleotide sequence represented by SEQ ID NO: 157 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 48, 157, and 714 (markers: hsa-miR-6131, hsa-miR-6765-5p, hsa-miR-4463, and hsa-miR-6757-5p);

(2) a combination of SEQ ID NOs: 7, 38, 148, and 157 (markers: hsa-miR-6131, hsa-miR-3622a-5p, hsa-miR-642a-3p, and hsa-miR-4463);

(3) a combination of SEQ ID NOs: 1, 44, 155, and 157 (markers: hsa-miR-1343-3p, hsa-miR-4665-5p, hsa-miR-3131, and hsa-miR-4463);

(4) a combination of SEQ ID NOs: 7, 76, 157, and 714 (markers: hsa-miR-6131, hsa-miR-3917, hsa-miR-4463, and hsa-miR-6757-5p); and (5) a combination of SEQ ID NOs: 7, 148, 157, and 189 (markers: hsa-miR-6131, hsa-miR-642a-3p, hsa-miR-4463, and hsa-miR-328-5p).

Non-limiting examples of the combination of the polynucleotide consisting of the nucleotide sequence represented by SEQ ID NO: 164 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 164 (markers: hsa-miR-6131, hsa-miR-7641, hsa-miR-642a-3p, and hsa-miR-3162-5p);

(2) a combination of SEQ ID NOs: 7, 76, 164, and 714 (markers: hsa-miR-6131, hsa-miR-3917, hsa-miR-3162-5p, and hsa-miR-6757-5p);

(3) a combination of SEQ ID NOs: 7, 38, 164, and 714 (markers: hsa-miR-6131, hsa-miR-3622a-5p, hsa-miR-3162-5p, and hsa-miR-6757-5p);

(4) a combination of SEQ ID NOs: 7, 38, 148, and 164 (markers: hsa-miR-6131, hsa-miR-3622a-5p, hsa-miR-642a-3p, and hsa-miR-3162-5p); and (5) a combination of SEQ ID NOs: 1, 7, 164, and 714 (markers: hsa-miR-1343-3p, hsa-miR-6131, hsa-miR-3162-5p, and hsa-miR-6757-5p).

Non-limiting examples of the combination of the polynucleotide consisting of the nucleotide sequence represented by SEQ ID NO: 167 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 167 (markers: hsa-miR-6131, hsa-miR-7641, hsa-miR-642a-3p, and hsa-miR-6724-5p);

(2) a combination of SEQ ID NOs: 1, 7, 167, and 714 (markers: hsa-miR-1343-3p, hsa-miR-6131, hsa-miR-6724-5p, and hsa-miR-6757-5p);

(3) a combination of SEQ ID NOs: 7, 151, 167, and 714 (markers: hsa-miR-6131, hsa-miR-5195-3p, hsa-miR-6724-5p, and hsa-miR-6757-5p);

(4) a combination of SEQ ID NOs: 7, 148, 167, and 189 (markers: hsa-miR-6131, hsa-miR-642a-3p, hsa-miR-6724-5p, and hsa-miR-328-5p); and (5) a combination of SEQ ID NOs: 7, 28, 167, and 714 (markers: hsa-miR-6131, hsa-miR-8069, hsa-miR-6724-5p, and hsa-miR-6757-5p).

Non-limiting examples of the combination of the polynucleotide consisting of the nucleotide sequence represented by SEQ ID NO: 172 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 172 (markers: hsa-miR-6131, hsa-miR-7641, hsa-miR-642a-3p, and hsa-miR-614);

(2) a combination of SEQ ID NOs: 7, 150, 172, and 714 (markers: hsa-miR-6131, hsa-miR-4728-5p, hsa-miR-614, and hsa-miR-6757-5p);

(3) a combination of SEQ ID NOs: 7, 172, 714, and 715 (markers: hsa-miR-6131, hsa-miR-614, hsa-miR-6757-5p, and hsa-miR-4448);

(4) a combination of SEQ ID NOs: 7, 38, 155, and 172 (markers: hsa-miR-6131, hsa-miR-3622a-5p, hsa-miR-3131, and hsa-miR-614); and (5) a combination of SEQ ID NOs: 1, 2, 155, and 172 (markers: hsa-miR-1343-3p, hsa-miR-6726-5p, hsa-miR-3131, and hsa-miR-614).

Non-limiting examples of the combination of the polynucleotide consisting of the nucleotide sequence represented by SEQ ID NO: 214 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 214 (markers: hsa-miR-6131, hsa-miR-7641, hsa-miR-642a-3p, and hsa-miR-4723-5p);

(2) a combination of SEQ ID NOs: 7, 148, 189, and 214 (markers: hsa-miR-6131, hsa-miR-642a-3p, hsa-miR-328-5p, and hsa-miR-4723-5p);

(3) a combination of SEQ ID NOs: 2, 7, 148, and 214 (markers: hsa-miR-6726-5p, hsa-miR-6131, hsa-miR-642a-3p, and hsa-miR-4723-5p);

(4) a combination of SEQ ID NOs: 1, 7, 214, and 714 (markers: hsa-miR-1343-3p, hsa-miR-6131, hsa-miR-4723-5p, and hsa-miR-6757-5p); and (5) a combination of SEQ ID NOs: 7, 39, 148, and 214 (markers: hsa-miR-6131, hsa-miR-615-5p, hsa-miR-642a-3p, and hsa-miR-4723-5p).

Non-limiting examples of the combination of the polynucleotide consisting of the nucleotide sequence represented by SEQ ID NO: 714 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 714 (markers: hsa-miR-6131, hsa-miR-7641, hsa-miR-642a-3p, and hsa-miR-6757-5p);

(2) a combination of SEQ ID NOs: 7, 54, 148, and 714 (markers: hsa-miR-6131, hsa-miR-6784-5p, hsa-miR-642a-3p, and hsa-miR-6757-5p);

(3) a combination of SEQ ID NOs: 7, 148, 151, and 714 (markers: hsa-miR-6131, hsa-miR-642a-3p, hsa-miR-5195-3p, and hsa-miR-6757-5p);

(4) a combination of SEQ ID NOs: 7, 38, 148, and 714 (markers: hsa-miR-6131, hsa-miR-3622a-5p, hsa-miR-642a-3p, and hsa-miR-6757-5p); and (5) a combination of SEQ ID NOs: 7, 28, 148, and 714 (markers: hsa-miR-6131, hsa-miR-8069, hsa-miR-642a-3p, and hsa-miR-6757-5p).

Non-limiting examples of the combination of the polynucleotide consisting of the nucleotide sequence represented by SEQ ID NO: 715 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 2, 7, 148, and 715 (markers: hsa-miR-6726-5p, hsa-miR-6131, hsa-miR-642a-3p, and hsa-miR-4448);

(2) a combination of SEQ ID NOs: 7, 9, 148, and 715 (markers: hsa-miR-6131, hsa-miR-7641, hsa-miR-642a-3p, and hsa-miR-4448);

(3) a combination of SEQ ID NOs: 7, 17, 148, and 715 (markers: hsa-miR-6131, hsa-miR-204-3p, hsa-miR-642a-3p, and hsa-miR-4448);

(4) a combination of SEQ ID NOs: 7, 38, 148, and 715 (markers: hsa-miR-6131, hsa-miR-3622a-5p, hsa-miR-642a-3p, and hsa-miR-4448); and (5) a combination of SEQ ID NOs: 7, 148, 715, and 725 (markers: hsa-miR-6131, hsa-miR-642a-3p, hsa-miR-6803-5p, and hsa-miR-4448).

Non-limiting examples of the combination of the polynucleotide consisting of the nucleotide sequence represented by SEQ ID NO: 716 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 716 (markers: hsa-miR-6131, hsa-miR-7641, hsa-miR-642a-3p, and hsa-miR-671-5p);

(2) a combination of SEQ ID NOs: 7, 148, 714, and 716 (markers: hsa-miR-6131, hsa-miR-642a-3p, hsa-miR-6757-5p, and hsa-miR-671-5p);

(3) a combination of SEQ ID NOs: 2, 7, 148, and 716 (markers: hsa-miR-6726-5p, hsa-miR-6131, hsa-miR-642a-3p, and hsa-miR-671-5p);

(4) a combination of SEQ ID NOs: 7, 38, 148, and 716 (markers: hsa-miR-6131, hsa-miR-3622a-5p, hsa-miR-642a-3p, and hsa-miR-671-5p); and (5) a combination of SEQ ID NOs: 7, 148, 715, and 716 (markers: hsa-miR-6131, hsa-miR-642a-3p, hsa-miR-4448, and hsa-miR-671-5p).

Non-limiting examples of the combination of the polynucleotide consisting of the nucleotide sequence represented by SEQ ID NO: 717 or a complementary sequence thereof with polynucleotides consisting of nucleotide sequences represented by SEQ ID NOs of three polynucleotides selected from the cancer type-specific polynucleotide group 1 or complementary sequences thereof are further listed below.

(1) a combination of SEQ ID NOs: 7, 9, 148, and 717 (markers: hsa-miR-6131, hsa-miR-7641, hsa-miR-642a-3p, and hsa-miR-3178);

(2) a combination of SEQ ID NOs: 7, 38, 148, and 717 (markers: hsa-miR-6131, hsa-miR-3622a-5p, hsa-miR-642a-3p, and hsa-miR-3178);

(3) a combination of SEQ ID NOs: 7, 27, 148, and 717 (markers: hsa-miR-6131, hsa-miR-6729-5p, hsa-miR-642a-3p, and hsa-miR-3178);

(4) a combination of SEQ ID NOs: 7, 44, 148, and 717 (markers: hsa-miR-6131, hsa-miR-4665-5p, hsa-miR-642a-3p, and hsa-miR-3178); and (5) a combination of SEQ ID NOs: 7, 148, 715, and 717 (markers: hsa-miR-6131, hsa-miR-642a-3p, hsa-miR-4448, and hsa-miR-3178).

The kit or the device of the present invention may also comprise a polynucleotide that is already known or that will be found in the future, to enable detection of liver cancer, in addition to the polynucleotide(s) (which can include variant(s), fragment(s), and derivative(s)) according to the present invention described above.

The kit of the present invention may also comprise an antibody for measuring a marker for liver cancer examination known in the art, such as AFP, CEA, CA19-9 and PIVKA-II, in addition to the polynucleotide(s) according to the present invention as described above.

These polynucleotides contained in the kit of the present invention may be packaged in different containers either individually or in any combination.

The kit of the present invention may comprise a kit for extracting a nucleic acid (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring a target nucleic acid through the use of hybridization using this array.

The kit or the device of the present invention comprises nucleic acids capable of specifically binding to the polynucleotides of at least one or more, preferably at least two or more, more preferably at least three or more, most preferably at least five or more to all of the liver cancer marker miRNAs, respectively, of the group 1 described above. The kit or the device of the present invention may optionally further comprise nucleic acids capable of specifically binding to the polynucleotides of at least one or more, preferably at least two or more, more preferably at least three or more, most preferably at least five or more to all of the liver cancer marker miRNAs, respectively, of the group 2 described above. The kit or the device of the present invention may optionally further comprise nucleic acids capable of specifically binding to the polynucleotides of at least one or more, preferably at least two or more, more preferably at least three or more, most preferably at least five or more to all of the liver cancer marker miRNAs, respectively, of the group 3 described above.

The kit or the device of the present invention can be used for detecting liver cancer as described in Section 4 below.

4. Method for Detecting Liver Cancer

The present invention further provides a method for detecting liver cancer, comprising using the kit or the device of the present invention (comprising the above-mentioned nucleic acid(s) that can be used in the present invention) described in Section 3 above to measure expression level(s) of one or more liver cancer-derived gene(s) being an expression level of liver cancer-derived gene(s) selected from the following group: miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR- 6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p; optionally an expression level of liver cancer-derived gene(s) selected from the following group: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a; and optionally an expression level of liver cancer-derived gene(s) selected from miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090 in a sample in vitro, further comparing, for example, the expression level(s) of the aforementioned gene(s) in the sample (e.g., blood, serum, or plasma) collected from a subject suspected of having liver cancer with a control expression level in the sample collected from a healthy subject (including a non-liver cancer patient), and evaluating the subject as having liver cancer when the expression level(s) of the target nucleic acid(s) is statistically significantly different between the samples.

This method of the present invention enables a limitedly invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored.

The method for extracting the liver cancer-derived gene from the sample such as blood, serum, or plasma according to the present invention is particularly preferably prepared by the addition of a reagent for RNA extraction in 3D-Gene® RNA extraction reagent from liquid sample kit (Toray Industries, Inc.). A general acidic phenol method (acid guanidinium-phenol-chloroform (AGPC)) may be used, or Trizol® (Life Technologies Corp.) may be used. The liver cancer-derived gene may be prepared by the addition of a reagent for RNA extraction containing acidic phenol, such as Trizol (Life Technologies Corp.) or Isogen (Nippon Gene Co., Ltd.). Alternatively, a kit such as miRNeasy® Mini Kit (Qiagen N.V.) can be used, though the method is not limited thereto.

The present invention also provides use of the kit or the device of the present invention for detecting in vitro an expression product of a liver cancer-derived miRNA gene in a sample derived from a subject.

In the method of the present invention, the kit or device described above comprising a single polynucleotide or any possible combination of the polynucleotides that can be used in the present invention as described above is used.

In the detection or (genetic) diagnosis of liver cancer according to the present invention, each polynucleotide contained in the kit or the device of the present invention can be used as a probe or a primer. In the case of using the polynucleotide as a primer, TaqMan® MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine of the subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of liver cancer or the detection of the presence or absence of liver cancer. Specifically, the detection of liver cancer using the kit or the device can be performed by detecting in vitro an expression level of a gene using the nucleic acid probe or the primer contained in the kit or the device in a sample such as blood, serum, plasma, or urine from a subject suspected of having liver cancer. The subject suspected of having liver cancer can be evaluated as having liver cancer when the expression level of a target miRNA marker measured using polynucleotide(s) (including variant(s), fragment(s), and derivative(s) thereof) consisting of a nucleotide sequence represented by at least one or more of SEQ ID NOs: 1 to 167 and 714 to 729 or a complementary sequence thereof, optionally a nucleotide sequence represented by one or more of SEQ ID NOs: 168 to 183 or a complementary sequence thereof, and optionally a nucleotide sequence represented by one or more of SEQ ID NOs: 184 to 224 or a complementary sequence thereof in the sample such as blood, serum, plasma, or urine of the subject is statistically significantly different compared with the expression level thereof in the sample such as blood, serum, or plasma, or urine of a healthy subject.

The method of the present invention can be combined with a diagnostic imaging method such as ultrasonography, CT scanning, MRI scanning, or angiography examination. The method of the present invention is capable of specifically detecting liver cancer and can substantially discriminate liver cancer from the other cancers.

The method for detecting the absence of an expression product of a liver cancer-derived gene or the presence of the expression product of a liver cancer-derived gene in a sample using the kit or the device of the present invention comprises collecting a body fluid such as blood, serum, plasma, or urine of a subject, and measuring the expression level of the target gene contained therein using one or more polynucleotide(s) (including variant(s), fragment(s), or derivative(s)) selected from the polynucleotide group of the present invention, to evaluate the presence or absence of liver cancer or to detect liver cancer. Using the method for detecting liver cancer according to the present invention, for example, the presence or absence of amelioration of the disease or the degree of amelioration thereof in a liver cancer patient when a therapeutic drug is administered to the patient for amelioration of the disease can be also evaluated or diagnosed.

The method of the present invention may comprise, for example, the following steps (a), (b), and (c):

(a) a step of contacting in vitro a sample derived from a subject with a polynucleotide in the kit or the device of the present invention;

(b) a step of measuring an expression level of the target nucleic acid in the sample using the polynucleotide as a nucleic acid probe or a primer; and (c) a step of evaluating the presence or absence of liver cancer (cells) in the subject on the basis of a measurement result obtained in the step (b).

Specifically, the present invention provides a method for detecting liver cancer, comprising measuring an expression level of a target nucleic acid in a sample of a subject using nucleic acid(s) capable of specifically binding to at least one or more (preferably at least two or more) polynucleotide(s) selected from the group consisting of miR-1343-3p, miR-6726-5p, miR-6515-3p, miR-4651, miR-4257, miR-3188, miR-6131, miR-6766-3p, miR-7641, miR-1249, miR-3679-3p, miR-6787-5p, miR-4454, miR-3135b, miR-6765-3p, miR-7975, miR-204-3p, miR-7977, miR-7110-5p, miR-6717-5p, miR-6870-5p, miR-663b, miR-6875-5p, miR-8072, miR-6816-5p, miR-4281, miR-6729-5p, miR-8069, miR-4706, miR-7108-5p, miR-4433b-3p, miR-6893-5p, miR-6857-5p, miR-1227-5p, miR-6741-5p, miR-451a, miR-8063, miR-3622a-5p, miR-615-5p, miR-128-1-5p, miR-6825-5p, miR-1260b, miR-4433-3p, miR-4665-5p, miR-7845-5p, miR-1908-5p, miR-6840-3p, miR-6765-5p, miR-296-5p, miR-3675-3p, miR-6781-5p, miR-423-5p, miR-3663-3p, miR-6784-5p, miR-6749-5p, miR-1231, miR-4746-3p, miR-6780b-5p, miR-4758-5p, miR-3679-5p, miR-3184-5p, miR-6125, miR-6721-5p, miR-6791-5p, miR-3185, miR-1260a, miR-3197, miR-6845-5p, miR-6887-5p, miR-6738-5p, miR-6872-3p, miR-4497, miR-1229-5p, miR-6820-5p, miR-6777-5p, miR-3917, miR-5787, miR-4286, miR-6877-5p, miR-1225-3p, miR-6088, miR-6800-5p, miR-1246, miR-4467, miR-4419b, miR-1914-3p, miR-4632-5p, miR-1915-5p, miR-3940-5p, miR-1185-2-3p, miR-6746-5p, miR-5001-5p, miR-1228-5p, miR-5572, miR-4327, miR-4638-5p, miR-6799-5p, miR-6861-5p, miR-6727-5p, miR-4513, miR-6805-3p, miR-6808-5p, miR-4449, miR-1199-5p, miR-1275, miR-4792, miR-4443, miR-6891-5p, miR-6826-5p, miR-6807-5p, miR-7150, miR-4534, miR-4476, miR-4649-5p, miR-4525, miR-1915-3p, miR-4516, miR-4417, miR-642b-3p, miR-3141, miR-5100, miR-6848-5p, miR-4739, miR-4459, miR-1237-5p, miR-296-3p, miR-4665-3p, miR-6786-5p, miR-4258, miR-6510-5p, miR-1343-5p, miR-1247-3p, miR-6805-5p, miR-4492, miR-1469, miR-1268b, miR-6858-5p, miR-3937, miR-939-5p, miR-3656, miR-744-5p, miR-4687-3p, miR-4763-3p, miR-3620-5p, miR-3195, miR-6842-5p, miR-4707-5p, miR-642a-3p, miR-7113-3p, miR-4728-5p, miR-5195-3p, miR-1185-1-3p, miR-6774-5p, miR-8059, miR-3131, miR-7847-3p, miR-4463, miR-128-2-5p, miR-4508, miR-6806-5p, miR-7111-5p, miR-6782-5p, miR-4734, miR-3162-5p, miR-887-3p, miR-6752-5p, miR-6724-5p, miR-6757-5p, miR-4448, miR-671-5p, miR-3178, miR-4725-3p, miR-940, miR-6789-5p, miR-4484, miR-4634, miR-4745-5p, miR-4730, miR-6803-5p, miR-6798-5p, miR-3648, miR-4783-3p and miR-6836-3p, and evaluating in vitro whether or not the subject has liver cancer using the measured expression level and a control expression level of a healthy subject measured in the same way as above.

The term "evaluation" used herein is evaluation support based on results of in vitro examination, not physician's judgment.

As described above, in a preferred embodiment of the method of the present invention, specifically, miR-1343-3p is hsa-miR-1343-3p, miR-6726-5p is hsa-miR-6726-5p, miR-6515-3p is hsa-miR-6515-3p, miR-4651 is hsa-miR-4651, miR-4257 is hsa-miR-4257, miR-3188 is hsa-miR-3188, miR-6131 is hsa-miR-6131, miR-6766-3p is hsa-miR-6766-3p, miR-7641 is hsa-miR-7641, miR-1249 is hsa-miR-1249, miR-3679-3p is hsa-miR-3679-3p, miR-6787-5p is hsa-miR-6787-5p, miR-4454 is hsa-miR-4454, miR-3135b is hsa-miR-3135b, miR-6765-3p is hsa-miR-6765-3p, miR-7975 is hsa-miR-7975, miR-204-3p is hsa-miR-204-3p, miR-7977 is hsa-miR-7977, miR-7110-5p is hsa-miR-7110-5p, miR-6717-5p is hsa-miR-6717-5p, miR-6870-5p is hsa-miR-6870-5p, miR-663b is hsa-miR-663b, miR-6875-5p is hsa-miR-6875-5p, miR-8072 is hsa-miR-8072, miR-6816-5p is hsa-miR-6816-5p, miR-4281 is hsa-miR-4281, miR-6729-5p is hsa-miR-6729-5p, miR-8069 is hsa-miR-8069, miR-4706 is hsa-miR-4706, miR-7108-5p is hsa-miR-7108-5p, miR-4433b-3p is hsa-miR-4433b-3p, miR-6893-5p is hsa-miR-6893-5p, miR-6857-5p is hsa-miR-6857-5p, miR-1227-5p is hsa-miR-1227-5p, miR-6741-5p is hsa-miR-6741-5p, miR-451a is hsa-miR-451a, miR-8063 is hsa-miR-8063, miR-3622a-5p is hsa-miR-3622a-5p, miR-615-5p is hsa-miR-615-5p, miR-128-1-5p is hsa-miR-128-1-5p, miR-6825-5p is hsa-miR-6825-5p, miR-1260b is hsa-miR-1260b, miR-4433-3p is hsa-miR-4433-3p, miR-4665-5p is hsa-miR-4665-5p, miR-7845-5p is hsa-miR-7845-5p, miR-1908-5p is hsa-miR-1908-5p, miR-6840-3p is hsa-miR-6840-3p, miR-6765-5p is hsa-miR-6765-5p, miR-296-5p is hsa-miR-296-5p, miR-3675-3p is hsa-miR-3675-3p, miR-6781-5p is hsa-miR-6781-5p, miR-423-5p is hsa-miR-423-5p, miR-3663-3p is hsa-miR-3663-3p, miR-6784-5p is hsa-miR-6784-5p, miR-6749-5p is hsa-miR-6749-5p, miR-1231 is hsa-miR-1231, miR-4746-3p is hsa-miR-4746-3p, miR-6780b-5p is hsa-miR-6780b-5p, miR-4758-5p is hsa-miR-4758-5p, miR-3679-5p is hsa-miR-3679-5p, miR-3184-5p is hsa-miR-3184-5p, miR-6125 is hsa-miR-6125, miR-6721-5p is hsa-miR-6721-5p, miR-6791-5p is hsa-miR-6791-5p, miR-3185 is hsa-miR-3185, miR-1260a is hsa-miR-1260a, miR-3197 is hsa-miR-3197, miR-6845-5p is hsa-miR-6845-5p, miR-6887-5p is hsa-miR-6887-5p, miR-6738-5p is hsa-miR-6738-5p, miR-6872-3p is hsa-miR-6872-3p, miR-4497 is hsa-miR-4497, miR-1229-5p is hsa-miR-1229-5p, miR-6820-5p is hsa-miR-6820-5p, miR-6777-5p is hsa-miR-6777-5p, miR-3917 is hsa-miR-3917, miR-5787 is hsa-miR-5787, miR-4286 is hsa-miR-4286, miR-6877-5p is hsa-miR-6877-5p, miR-1225-3p is hsa-miR-1225-3p, miR-6088 is hsa-miR-6088, miR-6800-5p is hsa-miR-6800-5p, miR-1246 is hsa-miR-1246, miR-4467 is hsa-miR-4467, miR-4419b is hsa-miR-4419b, miR-1914-3p is hsa-miR-1914-3p, miR-4632-5p is hsa-miR-4632-5p, miR-1915-5p is hsa-miR-1915-5p, miR-3940-5p is hsa-miR-3940-5p, miR-1185-2-3p is hsa-miR-1185-2-3p, miR-6746-5p is hsa-miR-6746-5p, miR-5001-5p is hsa-miR-5001-5p, miR-1228-5p is hsa-miR-1228-5p, miR-5572 is hsa-miR-5572, miR-4327 is hsa-miR-4327, miR-4638-5p is hsa-miR-4638-5p, miR-6799-5p is hsa-miR-6799-5p, miR-6861-5p is hsa-miR-6861-5p, miR-6727-5p is hsa-miR-6727-5p, miR-4513 is hsa-miR-4513, miR-6805-3p is hsa-miR-6805-3p, miR-6808-5p is hsa-miR-6808-5p, miR-4449 is hsa-miR-4449, miR-1199-5p is hsa-miR-1199-5p, miR-1275 is hsa-miR-1275, miR-4792 is hsa-miR-4792, miR-4443 is hsa-miR-4443, miR-6891-5p is hsa-miR-6891-5p, miR-6826-5p is hsa-miR-6826-5p, miR-6807-5p is hsa-miR-6807-5p, miR- 7150 is hsa-miR-7150, miR-4534 is hsa-miR-4534, miR-4476 is hsa-miR-4476, miR-4649-5p is hsa-miR-4649-5p, miR-4525 is hsa-miR-4525, miR-1915-3p is hsa-miR-1915-3p, miR-4516 is hsa-miR-4516, miR-4417 is hsa-miR-4417, miR-642b-3p is hsa-miR-642b-3p, miR-3141 is hsa-miR-3141, miR-5100 is hsa-miR-5100, miR-6848-5p is hsa-miR-6848-5p, miR-4739 is hsa-miR-4739, miR-4459 is hsa-miR-4459, miR-1237-5p is hsa-miR-1237-5p, miR-296-3p is hsa-miR-296-3p, miR-4665-3p is hsa-miR-4665-3p, miR-6786-5p is hsa-miR-6786-5p, miR-4258 is hsa-miR-4258, miR-6510-5p is hsa-miR-6510-5p, miR-1343-5p is hsa-miR-1343-5p, miR-1247-3p is hsa-miR-1247-3p, miR-6805-5p is hsa-miR-6805-5p, miR-4492 is hsa-miR-4492, miR-1469 is hsa-miR-1469, miR-1268b is hsa-miR-1268b, miR-6858-5p is hsa-miR-6858-5p, miR-3937 is hsa-miR-3937, miR-939-5p is hsa-miR-939-5p, miR-3656 is hsa-miR-3656, miR-744-5p is hsa-miR-744-5p, miR-4687-3p is hsa-miR-4687-3p, miR-4763-3p is hsa-miR-4763-3p, miR-3620-5p is hsa-miR-3620-5p, miR-3195 is hsa-miR-3195, miR-6842-5p is hsa-miR-6842-5p, miR-4707-5p is hsa-miR-4707-5p, miR-642a-3p is hsa-miR-642a-3p, miR-7113-3p is hsa-miR-7113-3p, miR-4728-5p is hsa-miR-4728-5p, miR-5195-3p is hsa-miR-5195-3p, miR-1185-1-3p is hsa-miR-1185-1-3p, miR-6774-5p is hsa-miR-6774-5p, miR-8059 is hsa-miR-8059, miR-3131 is hsa-miR-3131, miR-7847-3p is hsa-miR-7847-3p, miR-4463 is hsa-miR-4463, miR-128-2-5p is hsa-miR-128-2-5p, miR-4508 is hsa-miR-4508, miR-6806-5p is hsa-miR-6806-5p, miR-7111-5p is hsa-miR-7111-5p, miR-6782-5p is hsa-miR-6782-5p, miR-4734 is hsa-miR-4734, miR-3162-5p is hsa-miR-3162-5p, miR-887-3p is hsa-miR-887-3p, miR-6752-5p is hsa-miR-6752-5p, miR-6724-5p is hsa-miR-6724-5p, miR-6757-5p is hsa-miR-6757-5p, miR-4448 is hsa-miR-4448, miR-671-5p is hsa-miR-671-5p, miR-3178 is hsa-miR-3178, miR-4725-3p is hsa-miR-4725-3p, miR-940 is hsa-miR-940, miR-6789-5p is hsa-miR-6789-5p, miR-4484 is hsa-miR-4484, miR-4634 is hsa-miR-4634, miR-4745-5p is hsa-miR-4745-5p, miR-4730 is hsa-miR-4730, miR-6803-5p is hsa-miR-6803-5p, miR-6798-5p is hsa-miR-6798-5p, miR-3648 is hsa-miR-3648, miR-4783-3p is hsa-miR-4783-3p, and miR-6836-3p is hsa-miR-6836-3p.

In a preferred embodiment of the method of the present invention, specifically, the nucleic acid (specifically, probe or primer) is selected from the group consisting of the following polynucleotides (a) to (e):
(a) a polynucleotide consisting of a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 167 and 714 to 729,
(c) a polynucleotide consisting of a nucleotide sequence complementary to a nucleotide sequence represented by any of SEQ ID NOs: 1 to 167 and 714 to 729 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 167 and 714 to 729 or a nucleotide sequence derived from the nucleotide sequence by the replacement of u with t, and
(e) a polynucleotide hybridizing under stringent conditions to any of the polynucleotides (a) to (d).

In the method of the present invention, nucleic acid(s) capable of specifically binding to at least one or more polynucleotide(s) selected from the followings: miR-23b-3p, miR-23a-3p, miR-625-3p, miR-1228-3p, miR-614, miR-1913, miR-92a-2-5p, miR-187-5p, miR-16-5p, miR-92b-3p, miR-150-3p, miR-564, miR-125a-3p, miR-92b-5p, miR-92a-3p and miR-663a may be further used.

In a preferred embodiment, as for such an additional nucleic acid, specifically, miR-23b-3p is hsa-miR-23b-3p, miR-23a-3p is hsa-miR-23a-3p, miR-625-3p is hsa-miR-625-3p, miR-1228-3p is hsa-miR-1228-3p, miR-614 is hsa-miR-614, miR-1913 is hsa-miR-1913, miR-92a-2-5p is hsa-miR-92a-2-5p, miR-187-5p is hsa-miR-187-5p, miR-16-5p is hsa-miR-16-5p, miR-92b-3p is hsa-miR-92b-3p, miR-150-3p is hsa-miR-150-3p, miR-564 is hsa-miR-564, miR-125a-3p is hsa-miR-125a-3p, miR-92b-5p is hsa-miR-92b-5p, miR-92a-3p is hsa-miR-92a-3p, and miR-663a is hsa-miR-663a.

In a preferred embodiment, such a nucleic acid is specifically selected from the group consisting of the following polynucleotides (f) to (j):
(f) a polynucleotide consisting of a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 168 to 183,
(h) a polynucleotide consisting of a nucleotide sequence complementary to a nucleotide sequence represented by any of SEQ ID NOs: 168 to 183 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 168 to 183 or a nucleotide sequence derived from the nucleotide sequence by the replacement of u with t, and
(j) a polynucleotide hybridizing under stringent conditions to any of the polynucleotides (f) to (i).

In the method of the present invention, a nucleic acid capable of specifically binding to at least one or more polynucleotide(s) selected from the group consisting of miR-4688, miR-4648, miR-6085, miR-6126, miR-6880-5p, miR-328-5p, miR-6768-5p, miR-3180, miR-6087, miR-1273g-3p, miR-1225-5p, miR-3196, miR-4695-5p, miR-6732-5p, miR-638, miR-6813-5p, miR-665, miR-486-3p, miR-4466, miR-30c-1-3p, miR-3621, miR-6743-5p, miR-4298, miR-4741, miR-3619-3p, miR-6824-5p, miR-5698, miR-371a-5p, miR-4488, miR-1233-5p, miR-4723-5p, miR-24-3p, miR-1238-5p, miR-4442, miR-3928-3p, miR-6716-5p, miR-6089, miR-6124, miR-6778-5p, miR-557 and miR-6090 may be further used.

In a preferred embodiment, as for such an additional nucleic acid, specifically, miR-4688 is hsa-miR-4688, miR-4648 is hsa-miR-4648, miR-6085 is hsa-miR-6085, miR-6126 is hsa-miR-6126, miR-6880-5p is hsa-miR-6880-5p, miR-328-5p is hsa-miR-328-5p, miR-6768-5p is hsa-miR-6768-5p, miR-3180 is hsa-miR-3180, miR-6087 is hsa-miR-6087, miR-1273g-3p is hsa-miR-1273g-3p, miR-1225-5p is hsa-miR-1225-5p, miR-3196 is hsa-miR-3196, miR-4695-5p is hsa-miR-4695-5p, miR-6732-5p is hsa-miR-6732-5p, miR-638 is hsa-miR-638, miR-6813-5p is hsa-miR-6813-5p, miR-665 is hsa-miR-665, miR-486-3p is hsa-miR-486-3p, miR-4466 is hsa-miR-4466, miR-30c-1-3p is hsa-miR-30c-1-3p, miR-3621 is hsa-miR-3621, miR-6743-5p is hsamiR-6743-5p, miR-4298 is hsa-miR-4298, miR-4741 is hsa-miR-4741, miR-3619-3p is hsa-miR-3619-3p, miR-6824-5p is hsa-miR-6824-5p, miR-5698 is hsa-miR-5698, miR-371a-5p is hsa-miR-371a-5p, miR-4488 is hsa-miR-4488, miR-1233-5p is hsa-miR-1233-5p, miR-4723-5p is hsa-miR-4723-5p, miR-24-3p is hsa-miR-24-3p, miR-1238-5p is hsa-miR-1238-5p, miR-4442 is hsa-miR-4442, miR-3928-3p is hsa-miR-3928-3p, miR-6716-5p is hsa-miR-6716-5p, miR-6089 is hsa-miR-6089, miR-6124 is hsa-miR-6124, miR-6778-5p is hsa-miR-6778-5p, miR-557 is hsa-miR-557, and miR-6090 is hsa-miR-6090.

In a preferred embodiment, such a nucleic acid is specifically a polynucleotide selected from the group consisting of the following polynucleotides (k) to (o):

(k) a polynucleotide consisting of a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 184 to 224, (m) a polynucleotide consisting of a nucleotide sequence complementary to a nucleotide sequence represented by any of SEQ ID NOs: 184 to 224 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 184 to 224 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from a living tissue (preferably a liver tissue) or a body fluid such as blood, serum, plasma, or urine of the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse and a rat without any limitation, and is preferably a human.

The steps of the method of the present invention can be changed according to the type of the sample to be assayed.

In the case of using RNA as an analyte, the detection of liver cancer (cells) may comprise, for example, the following steps (a), (b), and (c):

(a) a step of binding RNA prepared from the sample of a subject or a complementary polynucleotide (cDNA) transcribed therefrom to a polynucleotide in the kit or the device of the present invention;

(b) a step of measuring the sample-derived RNA or the cDNA synthesized from the RNA, bound with the polynucleotide by hybridization using the polynucleotide as a nucleic acid probe or by quantitative RT-PCR using the polynucleotide as a primer; and (c) a step of evaluating the presence or absence of liver cancer (or liver cancer-derived gene expression) on the basis of the measurement results of the step (b).

For example, various hybridization methods can be used for detecting, examining, evaluating, or diagnosing liver cancer (or liver cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which comprises labeling the nucleic acid probe (a complementary strand) with a radioisotope ($^{32}$P, $^{33}$P, $^{35}$S, etc.), a fluorescent material, or the like, hybridizing the labeled product with the living tissue-derived RNA from the subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNA from the living tissue-derived RNA of the subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention are attached to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of them. 3D-Gene® Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probes using an image detector (examples thereof can include Typhoon 9410 (GE Healthcare Japan Corp.) and 3D-Gene® scanner (Toray Industries, Inc.)).

The "stringent conditions" used herein are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by hybridization and subsequent washing conditions. Examples of the hybridization conditions include, but not limited to, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3 to 10×SSC and 0.1 to 1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state even with a target plus strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include treatment for approximately 15 seconds to 1 minute at 5 to 10° C. plus a Tm value calculated from the sequence of the primer, using a PCR buffer with composition such as 10 mM Tris-HCL (pH 8.3), 50 mM KCL, and 1 to 2 mM MgCl$_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan® MicroRNA Assays (Life Technologies Corp.); LNA®-based MicroRNA PCR (Exiqon); or Ncode® miRNA qRT-PCT kit (Invitrogen Corp.) may be used.

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a liver cancer patient and a sample derived from a healthy subject as supervising samples, and determining or evaluating the presence and/or absence of the liver cancer-derived gene in the sample.

Specifically, the present invention further provides the method comprising: a first step of measuring in vitro an expression level of a target gene (target nucleic acids) in multiple samples known to determine or evaluate the presence or absence of the liver cancer-derived gene in the samples, using the polynucleotide, the kit, or the device (e.g., chip) for detection of the present invention, or a combination thereof; a second step of constructing a discriminant with the measurement values of the expression level of the target gene obtained in the first step as supervising samples; a third step of measuring in vitro an expression level of the target gene in a sample derived from a subject in the same way as in the first step; and a fourth step of substituting the measurement value of the expression level of the target gene obtained in the third step into the discriminant obtained in the second step, and determining or evaluating the presence or absence of the liver cancer-derived gene in the sample on the basis of the results obtained from the discriminant, wherein the target gene can be detected using the polynucleotide or using a polynucleotide for detection contained in the kit or the device (e.g., chip). In this context, the discriminant can be prepared by use of Fisher's linear discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In this formula, x represents an explanatory variable, w represents a coefficient of the explanatory variable, and $w_0$ represents a constant term.

$$f(x) = w_0 + \sum_{i=1}^{n} w_i x_i \quad \text{Formula 1}$$

Values obtained from the discriminant are referred to as discriminant scores. The measurement values of a newly offered data set can be substituted as explanatory variables into the discriminant to determine clusters on the basis of the signs of the discriminant scores.

The Fisher's linear discriminant analysis, one type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer., 2002). In the Fisher's linear discriminant analysis, direction w of projection is determined so as to maximize Formula 2. In this formula, μ represents an average input, ng represents the number of data associated with class g, and μg represents an average input of the data associated with class g. The numerator and the denominator are interclass variance and intraclass variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i: y_i=g} (w^T x_i - w^T \mu_g)(w^T x_i - w^T \mu_g)}$$ Formula 2

$$\text{subject to } \mu = \sum_{i=1}^{n} \frac{x_i}{n}, \mu_g = \sum_{i: u_i=g}^{n} \frac{x_i}{n_g}$$

The Mahalanobis' distance is calculated according to Formula 3 in consideration of data correlation and can be used as nonlinear discriminant analysis for determining an associated cluster, based on a closer Mahalanobis' distance from each cluster. In this Formula 3, μ represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x-\mu)^t S^{-1}(x-\mu)\}^{\frac{1}{2}}$$ Formula 3

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be substituted as explanatory variables into the discriminant to determine classes. In this respect, the result of the discriminant analysis may be classes, may be a probability of data to be classified into correct classes, or may be the distance from the hyperplane. In SVM, a method of nonlinearly converting a feature vector to a high dimension and performing linear discriminant analysis in the space is known as a method for tackling nonlinear problems. A formula in which an inner product of two factors in a nonlinearly mapped space is expressed only by inputs in their original spaces is called kernel. Examples of the kernel can include a linear kernel, a RBF (radial basis function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, comprises preparing a hyperplane by supervising with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a liver cancer patient group and a healthy subject group. For example, liver tissue examination can be used for confirming each subject either as a liver cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a$$ Formula 4 subject to $y^T a = 0, 0 \leq a_i \leq C, i = 1, \ldots, l,$

Formula 5 is a finally obtained discriminant, and a group to which the data point is associated can be determined on the basis of the sign of a value obtained according to the discriminant. In this formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right)$$ Formula 5

For example, a RBF kernel defined by Formula 6 can be used as the kernel function. In this formula, x represents a support vector, and γ represents a kernel parameter for adjusting the complexity of the hyperplane.

$$K(x_i, x_j) = \exp(-r\|x_i - x_j\|^2), r < 0$$ Formula 6

In addition, an approach such as neural network, k-nearest neighbor algorithms, decision trees, or logistic regression analysis can be selected as a method for determining or evaluating the presence and/or absence of expression of a liver cancer-derived target gene in a sample derived from a subject, or for evaluating the expression level thereof by comparison with a control derived from a healthy subject.

The method of the present invention can comprise, for example, the following steps (a), (b), and (c):

(a) measuring an expression level of a target gene in tissues containing liver cancer-derived genes derived from liver cancer patients and/or samples that are already known to contain no liver cancer-derived gene derived from healthy subjects, using the polynucleotide, the kit, or the device (e.g., DNA chip) for detection according to the present invention;

(b) preparing the discriminants of Formulae 1 to 3, 5, and 6 described above from the measurement values of the expression level measured in the step (a); and (c) measuring an expression level of the target gene in a sample derived from a subject using the polynucleotide, the kit, or the device (e.g., DNA chip) for detection according to the present invention, substituting the obtained measurement value into the discriminants prepared in the step (b), and determining or evaluating the presence and/or absence of the liver cancer-derived target gene in the sample, or evaluating the expression level thereof by comparison with a healthy subject-derived control, on the basis of the obtained results. In this context, in the discriminants of Formulae 1 to 3, 5, and 6, x represents an explanatory variable and includes a value obtained by measuring a polynucleotide selected from the polynucleotides described above in the Section 2, or a fragment thereof, etc. Specifically, the explanatory variable for discriminating a liver cancer patient from a healthy subject according to the present invention is a gene expression level selected from, for example, the following expression levels (1) to (3):

(1) a gene expression level in the serum of a pancreatic cancer patient or a healthy subject measured by any of DNA comprising 15 or more consecutive nucleotides in a nucleotide sequence represented by any of SEQ ID NOs: 1 to 167 and 714 to 729 or a complementary sequence thereof, (2) a gene expression level in the serum of a pancreatic cancer patient or a healthy subject measured by any of DNA comprising 15 or more consecutive nucleotides in a nucleotide sequence represented by any of SEQ ID NOs: 168 to 183 or a complementary sequence thereof, and (3) a gene expression level in the serum of a liver cancer patient or a healthy subject measured by any DNA comprising 15 or more consecutive nucleotides in a nucleotide sequence represented by any of SEQ ID NOs: 184 to 224 or a complementary sequence thereof.

As described above, for the method for determining or evaluating the presence and/or absence of a liver cancer-derived gene in a sample derived from a subject, the preparation of a discriminant requires a discriminant prepared in a training cohort. For enhancing the discriminant accuracy of the discriminant, it is necessary for the discriminant to use genes that show clear difference between two groups in the training cohort when preparing the discriminant.

Each gene that is used for an explanatory variable in a discriminant is preferably determined as follows. First, comprehensive gene expression levels of a liver cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a liver cancer patient group and gene expression levels of a healthy subject group may be calculated to select a gene that is used for an explanatory variable in a discriminant. Alternatively, ROC curves may be prepared using gene expression levels of a liver cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level of P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). A gene expression level of another independent liver cancer patient or healthy subject is substituted as an explanatory variable into this discriminant to calculate discrimination results of the group to which this independent liver cancer patient or healthy subject belongs. Specifically, the found gene set for diagnosis and the discriminant constructed using the gene set for diagnosis can be evaluated in an independent sample cohort to find a more universal gene set for diagnosis capable of detecting liver cancer and a more universal method for discriminating liver cancer.

Split-sample method is preferably used for evaluating the discriminant performance (generality) of the discriminant. Specifically, a data set is divided into a training cohort and a validation cohort, and gene selection by a statistical test and discriminant preparation are performed using the training cohort. Accuracy, sensitivity, and specificity are calculated using results of discriminating a validation cohort according to the discriminant and a true group to which the validation cohort associates, to evaluate the discriminant performance. On the other hand, instead of dividing a data set, the gene selection by a statistical test and discriminant preparation may be performed using all of samples, and accuracy, sensitivity, and specificity can be calculated by the discriminant analysis using a newly prepared samples cohort for evaluation of the discriminant performance.

The present invention provides a polynucleotide for detection or for disease diagnosis useful in the diagnosis and treatment of liver cancer, a method for detecting liver cancer using the polynucleotide, and a kit and a device for the detection of liver cancer, comprising the polynucleotide. Particularly, in order to select a gene for diagnosis and prepare a discriminant so as to exhibit accuracy beyond a liver cancer diagnosis method using an existing tumor marker CEA, a gene set for diagnosis and a discriminant for the method of the present invention, that exhibit accuracy beyond AFP, CEA, CA19-9 and/or PIVKA-II, can be constructed, for example, by comparing expressed genes in serum derived from a patient confirmed to be negative using AFP, CEA, CA19-9, and/or PIVKA-II but finally found to have liver cancer by detailed examination such as computed tomography using a contrast medium, with genes expressed in serum derived from a patient having no liver cancer.

For example, the gene set for diagnosis is set to any combination selected from one or two or more of the polynucleotides based on a nucleotide sequence represented by any of SEQ ID NOs: 1 to 167 and 714 to 729 or a complementary sequence thereof as described above, optionally one or two or more of the polynucleotides based on a nucleotide sequence represented by any of SEQ ID NOs: 168 to 183 or a complementary sequence thereof, and optionally one or two or more of the polynucleotides based on a nucleotide sequence represented by any of SEQ ID NOs: 184 to 224 or a complementary sequence thereof. Further, a discriminant is constructed using expression levels of the gene set for diagnosis in samples derived from class I liver cancer patients as a result of tissue diagnosis and samples derived from class II healthy subjects as a result of tissue diagnosis. As a result, the presence or absence of liver cancer-derived genes in an unknown sample can be determined with 100% accuracy at the maximum by measuring expression levels of the gene set for diagnosis in an unknown sample.

EXAMPLES

Hereinafter, the present invention is described further specifically with reference to Examples below. However, the scope of the present invention is not intended to be limited by these Examples.

Reference Example 1

Collection of Samples from Liver Cancer Patients and Healthy Subjects

Sera were collected using VENOJECT II vacuum blood collecting tube VP-AS109K60 (Terumo Corp.) from 100 healthy subjects and 34 liver cancer patients (15 cases with stage I, 9 cases with stage II, 5 cases with stage IIIA, 2 cases with stage IIIB, 1 case with stage IIIC, and 2 cases with stage IV) confirmed to have no primary cancer other than liver cancer after acquisition of informed consent, and used as a training cohort. Likewise, sera were collected using VENOJECT II vacuum blood collecting tube VP-AS109K60 (Terumo Corp.) from 50 healthy subjects and 16 liver cancer patients (9 cases with stage I, 5 cases with stage II, and 2 cases with stage IIIA) confirmed to have no primary cancer other than liver cancer after acquisition of informed consent, and used as a validation cohort.

Extraction of Total RNA

Total RNA was obtained from 300 µL of the serum sample obtained from each of 200 persons in total of 150 healthy subjects and 50 liver cancer patients included in the training cohort and the validation cohort, using a reagent for RNA extraction in 3D-Gene® RNA extraction reagent from liquid sample kit (Toray Industries, Inc.) according to the protocol provided by the manufacturer.

Measurement of Gene Expression Level miRNAs in the total RNA obtained from the serum sample of each of 200 persons in total of 150 healthy subjects and 50 liver cancer patients included in the training cohort and the validation cohort were fluorescently labeled using 3D-Gene® miRNA Labeling kit (Toray Industries, Inc.) according to the protocol (ver 2.20) provided by the manufacturer. The oligo DNA chip used was 3D-Gene® Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene® scanner (Toray Industries, Inc.) to obtain images. Fluorescence intensity was digitized using 3D-Gene® Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 150 liver cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

Collection of Samples from Patients with Cancers Other than Liver Cancer

Sera were collected using VENOJECT II vacuum blood collecting tube VP-AS109K60 (Terumo Corp.) from each of 72 pancreatic cancer patients, 61 bile duct cancer patients, 38 stomach cancer patients, 25 esophageal cancer patients, 35 colorectal cancer patients, and 16 benign pancreaticobiliary disease patients confirmed to have no cancer in other organs after acquisition of informed consent, and used as a training cohort together with the samples of 35 liver cancer patients and 99 healthy subjects of Reference Example 1. Likewise, sera were collected using VENOJECT II vacuum blood collecting tube VP-AS109K60 (Terumo Corp.) from each of 28 pancreatic cancer patients, 37 bile duct cancer patients, 12 stomach cancer patients, 25 esophageal cancer patients, 15 colorectal cancer patients, and 5 benign pancreaticobiliary disease patients confirmed to have no cancer in other organs after acquisition of informed consent, and used as a validation cohort together with the samples of 17 liver cancer patients confirmed to have no cancer in organs except for liver cancer and 51 healthy subjects of Reference Example 1. Subsequent operations were conducted in the same way as in Reference Example 1.

Example 1

Selection of Gene Marker Using Samples in the Training Cohort, and Method for Evaluating Liver Cancer Discriminant Performance of the Single Gene Marker Using Samples in the Validation Cohort In this Example, a gene marker for discriminating a liver cancer patient from a healthy subject was selected from the training cohort, and studied in samples of the validation cohort independent of the training cohort, for a method for evaluating liver cancer discriminant performance of each selected gene marker alone.

Specifically, first, the miRNA expression levels in the training cohort and the validation cohort obtained in the above-mentioned Reference Examples were combined and normalized by quantile normalization.

Next, genes for diagnosis were selected in the training cohort. Here, in order to acquire diagnostic markers with higher reliability, only genes having the gene expression level of $2^6$ or higher in 50% or more of the samples in either of the liver cancer patient group in the training cohort or the healthy subject group of the training cohort were selected. In order to further acquire statistically significant genes for discriminating a liver cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant and described in Table 2.

In this way, hsa-miR-1343-3p, hsa-miR-6726-5p, hsa-miR-6515-3p, hsa-miR-4651, hsa-miR-4257, hsa-miR-3188, hsa-miR-6131, hsa-miR-6766-3p, hsa-miR-7641, hsa-miR-1249, hsa-miR-3679-3p, hsa-miR-6787-5p, hsa-miR-4454, hsa-miR-3135b, hsa-miR-6765-3p, hsa-miR-7975, hsa-miR-204-3p, hsa-miR-7977, hsa-miR-7110-5p, hsa-miR-6717-5p, hsa-miR-6870-5p, hsa-miR-663b, hsa-miR-6875-5p, hsa-miR-8072, hsa-miR-6816-5p, hsa-miR-4281, hsa-miR-6729-5p, hsa-miR-8069, hsa-miR-4706, hsa-miR-7108-5p, hsa-miR-4433b-3p, hsa-miR-6893-5p, hsa-miR-6857-5p, hsa-miR-1227-5p, hsa-miR-6741-5p, hsa-miR-451a, hsa-miR-8063, hsa-miR-3622a-5p, hsa-miR-615-5p, hsa-miR-128-1-5p, hsa-miR-6825-5p, hsa-miR-1260b, hsa-miR-4433-3p, hsa-miR-4665-5p, hsa-miR-7845-5p, hsa-miR-1908-5p, hsa-miR-6840-3p, hsa-miR-6765-5p, hsa-miR-296-5p, hsa-miR-3675-3p, hsa-miR-6781-5p, hsa-miR-423-5p, hsa-miR-3663-3p, hsa-miR-6784-5p, hsa-miR-6749-5p, hsa-miR-1231, hsa-miR-4746-3p, hsa-miR-6780b-5p, hsa-miR-4758-5p, hsa-miR-3679-5p, hsa-miR-3184-5p, hsa-miR-6125, hsa-miR-6721-5p, hsa-miR-6791-5p, hsa-miR-3185, hsa-miR-1260a, hsa-miR-3197, hsa-miR-6845-5p, hsa-miR-6887-5p, hsa-miR-6738-5p, hsa-miR-6872-3p, hsa-miR-4497, hsa-miR-1229-5p, hsa-miR-6820-5p, hsa-miR-6777-5p, hsa-miR-3917, hsa-miR-5787, hsa-miR-4286, hsa-miR-6877-5p, hsa-miR-1225-3p, hsa-miR-6088, hsa-miR-6800-5p, hsa-miR-1246, hsa-miR-4467, hsa-miR-4419b, hsa-miR-1914-3p, hsa-miR-4632-5p, hsa-miR-1915-5p, hsa-miR-3940-5p, hsa-miR-1185-2-3p, hsa-miR-6746-5p, hsa-miR-5001-5p, hsa-miR-1228-5p, hsa-miR-5572, hsa-miR-4327, hsa-miR-4638-5p, hsa-miR-6799-5p, hsa-miR-6861-5p, hsa-miR-6727-5p, hsa-miR-4513, hsa-miR-6805-3p, hsa-miR-6808-5p, hsa-miR-4449, hsa-miR-1199-5p, hsa-miR-1275, hsa-miR-4792, hsa-miR-4443, hsa-miR-6891-5p, hsa-miR-6826-5p, hsa-miR-6807-5p, hsa-miR-7150, hsa-miR-4534, hsa-miR-4476, hsa-miR-4649-5p, hsa-miR-4525, hsa-miR-1915-3p, hsa-miR-4516, hsa-miR-4417, hsa-miR-642b-3p, hsa-miR-3141, hsa-miR-5100, hsa-miR-6848-5p, hsa-miR-4739, hsa-miR-4459, hsa-miR-1237-5p, hsa-miR-296-3p, hsa-miR-4665-3p, hsa-miR-6786-5p, hsa-miR-4258, hsa-miR-6510-5p, hsa-miR-1343-5p, hsa-miR-1247-3p, hsa-miR-6805-5p, hsa-miR-4492, hsa-miR-1469, hsa-miR-1268b, hsa-miR-6858-5p, hsa-miR-3937, hsa-miR-939-5p, hsa-miR-3656, hsa-miR-744-5p, hsa-miR-4687-3p, hsa-miR-4763-3p, hsa-miR-3620-5p, hsa-miR-3195, hsa-miR-6842-5p, hsa-miR-4707-5p, hsa-miR-642a-3p, hsa-miR-7113-3p, hsa-miR-4728-5p, hsa-miR-5195-3p, hsa-miR-1185-1-3p, hsa-miR-6774-5p, hsa-miR-8059, hsa-miR-3131, hsa-miR-7847-3p, hsa-miR-4463, hsa-miR-128-2-5p, hsa-miR-4508, hsa-miR-6806-5p, hsa-miR-7111-5p, hsa-miR-6782-5p, hsa-miR-4734, hsa-miR-3162-5p, hsa-miR-887-3p, hsa-miR-6752-5p, hsa-miR-6724-5p, hsa-miR-23b-3p, hsa-miR-23a-3p, hsa-miR-625-3p, hsa-miR-1228-3p, hsa-miR-614, hsa-miR-1913, hsa-miR-92a-2-5p, hsa-miR-187-5p, hsa-miR-16-5p, hsa-miR-92b-3p, hsa-miR-150-3p, hsa-miR-564, hsa-miR-125a-3p, hsa-miR-92b-5p, hsa-miR-92a-3p, and hsa-miR-663a genes represented by SEQ ID NOs: 1 to 183 were found as liver cancer markers relative to the healthy subjects.

Among them, genes newly found as markers for examining the presence or absence of liver cancer are polynucleotides consisting of the nucleotide sequences represented by SEQ ID NOs: 1 to 167.

A discriminant for determining the presence or absence of liver cancer was further prepared by Fisher's linear discriminant analysis with the expression levels of these genes as an indicator. Specifically, any newly found polynucleotide consisting of a nucleotide sequence represented by any of SEQ ID NOs: 1 to 183 in the training cohort was input to Formula 2 to construct a discriminant. Calculated accuracy, sensitivity, and specificity are shown in Table 3. In this respect, a discriminant coefficient and a constant term are shown in Table 4.

Figure 2:
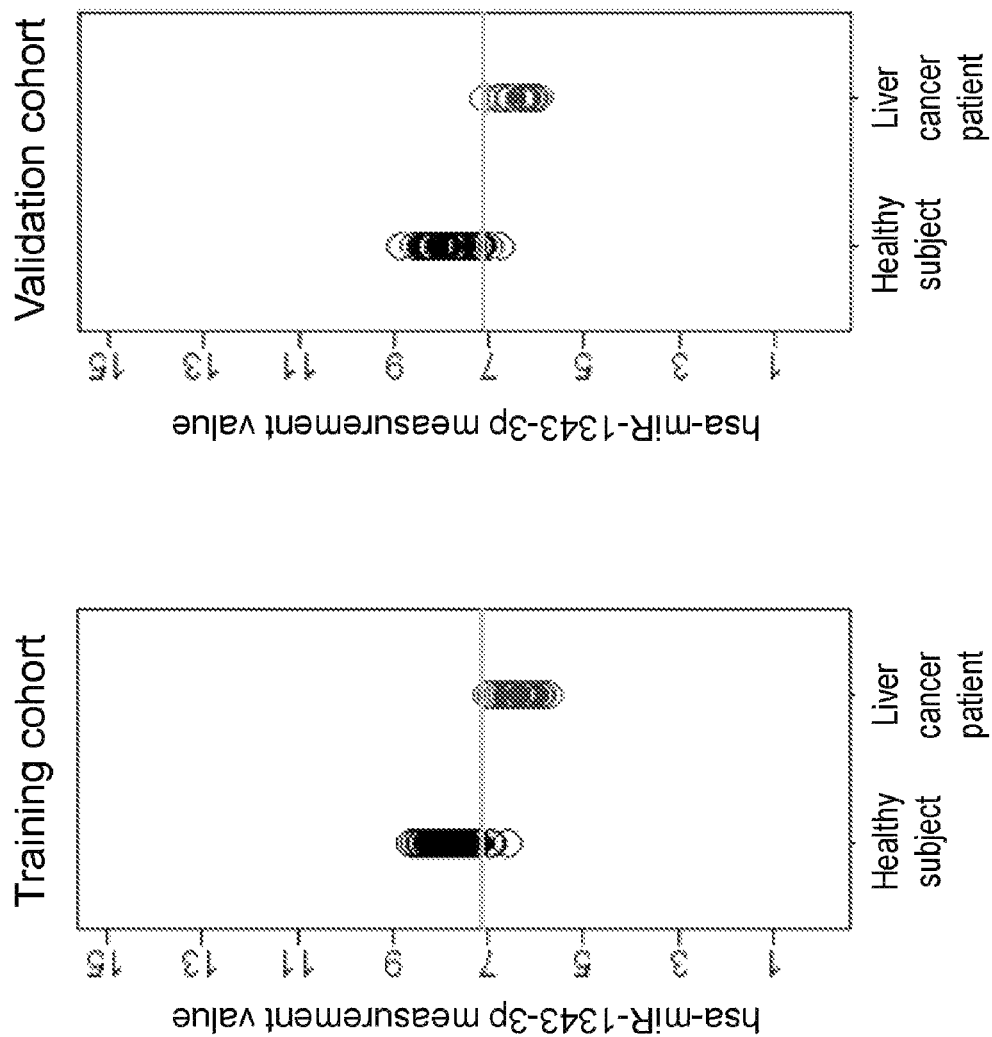
FIG. 2 Left diagram: the measurement values of hsa-miR-1343-3p (SEQ ID NO: 1) in healthy subjects (100 persons) and liver cancer patients (34 persons) selected as a training cohort were each plotted on the ordinate. The horizontal line in the diagram depicts a threshold (7.09) that was optimized by Fisher's linear discriminant analysis and discriminated between the two groups. Right diagram: the measurement values of hsa-miR-1343-3p (SEQ ID NO: 1) in healthy subjects (50 persons) and liver cancer patients (16 persons) selected as a validation cohort were each plotted on the ordinate. The horizontal line in the diagram depicts the threshold (7.09) that was set in the training cohort and discriminated between the two groups.

Accuracy, sensitivity, and specificity in the validation cohort were calculated using the discriminant thus prepared, and the discriminant performance of the selected polynucleotides was validated using independent samples (Table 3). For example, the expression level measurement value of the nucleotide sequence represented by SEQ ID NO: 1 was compared between the healthy subjects (100 persons) and the liver cancer patients (34 persons) in the training cohort. As a result, the gene expression level measurement values were found to be significantly lower in the liver cancer patient group than in the healthy subject group (see the left diagram of FIG. 2). These results were also reproducible for the healthy subjects (50 persons) and the liver cancer patients (16 persons) in the validation cohort (see the right diagram of FIG. 2). Likewise, the results obtained about the other polynucleotides shown in SEQ ID NOs: 2 to 183 showed that the gene expression level measurement values were significantly lower (−) or higher (+) in the liver cancer patient group than in the healthy subject group (Table 2). These results were able to be validated in the validation cohort. For example, as for this nucleotide sequence represented by SEQ ID NO: 1, the number of samples that were correctly identified in the detection of liver cancer was calculated using the threshold (7.09) that was set in the training cohort and discriminated between the two groups. As a result, 15 true positives, 49 true negatives, 1 false positive, and 1 false negatives were obtained in the validation cohort. From these values, 97% accuracy, 94% sensitivity, and 98% specificity were obtained as the detection performance. In this way, the detection performance was calculated as to all of the polynucleotides shown in SEQ ID NOs: 1 to 183, and described in Table 3.

Likewise, 72 polynucleotides consisting of the nucleotide sequences represented by SEQ ID NOs: 1, 2, 3, 4, 5, 6, 7, 8, 9, 10, 11, 12, 13, 14, 15, 16, 17, 19, 21, 22, 23, 24, 25, 27, 28, 29, 30, 31, 32, 33, 34, 35, 37, 39, 40, 41, 43, 44, 45, 46, 47, 48, 50, 51, 54, 55, 56, 57, 58, 60, 61, 62, 63, 64, 65, 68, 73, 80, 86, 88, 91, 93, 94, 99, 114, 117, 170, 171, 172, 173, 174 and 175 exhibited sensitivity of 93.8%, 93.8%, 93.8%, 87.5%, 75%, 87.5%, 62.5%, 81.2%, 93.8%, 93.8%, 75%, 93.8%, 62.5%, 93.8%, 56.2%, 56.2%, 56.2%, 93.8%, 68.8%, 87.5%, 93.8%, 81.2%, 87.5%, 62.5%, 56.2%, 68.8%, 81.2%, 81.2%, 62.5%, 87.5%, 68.8%, 75%, 75%, 75%, 62.5%, 93.8%, 75%, 56.2%, 62.5%, 62.5%, 68.8%, 87.5%, 75%, 62.5%, 75%, 68.8%, 62.5%, 68.8%, 68.8%, 68.8%, 62.5%, 62.5%, 75%, 62.5%, 75%, 68.8%, 56.2%, 81.2%, 68.8%, 56.2%, 62.5%, 56.2%, 56.2%, 68.8%, 56.2%, 62.5%, 87.5%, 87.5%, 75%, 68.8%, 62.5% and 81.2% respectively, in the validation cohort (Table 3). As seen from Comparative Example mentioned later, AFP, which had the highest sensitivity among four existing markers, had sensitivity of 53.3% in the validation cohort (Table 5), demonstrating that, for example, the 72 polynucleotides consisting of the nucleotide sequences represented by SEQ ID NOs: 1, 2, 3, 4, 5, 6, 7, 8, 9, 10, 11, 12, 13, 14, 15, 16, 17, 19, 21, 22, 23, 24, 25, 27, 28, 29, 30, 31, 32, 33, 34, 35, 37, 39, 40, 41, 43, 44, 45, 46, 47, 48, 50, 51, 54, 55, 56, 57, 58, 60, 61, 62, 63, 64, 65, 68, 73, 80, 86, 88, 91, 93, 94, 99, 114, 117, 170, 171, 172, 173, 174 and 175 can discriminate, each alone, liver cancer in the validation cohort with sensitivity beyond AFP.

Also, for example, 7 polynucleotides consisting of the nucleotide sequences represented by SEQ ID NOs: 1, 6, 15, 31, 46, 50, and 58 were able to correctly determine all of the nine stage 1 liver cancer samples contained in the validation cohort to have liver cancer. Thus, these polynucleotides can detect even early liver cancer and contribute to the early diagnosis of liver cancer.

Example 2

Method for Evaluating Liver Cancer Discriminant Performance by Combination of Multiple Gene Markers Using Samples in the Validation Cohort In this Example, a method for evaluating liver cancer discriminant performance by a combination of the gene markers selected in Example 1 was studied. Specifically, Fisher's linear discriminant analysis was conducted as to 16,533 combinations of two expression level measurement values comprising at least one or more of the expression level measurement values of the newly found polynucleotides consisting of the nucleotide sequences represented by SEQ ID NOs: 1 to 167 among the polynucleotides consisting of the nucleotide sequences represented by SEQ ID NOs: 1 to 183 selected in Example 1, to construct a discriminant for determining the presence or absence of liver cancer. Next, accuracy, sensitivity, and specificity in the validation cohort were calculated using the discriminant thus prepared, and the discriminant performance of the selected polynucleotides was validated using the independent samples.

Figure 3:
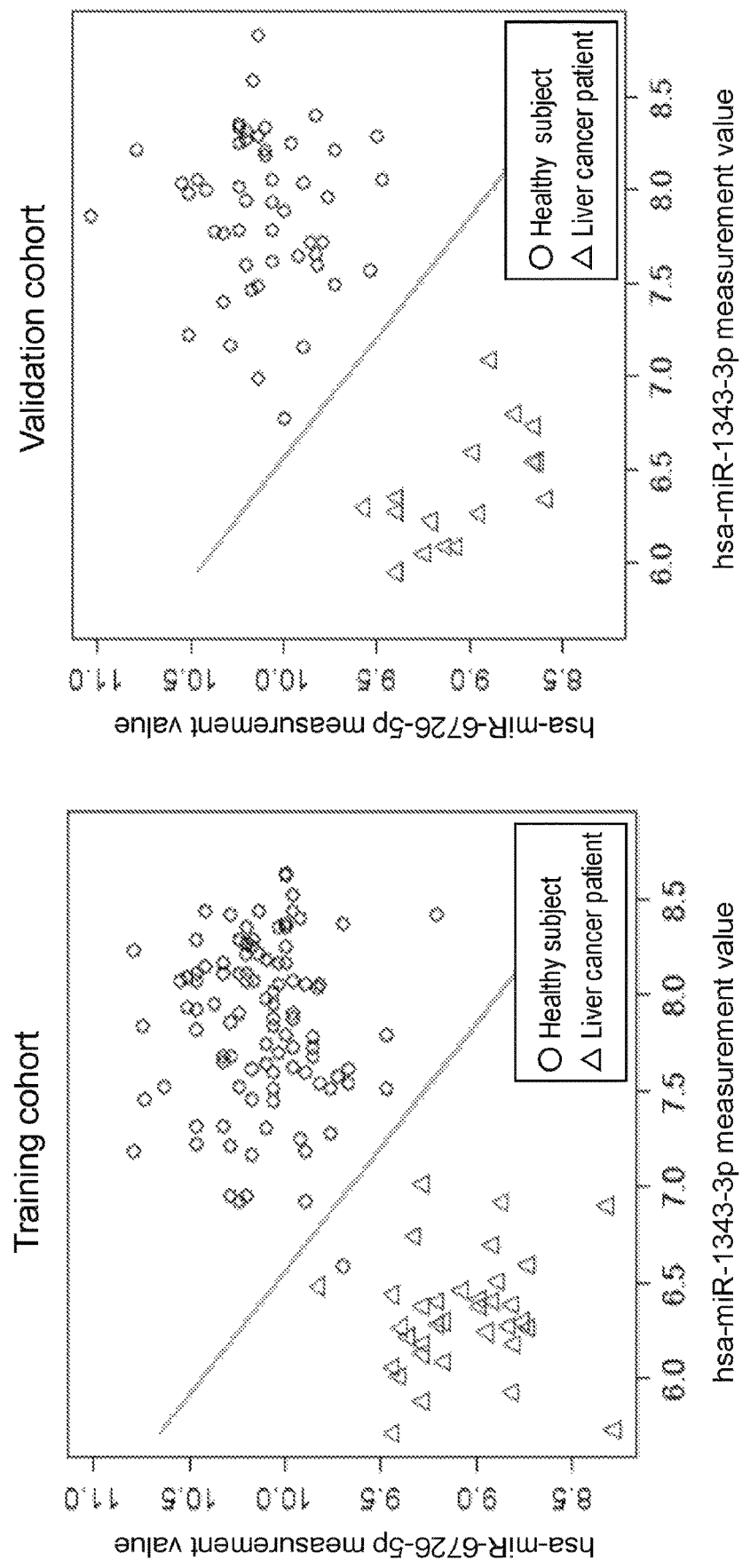
FIG. 3 Left diagram: the measurement values of hsa-miR-1343-3p (SEQ ID NO: 1) in healthy subjects (100 persons, circles) and liver cancer patients (34 persons, triangles) selected as a training cohort were each plotted on the abscissa against their measurement values of hsa-miR-6'726-5p (SEQ ID NO: 2) on the ordinate. The line in the diagram depicts a discriminant function (0=0.77x+y−15.07) that was optimized by Fisher's linear discriminant analysis and discriminated between the two groups. Right diagram: the measurement values of hsa-miR-1343-3p (SEQ ID NO: 1) in healthy subjects (50 persons, circles) and liver cancer patients (16 persons, triangles) selected as a validation cohort were each plotted on the abscissa against their measurement values of hsa-miR-6726-5p (SEQ ID NO: 2) on the ordinate. The line in the diagram depicts the threshold (0=0.77x+y−15.07) that was set in the training cohorts and discriminated between the two groups.

For example, the expression level measurement values of polynucleotides consisting of the nucleotide sequences represented by SEQ ID NO: 1 and SEQ ID NO: 2 were compared between the healthy subjects (100 persons) and the liver cancer patients (34 persons) in the training cohort. As a result, a scatter diagram that significantly separated the expression level measurement values of the liver cancer patient group from those of the healthy subject group was obtained (see the left diagram of FIG. 3). These results were also reproducible for the healthy subjects (50 persons) and the liver cancer patients (16 persons) in the validation cohort (see the right diagram of FIG. 3). Likewise, a scatter diagram that significantly separated the expression level measurement values of the liver cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 167 among the polynucleotides consisting of the nucleotide sequences represented by SEQ ID NOs: 1 to 183. These results were able to be validated in the validation cohort. For example, as for these nucleotide sequences represented by SEQ ID NO: 1 and SEQ ID NO: 2, the number of correctly or incorrectly identified samples in the detection of liver cancer was calculated using the function ($0=0.77x+y-15.07$) that was set in the training cohort and discriminated between the two groups. As a result, 16 true positives, 50 true negatives, 0 false positives, and 0 false negatives were obtained. From these values, 100% accuracy, 100% sensitivity, and 100% specificity were obtained as the detection performance. In this way, the detection performance was calculated for all combinations of two expression level measurement values comprising at least one more of the expression level measurement values of any of the newly found polynucleotides consisting of the nucleotide sequences represented by SEQ ID NOs: 1 to 167 among the polynucleotides consisting of the nucleotide sequences represented by SEQ ID NOs: 1 to 183. Among them, 182 combinations comprising the expression level measurement value of the polynucleotide consisting of the nucleotide sequence represented by SEQ ID NO: 1 and the detection performance thereof were described in Table 6 as an example. For example, all of combinations of the expression level measurement values of the polynucleotides consisting of the nucleotide sequences represented by SEQ ID NOs: 1 and 2, SEQ ID NOs: 1 and 3, SEQ ID NOs: 1 and 4, and SEQ ID NOs: 1 and 5 exhibited sensitivity of 100%, 100%, 100%, 94%, and 94%, respectively, in the validation cohort. Likewise, the sensitivity was also calculated as to the combinations of two polynucleotides consisting of the nucleotide sequences represented by SEQ ID NO: 1 and any of SEQ ID NOs: 6 to 251. As a result, all of these combinations exhibited sensitivity of 88% or higher (Table 6), which was beyond the sensitivity (53.3%) of the existing liver cancer marker AFP (Table 5). Thus, a combination of two of the polynucleotides consisting of the nucleotide sequences represented by SEQ ID NOs: 1 to 183 also produced excellent liver cancer detection sensitivity.

In addition, markers for the detection of liver cancer with more excellent sensitivity are obtained by combining the expression level measurement values of 3, 4, 5, 6, 7, 8, 9, 10 or more of the polynucleotides consisting of the nucleotide sequences represented by SEQ ID NOs: 1 to 183. For example, the newly found polynucleotides consisting of the nucleotide sequences represented by SEQ ID NOs: 1 to 167 among the polynucleotides consisting of the nucleotide sequences represented by SEQ ID NOs: 1 to 183 selected in Example 1 were measured to obtain their expression levels of the healthy subject group and the liver cancer group in the validation cohort. All of the polynucleotides were ranked in the descending order of their P values based on the Student's t-test which indicate statistical significance of difference between groups (i.e., one having the lowest P value was ranked in the first place), and liver cancer detection sensitivity was evaluated for each of combinations of one or more polynucleotides to which the polynucleotides were added one by one from the top to the bottom according to the rank. In short, the order in terms of SEQ ID NOs in which the polynucleotides were combined in this evaluation is in reverse in terms of SEQ ID NO: 167 to SEQ ID NOs: 166, 165, . . . shown in Table 2 in order. As a result, the sensitivity in the validation cohort was 12.5% for 1 polynucleotide (SEQ ID NO: 167), 43.8% for 2 polynucleotides (SEQ ID NOs: 166 and 167), 68.8% for 4 polynucleotides (SEQ ID NOs: 164 to 167), 87.5% for 6 polynucleotides (SEQ ID NOs: 162 to 167), 93.8% for 10 polynucleotides (SEQ ID NOs: 158 to 167), 100% for 20 polynucleotides (SEQ ID NOs: 148 to 167), 100% for 30 polynucleotides (SEQ ID NOs: 138 to 167), 100% for 50 polynucleotides (SEQ ID NOs: 118 to 167), 100% for 80 polynucleotides (SEQ ID NOs: 88 to 167), 100% for 110 polynucleotides (SEQ ID NOs: 58 to 167), 100% for 150 polynucleotides (SEQ ID NOs: 18 to 167), and 100% for 167 polynucleotides (SEQ ID NOs: 1 to 167).

These results demonstrated that a combination of a plurality of polynucleotides can produce higher liver cancer discriminant performance than that of each polynucleotide alone or a combination of a fewer number of polynucleotides. In this context, the combinations of a plurality of polynucleotides are not limited to the combinations of the polynucleotides added in the order of statistically significant difference as described above, and any combination of a plurality of polynucleotides can be used in the detection of liver cancer.

From these results, it can be concluded that all of the polynucleotides consisting of the nucleotide sequences represented by SEQ ID NOs: 1 to 183 serve as excellent markers for the detection of liver cancer.

TABLE 2

| SEQ ID NO: | Gene name | P value after Bonferroni correction | Expression level in liver cancer patient relative to healthy subject |
|---|---|---|---|
| 1 | hsa-miR-1343-3p | 6.65.E−37 | − |
| 2 | hsa-miR-6726-5p | 2.01.E−34 | − |
| 3 | hsa-miR-6515-3p | 4.26.E−28 | + |
| 4 | hsa-miR-4651 | 1.83.E−27 | − |
| 5 | hsa-miR-4257 | 5.63.E−27 | − |
| 6 | hsa-miR-3188 | 1.06.E−25 | + |
| 7 | hsa-miR-6131 | 4.08.E−25 | − |
| 8 | hsa-miR-6766-3p | 1.86.E−24 | + |
| 9 | hsa-miR-7641 | 5.24.E−24 | − |
| 10 | hsa-miR-1249 | 1.67.E−23 | + |
| 11 | hsa-miR-3679-3p | 3.33.E−23 | + |
| 12 | hsa-miR-6787-5p | 5.69.E−23 | − |
| 13 | hsa-miR-4454 | 6.89.E−23 | − |
| 14 | hsa-miR-3135b | 3.83.E−21 | − |
| 15 | hsa-miR-6765-3p | 2.37.E−20 | − |
| 16 | hsa-miR-7975 | 1.57.E−19 | − |
| 17 | hsa-miR-204-3p | 2.58.E−19 | − |
| 18 | hsa-miR-7977 | 5.17.E−18 | − |
| 19 | hsa-miR-7110-5p | 1.34.E−16 | + |
| 20 | hsa-miR-6717-5p | 1.77.E−16 | − |
| 21 | hsa-miR-6870-5p | 1.86.E−16 | + |
| 22 | hsa-miR-663b | 1.91.E−16 | − |

TABLE 2-continued

| SEQ ID NO: | Gene name | P value after Bonferroni correction | Expression level in liver cancer patient relative to healthy subject |
|---|---|---|---|
| 23 | hsa-miR-6875-5p | 1.98.E−16 | + |
| 24 | hsa-miR-8072 | 2.20.E−16 | + |
| 25 | hsa-miR-6816-5p | 4.02.E−16 | + |
| 26 | hsa-miR-4281 | 1.18.E−15 | − |
| 27 | hsa-miR-6729-5p | 1.90.E−15 | + |
| 28 | hsa-miR-8069 | 4.12.E−15 | + |
| 29 | hsa-miR-4706 | 9.80.E−15 | − |
| 30 | hsa-miR-7108-5p | 1.34.E−14 | + |
| 31 | hsa-miR-4433b-3p | 1.44.E−14 | + |
| 32 | hsa-miR-6893-5p | 2.25.E−14 | − |
| 33 | hsa-miR-6857-5p | 3.37.E−14 | + |
| 34 | hsa-miR-1227-5p | 5.86.E−14 | + |
| 35 | hsa-miR-6741-5p | 1.52.E−13 | − |
| 36 | hsa-miR-451a | 1.99.E−13 | − |
| 37 | hsa-miR-8063 | 2.08.E−13 | − |
| 38 | hsa-miR-3622a-5p | 2.29.E−13 | − |
| 39 | hsa-miR-615-5p | 2.47.E−13 | − |
| 40 | hsa-miR-128-1-5p | 6.21.E−13 | + |
| 41 | hsa-miR-6825-5p | 1.19.E−12 | + |
| 42 | hsa-miR-1260b | 2.03.E−12 | − |
| 43 | hsa-miR-4433-3p | 2.67.E−12 | + |
| 44 | hsa-miR-4665-5p | 3.11.E−12 | − |
| 45 | hsa-miR-7845-5p | 3.97.E−12 | + |
| 46 | hsa-miR-1908-5p | 4.05.E−12 | + |
| 47 | hsa-miR-6840-3p | 5.71.E−12 | − |
| 48 | hsa-miR-6765-5p | 5.84.E−12 | + |
| 49 | hsa-miR-296-5p | 6.23.E−12 | − |
| 50 | hsa-miR-3675-3p | 1.58.E−11 | + |
| 51 | hsa-miR-6781-5p | 5.32.E−11 | + |
| 52 | hsa-miR-423-5p | 5.46.E−11 | − |
| 53 | hsa-miR-3663-3p | 5.53.E−11 | − |
| 54 | hsa-miR-6784-5p | 5.78.E−11 | + |
| 55 | hsa-miR-6749-5p | 7.92.E−11 | − |
| 56 | hsa-miR-1231 | 1.43.E−10 | + |
| 57 | hsa-miR-4746-3p | 1.47.E−10 | + |
| 58 | hsa-miR-6780b-5p | 1.80.E−10 | + |
| 59 | hsa-miR-4758-5p | 1.80.E−10 | − |
| 60 | hsa-miR-3679-5p | 2.45.E−10 | + |
| 61 | hsa-miR-3184-5p | 3.79.E−10 | + |
| 62 | hsa-miR-6125 | 4.04.E−10 | + |
| 63 | hsa-miR-6721-5p | 9.40.E−10 | + |
| 64 | hsa-miR-6791-5p | 1.05.E−09 | + |
| 65 | hsa-miR-3185 | 1.24.E−09 | + |
| 66 | hsa-miR-1260a | 1.37.E−09 | − |
| 67 | hsa-miR-3197 | 1.86.E−09 | + |
| 68 | hsa-miR-6845-5p | 2.23.E−09 | + |
| 69 | hsa-miR-6887-5p | 2.95.E−09 | − |
| 70 | hsa-miR-6738-5p | 5.06.E−09 | − |
| 71 | hsa-miR-6872-3p | 5.23.E−09 | − |
| 72 | hsa-miR-4497 | 5.30.E−09 | − |
| 73 | hsa-miR-1229-5p | 6.30.E−09 | + |
| 74 | hsa-miR-6820-5p | 6.66.E−09 | − |
| 75 | hsa-miR-6777-5p | 7.32.E−09 | − |
| 76 | hsa-miR-3917 | 7.71.E−09 | − |
| 77 | hsa-miR-5787 | 7.78.E−09 | + |
| 78 | hsa-miR-4286 | 1.22.E−08 | − |
| 79 | hsa-miR-6877-5p | 1.34.E−08 | − |
| 80 | hsa-miR-1225-3p | 1.56.E−08 | + |
| 81 | hsa-miR-6088 | 1.57.E−08 | − |
| 82 | hsa-miR-6800-5p | 1.94.E−08 | + |
| 83 | hsa-miR-1246 | 3.37.E−08 | − |
| 84 | hsa-miR-4467 | 4.44.E−08 | + |
| 85 | hsa-miR-4419b | 5.34.E−08 | − |
| 86 | hsa-miR-1914-3p | 6.12.E−08 | − |
| 87 | hsa-miR-4632-5p | 7.12.E−08 | + |
| 88 | hsa-miR-1915-5p | 7.21.E−08 | − |
| 89 | hsa-miR-3940-5p | 7.68.E−08 | + |
| 90 | hsa-miR-1185-2-3p | 8.95.E−08 | + |
| 91 | hsa-miR-6746-5p | 1.20.E−07 | − |
| 92 | hsa-miR-5001-5p | 1.89.E−07 | − |
| 93 | hsa-miR-1228-5p | 2.11.E−07 | + |
| 94 | hsa-miR-5572 | 2.20.E−07 | + |
| 95 | hsa-miR-4327 | 2.34.E−07 | + |

TABLE 2-continued

| SEQ ID NO: | Gene name | P value after Bonferroni correction | Expression level in liver cancer patient relative to healthy subject |
|---|---|---|---|
| 96 | hsa-miR-4638-5p | 2.46.E−07 | − |
| 97 | hsa-miR-6799-5p | 3.24.E−07 | + |
| 98 | hsa-miR-6861-5p | 5.31.E−07 | − |
| 99 | hsa-miR-6727-5p | 5.46.E−07 | − |
| 100 | hsa-miR-4513 | 7.37.E−07 | − |
| 101 | hsa-miR-6805-3p | 1.20.E−06 | + |
| 102 | hsa-miR-6808-5p | 1.48.E−06 | + |
| 103 | hsa-miR-4449 | 1.92.E−06 | + |
| 104 | hsa-miR-1199-5p | 1.96.E−06 | − |
| 105 | hsa-miR-1275 | 2.60.E−06 | + |
| 106 | hsa-miR-4792 | 3.93.E−06 | + |
| 107 | hsa-miR-4443 | 4.56.E−06 | + |
| 108 | hsa-miR-6891-5p | 4.68.E−06 | + |
| 109 | hsa-miR-6826-5p | 5.09.E−06 | − |
| 110 | hsa-miR-6807-5p | 5.61.E−06 | + |
| 111 | hsa-miR-7150 | 5.87.E−06 | + |
| 112 | hsa-miR-4534 | 6.23.E−06 | + |
| 113 | hsa-miR-4476 | 6.58.E−06 | − |
| 114 | hsa-miR-4649-5p | 6.78.E−06 | − |
| 115 | hsa-miR-4525 | 6.95.E−06 | − |
| 116 | hsa-miR-1915-3p | 7.86.E−06 | + |
| 117 | hsa-miR-4516 | 9.89.E−06 | − |
| 118 | hsa-miR-4417 | 1.02.E−05 | + |
| 119 | hsa-miR-642b-3p | 1.44.E−05 | − |
| 120 | hsa-miR-3141 | 1.52.E−05 | + |
| 121 | hsa-miR-5100 | 1.70.E−05 | − |
| 122 | hsa-miR-6848-5p | 2.10.E−05 | + |
| 123 | hsa-miR-4739 | 2.86.E−05 | + |
| 124 | hsa-miR-4459 | 3.57.E−05 | + |
| 125 | hsa-miR-1237-5p | 3.74.E−05 | + |
| 126 | hsa-miR-296-3p | 4.27.E−05 | − |
| 127 | hsa-miR-4665-3p | 4.37.E−05 | + |
| 128 | hsa-miR-6786-5p | 6.36.E−05 | + |
| 129 | hsa-miR-4258 | 7.87.E−05 | − |
| 130 | hsa-miR-6510-5p | 8.68.E−05 | + |
| 131 | hsa-miR-1343-5p | 8.90.E−05 | + |
| 132 | hsa-miR-1247-3p | 1.33.E−04 | + |
| 133 | hsa-miR-6805-5p | 1.34.E−04 | + |
| 134 | hsa-miR-4492 | 1.62.E−04 | + |
| 135 | hsa-miR-1469 | 1.93.E−04 | + |
| 136 | hsa-miR-1268b | 2.29.E−04 | + |
| 137 | hsa-miR-6858-5p | 2.37.E−04 | + |
| 138 | hsa-miR-3937 | 3.14.E−04 | + |
| 139 | hsa-miR-939-5p | 3.53.E−04 | + |
| 140 | hsa-miR-3656 | 3.91.E−04 | + |
| 141 | hsa-miR-744-5p | 4.32.E−04 | + |
| 142 | hsa-miR-4687-3p | 4.42.E−04 | + |
| 143 | hsa-miR-4763-3p | 4.53.E−04 | + |
| 144 | hsa-miR-3620-5p | 5.43.E−04 | + |
| 145 | hsa-miR-3195 | 6.21.E−04 | + |
| 146 | hsa-miR-6842-5p | 6.44.E−04 | + |
| 147 | hsa-miR-4707-5p | 7.50.E−04 | + |
| 148 | hsa-miR-642a-3p | 8.01.E−04 | + |
| 149 | hsa-miR-7113-3p | 8.81.E−04 | + |
| 150 | hsa-miR-4728-5p | 1.13.E−03 | − |
| 151 | hsa-miR-5195-3p | 1.39.E−03 | − |
| 152 | hsa-miR-1185-1-3p | 1.99.E−03 | + |
| 153 | hsa-miR-6774-5p | 2.01.E−03 | + |
| 154 | hsa-miR-8059 | 2.34.E−03 | − |
| 155 | hsa-miR-3131 | 2.51.E−03 | − |
| 156 | hsa-miR-7847-3p | 2.78.E−03 | − |
| 157 | hsa-miR-4463 | 3.86.E−03 | + |
| 158 | hsa-miR-128-2-5p | 4.01.E−03 | − |
| 159 | hsa-miR-4508 | 4.42.E−03 | + |
| 160 | hsa-miR-6806-5p | 4.85.E−03 | − |
| 161 | hsa-miR-7111-5p | 5.18.E−03 | + |
| 162 | hsa-miR-6782-5p | 5.20.E−03 | + |
| 163 | hsa-miR-4734 | 6.28.E−03 | + |
| 164 | hsa-miR-3162-5p | 8.46.E−03 | + |
| 165 | hsa-miR-887-3p | 8.47.E−03 | + |
| 166 | hsa-miR-6752-5p | 8.98.E−03 | + |
| 167 | hsa-miR-6724-5p | 9.90.E−03 | + |
| 168 | hsa-miR-23b-3p | 4.55.E−23 | − |
| 169 | hsa-miR-23a-3p | 4.37.E−21 | − |
| 170 | hsa-miR-625-3p | 8.87.E−20 | + |
| 171 | hsa-miR-1228-3p | 1.35.E−19 | + |
| 172 | hsa-miR-614 | 2.37.E−18 | − |
| 173 | hsa-miR-1913 | 5.84.E−18 | + |
| 174 | hsa-miR-92a-2-5p | 9.35.E−16 | + |
| 175 | hsa-miR-187-5p | 1.18.E−15 | − |
| 176 | hsa-miR-16-5p | 2.32.E−14 | − |
| 177 | hsa-miR-92b-3p | 2.82.E−12 | − |
| 178 | hsa-miR-150-3p | 8.73.E−11 | − |
| 179 | hsa-miR-564 | 1.08.E−09 | − |
| 180 | hsa-miR-125a-3p | 1.64.E−07 | − |
| 181 | hsa-miR-92b-5p | 5.34.E−07 | + |
| 182 | hsa-miR-92a-3p | 6.00.E−06 | − |
| 183 | hsa-miR-663a | 7.49.E−04 | + |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 95.5 | 97.1 | 95 | 97 | 93.8 | 98 |
| 2 | 97 | 97.1 | 97 | 95.5 | 93.8 | 96 |
| 3 | 91.8 | 82.4 | 95 | 90.9 | 93.8 | 90 |
| 4 | 96.3 | 91.2 | 98 | 95.5 | 87.5 | 98 |
| 5 | 96.3 | 88.2 | 99 | 92.4 | 75 | 98 |
| 6 | 94.8 | 88.2 | 97 | 95.5 | 87.5 | 98 |
| 7 | 92.5 | 73.5 | 99 | 90.9 | 62.5 | 100 |
| 8 | 94.8 | 88.2 | 97 | 92.4 | 81.2 | 96 |
| 9 | 91.8 | 82.4 | 95 | 95.5 | 93.8 | 96 |
| 10 | 94.7 | 94.1 | 94.9 | 92.4 | 93.8 | 92 |
| 11 | 94 | 91.2 | 95 | 86.4 | 75 | 90 |
| 12 | 91.8 | 76.5 | 97 | 93.9 | 93.8 | 94 |
| 13 | 91.8 | 70.6 | 99 | 89.4 | 62.5 | 98 |
| 14 | 97 | 91.2 | 99 | 97 | 93.8 | 98 |
| 15 | 91.8 | 73.5 | 98 | 87.9 | 56.2 | 98 |
| 16 | 90.3 | 64.7 | 99 | 87.9 | 56.2 | 98 |
| 17 | 90.3 | 67.6 | 98 | 81.8 | 56.2 | 90 |
| 18 | 88.1 | 58.8 | 98 | 84.8 | 43.8 | 98 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 19 | 88.1 | 76.5 | 92 | 90.9 | 93.8 | 90 |
| 20 | 92.5 | 73.5 | 99 | 86.4 | 50 | 98 |
| 21 | 92.5 | 79.4 | 97 | 92.4 | 68.8 | 100 |
| 22 | 88.8 | 58.8 | 99 | 97 | 87.5 | 100 |
| 23 | 91 | 73.5 | 97 | 90.9 | 93.8 | 90 |
| 24 | 91.8 | 79.4 | 96 | 84.8 | 81.2 | 86 |
| 25 | 89.6 | 82.4 | 92 | 93.9 | 87.5 | 96 |
| 26 | 88.8 | 76.5 | 93 | 84.8 | 50 | 96 |
| 27 | 91.8 | 73.5 | 98 | 89.4 | 62.5 | 98 |
| 28 | 83.6 | 50 | 95 | 86.4 | 56.2 | 96 |
| 29 | 88.8 | 73.5 | 94 | 87.9 | 68.8 | 94 |
| 30 | 85.8 | 64.7 | 93 | 86.4 | 81.2 | 88 |
| 31 | 88.8 | 76.5 | 93 | 83.3 | 81.2 | 84 |
| 32 | 89.6 | 61.8 | 99 | 89.4 | 62.5 | 98 |
| 33 | 89.6 | 79.4 | 93 | 92.4 | 87.5 | 94 |
| 34 | 86.6 | 64.7 | 94 | 84.8 | 68.8 | 90 |
| 35 | 88.1 | 64.7 | 96 | 87.9 | 75 | 92 |
| 36 | 86.6 | 50 | 99 | 80.3 | 31.2 | 96 |
| 37 | 84.3 | 64.7 | 91 | 89.4 | 75 | 94 |
| 38 | 85.8 | 50 | 98 | 86.4 | 43.8 | 100 |
| 39 | 87.3 | 52.9 | 99 | 92.4 | 75 | 98 |
| 40 | 85.1 | 64.7 | 92 | 78.8 | 62.5 | 84 |
| 41 | 94 | 85.3 | 97 | 93.9 | 93.8 | 94 |
| 42 | 85.8 | 52.9 | 97 | 84.8 | 50 | 96 |
| 43 | 82.1 | 64.7 | 88 | 86.4 | 75 | 90 |
| 44 | 82.1 | 50 | 93 | 80.3 | 56.2 | 88 |
| 45 | 88.1 | 70.6 | 94 | 84.8 | 62.5 | 92 |
| 46 | 82.8 | 52.9 | 93 | 86.4 | 62.5 | 94 |
| 47 | 86.6 | 55.9 | 97 | 89.4 | 68.8 | 96 |
| 48 | 88.1 | 67.6 | 95 | 92.4 | 87.5 | 94 |
| 49 | 82.8 | 50 | 94 | 72.7 | 25 | 88 |
| 50 | 94 | 85.3 | 97 | 89.4 | 75 | 94 |
| 51 | 84.3 | 55.9 | 94 | 83.3 | 62.5 | 90 |
| 52 | 83.6 | 41.2 | 98 | 86.4 | 43.8 | 100 |
| 53 | 85.8 | 52.9 | 97 | 84.8 | 43.8 | 98 |
| 54 | 91 | 79.4 | 95 | 87.9 | 75 | 92 |
| 55 | 86.6 | 58.8 | 96 | 90.9 | 68.8 | 98 |
| 56 | 83.6 | 55.9 | 93 | 84.8 | 62.5 | 92 |
| 57 | 86.6 | 67.6 | 93 | 89.4 | 68.8 | 96 |
| 58 | 85.1 | 55.9 | 95 | 92.4 | 68.8 | 100 |
| 59 | 85.1 | 47.1 | 98 | 81.8 | 31.2 | 98 |
| 60 | 82.1 | 50 | 93 | 89.4 | 68.8 | 96 |
| 61 | 86.6 | 67.6 | 93 | 86.4 | 62.5 | 94 |
| 62 | 85.8 | 61.8 | 94 | 87.9 | 62.5 | 96 |
| 63 | 82.1 | 58.8 | 90 | 84.8 | 75 | 88 |
| 64 | 83.6 | 61.8 | 91 | 89.4 | 62.5 | 98 |
| 65 | 85.1 | 64.7 | 92 | 89.4 | 75 | 94 |
| 66 | 85.8 | 52.9 | 97 | 78.8 | 31.2 | 94 |
| 67 | 84.3 | 58.8 | 93 | 83.3 | 50 | 94 |
| 68 | 84.3 | 47.1 | 97 | 90.9 | 68.8 | 98 |
| 69 | 80.6 | 26.5 | 99 | 80.3 | 18.8 | 100 |
| 70 | 86.6 | 55.9 | 97 | 83.3 | 50 | 94 |
| 71 | 83.6 | 38.2 | 99 | 84.8 | 37.5 | 100 |
| 72 | 79.1 | 41.2 | 92 | 74.2 | 31.2 | 88 |
| 73 | 85.1 | 55.9 | 95 | 86.4 | 56.2 | 96 |
| 74 | 85.8 | 47.1 | 99 | 81.8 | 31.2 | 98 |
| 75 | 82.1 | 32.4 | 99 | 83.3 | 31.2 | 100 |
| 76 | 82.1 | 32.4 | 99 | 81.8 | 37.5 | 96 |
| 77 | 81.3 | 32.4 | 98 | 87.9 | 50 | 100 |
| 78 | 82.1 | 38.2 | 97 | 78.8 | 25 | 96 |
| 79 | 79.1 | 41.2 | 92 | 78.8 | 37.5 | 92 |
| 80 | 88.8 | 64.7 | 97 | 95.5 | 81.2 | 100 |
| 81 | 79.1 | 47.1 | 90 | 80.3 | 43.8 | 92 |
| 82 | 84.3 | 52.9 | 95 | 81.8 | 50 | 92 |
| 83 | 82.1 | 41.2 | 96 | 78.8 | 31.2 | 94 |
| 84 | 76.1 | 41.2 | 88 | 84.8 | 50 | 96 |
| 85 | 79.9 | 32.4 | 96 | 78.8 | 18.8 | 98 |
| 86 | 83.6 | 55.9 | 93 | 83.3 | 68.8 | 88 |
| 87 | 86.6 | 50 | 99 | 80.3 | 18.8 | 100 |
| 88 | 82.1 | 41.2 | 96 | 86.4 | 56.2 | 96 |
| 89 | 82.1 | 38.2 | 97 | 80.3 | 37.5 | 94 |
| 90 | 83.6 | 50 | 95 | 80.3 | 43.8 | 92 |
| 91 | 78.4 | 44.1 | 90 | 84.8 | 62.5 | 92 |
| 92 | 88.1 | 64.7 | 96 | 81.8 | 37.5 | 96 |
| 93 | 82.8 | 50 | 94 | 84.8 | 56.2 | 94 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 94 | 88.1 | 67.6 | 95 | 84.8 | 56.2 | 94 |
| 95 | 82.8 | 50 | 94 | 77.3 | 31.2 | 92 |
| 96 | 82.1 | 35.3 | 98 | 80.3 | 18.8 | 100 |
| 97 | 84.3 | 50 | 96 | 77.3 | 18.8 | 96 |
| 98 | 79.1 | 41.2 | 92 | 78.8 | 37.5 | 92 |
| 99 | 83.6 | 55.9 | 93 | 90.9 | 68.8 | 98 |
| 100 | 76.1 | 14.7 | 97 | 81.8 | 31.2 | 98 |
| 101 | 78.4 | 44.1 | 90 | 78.8 | 31.2 | 94 |
| 102 | 79.9 | 32.4 | 96 | 77.3 | 31.2 | 92 |
| 103 | 81.3 | 41.2 | 95 | 75.8 | 12.5 | 96 |
| 104 | 82.1 | 44.1 | 95 | 84.8 | 50 | 96 |
| 105 | 77.6 | 32.4 | 93 | 77.3 | 25 | 94 |
| 106 | 84.3 | 50 | 96 | 86.4 | 50 | 98 |
| 107 | 85.1 | 50 | 97 | 86.4 | 50 | 98 |
| 108 | 82.1 | 47.1 | 94 | 87.9 | 50 | 100 |
| 109 | 79.9 | 26.5 | 98 | 77.3 | 6.2 | 100 |
| 110 | 79.1 | 35.3 | 94 | 78.8 | 31.2 | 94 |
| 111 | 84.3 | 44.1 | 98 | 83.3 | 31.2 | 100 |
| 112 | 80.6 | 35.3 | 96 | 75.8 | 12.5 | 96 |
| 113 | 78.4 | 20.6 | 98 | 81.8 | 25 | 100 |
| 114 | 83.6 | 47.1 | 96 | 86.4 | 56.2 | 96 |
| 115 | 79.1 | 38.2 | 93 | 80.3 | 25 | 98 |
| 116 | 82.1 | 44.1 | 95 | 78.8 | 31.2 | 94 |
| 117 | 84.3 | 50 | 96 | 87.9 | 62.5 | 96 |
| 118 | 82.8 | 41.2 | 97 | 83.3 | 43.8 | 96 |
| 119 | 82.8 | 41.2 | 97 | 83.3 | 31.2 | 100 |
| 120 | 79.1 | 23.5 | 98 | 75.8 | 18.8 | 94 |
| 121 | 82 | 39.4 | 96 | 74.2 | 12.5 | 94 |
| 122 | 77.6 | 32.4 | 93 | 74.2 | 31.2 | 88 |
| 123 | 82.1 | 38.2 | 97 | 80.3 | 31.2 | 96 |
| 124 | 80.6 | 32.4 | 97 | 83.3 | 37.5 | 98 |
| 125 | 76.9 | 20.6 | 96 | 78.8 | 18.8 | 98 |
| 126 | 77.6 | 20.6 | 97 | 78.8 | 25 | 96 |
| 127 | 82.8 | 35.3 | 99 | 83.3 | 37.5 | 98 |
| 128 | 79.9 | 32.4 | 96 | 71.2 | 37.5 | 82 |
| 129 | 82.8 | 38.2 | 98 | 81.8 | 31.2 | 98 |
| 130 | 82.1 | 32.4 | 99 | 83.3 | 31.2 | 100 |
| 131 | 83.6 | 44.1 | 97 | 83.3 | 37.5 | 98 |
| 132 | 85.8 | 44.1 | 100 | 84.8 | 43.8 | 98 |
| 133 | 78.4 | 26.5 | 96 | 81.8 | 43.8 | 94 |
| 134 | 79.9 | 35.3 | 95 | 77.3 | 31.2 | 92 |
| 135 | 78.4 | 14.7 | 100 | 72.7 | 0 | 96 |
| 136 | 69.4 | 8.8 | 90 | 68.2 | 6.2 | 88 |
| 137 | 77.6 | 14.7 | 99 | 72.7 | 0 | 96 |
| 138 | 77.6 | 29.4 | 94 | 78.8 | 25 | 96 |
| 139 | 82.1 | 32.4 | 99 | 80.3 | 31.2 | 96 |
| 140 | 75.4 | 20.6 | 94 | 77.3 | 12.5 | 98 |
| 141 | 76.9 | 20.6 | 96 | 83.3 | 31.2 | 100 |
| 142 | 74.6 | 20.6 | 93 | 81.8 | 31.2 | 98 |
| 143 | 77.6 | 23.5 | 96 | 80.3 | 25 | 98 |
| 144 | 78.4 | 29.4 | 95 | 77.3 | 31.2 | 92 |
| 145 | 76.9 | 23.5 | 95 | 74.2 | 12.5 | 94 |
| 146 | 81.3 | 29.4 | 99 | 86.4 | 50 | 98 |
| 147 | 73.1 | 8.8 | 95 | 72.7 | 0 | 96 |
| 148 | 79.9 | 26.5 | 98 | 77.3 | 12.5 | 98 |
| 149 | 78.4 | 17.6 | 99 | 75.8 | 12.5 | 96 |
| 150 | 74.6 | 23.5 | 92 | 74.2 | 18.8 | 92 |
| 151 | 73.9 | 8.8 | 96 | 75.8 | 6.2 | 98 |
| 152 | 79.9 | 29.4 | 97 | 74.2 | 12.5 | 94 |
| 153 | 73.9 | 11.8 | 95 | 72.7 | 0 | 96 |
| 154 | 75.4 | 14.7 | 96 | 75.8 | 12.5 | 96 |
| 155 | 79.1 | 23.5 | 98 | 77.3 | 12.5 | 98 |
| 156 | 75.4 | 5.9 | 99 | 77.3 | 6.2 | 100 |
| 157 | 76.1 | 20.6 | 95 | 77.3 | 18.8 | 96 |
| 158 | 80.6 | 29.4 | 98 | 78.8 | 12.5 | 100 |
| 159 | 73.9 | 11.8 | 95 | 75.8 | 31.2 | 90 |
| 160 | 76.1 | 5.9 | 100 | 75.8 | 0 | 100 |
| 161 | 79.1 | 23.5 | 98 | 78.8 | 12.5 | 100 |
| 162 | 79.1 | 17.6 | 100 | 77.3 | 18.8 | 96 |
| 163 | 72.4 | 8.8 | 94 | 78.8 | 31.2 | 94 |
| 164 | 75.4 | 14.7 | 96 | 72.7 | 6.2 | 94 |
| 165 | 70.9 | 2.9 | 94 | 68.2 | 0 | 90 |
| 166 | 76.1 | 14.7 | 97 | 72.7 | 6.2 | 94 |
| 167 | 76.9 | 23.5 | 95 | 74.2 | 12.5 | 94 |
| 168 | 88.8 | 64.7 | 97 | 81.8 | 43.8 | 94 |

TABLE 3-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 169 | 87.3 | 58.8 | 97 | 80.3 | 37.5 | 94 |
| 170 | 91 | 76.5 | 96 | 90.9 | 87.5 | 92 |
| 171 | 91.8 | 85.3 | 94 | 89.4 | 87.5 | 90 |
| 172 | 87.3 | 79.4 | 90 | 89.4 | 75 | 94 |
| 173 | 88.8 | 79.4 | 92 | 87.7 | 68.8 | 93.9 |
| 174 | 89.6 | 76.5 | 94 | 84.8 | 62.5 | 92 |
| 175 | 90.3 | 70.6 | 97 | 93.9 | 81.2 | 98 |
| 176 | 85.8 | 55.9 | 96 | 83.3 | 43.8 | 96 |
| 177 | 86.6 | 52.9 | 98 | 83.3 | 37.5 | 98 |
| 178 | 83.6 | 38.2 | 99 | 81.8 | 50 | 92 |
| 179 | 82.8 | 41.2 | 97 | 84.8 | 43.8 | 98 |
| 180 | 84.3 | 41.2 | 99 | 87.9 | 50 | 100 |
| 181 | 82.1 | 32.4 | 99 | 75.8 | 0 | 100 |
| 182 | 82.1 | 32.4 | 99 | 78.8 | 18.8 | 98 |
| 183 | 76.9 | 14.7 | 98 | 77.3 | 6.2 | 100 |

TABLE 4

| SEQ ID NO: | Discriminant coefficient | Constant term |
|---|---|---|
| 1 | 2.471 | 17.511 |
| 2 | 3.389 | 32.503 |
| 3 | 4.221 | 29.467 |
| 4 | 5.669 | 61.422 |
| 5 | 2.340 | 14.902 |
| 6 | 3.403 | 21.347 |
| 7 | 1.666 | 16.714 |
| 8 | 3.780 | 23.286 |
| 9 | 1.162 | 7.705 |
| 10 | 3.871 | 23.895 |
| 11 | 3.327 | 20.777 |
| 12 | 3.912 | 32.887 |
| 13 | 1.850 | 20.690 |
| 14 | 2.777 | 21.161 |
| 15 | 1.469 | 12.157 |
| 16 | 1.640 | 15.602 |
| 17 | 1.594 | 20.057 |
| 18 | 1.741 | 16.417 |
| 19 | 1.740 | 14.012 |
| 20 | 2.167 | 12.838 |
| 21 | 3.215 | 24.454 |
| 22 | 2.867 | 24.605 |
| 23 | 3.272 | 30.031 |
| 24 | 5.400 | 67.222 |
| 25 | 4.398 | 44.949 |
| 26 | 4.110 | 47.240 |
| 27 | 8.336 | 105.482 |
| 28 | 6.984 | 90.484 |
| 29 | 3.912 | 29.950 |
| 30 | 4.452 | 41.269 |
| 31 | 3.737 | 30.649 |
| 32 | 1.541 | 12.525 |
| 33 | 1.731 | 9.319 |
| 34 | 6.775 | 65.355 |
| 35 | 4.246 | 28.999 |
| 36 | 0.707 | 5.520 |
| 37 | 2.475 | 20.255 |
| 38 | 1.782 | 9.870 |
| 39 | 1.749 | 10.960 |
| 40 | 2.724 | 20.676 |
| 41 | 1.635 | 11.008 |
| 42 | 2.017 | 16.782 |
| 43 | 3.750 | 27.935 |
| 44 | 3.268 | 30.852 |
| 45 | 3.074 | 20.807 |
| 46 | 4.135 | 48.094 |
| 47 | 2.722 | 23.696 |
| 48 | 4.645 | 49.638 |
| 49 | 4.364 | 34.762 |
| 50 | 2.395 | 13.357 |
| 51 | 5.700 | 60.009 |
| 52 | 1.785 | 12.550 |
| 53 | 3.691 | 44.502 |
| 54 | 3.410 | 43.229 |
| 55 | 4.359 | 43.584 |
| 56 | 3.783 | 25.006 |
| 57 | 2.734 | 18.058 |
| 58 | 2.978 | 26.851 |
| 59 | 6.061 | 51.915 |
| 60 | 2.729 | 18.883 |
| 61 | 2.150 | 17.585 |
| 62 | 5.256 | 63.263 |
| 63 | 3.936 | 30.117 |
| 64 | 4.508 | 41.792 |
| 65 | 2.386 | 16.961 |
| 66 | 1.810 | 12.154 |
| 67 | 2.969 | 28.301 |
| 68 | 3.512 | 34.056 |
| 69 | 1.951 | 12.101 |
| 70 | 3.135 | 22.180 |
| 71 | 1.606 | 9.267 |
| 72 | 2.696 | 34.139 |
| 73 | 4.474 | 34.903 |
| 74 | 2.012 | 14.274 |
| 75 | 1.959 | 12.395 |
| 76 | 2.215 | 12.602 |
| 77 | 5.057 | 66.741 |
| 78 | 1.620 | 11.678 |
| 79 | 4.288 | 30.633 |
| 80 | 2.430 | 13.696 |
| 81 | 3.351 | 33.938 |
| 82 | 3.921 | 34.024 |
| 83 | 1.278 | 9.389 |
| 84 | 2.183 | 21.651 |
| 85 | 1.944 | 11.599 |
| 86 | 4.824 | 36.279 |
| 87 | 3.858 | 31.074 |
| 88 | 1.277 | 7.779 |
| 89 | 4.555 | 56.233 |
| 90 | 1.520 | 8.345 |
| 91 | 3.667 | 23.791 |
| 92 | 3.455 | 26.548 |
| 93 | 3.821 | 45.609 |
| 94 | 1.784 | 12.053 |
| 95 | 4.842 | 42.664 |
| 96 | 1.392 | 8.122 |
| 97 | 3.251 | 27.595 |
| 98 | 4.026 | 29.199 |
| 99 | 5.471 | 69.803 |
| 100 | 2.281 | 13.200 |
| 101 | 2.499 | 18.849 |
| 102 | 5.118 | 35.429 |

TABLE 4-continued

| SEQ ID NO: | Discriminant coefficient | Constant term |
|---|---|---|
| 103 | 3.691 | 24.076 |
| 104 | 2.471 | 16.246 |
| 105 | 2.973 | 21.963 |
| 106 | 1.588 | 10.669 |
| 107 | 2.017 | 13.094 |
| 108 | 4.206 | 32.002 |
| 109 | 1.659 | 9.895 |
| 110 | 2.739 | 16.192 |
| 111 | 3.174 | 24.976 |
| 112 | 2.780 | 19.682 |
| 113 | 1.225 | 8.488 |
| 114 | 2.404 | 24.762 |
| 115 | 2.895 | 19.963 |
| 116 | 4.205 | 46.806 |
| 117 | 4.490 | 59.177 |
| 118 | 5.016 | 41.382 |
| 119 | 2.142 | 20.182 |
| 120 | 4.030 | 28.787 |
| 121 | 2.093 | 21.502 |
| 122 | 4.832 | 36.040 |
| 123 | 3.672 | 42.382 |
| 124 | 3.305 | 27.456 |
| 125 | 4.919 | 62.904 |
| 126 | 1.924 | 11.325 |
| 127 | 2.696 | 15.869 |
| 128 | 7.275 | 92.098 |
| 129 | 1.903 | 17.010 |
| 130 | 1.935 | 12.644 |
| 131 | 3.379 | 35.351 |
| 132 | 2.384 | 15.077 |
| 133 | 6.549 | 74.981 |
| 134 | 5.238 | 55.302 |
| 135 | 2.785 | 28.718 |
| 136 | 3.118 | 31.040 |
| 137 | 3.097 | 23.331 |
| 138 | 4.424 | 38.383 |
| 139 | 1.611 | 12.320 |
| 140 | 4.840 | 56.003 |
| 141 | 2.484 | 17.251 |
| 142 | 3.851 | 37.749 |
| 143 | 3.720 | 31.374 |
| 144 | 3.991 | 31.836 |
| 145 | 4.065 | 33.772 |
| 146 | 2.441 | 14.617 |
| 147 | 3.795 | 27.973 |
| 148 | 2.362 | 18.895 |
| 149 | 2.354 | 13.716 |
| 150 | 5.065 | 35.714 |
| 151 | 2.922 | 20.137 |
| 152 | 1.539 | 9.313 |
| 153 | 4.631 | 31.436 |
| 154 | 3.326 | 25.477 |
| 155 | 2.223 | 15.649 |
| 156 | 2.416 | 15.308 |
| 157 | 4.655 | 51.632 |
| 158 | 2.552 | 27.736 |
| 159 | 6.563 | 85.503 |
| 160 | 2.281 | 14.772 |
| 161 | 5.241 | 39.899 |
| 162 | 2.291 | 14.195 |
| 163 | 6.256 | 74.602 |
| 164 | 2.920 | 22.423 |
| 165 | 2.285 | 16.474 |
| 166 | 3.720 | 42.108 |
| 167 | 4.806 | 47.920 |
| 168 | 1.156 | 5.990 |
| 169 | 1.212 | 6.218 |
| 170 | 3.292 | 19.092 |
| 171 | 4.244 | 27.332 |
| 172 | 1.867 | 12.024 |
| 173 | 3.494 | 22.197 |
| 174 | 2.062 | 19.948 |
| 175 | 1.942 | 18.936 |
| 176 | 0.886 | 4.794 |
| 177 | 1.182 | 6.543 |
| 178 | 1.678 | 10.850 |
| 179 | 1.358 | 7.646 |
| 180 | 1.032 | 6.311 |
| 181 | 2.498 | 20.322 |
| 182 | 1.203 | 7.922 |
| 183 | 2.779 | 28.552 |

TABLE 5-1

Training cohort

| Sample name | Cancer stage | AFP (ng/mL) | CEA (ng/mL) | CA19-9 (U/mL) | PIVKA-II (mAU/mL) |
|---|---|---|---|---|---|
| HC03 | I | 13.2 | 3.1 | — | 99 |
| HC04 | I | 37210 | 1 | — | 13550 |
| HC05 | IV | 3 | — | — | 18 |
| HC06 | I | 26.1 | 5.7 | — | 136 |
| HC07 | III | 3.2 | 3.4 | — | 2452 |
| HC09 | II | 34.7 | 5 | 26.2 | 1932 |
| HC10 | I | 74 | 2.6 | — | 10 |
| HC12 | I | 3.4 | — | — | 39 |
| HC13 | III | — | 0.6 | 5.1 | — |
| HC15 | II | — | 1.9 | 0.1 | — |
| HC17 | II | 2.3 | — | — | 556 |
| HC18 | IV | 36145 | — | — | 167 |
| HC19 | I | 8.5 | 3.7 | — | 13 |
| HC20 | I | 4.6 | 3.2 | 6.4 | 344 |
| HC23 | III | 151.3 | 1.9 | — | 29521 |
| HC24 | III | 103299 | 1.9 | — | 55837 |
| HC25 | I | 179.7 | 12.1 | — | 220 |
| HC26 | I | 25.3 | 1.4 | — | 36 |
| HC27 | I | 8.5 | 4.7 | — | 28 |
| HC29 | I | 29.2 | — | — | 979 |
| HC30 | IIIB | 77.4 | — | — | 176940 |
| HC31 | II | 7 | — | — | 34 |
| HC32 | III | 2.2 | 1.8 | — | 40 |
| HC34 | II | 6.9 | — | — | 688 |
| HC36 | II | 25.3 | 1.9 | — | 3481 |
| HC38 | I | 5.4 | 4.8 | — | 92 |
| HC40 | IIIB | 5.7 | — | — | 95 |
| HC41 | II | 93.7 | 5.8 | 104.9 | 26 |
| HC42 | I | 1.9 | 6.5 | — | 25 |
| HC45 | II | 10.3 | — | — | 51 |
| HC47 | IIIC | 235.5 | — | — | 3601 |
| HC48 | I | 107.9 | — | — | 52 |
| HC49 | I | 4.5 | 4.3 | 26.7 | 22 |
| HC50 | II | 133338 | 2.9 | — | 829 |
| Sensitivity | | 56.3% | 18.2% | 16.7% | 65.6% |

TABLE 5-2

Validation cohort

| Sample name | Cancer stage | AFP (ng/mL) | CEA (ng/mL) | CA19-9 (U/mL) | PIVKA-II (mAU/mL) |
|---|---|---|---|---|---|
| HC01 | II | 10.8 | 2.8 | — | 678 |
| HC02 | I | 3.8 | 1.4 | 11.4 | 26 |
| HC08 | I | 13 | 3 | — | 245 |
| HC11 | I | 17.2 | 3.4 | — | 15 |
| HC14 | I | 1.8 | 5.7 | — | 18 |
| HC16 | I | 6 | — | — | 21 |
| HC21 | II | 5.3 | 5.3 | 14.8 | 22 |
| HC22 | I | 1.7 | — | — | 76 |
| HC28 | I | — | 4.4 | 11 | — |
| HC33 | III | 40 | 1.1 | — | 25 |
| HC35 | II | 4.2 | 5.2 | — | 20 |
| HC37 | III | 59992 | — | — | 14358 |
| HC39 | II | 555 | — | — | 194 |
| HC43 | I | 18 | — | — | 32 |
| HC44 | I | 7.5 | 1 | 32.7 | 462 |
| HC46 | I | 1075 | — | — | 46 |
| Sensitivity | | 53.3% | 30.0% | 0.0% | 46.7% |

The reference values of AFP, CEA, CA19-9, and PIVKA-II were 10 ng/mL, 5 ng/mL, 37 U/mL, and 40 mAU/mL, respectively. Each sample that exhibited a measurement value equal to or higher than the reference values was determined to be positive, and the sensitivity of each tumor marker was calculated.

TABLE 6

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 1_2 | 99.3 | 100 | 99 | 100 | 100 | 100 |
| 1_3 | 100 | 100 | 100 | 98.5 | 100 | 98 |
| 1_4 | 99.3 | 100 | 99 | 100 | 100 | 100 |
| 1_5 | 97.8 | 97.1 | 98 | 97 | 93.8 | 98 |
| 1_6 | 99.3 | 97.1 | 100 | 97 | 93.8 | 98 |
| 1_7 | 96.3 | 91.2 | 98 | 97 | 87.5 | 100 |
| 1_8 | 100 | 100 | 100 | 97 | 93.8 | 98 |
| 1_9 | 97.8 | 97.1 | 98 | 97 | 100 | 96 |
| 1_10 | 99.2 | 100 | 99 | 100 | 100 | 100 |
| 1_11 | 98.5 | 100 | 98 | 97 | 93.8 | 98 |
| 1_12 | 97.8 | 100 | 97 | 97 | 93.8 | 98 |
| 1_13 | 98.5 | 97.1 | 99 | 98.5 | 93.8 | 100 |
| 1_14 | 99.3 | 100 | 99 | 98.5 | 93.8 | 100 |
| 1_15 | 97.8 | 94.1 | 99 | 98.5 | 93.8 | 100 |
| 1_16 | 97.8 | 94.1 | 99 | 97 | 93.8 | 98 |
| 1_17 | 99.3 | 100 | 99 | 97 | 100 | 96 |
| 1_18 | 97.8 | 97.1 | 98 | 97 | 93.8 | 98 |
| 1_19 | 96.3 | 94.1 | 97 | 97 | 93.8 | 98 |
| 1_20 | 96.3 | 94.1 | 97 | 97 | 93.8 | 98 |
| 1_21 | 95.5 | 94.1 | 96 | 97 | 93.8 | 98 |
| 1_22 | 97 | 94.1 | 98 | 97 | 93.8 | 98 |
| 1_23 | 97.8 | 97.1 | 98 | 98.5 | 100 | 98 |
| 1_24 | 98.5 | 100 | 98 | 97 | 93.8 | 98 |
| 1_25 | 97.8 | 97.1 | 98 | 97 | 93.8 | 98 |
| 1_26 | 97 | 97.1 | 97 | 97 | 93.8 | 98 |
| 1_27 | 97.8 | 97.1 | 98 | 95.5 | 93.8 | 96 |
| 1_28 | 97.8 | 100 | 97 | 97 | 93.8 | 98 |
| 1_29 | 97.8 | 100 | 97 | 97 | 100 | 96 |
| 1_30 | 98.5 | 97.1 | 99 | 93.9 | 87.5 | 96 |
| 1_31 | 95.5 | 91.2 | 97 | 97 | 93.8 | 98 |
| 1_32 | 99.3 | 100 | 99 | 97 | 100 | 96 |
| 1_33 | 96.3 | 94.1 | 97 | 97 | 93.8 | 98 |
| 1_34 | 96.3 | 97.1 | 96 | 97 | 93.8 | 98 |
| 1_35 | 97.8 | 97.1 | 98 | 97 | 93.8 | 98 |
| 1_36 | 99.3 | 100 | 99 | 98.5 | 93.8 | 100 |
| 1_37 | 97 | 94.1 | 98 | 97 | 93.8 | 98 |
| 1_38 | 98.5 | 97.1 | 99 | 97 | 93.8 | 98 |
| 1_39 | 99.3 | 97.1 | 100 | 100 | 100 | 100 |
| 1_40 | 97 | 97.1 | 97 | 97 | 93.8 | 98 |
| 1_41 | 95.5 | 94.1 | 96 | 97 | 93.8 | 98 |
| 1_42 | 96.3 | 97.1 | 96 | 97 | 93.8 | 98 |
| 1_43 | 96.3 | 94.1 | 97 | 97 | 93.8 | 98 |
| 1_44 | 98.5 | 100 | 98 | 97 | 100 | 96 |
| 1_45 | 97.8 | 97.1 | 98 | 97 | 93.8 | 98 |
| 1_46 | 97 | 97.1 | 97 | 97 | 93.8 | 98 |
| 1_47 | 97 | 94.1 | 98 | 97 | 93.8 | 98 |
| 1_48 | 97.8 | 97.1 | 98 | 97 | 93.8 | 98 |
| 1_49 | 98.5 | 97.1 | 99 | 98.5 | 93.8 | 100 |
| 1_50 | 96.3 | 97.1 | 96 | 97 | 93.8 | 98 |
| 1_51 | 97 | 97.1 | 97 | 97 | 93.8 | 98 |
| 1_52 | 99.3 | 100 | 99 | 98.5 | 100 | 98 |
| 1_53 | 95.5 | 97.1 | 95 | 97 | 93.8 | 98 |
| 1_54 | 96.3 | 94.1 | 97 | 97 | 93.8 | 98 |
| 1_55 | 97.8 | 97.1 | 98 | 97 | 93.8 | 98 |
| 1_56 | 96.3 | 97.1 | 96 | 97 | 93.8 | 98 |
| 1_57 | 97 | 94.1 | 98 | 97 | 93.8 | 98 |
| 1_58 | 96.3 | 94.1 | 97 | 97 | 93.8 | 98 |
| 1_59 | 97 | 94.1 | 98 | 98.5 | 93.8 | 100 |
| 1_60 | 97 | 97.1 | 97 | 97 | 93.8 | 98 |
| 1_61 | 95.5 | 94.1 | 96 | 97 | 93.8 | 98 |
| 1_62 | 97 | 94.1 | 98 | 97 | 93.8 | 98 |
| 1_63 | 96.3 | 94.1 | 97 | 97 | 93.8 | 98 |
| 1_64 | 97.8 | 94.1 | 99 | 97 | 93.8 | 98 |
| 1_65 | 97.8 | 97.1 | 98 | 97 | 93.8 | 98 |
| 1_66 | 97.8 | 97.1 | 98 | 97 | 93.8 | 98 |
| 1_67 | 97 | 94.1 | 98 | 97 | 93.8 | 98 |
| 1_68 | 98.5 | 100 | 98 | 98.5 | 100 | 98 |
| 1_69 | 96.3 | 94.1 | 97 | 97 | 93.8 | 98 |
| 1_70 | 97.8 | 94.1 | 99 | 97 | 93.8 | 98 |
| 1_71 | 97.8 | 97.1 | 98 | 97 | 93.8 | 98 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_72 | 97.8 | 100 | 97 | 95.5 | 100 | 94 |
| 1_73 | 95.5 | 94.1 | 96 | 97 | 93.8 | 98 |
| 1_74 | 99.3 | 100 | 99 | 98.5 | 100 | 98 |
| 1_75 | 98.5 | 100 | 98 | 97 | 93.8 | 98 |
| 1_76 | 96.3 | 97.1 | 96 | 97 | 93.8 | 98 |
| 1_77 | 97.8 | 97.1 | 98 | 97 | 93.8 | 98 |
| 1_78 | 97 | 97.1 | 97 | 97 | 93.8 | 98 |
| 1_79 | 97 | 97.1 | 97 | 97 | 93.8 | 98 |
| 1_80 | 97 | 94.1 | 98 | 95.5 | 87.5 | 98 |
| 1_81 | 98.5 | 97.1 | 99 | 95.5 | 93.8 | 96 |
| 1_82 | 95.5 | 97.1 | 95 | 97 | 93.8 | 98 |
| 1_83 | 96.3 | 91.2 | 98 | 97 | 93.8 | 98 |
| 1_84 | 97.8 | 97.1 | 98 | 97 | 93.8 | 98 |
| 1_85 | 96.3 | 97.1 | 96 | 97 | 93.8 | 98 |
| 1_86 | 97 | 97.1 | 97 | 95.5 | 93.8 | 96 |
| 1_87 | 97 | 97.1 | 97 | 97 | 93.8 | 98 |
| 1_88 | 96.3 | 94.1 | 97 | 98.5 | 100 | 98 |
| 1_89 | 95.5 | 97.1 | 95 | 95.5 | 93.8 | 96 |
| 1_90 | 98.5 | 100 | 98 | 95.5 | 93.8 | 96 |
| 1_91 | 96.3 | 97.1 | 96 | 97 | 93.8 | 98 |
| 1_92 | 97 | 97.1 | 97 | 97 | 93.8 | 98 |
| 1_93 | 97 | 100 | 96 | 95.5 | 93.8 | 96 |
| 1_94 | 96.3 | 94.1 | 97 | 97 | 93.8 | 98 |
| 1_95 | 97 | 97.1 | 97 | 97 | 93.8 | 98 |
| 1_96 | 99.3 | 100 | 99 | 97 | 100 | 96 |
| 1_97 | 97 | 100 | 96 | 95.5 | 93.8 | 96 |
| 1_98 | 97 | 100 | 96 | 95.5 | 93.8 | 96 |
| 1_99 | 97 | 97.1 | 97 | 97 | 93.8 | 98 |
| 1_100 | 98.5 | 100 | 98 | 95.5 | 93.8 | 96 |
| 1_101 | 97.8 | 100 | 97 | 93.9 | 93.8 | 94 |
| 1_102 | 97.8 | 100 | 97 | 97 | 93.8 | 98 |
| 1_103 | 97 | 97.1 | 97 | 97 | 93.8 | 98 |
| 1_104 | 97.8 | 97.1 | 98 | 97 | 93.8 | 98 |
| 1_105 | 96.3 | 97.1 | 96 | 97 | 93.8 | 98 |
| 1_106 | 97 | 100 | 96 | 95.5 | 93.8 | 96 |
| 1_107 | 96.3 | 97.1 | 96 | 97 | 93.8 | 98 |
| 1_108 | 96.3 | 97.1 | 96 | 95.5 | 93.8 | 96 |
| 1_109 | 96.3 | 97.1 | 96 | 97 | 93.8 | 98 |
| 1_110 | 97 | 97.1 | 97 | 98.5 | 100 | 98 |
| 1_111 | 97.8 | 100 | 97 | 97 | 100 | 96 |
| 1_112 | 96.3 | 97.1 | 96 | 97 | 93.8 | 98 |
| 1_113 | 98.5 | 100 | 98 | 97 | 100 | 96 |
| 1_114 | 96.3 | 100 | 95 | 95.5 | 93.8 | 96 |
| 1_115 | 97.8 | 97.1 | 98 | 98.5 | 100 | 98 |
| 1_116 | 95.5 | 97.1 | 95 | 97 | 93.8 | 98 |
| 1_117 | 97 | 94.1 | 98 | 97 | 93.8 | 98 |
| 1_118 | 95.5 | 97.1 | 95 | 97 | 93.8 | 98 |
| 1_119 | 97 | 97.1 | 97 | 97 | 93.8 | 98 |
| 1_120 | 95.5 | 97.1 | 95 | 97 | 93.8 | 98 |
| 1_121 | 97 | 97 | 97 | 97 | 93.8 | 98 |
| 1_122 | 95.5 | 97.1 | 95 | 97 | 93.8 | 98 |
| 1_123 | 97 | 97.1 | 97 | 98.5 | 100 | 98 |
| 1_124 | 95.5 | 97.1 | 95 | 97 | 93.8 | 98 |
| 1_125 | 98.5 | 97.1 | 99 | 97 | 93.8 | 98 |
| 1_126 | 96.3 | 94.1 | 97 | 93.9 | 93.8 | 94 |
| 1_127 | 97 | 97.1 | 97 | 98.5 | 100 | 98 |
| 1_128 | 96.3 | 97.1 | 96 | 95.5 | 93.8 | 96 |
| 1_129 | 97 | 100 | 96 | 97 | 100 | 96 |
| 1_130 | 95.5 | 97.1 | 95 | 97 | 93.8 | 98 |
| 1_131 | 97 | 100 | 96 | 93.9 | 93.8 | 94 |
| 1_132 | 96.3 | 94.1 | 97 | 97 | 93.8 | 98 |
| 1_133 | 96.3 | 97.1 | 96 | 95.5 | 93.8 | 96 |
| 1_134 | 98.5 | 100 | 98 | 97 | 93.8 | 98 |
| 1_135 | 98.5 | 97.1 | 99 | 95.5 | 93.8 | 96 |
| 1_136 | 97 | 97.1 | 97 | 97 | 93.8 | 98 |
| 1_137 | 97 | 97.1 | 97 | 98.5 | 100 | 98 |
| 1_138 | 96.3 | 97.1 | 96 | 97 | 93.8 | 98 |
| 1_139 | 96.3 | 94.1 | 97 | 97 | 93.8 | 98 |
| 1_140 | 96.3 | 97.1 | 96 | 97 | 93.8 | 98 |
| 1_141 | 97.8 | 97.1 | 98 | 97 | 100 | 96 |
| 1_142 | 95.5 | 94.1 | 96 | 97 | 93.8 | 98 |
| 1_143 | 95.5 | 97.1 | 95 | 97 | 93.8 | 98 |
| 1_144 | 95.5 | 97.1 | 95 | 97 | 93.8 | 98 |
| 1_145 | 97 | 94.1 | 98 | 97 | 93.8 | 98 |
| 1_146 | 95.5 | 94.1 | 96 | 97 | 93.8 | 98 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_147 | 98.5 | 97.1 | 99 | 97 | 93.8 | 98 |
| 1_148 | 96.3 | 94.1 | 97 | 97 | 93.8 | 98 |
| 1_149 | 95.5 | 97.1 | 95 | 97 | 93.8 | 98 |
| 1_150 | 95.5 | 97.1 | 95 | 97 | 93.8 | 98 |
| 1_151 | 97.8 | 97.1 | 98 | 95.5 | 93.8 | 96 |
| 1_152 | 96.3 | 97.1 | 96 | 97 | 93.8 | 98 |
| 1_153 | 97.8 | 100 | 97 | 97 | 93.8 | 98 |
| 1_154 | 97.8 | 97.1 | 98 | 95.5 | 93.8 | 96 |
| 1_155 | 98.5 | 97.1 | 99 | 97 | 93.8 | 98 |
| 1_156 | 96.3 | 97.1 | 96 | 97 | 93.8 | 98 |
| 1_157 | 97 | 97.1 | 97 | 95.5 | 93.8 | 96 |
| 1_158 | 96.3 | 100 | 95 | 97 | 100 | 96 |
| 1_159 | 95.5 | 97.1 | 95 | 97 | 93.8 | 98 |
| 1_160 | 97 | 97.1 | 97 | 97 | 93.8 | 98 |
| 1_161 | 96.3 | 94.1 | 97 | 97 | 93.8 | 98 |
| 1_162 | 96.3 | 97.1 | 96 | 97 | 93.8 | 98 |
| 1_163 | 95.5 | 97.1 | 95 | 97 | 100 | 96 |
| 1_164 | 95.5 | 97.1 | 95 | 97 | 93.8 | 98 |
| 1_165 | 96.3 | 94.1 | 97 | 97 | 93.8 | 98 |
| 1_166 | 97 | 97.1 | 97 | 97 | 93.8 | 98 |
| 1_167 | 96.3 | 97.1 | 96 | 97 | 93.8 | 98 |
| 1_168 | 97 | 94.1 | 98 | 98.5 | 93.8 | 100 |
| 1_169 | 98.5 | 97.1 | 99 | 97 | 93.8 | 98 |
| 1_170 | 100 | 100 | 100 | 97 | 93.8 | 98 |
| 1_171 | 99.3 | 100 | 99 | 98.5 | 100 | 98 |
| 1_172 | 96.3 | 97.1 | 96 | 97 | 93.8 | 98 |
| 1_173 | 98.5 | 100 | 98 | 98.5 | 100 | 98 |
| 1_174 | 95.5 | 94.1 | 96 | 97 | 93.8 | 98 |
| 1_175 | 97 | 97.1 | 97 | 97 | 93.8 | 98 |
| 1_176 | 98.5 | 100 | 98 | 98.5 | 93.8 | 100 |
| 1_177 | 97.8 | 97.1 | 98 | 97 | 93.8 | 98 |
| 1_178 | 99.3 | 100 | 99 | 97 | 100 | 96 |
| 1_179 | 98.5 | 100 | 98 | 98.5 | 100 | 98 |
| 1_180 | 99.3 | 100 | 99 | 97 | 100 | 96 |
| 1_181 | 97.8 | 97.1 | 98 | 97 | 93.8 | 98 |
| 1_182 | 97 | 97.1 | 97 | 97 | 93.8 | 98 |
| 1_183 | 99.3 | 100 | 99 | 100 | 100 | 100 |

Example 3

Selection of Gene Marker Using all Samples and Method for Evaluating Liver Cancer Discriminant Performance of Acquired Gene Marker In this Example, the samples in the training cohort and the validation cohort used in Examples 1 and 2 were integrated, and selection of a gene marker and evaluation of its liver cancer discriminant performance were conducted using all of the samples.

Specifically, the miRNA expression levels in the serum of the 50 liver cancer patients and the 150 healthy subjects obtained in the above-mentioned Reference Examples were normalized by quantile normalization. In order to acquire diagnostic markers with higher reliability, only genes having a gene expression level of $2^6$ or higher in 50% or more of the samples in either of the liver cancer patient group or the healthy subject group were selected in the gene marker selection. In order to further acquire statistical significance for discriminating a liver cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant. The acquired genes are described in Table 7. In this way, hsa-miR-4688, hsa-miR-4648, hsa-miR-6085, hsa-miR-6126, hsa-miR-6880-5p, hsa-miR-328-5p, hsa-miR-6768-5p, hsa-miR-3180, hsa-miR-6087, hsa-miR-1273g-3p, hsa-miR-1225-5p, hsa-miR-3196, hsa-miR-4695-5p, hsa-miR-6732-5p, hsa-miR-638, hsa-miR-6813-5p, hsa-miR-665, hsa-miR-486-3p, hsa-miR-4466, hsa-miR-30c-1-3p, hsa-miR-3621, hsa-miR-6743-5p, hsa-miR-4298, hsa-miR-4741, hsa-miR-3619-3p, hsa-miR-6824-5p, hsa-miR-5698, hsa-miR-371a-5p, hsa-miR-4488, hsa-miR-1233-5p, hsa-miR-4723-5p, hsa-miR-24-3p, hsa-miR-1238-5p, hsa-miR-4442, hsa-miR-3928-3p, hsa-miR-6716-5p, hsa-miR-6089, hsa-miR-6124, hsa-miR-6778-5p, hsa-miR-557 and hsa-miR-6090 genes represented by SEQ ID NOs: 184 to 224 were found as liver cancer markers relative to the healthy subjects, in addition to the genes described in Table 2. As with the polynucleotides shown in SEQ ID NOs: 1 to 183, the results obtained about the polynucleotides shown in SEQ ID NOs: 184 to 224 also showed that the expression level measurement values were significantly lower (−) or higher (+) in the liver cancer patient group than in the healthy subject group (Table 7). These results were able to be validated in the validation cohort. Thus, the presence or absence of liver cancer in the newly obtained samples can be determined by the methods described in Examples 1 and 2 by using the gene expression level measurement values described in Table 7 either alone or in combination with the gene expression level measurement values described in Table 2.

TABLE 7

| SEQ ID NO: | Gene name | P value after Bonferroni correction | Expression level in liver cancer patient relative to healthy subject |
|---|---|---|---|
| 1 | hsa-miR-1343-3p | 7.76.E−56 | − |
| 2 | hsa-miR-6726-5p | 1.12.E−51 | − |
| 3 | hsa-miR-6515-3p | 4.93.E−36 | + |
| 4 | hsa-miR-4651 | 9.12.E−42 | − |
| 5 | hsa-miR-4257 | 2.81.E−42 | − |
| 6 | hsa-miR-3188 | 1.06.E−41 | + |
| 7 | hsa-miR-6131 | 1.97.E−37 | − |
| 8 | hsa-miR-6766-3p | 4.59.E−35 | + |
| 9 | hsa-miR-7641 | 2.35.E−36 | − |
| 10 | hsa-miR-1249 | 2.50.E−34 | + |
| 11 | hsa-miR-3679-3p | 5.67.E−31 | + |
| 12 | hsa-miR-6787-5p | 9.25.E−36 | − |
| 13 | hsa-miR-4454 | 1.38.E−34 | − |
| 14 | hsa-miR-3135b | 3.23.E−23 | − |
| 15 | hsa-miR-6765-3p | 8.15.E−32 | − |
| 16 | hsa-miR-7975 | 4.38.E−28 | − |
| 17 | hsa-miR-204-3p | 2.40.E−25 | − |
| 18 | hsa-miR-7977 | 6.65.E−27 | − |
| 19 | hsa-miR-7110-5p | 2.91.E−28 | + |
| 20 | hsa-miR-6717-5p | 4.18.E−23 | − |
| 21 | hsa-miR-6870-5p | 2.08.E−27 | + |
| 22 | hsa-miR-663b | 1.18.E−29 | − |
| 23 | hsa-miR-6875-5p | 1.80.E−24 | + |
| 24 | hsa-miR-8072 | 1.13.E−21 | + |
| 25 | hsa-miR-6816-5p | 9.86.E−26 | + |
| 26 | hsa-miR-4281 | 1.18.E−24 | − |
| 27 | hsa-miR-6729-5p | 1.39.E−22 | + |
| 28 | hsa-miR-8069 | 9.35.E−19 | + |
| 29 | hsa-miR-4706 | 1.28.E−23 | − |
| 30 | hsa-miR-7108-5p | 3.30.E−21 | + |
| 31 | hsa-miR-4433b-3p | 1.04.E−21 | + |
| 32 | hsa-miR-6893-5p | 7.87.E−23 | − |
| 33 | hsa-miR-6857-5p | 1.05.E−22 | + |
| 34 | hsa-miR-1227-5p | 5.00.E−23 | + |
| 35 | hsa-miR-6741-5p | 2.98.E−21 | − |
| 36 | hsa-miR-451a | 1.60.E−19 | − |
| 37 | hsa-miR-8063 | 1.20.E−22 | − |
| 38 | hsa-miR-3622a-5p | 8.16.E−21 | − |
| 39 | hsa-miR-615-5p | 1.17.E−21 | − |
| 40 | hsa-miR-128-1-5p | 8.49.E−17 | + |
| 41 | hsa-miR-6825-5p | 4.10.E−25 | + |
| 42 | hsa-miR-1260b | 4.23.E−20 | − |
| 43 | hsa-miR-4433-3p | 7.63.E−20 | + |
| 44 | hsa-miR-4665-5p | 1.92.E−15 | − |
| 45 | hsa-miR-7845-5p | 9.71.E−18 | + |
| 46 | hsa-miR-1908-5p | 6.59.E−21 | + |
| 47 | hsa-miR-6840-3p | 1.70.E−20 | − |
| 48 | hsa-miR-6765-5p | 3.32.E−19 | + |
| 49 | hsa-miR-296-5p | 5.14.E−14 | + |
| 51 | hsa-miR-6781-5p | 6.41.E−18 | + |
| 52 | hsa-miR-423-5p | 1.91.E−15 | − |
| 53 | hsa-miR-3663-3p | 1.67.E−16 | − |
| 54 | hsa-miR-6784-5p | 8.43.E−18 | + |
| 55 | hsa-miR-6749-5p | 2.59.E−20 | − |
| 56 | hsa-miR-1231 | 1.33.E−14 | + |
| 57 | hsa-miR-4746-3p | 3.47.E−19 | + |
| 58 | hsa-miR-6780b-5p | 2.82.E−21 | + |
| 59 | hsa-miR-4758-5p | 4.87.E−15 | − |
| 60 | hsa-miR-3679-5p | 1.59.E−19 | + |
| 61 | hsa-miR-3184-5p | 6.75.E−18 | + |
| 62 | hsa-miR-6125 | 8.43.E−17 | + |
| 63 | hsa-miR-6721-5p | 3.93.E−15 | + |
| 64 | hsa-miR-6791-5p | 1.78.E−17 | + |
| 65 | hsa-miR-3185 | 5.38.E−17 | + |
| 66 | hsa-miR-1260a | 7.87.E−15 | − |
| 67 | hsa-miR-3197 | 1.51.E−14 | + |
| 68 | hsa-miR-6845-5p | 2.09.E−16 | + |
| 69 | hsa-miR-6887-5p | 3.08.E−15 | − |
| 70 | hsa-miR-6738-5p | 1.83.E−16 | − |
| 71 | hsa-miR-6872-3p | 5.80.E−14 | − |
| 72 | hsa-miR-4497 | 2.63.E−10 | − |
| 73 | hsa-miR-1229-5p | 1.21.E−14 | + |
| 74 | hsa-miR-6820-5p | 5.60.E−13 | − |
| 75 | hsa-miR-6777-5p | 7.03.E−15 | − |
| 76 | hsa-miR-3917 | 7.63.E−13 | − |
| 77 | hsa-miR-5787 | 5.42.E−15 | + |
| 78 | hsa-miR-4286 | 1.57.E−12 | − |
| 79 | hsa-miR-6877-5p | 1.83.E−14 | − |
| 80 | hsa-miR-1225-3p | 4.77.E−11 | + |
| 81 | hsa-miR-6088 | 4.12.E−13 | − |
| 82 | hsa-miR-6800-5p | 1.01.E−13 | + |
| 83 | hsa-miR-1246 | 1.20.E−10 | − |
| 84 | hsa-miR-4467 | 2.24.E−15 | + |
| 85 | hsa-miR-4419b | 3.03.E−12 | − |
| 86 | hsa-miR-1914-3p | 3.27.E−13 | − |
| 87 | hsa-miR-4632-5p | 6.04.E−12 | + |
| 88 | hsa-miR-1915-5p | 7.61.E−15 | − |
| 89 | hsa-miR-3940-5p | 7.23.E−12 | + |
| 91 | hsa-miR-6746-5p | 5.54.E−13 | − |
| 92 | hsa-miR-5001-5p | 2.14.E−13 | − |
| 93 | hsa-miR-1228-5p | 7.95.E−13 | + |
| 94 | hsa-miR-5572 | 5.18.E−16 | + |
| 95 | hsa-miR-4327 | 2.61.E−09 | + |
| 96 | hsa-miR-4638-5p | 1.48.E−10 | − |
| 97 | hsa-miR-6799-5p | 1.10.E−10 | + |
| 98 | hsa-miR-6861-5p | 8.44.E−11 | − |
| 99 | hsa-miR-6727-5p | 2.38.E−13 | − |
| 100 | hsa-miR-4513 | 8.83.E−12 | − |
| 101 | hsa-miR-6805-3p | 1.08.E−12 | + |
| 102 | hsa-miR-6808-5p | 3.32.E−10 | + |
| 103 | hsa-miR-4449 | 4.13.E−09 | + |
| 104 | hsa-miR-1199-5p | 1.45.E−11 | − |
| 105 | hsa-miR-1275 | 2.47.E−08 | + |
| 106 | hsa-miR-4792 | 9.54.E−13 | + |
| 107 | hsa-miR-4443 | 4.44.E−10 | + |
| 108 | hsa-miR-6891-5p | 3.67.E−12 | + |
| 109 | hsa-miR-6826-5p | 5.10.E−11 | − |
| 110 | hsa-miR-6807-5p | 1.03.E−09 | + |
| 111 | hsa-miR-7150 | 1.05.E−09 | + |
| 112 | hsa-miR-4534 | 1.61.E−09 | + |
| 113 | hsa-miR-4476 | 6.66.E−08 | − |
| 114 | hsa-miR-4649-5p | 1.12.E−10 | − |
| 115 | hsa-miR-4525 | 4.68.E−12 | − |
| 116 | hsa-miR-1915-3p | 1.92.E−10 | + |
| 117 | hsa-miR-4516 | 1.95.E−10 | − |
| 118 | hsa-miR-4417 | 3.89.E−10 | + |
| 119 | hsa-miR-642b-3p | 3.82.E−10 | − |
| 120 | hsa-miR-3141 | 1.02.E−08 | + |
| 121 | hsa-miR-5100 | 4.74.E−08 | − |
| 122 | hsa-miR-6848-5p | 7.00.E−10 | + |
| 123 | hsa-miR-4739 | 1.94.E−08 | + |
| 124 | hsa-miR-4459 | 1.30.E−08 | + |
| 125 | hsa-miR-1237-5p | 1.04.E−08 | + |
| 126 | hsa-miR-296-3p | 9.28.E−08 | − |
| 127 | hsa-miR-4665-3p | 9.58.E−12 | + |
| 128 | hsa-miR-6786-5p | 7.26.E−06 | + |
| 129 | hsa-miR-4258 | 4.38.E−08 | − |
| 130 | hsa-miR-6510-5p | 4.93.E−11 | + |
| 131 | hsa-miR-1343-5p | 1.77.E−10 | + |
| 132 | hsa-miR-1247-3p | 3.69.E−11 | + |
| 133 | hsa-miR-6805-5p | 1.78.E−09 | + |
| 134 | hsa-miR-4492 | 1.28.E−07 | + |
| 135 | hsa-miR-1469 | 8.04.E−06 | + |
| 136 | hsa-miR-1268b | 7.93.E−07 | + |
| 137 | hsa-miR-6858-5p | 2.19.E−06 | + |
| 138 | hsa-miR-3937 | 5.07.E−06 | + |
| 139 | hsa-miR-939-5p | 3.71.E−10 | + |
| 140 | hsa-miR-3656 | 9.45.E−10 | + |
| 141 | hsa-miR-744-5p | 6.81.E−08 | + |
| 142 | hsa-miR-4687-3p | 1.70.E−07 | + |
| 143 | hsa-miR-4763-3p | 1.79.E−06 | + |
| 144 | hsa-miR-3620-5p | 2.74.E−06 | + |
| 145 | hsa-miR-3195 | 1.35.E−04 | + |
| 146 | hsa-miR-6842-5p | 9.98.E−12 | + |
| 147 | hsa-miR-4707-5p | 7.25.E−06 | + |
| 148 | hsa-miR-642a-3p | 1.31.E−06 | + |
| 149 | hsa-miR-7113-3p | 2.95.E−07 | + |
| 150 | hsa-miR-4728-5p | 3.51.E−06 | − |
| 151 | hsa-miR-5195-3p | 9.06.E−07 | − |
| 152 | hsa-miR-1185-1-3p | 3.35.E−05 | + |

TABLE 7-continued

| SEQ ID NO: | Gene name | P value after Bonferroni correction | Expression level in liver cancer patient relative to healthy subject |
|---|---|---|---|
| 153 | hsa-miR-6774-5p | 5.14.E−04 | + |
| 154 | hsa-miR-8059 | 1.37.E−05 | − |
| 155 | hsa-miR-3131 | 6.97.E−08 | − |
| 156 | hsa-miR-7847-3p | 6.35.E−06 | − |
| 157 | hsa-miR-4463 | 1.04.E−07 | + |
| 158 | hsa-miR-128-2-5p | 3.84.E−06 | − |
| 159 | hsa-miR-4508 | 3.57.E−05 | + |
| 160 | hsa-miR-6806-5p | 2.04.E−06 | − |
| 161 | hsa-miR-7111-5p | 6.31.E−05 | + |
| 162 | hsa-miR-6782-5p | 2.11.E−07 | + |
| 163 | hsa-miR-4734 | 1.79.E−05 | + |
| 164 | hsa-miR-3162-5p | 7.73.E−04 | + |
| 165 | hsa-miR-887-3p | 7.67.E−05 | + |
| 166 | hsa-miR-6752-5p | 7.74.E−05 | + |
| 167 | hsa-miR-6724-5p | 4.17.E−05 | + |
| 168 | hsa-miR-23b-3p | 1.17.E−30 | − |
| 169 | hsa-miR-23a-3p | 5.61.E−28 | − |
| 170 | hsa-miR-625-3p | 1.19.E−16 | + |
| 171 | hsa-miR-1228-3p | 7.80.E−28 | + |
| 172 | hsa-miR-614 | 7.24.E−27 | − |
| 173 | hsa-miR-1913 | 1.52.E−26 | + |
| 174 | hsa-miR-92a-2-5p | 5.94.E−24 | + |
| 175 | hsa-miR-187-5p | 1.72.E−26 | − |
| 176 | hsa-miR-16-5p | 4.14.E−20 | − |
| 177 | hsa-miR-92b-3p | 1.09.E−17 | − |
| 178 | hsa-miR-150-3p | 1.47.E−13 | − |
| 179 | hsa-miR-564 | 2.36.E−15 | − |
| 180 | hsa-miR-125a-3p | 7.07.E−12 | − |
| 181 | hsa-miR-92b-5p | 8.01.E−10 | + |
| 182 | hsa-miR-92a-3p | 3.99.E−09 | − |
| 183 | hsa-miR-663a | 1.34.E−06 | + |
| 184 | hsa-miR-4688 | 4.97.E−07 | − |
| 185 | hsa-miR-4648 | 2.21.E−05 | + |
| 186 | hsa-miR-6085 | 2.31.E−05 | + |
| 187 | hsa-miR-6126 | 2.31.E−05 | + |
| 188 | hsa-miR-6880-5p | 2.44.E−05 | + |
| 189 | hsa-miR-328-5p | 2.90.E−05 | + |
| 190 | hsa-miR-6768-5p | 4.36.E−05 | + |
| 191 | hsa-miR-3180 | 6.14.E−05 | + |
| 192 | hsa-miR-6087 | 8.15.E−05 | − |
| 193 | hsa-miR-1273g-3p | 1.23.E−04 | − |
| 194 | hsa-miR-1225-5p | 1.23.E−04 | + |
| 195 | hsa-miR-3196 | 1.32.E−04 | + |
| 196 | hsa-miR-4695-5p | 1.47.E−04 | + |
| 197 | hsa-miR-6732-5p | 2.45.E−04 | + |
| 198 | hsa-miR-638 | 2.98.E−04 | − |
| 199 | hsa-miR-6813-5p | 3.27.E−04 | + |
| 200 | hsa-miR-665 | 3.46.E−04 | + |
| 201 | hsa-miR-486-3p | 4.04.E−04 | − |
| 202 | hsa-miR-4466 | 4.22.E−04 | − |
| 203 | hsa-miR-30c-1-3p | 5.71.E−04 | + |
| 204 | hsa-miR-3621 | 8.32.E−04 | − |
| 205 | hsa-miR-6743-5p | 8.89.E−04 | + |
| 206 | hsa-miR-4298 | 1.05.E−03 | − |
| 207 | hsa-miR-4741 | 1.07.E−03 | + |
| 208 | hsa-miR-3619-3p | 1.11.E−03 | + |
| 209 | hsa-miR-6824-5p | 1.17.E−03 | + |
| 210 | hsa-miR-5698 | 1.30.E−03 | − |
| 211 | hsa-miR-371a-5p | 1.51.E−03 | − |
| 212 | hsa-miR-4488 | 1.85.E−03 | − |
| 213 | hsa-miR-1233-5p | 1.90.E−03 | − |
| 214 | hsa-miR-4723-5p | 2.05.E−03 | + |
| 215 | hsa-miR-24-3p | 2.09.E−03 | − |
| 216 | hsa-miR-1238-5p | 2.18.E−03 | + |
| 217 | hsa-miR-4442 | 2.48.E−03 | − |
| 218 | hsa-miR-3928-3p | 2.71.E−03 | + |
| 219 | hsa-miR-6716-5p | 2.96.E−03 | + |
| 220 | hsa-miR-6089 | 3.43.E−03 | + |
| 221 | hsa-miR-6124 | 3.68.E−03 | + |
| 222 | hsa-miR-6778-5p | 4.10.E−03 | − |
| 223 | hsa-miR-557 | 6.88.E−03 | + |
| 224 | hsa-miR-6090 | 9.92.E−03 | + |

Example 4

Method for Evaluating Liver Cancer-Specific Discriminant Performance by Combination of Multiple Gene Markers Using Samples in the Validation Cohort In this Example, novel additional gene markers for diagnosis were selected by comparing gene expression levels of miRNAs in sera of liver cancer patients with those of a control group consisting of healthy subjects, pancreatic cancer patients, bile duct cancer patients, stomach cancer patients, esophageal cancer patients, colorectal cancer patients, and benign pancreaticobiliary disease patients, in the same way as the method described in Example 1, and targeting the training cohort as the sample group described in Reference Example 2. One or two or more markers selected from the group consisting of the polynucleotides consisting of the nucleotide sequences represented by SEQ ID NOs: 714 to 729 thus selected and the gene markers selected in Example 1 were used to evaluate liver cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 4 expression level measurement values comprising at least one or more of the expression level measurement values of the polynucleotides consisting of the nucleotide sequences represented by SEQ ID NOs: 1 to 167 and 714 to 729, to construct a discriminant for determining the presence or absence of liver cancer. Next, accuracy, sensitivity, and specificity in the validation cohort were calculated using the discriminant thus prepared, with the liver cancer patient group as a positive sample group and, on the other hand, the healthy subject group, the pancreatic cancer patient group, the bile duct cancer patient group, the stomach cancer patient group, the esophageal cancer patient group, the colorectal cancer patient group, and the benign pancreaticobiliary disease patient group as negative sample groups. The discriminant performance of the selected polynucleotides was validated using independent samples.

Most of polynucleotides consisting of the nucleotide sequences represented by these SEQ ID NOs (SEQ ID NOs: 1 to 224 and 714 to 729 corresponding to the miRNA markers of Table 1) or complementary sequences thereof mentioned above were able to provide relatively high accuracy, sensitivity, and specificity in the determination of the presence or absence of liver cancer, and furthermore, were able to specifically discriminate liver cancer from other cancers. For example, among the combinations of a plurality of polynucleotides selected from the group consisting of polynucleotides consisting of the nucleotide sequences represented by SEQ ID NOs: 1, 2, 3, 5, 7, 9, 12, 17, 20, 22, 27, 28, 29, 38, 39, 44, 46, 48, 51, 54, 61, 76, 89, 93, 101, 109, 116, 123, 132, 134, 136, 148, 150, 151, 155, 157, 164, 166, 167, 172, 180, 186, 188, 189, 197, 198, 214, 216, 714, 715, 716, 717, 718, 719, 720, 721, 722, 723, 724, 725, 726, 727, 728 and 729 or complementary sequences thereof (the cancer type-specific polynucleotide group 1) as polynucleotides capable of specifically binding to target markers, combinations comprising at least one or more polynucleotide(s) selected from the group consisting of polynucleotides consisting of the nucleotide sequences represented by SEQ ID NOs: 1, 3, 7, 9, 22, 38, 44, 134, 148, 155, 157, 164, 167, 172, 214, 714, 715, 716, and 717 or complementary sequences thereof (the cancer type-specific polynucleotide group 2) were able to specifically discriminate liver cancer from other cancers with high accuracy.

The number of the polynucleotides with cancer type specificity in the combination mentioned above can be 1, 2, 3, 4, 5, 6, 7, 8, 9, 10 or more for the combination. The combinations of 4 or more polynucleotides were able to exhibit discriminant accuracy of 90% or higher.

Specifically, the discriminant accuracy of the measurement using the polynucleotide consisting of the nucleotide sequence represented by SEQ ID NO: 1 or a complementary sequence thereof is shown in Table 8-1. In Table 8-1, "SEQ ID NO" represents one polynucleotide or a combination of a plurality of polynucleotides used with the number of SEQ ID NO: (the same holds true for Tables 8-2 to 8-19). The measurement using, alone (one), the polynucleotide consisting of the nucleotide sequence represented by SEQ ID NO: 1 or a complementary sequence thereof exhibited accuracy of 71.2% in the training cohort and accuracy of 73.2% in the validation cohort. Also, for example, the measurement using the combinations of two polynucleotides comprising at least one polynucleotide consisting of the nucleotide sequence represented by SEQ ID NO: 1 or a complementary sequence thereof exhibited the highest accuracy of 88.1% in the training cohort and accuracy of 90% in the validation cohort. Furthermore, for example, the measurement using the combinations of three polynucleotides comprising at least one polynucleotide consisting of the nucleotide sequence represented by SEQ ID NO: 1 or a complementary sequence thereof exhibited the highest accuracy of 90.2% in the training cohort and accuracy of 90.5% in the validation cohort. Furthermore, for example, the measurement using the combinations of four polynucleotides comprising at least one polynucleotide consisting of the nucleotide sequence represented by SEQ ID NO: 1 or a complementary sequence thereof exhibited the highest accuracy of 92.3% in the training cohort and accuracy of 93.2% in the validation cohort.

The discriminant accuracy of the measurement using the polynucleotide consisting of the nucleotide sequence represented by SEQ ID NO: 3 or a complementary sequence thereof is shown in Table 8-2. The measurement using, alone (one), the polynucleotide consisting of the nucleotide sequence represented by SEQ ID NO: 3 or a complementary sequence thereof exhibited accuracy of 78.7% in the training cohort and accuracy of 73.2% in the validation cohort. Also, for example, the measurement using the combinations of two polynucleotides comprising at least one polynucleotide consisting of the nucleotide sequence represented by SEQ ID NO: 3 or a complementary sequence thereof exhibited the highest accuracy of 88.7% in the training cohort and accuracy of 87.4% in the validation cohort. Furthermore, for example, the measurement using the combinations of three polynucleotides comprising at least one polynucleotide consisting of the nucleotide sequence represented by SEQ ID NO: 3 or a complementary sequence thereof exhibited the highest accuracy of 91.8% in the training cohort and accuracy of 87.9% in the validation cohort. Furthermore, for example, the measurement using the combinations of four polynucleotides comprising at least one polynucleotide consisting of the nucleotide sequence represented by SEQ ID NO: 3 or a complementary sequence thereof exhibited the highest accuracy of 92.9% in the training cohort and accuracy of 93.2% in the validation cohort.

The discriminant accuracy of the measurement using the polynucleotide consisting of the nucleotide sequence represented by SEQ ID NO: 7 or a complementary sequence thereof is shown in Table 8-3. The measurement using, alone (one), the polynucleotide consisting of the nucleotide sequence represented by SEQ ID NO: 7 or a complementary sequence thereof exhibited accuracy of 85.5% in the training cohort and accuracy of 84.7% in the validation cohort. Also, for example, the measurement using the combinations of two polynucleotides comprising at least one polynucleotide consisting of the nucleotide sequence represented by SEQ ID NO: 7 or a complementary sequence thereof exhibited the highest accuracy of 91.5% in the training cohort and accuracy of 90.5% in the validation cohort. Furthermore, for example, the measurement using the combinations of three polynucleotides comprising at least one polynucleotide consisting of the nucleotide sequence represented by SEQ ID NO: 7 or a complementary sequence thereof exhibited the highest accuracy of 93.7% in the training cohort and accuracy of 92.1% in the validation cohort. Furthermore, for example, the measurement using the combinations of four polynucleotides comprising at least one polynucleotide consisting of the nucleotide sequence represented by SEQ ID NO: 7 or a complementary sequence thereof exhibited the highest accuracy of 94.4% in the training cohort and accuracy of 92.6% in the validation cohort.

The discriminant accuracy of the measurement using the polynucleotide consisting of the nucleotide sequence represented by SEQ ID NO: 9 or a complementary sequence thereof is shown in Table 8-4. The measurement using, alone (one), the polynucleotide consisting of the nucleotide sequence represented by SEQ ID NO: 9 or a complementary sequence thereof exhibited accuracy of 59.7% in the training cohort and accuracy of 59.5% in the validation cohort. Also, for example, the measurement using the combinations of two polynucleotides comprising at least one polynucleotide consisting of the nucleotide sequence represented by SEQ ID NO: 9 or a complementary sequence thereof exhibited the highest accuracy of 86% in the training cohort and accuracy of 81.1% in the validation cohort. Furthermore, for example, the measurement using the combinations of three polynucleotides comprising at least one polynucleotide consisting of the nucleotide sequence represented by SEQ ID NO: 9 or a complementary sequence thereof exhibited the highest accuracy of 91.8% in the training cohort and accuracy of 84.7% in the validation cohort. Furthermore, for example, the measurement using the combinations of four polynucleotides comprising at least one polynucleotide consisting of the nucleotide sequence represented by SEQ ID NO: 9 or a complementary sequence thereof exhibited the highest accuracy of 94.7% in the training cohort and accuracy of 92.1% in the validation cohort.

The discriminant accuracy of the measurement using the polynucleotide consisting of the nucleotide sequence represented by SEQ ID NO: 22 or a complementary sequence thereof is shown in Table 8-5. The measurement using, alone (one), the polynucleotide consisting of the nucleotide sequence represented by SEQ ID NO: 22 or a complementary sequence thereof exhibited accuracy of 76.5% in the training cohort and accuracy of 78.9% in the validation cohort. Also, for example, the measurement using the combinations of two polynucleotides comprising at least one polynucleotide consisting of the nucleotide sequence represented by SEQ ID NO: 22 or a complementary sequence thereof exhibited the highest accuracy of 85.8% in the training cohort and accuracy of 84.7% in the validation cohort. Furthermore, for example, the measurement using the combinations of three polynucleotides comprising at least one polynucleotide consisting of the nucleotide sequence represented by SEQ ID NO: 22 or a complementary sequence thereof exhibited the highest accuracy of 91.3% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 22 or a complementary sequence thereof exhibited the highest accuracy of 93.7% in the training cohort and accuracy of 93.7% in the validation cohort.

The discriminant accuracy of the measurement using the polynucleotide consisting of the nucleotide sequence represented by SEQ ID NO: 38 or a complementary sequence thereof is shown in Table 8-6. The measurement using, alone (one), the polynucleotide consisting of the nucleotide sequence represented by SEQ ID NO: 38 or a complementary sequence thereof exhibited accuracy of 65.5% in the training cohort and accuracy of 65.8% in the validation cohort. Also, for example, the measurement using the combinations of two polynucleotides comprising at least one polynucleotide consisting of the nucleotide sequence represented by SEQ ID NO: 38 or a complementary sequence thereof exhibited the highest accuracy of 86.3% in the training cohort and accuracy of 84.2% in the validation cohort. Furthermore, for example, the measurement using the combinations of three polynucleotides comprising at least one polynucleotide consisting of the nucleotide sequence represented by SEQ ID NO: 38 or a complementary sequence thereof exhibited the highest accuracy of 92.3% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 38 or a complementary sequence thereof exhibited the highest accuracy of 94.2% in the training cohort and accuracy of 92.1% in the validation cohort.

The discriminant accuracy of the measurement using the polynucleotide consisting of the nucleotide sequence represented by SEQ ID NO: 44 or a complementary sequence thereof is shown in Table 8-7. The measurement using, alone (one), the polynucleotide consisting of the nucleotide sequence represented by SEQ ID NO: 44 or a complementary sequence thereof exhibited accuracy of 62.6% in the training cohort and accuracy of 62.1% in the validation cohort. Also, for example, the measurement using the combinations of two polynucleotides comprising at least one polynucleotide consisting of the nucleotide sequence represented by SEQ ID NO: 44 or a complementary sequence thereof exhibited the highest accuracy of 90.5% in the training cohort and accuracy of 86.3% in the validation cohort. Furthermore, for example, the measurement using the combinations of three polynucleotides comprising at least one polynucleotide consisting of the nucleotide sequence represented by SEQ ID NO: 44 or a complementary sequence thereof exhibited the highest accuracy of 92.9% in the training cohort and accuracy of 91.1% in the validation cohort. Furthermore, for example, the measurement using the combinations of four polynucleotides comprising at least one polynucleotide consisting of the nucleotide sequence represented by SEQ ID NO: 44 or a complementary sequence thereof exhibited the highest accuracy of 93.7% in the training cohort and accuracy of 91.6% in the validation cohort.

The discriminant accuracy of the measurement using the polynucleotide consisting of the nucleotide sequence represented by SEQ ID NO: 134 or a complementary sequence thereof is shown in Table 8-8. The measurement using, alone (one), the polynucleotide consisting of the nucleotide sequence represented by SEQ ID NO: 134 or a complementary sequence thereof exhibited accuracy of 53.4% in the training cohort and accuracy of 58.9% in the validation cohort. Also, for example, the measurement using the combinations of two polynucleotides comprising at least one polynucleotide consisting of the nucleotide sequence represented by SEQ ID NO: 134 or a complementary sequence thereof exhibited the highest accuracy of 87.3% in the training cohort and accuracy of 84.2% in the validation cohort. Furthermore, for example, the measurement using the combinations of three polynucleotides comprising at least one polynucleotide consisting of the nucleotide sequence represented by SEQ ID NO: 134 or a complementary sequence thereof exhibited the highest accuracy of 92.9% in the training cohort and accuracy of 91.1% in the validation cohort. Furthermore, for example, the measurement using the combinations of four polynucleotides comprising at least one polynucleotide consisting of the nucleotide sequence represented by SEQ ID NO: 134 or a complementary sequence thereof exhibited the highest accuracy of 93.7% in the training cohort and accuracy of 92.1% in the validation cohort.

The discriminant accuracy of the measurement using the polynucleotide consisting of the nucleotide sequence represented by SEQ ID NO: 148 or a complementary sequence thereof is shown in Table 8-9. The measurement using, alone (one), the polynucleotide consisting of the nucleotide sequence represented by SEQ ID NO: 148 or a complementary sequence thereof exhibited accuracy of 73.6% in the training cohort and accuracy of 75.3% in the validation cohort. Also, for example, the measurement using the combinations of two polynucleotides comprising at least one polynucleotide consisting of the nucleotide sequence represented by SEQ ID NO: 148 or a complementary sequence thereof exhibited the highest accuracy of 86.3% in the training cohort and accuracy of 85.3% in the validation cohort. Furthermore, for example, the measurement using the combinations of three polynucleotides comprising at least one polynucleotide consisting of the nucleotide sequence represented by SEQ ID NO: 148 or a complementary sequence thereof exhibited the highest accuracy of 93.7% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 148 or a complementary sequence thereof exhibited the highest accuracy of 93.7% in the training cohort and accuracy of 92.1% in the validation cohort.

The discriminant accuracy of the measurement using the polynucleotide consisting of the nucleotide sequence represented by SEQ ID NO: 155 or a complementary sequence thereof is shown in Table 8-10. The measurement using, alone (one), the polynucleotide consisting of the nucleotide sequence represented by SEQ ID NO: 155 or a complementary sequence thereof exhibited accuracy of 60.8% in the training cohort and accuracy of 58.9% in the validation cohort. Also, for example, the measurement using the combinations of two polynucleotides comprising at least one polynucleotide consisting of the nucleotide sequence represented by SEQ ID NO: 155 or a complementary sequence thereof exhibited the highest accuracy of 86.5% in the training cohort and accuracy of 85.8% in the validation cohort. Furthermore, for example, the measurement using the combinations of three polynucleotides comprising at least one polynucleotide consisting of the nucleotide sequence represented by SEQ ID NO: 155 or a complementary sequence thereof exhibited the highest accuracy of 90.5% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 155 or a complementary sequence thereof exhibited the highest accuracy of 93.4% in the training cohort and accuracy of 91.6% in the validation cohort.

The discriminant accuracy of the measurement using the polynucleotide consisting of the nucleotide sequence represented by SEQ ID NO: 157 or a complementary sequence thereof is shown in Table 8-11. The measurement using, alone (one), the polynucleotide consisting of the nucleotide sequence represented by SEQ ID NO: 157 or a complementary sequence thereof exhibited accuracy of 70.3% in the training cohort and accuracy of 68.9% in the validation cohort. Also, for example, the measurement using the combinations of two polynucleotides comprising at least one polynucleotide consisting of the nucleotide sequence represented by SEQ ID NO: 157 or a complementary sequence thereof exhibited the highest accuracy of 86.5% in the training cohort and accuracy of 83.2% in the validation cohort. Furthermore, for example, the measurement using the combinations of three polynucleotides comprising at least one polynucleotide consisting of the nucleotide sequence represented by SEQ ID NO: 157 or a complementary sequence thereof exhibited the highest accuracy of 91% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 157 or a complementary sequence thereof exhibited the highest accuracy of 93.9% in the training cohort and accuracy of 92.6% in the validation cohort.

The discriminant accuracy of the measurement using the polynucleotide consisting of the nucleotide sequence represented by SEQ ID NO: 164 or a complementary sequence thereof is shown in Table 8-12. The measurement using, alone (one), the polynucleotide consisting of the nucleotide sequence represented by SEQ ID NO: 164 or a complementary sequence thereof exhibited accuracy of 72.4% in the training cohort and accuracy of 65.8% in the validation cohort. Also, for example, the measurement using the combinations of two polynucleotides comprising at least one polynucleotide consisting of the nucleotide sequence represented by SEQ ID NO: 164 or a complementary sequence thereof exhibited the highest accuracy of 87.6% in the training cohort and accuracy of 87.4% in the validation cohort. Furthermore, for example, the measurement using the combinations of three polynucleotides comprising at least one polynucleotide consisting of the nucleotide sequence represented by SEQ ID NO: 164 or a complementary sequence thereof exhibited the highest accuracy of 91.5% in the training cohort and accuracy of 92.1% in the validation cohort. Furthermore, for example, the measurement using the combinations of four polynucleotides comprising at least one polynucleotide consisting of the nucleotide sequence represented by SEQ ID NO: 164 or a complementary sequence thereof exhibited the highest accuracy of 92.6% in the training cohort and accuracy of 90.5% in the validation cohort.

The discriminant accuracy of the measurement using the polynucleotide consisting of the nucleotide sequence represented by SEQ ID NO: 167 or a complementary sequence thereof is shown in Table 8-13. The measurement using, alone (one), the polynucleotide consisting of the nucleotide sequence represented by SEQ ID NO: 167 or a complementary sequence thereof exhibited accuracy of 62.1% in the training cohort and accuracy of 57.4% in the validation cohort. Also, for example, the measurement using the combinations of two polynucleotides comprising at least one polynucleotide consisting of the nucleotide sequence represented by SEQ ID NO: 167 or a complementary sequence thereof exhibited the highest accuracy of 89.2% in the training cohort and accuracy of 87.4% in the validation cohort. Furthermore, for example, the measurement using the combinations of three polynucleotides comprising at least one polynucleotide consisting of the nucleotide sequence represented by SEQ ID NO: 167 or a complementary sequence thereof exhibited the highest accuracy of 92.1% in the training cohort and accuracy of 90% in the validation cohort. Furthermore, for example, the measurement using the combinations of four polynucleotides comprising at least one polynucleotide consisting of the nucleotide sequence represented by SEQ ID NO: 167 or a complementary sequence thereof exhibited the highest accuracy of 93.4% in the training cohort and accuracy of 91.1% in the validation cohort.

The discriminant accuracy of the measurement using the polynucleotide consisting of the nucleotide sequence represented by SEQ ID NO: 172 or a complementary sequence thereof is shown in Table 8-14. The measurement using, alone (one), the polynucleotide consisting of the nucleotide sequence represented by SEQ ID NO: 172 or a complementary sequence thereof exhibited accuracy of 76.8% in the training cohort and accuracy of 75.8% in the validation cohort. Also, for example, the measurement using the combinations of two polynucleotides comprising at least one polynucleotide consisting of the nucleotide sequence represented by SEQ ID NO: 172 or a complementary sequence thereof exhibited the highest accuracy of 86.3% in the training cohort and accuracy of 83.7% in the validation cohort. Furthermore, for example, the measurement using the combinations of three polynucleotides comprising at least one polynucleotide consisting of the nucleotide sequence represented by SEQ ID NO: 172 or a complementary sequence thereof exhibited the highest accuracy of 90.2% in the training cohort and accuracy of 90.5% in the validation cohort. Furthermore, for example, the measurement using the combinations of four polynucleotides comprising at least one polynucleotide consisting of the nucleotide sequence represented by SEQ ID NO: 172 or a complementary sequence thereof exhibited the highest accuracy of 92.1% in the training cohort and accuracy of 93.2% in the validation cohort.

The discriminant accuracy of the measurement using the polynucleotide consisting of the nucleotide sequence represented by SEQ ID NO: 214 or a complementary sequence thereof is shown in Table 8-15. The measurement using, alone (one), the polynucleotide consisting of the nucleotide sequence represented by SEQ ID NO: 214 or a complementary sequence thereof exhibited accuracy of 69.5% in the training cohort and accuracy of 67.4% in the validation cohort. Also, for example, the measurement using the combinations of two polynucleotides comprising at least one polynucleotide consisting of the nucleotide sequence represented by SEQ ID NO: 214 or a complementary sequence thereof exhibited the highest accuracy of 89.2% in the training cohort and accuracy of 87.9% in the validation cohort. Furthermore, for example, the measurement using the combinations of three polynucleotides comprising at least one polynucleotide consisting of the nucleotide sequence represented by SEQ ID NO: 214 or a complementary sequence thereof exhibited the highest accuracy of 91.5% in the training cohort and accuracy of 90.5% in the validation cohort. Furthermore, for example, the measurement using the combinations of four polynucleotides comprising at least one polynucleotide consisting of the nucleotide sequence represented by SEQ ID NO: 214 or a complementary sequence thereof exhibited the highest accuracy of 93.4% in the training cohort and accuracy of 92.6% in the validation cohort.

The discriminant accuracy of the measurement using the polynucleotide consisting of the nucleotide sequence represented by SEQ ID NO: 714 or a complementary sequence thereof is shown in Table 8-16. The measurement using, alone (one), the polynucleotide consisting of the nucleotide sequence represented by SEQ ID NO: 714 or a complementary sequence thereof exhibited accuracy of 44.7% in the training cohort and accuracy of 46.8% in the validation cohort. Also, for example, the measurement using the combinations of two polynucleotides comprising at least one polynucleotide consisting of the nucleotide sequence represented by SEQ ID NO: 714 or a complementary sequence thereof exhibited the highest accuracy of 90.2% in the training cohort and accuracy of 87.4% in the validation cohort. Furthermore, for example, the measurement using the combinations of three polynucleotides comprising at least one polynucleotide consisting of the nucleotide sequence represented by SEQ ID NO: 714 or a complementary sequence thereof exhibited the highest accuracy of 92.1% in the training cohort and accuracy of 91.1% in the validation cohort. Furthermore, for example, the measurement using the combinations of four polynucleotides comprising at least one polynucleotide consisting of the nucleotide sequence represented by SEQ ID NO: 714 or a complementary sequence thereof exhibited the highest accuracy of 94.4% in the training cohort and accuracy of 94.2% in the validation cohort.

The discriminant accuracy of the measurement using the polynucleotide consisting of the nucleotide sequence represented by SEQ ID NO: 715 or a complementary sequence thereof is shown in Table 8-17. The measurement using, alone (one), the polynucleotide consisting of the nucleotide sequence represented by SEQ ID NO: 715 or a complementary sequence thereof exhibited accuracy of 64.2% in the training cohort and accuracy of 65.8% in the validation cohort. Also, for example, the measurement using the combinations of two polynucleotides comprising at least one polynucleotide consisting of the nucleotide sequence represented by SEQ ID NO: 715 or a complementary sequence thereof exhibited the highest accuracy of 87.9% in the training cohort and accuracy of 86.8% in the validation cohort. Furthermore, for example, the measurement using the combinations of three polynucleotides comprising at least one polynucleotide consisting of the nucleotide sequence represented by SEQ ID NO: 715 or a complementary sequence thereof exhibited the highest accuracy of 91.8% in the training cohort and accuracy of 91.1% in the validation cohort. Furthermore, for example, the measurement using the combinations of four polynucleotides comprising at least one polynucleotide consisting of the nucleotide sequence represented by SEQ ID NO: 715 or a complementary sequence thereof exhibited the highest accuracy of 93.9% in the training cohort and accuracy of 93.2% in the validation cohort.

The discriminant accuracy of the measurement using the polynucleotide consisting of the nucleotide sequence represented by SEQ ID NO: 716 or a complementary sequence thereof is shown in Table 8-18. The measurement using, alone (one), the polynucleotide consisting of the nucleotide sequence represented by SEQ ID NO: 716 or a complementary sequence thereof exhibited accuracy of 62.6% in the training cohort and accuracy of 58.9% in the validation cohort. Also, for example, the measurement using the combinations of two polynucleotides comprising at least one polynucleotide consisting of the nucleotide sequence represented by SEQ ID NO: 716 or a complementary sequence thereof exhibited the highest accuracy of 90.2% in the training cohort and accuracy of 86.3% in the validation cohort. Furthermore, for example, the measurement using the combinations of three polynucleotides comprising at least one polynucleotide consisting of the nucleotide sequence represented by SEQ ID NO: 716 or a complementary sequence thereof exhibited the highest accuracy of 91.3% in the training cohort and accuracy of 91.6% in the validation cohort. Furthermore, for example, the measurement using the combinations of four polynucleotides comprising at least one polynucleotide consisting of the nucleotide sequence represented by SEQ ID NO: 716 or a complementary sequence thereof exhibited the highest accuracy of 93.7% in the training cohort and accuracy of 92.1% in the validation cohort.

The discriminant accuracy of the measurement using the polynucleotide consisting of the nucleotide sequence represented by SEQ ID NO: 717 or a complementary sequence thereof is shown in Table 8-19. The measurement using, alone (one), the polynucleotide consisting of the nucleotide sequence represented by SEQ ID NO: 717 or a complementary sequence thereof exhibited accuracy of 70.3% in the training cohort and accuracy of 66.3% in the validation cohort. Also, for example, the measurement using the combinations of two polynucleotides comprising at least one polynucleotide consisting of the nucleotide sequence represented by SEQ ID NO: 717 or a complementary sequence thereof exhibited the highest accuracy of 86.8% in the training cohort and accuracy of 84.7% in the validation cohort. Furthermore, for example, the measurement using the combinations of three polynucleotides comprising at least one polynucleotide consisting of the nucleotide sequence represented by SEQ ID NO: 717 or a complementary sequence thereof exhibited the highest accuracy of 92.3% in the training cohort and accuracy of 90.5% in the validation cohort. Furthermore, for example, the measurement using the combinations of four polynucleotides comprising at least one polynucleotide consisting of the nucleotide sequence represented by SEQ ID NO: 717 or a complementary sequence thereof exhibited the highest accuracy of 93.1% in the training cohort and accuracy of 92.6% in the validation cohort.

Figure 4:
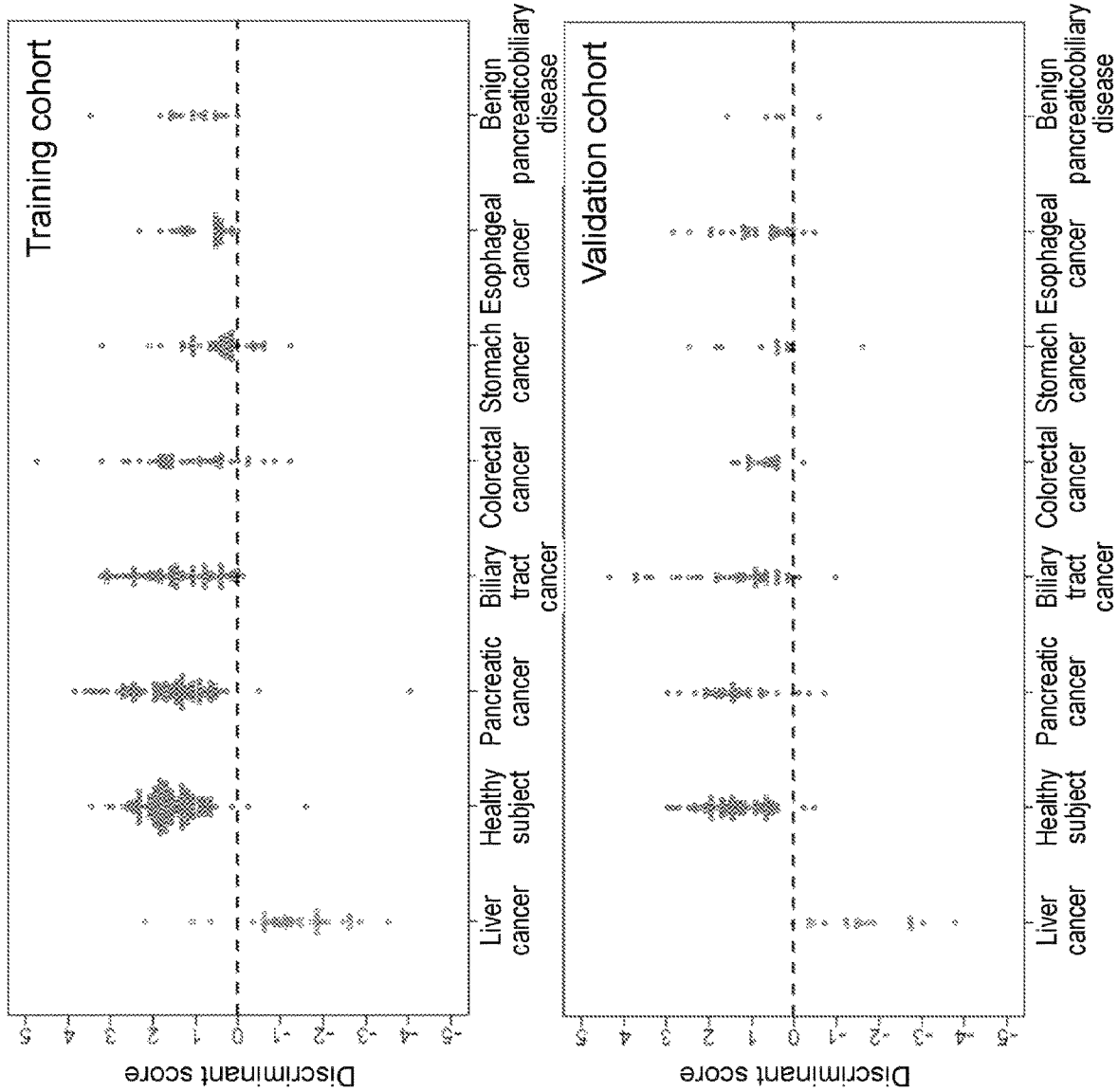
FIG. 4 Upper diagram: a discriminant (0.88×hsa-miR-6131−1.58×hsa-miR-642a-3p+0.39×hsa-miR-7641−0.33×hsa-miR-6729-5p+5.19) was prepared by use of Fisher's linear discriminant analysis from the measurement values of hsa-miR-6131 (SEQ ID NO: 7), hsa-miR-642a-3p (SEQ ID NO: 148), hsa-miR-7641 (SEQ ID NO: 9), and hsa-miR-6'729-5p (SEQ ID NO: 27) in 35 liver cancer patients, 99 healthy subjects, 72 pancreatic cancer patients, 61 bile duct cancer patients, 35 colorectal cancer patients, 38 stomach cancer patients, 25 esophageal cancer patients, and 16 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared from the training cohorts as to the measurement values of hsa-miR-6131 (SEQ ID NO: 7), hsa-miR-642a-3p (SEQ ID NO: 148), hsa-miR-7641 (SEQ ID NO: 9), and hsa-miR-6729-5p (SEQ ID NO: 27) in 17 liver cancer patients, 51 healthy subjects, 28 pancreatic cancer patients, 37 bile duct cancer patients, 15 colorectal cancer patients, 12 stomach cancer patients, 25 esophageal cancer patients, and 5 benign pancreaticobiliary disease patients selected as a validation cohort were plotted on the ordinate against the sample groups on the abscissa. The dotted line in the diagram depicts the discriminant boundary that offered a discriminant score of 0 and discriminated between the two groups.

The expression level measurement values of the nucleotide sequences represented by SEQ ID NOs: 7, 9, 27, and 148 were compared among 35 liver cancer patients, 99 healthy subjects, 72 pancreatic cancer patients, 61 bile duct cancer patients, 38 stomach cancer patients, 25 esophageal cancer patients, 35 colorectal cancer patients, and 16 benign pancreaticobiliary disease patients in the training cohort. As a result, a scatter diagram that significantly separated the discriminant score of the liver cancer patient group from the discriminant scores of the other groups was obtained in the training cohort (see the upper diagram of FIG. 4). These results were also reproducible in the validation cohort (see the lower diagram of FIG. 4).

TABLE 8-1

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1 | 71.2 | 94.3 | 68.9 | 73.2 | 100 | 70.5 |
| 1_155 | 88.1 | 91.4 | 87.8 | 90 | 88.2 | 90.2 |
| 1_7_155 | 90.2 | 88.6 | 90.4 | 90.5 | 88.2 | 90.8 |
| 1_7_9_148 | 92.3 | 91.4 | 92.4 | 93.2 | 100 | 92.5 |
| 1_9_155_172 | 91.3 | 94.3 | 91 | 91.6 | 94.1 | 91.3 |
| 1_9_148_155 | 90.2 | 91.4 | 90.1 | 90.5 | 100 | 89.6 |
| 1_155_172_715 | 91 | 91.4 | 91 | 93.2 | 100 | 92.5 |
| 1_155_164_715 | 90.8 | 94.3 | 90.4 | 93.7 | 100 | 93.1 |

TABLE 8-2

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 3 | 78.7 | 85.7 | 78 | 73.2 | 82.4 | 72.3 |
| 3_7 | 88.7 | 85.7 | 89 | 87.4 | 82.4 | 87.9 |
| 3_7_718 | 91.8 | 88.6 | 92.2 | 87.9 | 88.2 | 87.9 |
| 3_7_9_148 | 92.9 | 88.6 | 93.3 | 93.2 | 94.1 | 93.1 |
| 3_22_27_46 | 90.8 | 91.4 | 90.7 | 91.1 | 94.1 | 90.8 |
| 1_3_29_155 | 91 | 88.6 | 91.3 | 95.3 | 94.1 | 95.4 |
| 1_3_151_155 | 90.7 | 88.6 | 91 | 95.8 | 94.1 | 96 |
| 3_7_148_715 | 92.3 | 88.6 | 92.7 | 90 | 94.1 | 89.6 |

TABLE 8-3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 7 | 85.5 | 85.7 | 85.5 | 84.7 | 82.4 | 85 |
| 7_148 | 91.5 | 85.7 | 92.1 | 90.5 | 88.2 | 90.8 |
| 7_9_148 | 93.7 | 91.4 | 93.9 | 92.1 | 100 | 91.3 |
| 7_28_148_717 | 94.2 | 91.4 | 94.5 | 92.1 | 100 | 91.3 |
| 7_9_148_186 | 93.4 | 91.4 | 93.6 | 91.6 | 94.1 | 91.3 |
| 7_148_172_715 | 92.1 | 88.6 | 92.4 | 92.6 | 100 | 91.9 |
| 7_9_148_723 | 93.4 | 91.4 | 93.6 | 92.1 | 100 | 91.3 |
| 7_9_28_148 | 94.4 | 91.4 | 94.8 | 92.6 | 100 | 91.9 |

TABLE 8-4

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 9 | 59.7 | 62.9 | 59.4 | 59.5 | 94.1 | 56.1 |
| 7_9 | 86 | 88.6 | 85.8 | 81.1 | 82.4 | 80.9 |
| 7_9_714 | 91.8 | 85.7 | 92.4 | 84.7 | 76.5 | 85.5 |
| 7_9_148_157 | 93.4 | 91.4 | 93.6 | 92.1 | 100 | 91.3 |
| 7_9_148_722 | 93.9 | 91.4 | 94.2 | 91.6 | 94.1 | 91.3 |
| 7_9_27_148 | 94.7 | 91.4 | 95 | 92.1 | 94.1 | 91.9 |
| 7_9_148_725 | 93.7 | 91.4 | 93.9 | 92.1 | 100 | 91.3 |
| 7_9_148_729 | 93.7 | 91.4 | 93.9 | 91.1 | 94.1 | 90.8 |

TABLE 8-5

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 22 | 76.5 | 77.1 | 76.5 | 78.9 | 76.5 | 79.2 |
| 3_22 | 85.8 | 88.6 | 85.5 | 84.7 | 88.2 | 84.4 |

TABLE 8-5-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 7__22__148 | 91.3 | 88.6 | 91.5 | 91.6 | 88.2 | 91.9 |
| 7__9__22__148 | 93.7 | 91.4 | 93.9 | 93.7 | 100 | 93.1 |
| 7__22__28__148 | 93.7 | 91.4 | 93.9 | 92.6 | 94.1 | 92.5 |
| 7__22__148__189 | 91.8 | 85.7 | 92.4 | 92.1 | 88.2 | 92.5 |
| 2__7__22__148 | 92.1 | 91.4 | 92.1 | 92.6 | 100 | 91.9 |
| 7__22__148__720 | 92.3 | 82.9 | 93.3 | 93.2 | 88.2 | 93.6 |

TABLE 8-6

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 38 | 65.5 | 51.4 | 67 | 65.8 | 76.5 | 64.7 |
| 7__38 | 86.3 | 85.7 | 86.3 | 84.2 | 82.4 | 84.4 |
| 7__38__148 | 92.3 | 88.6 | 92.7 | 91.6 | 94.1 | 91.3 |
| 7__9__38__148 | 94.2 | 91.4 | 94.5 | 92.1 | 100 | 91.3 |
| 7__38__51__148 | 93.1 | 88.6 | 93.6 | 91.6 | 94.1 | 91.3 |
| 7__38__148__718 | 92.9 | 88.6 | 93.3 | 92.6 | 94.1 | 92.5 |
| 7__38__148__216 | 92.3 | 88.6 | 92.7 | 93.2 | 94.1 | 93.1 |
| 7__38__148__728 | 91.5 | 88.6 | 91.8 | 92.1 | 94.1 | 91.9 |

TABLE 8-7

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 44 | 62.6 | 62.9 | 62.6 | 62.1 | 94.1 | 59 |
| 7__44 | 90.5 | 85.7 | 91 | 86.3 | 88.2 | 86.1 |
| 7__44__148 | 92.9 | 91.4 | 93 | 91.1 | 100 | 90.2 |
| 7__9__44__148 | 93.7 | 91.4 | 93.9 | 91.6 | 100 | 90.8 |
| 7__44__123__148 | 93.4 | 91.4 | 93.6 | 91.1 | 100 | 90.2 |
| 7__38__44__148 | 92.9 | 91.4 | 93 | 91.1 | 100 | 90.2 |
| 7__44__148__723 | 93.1 | 91.4 | 93.3 | 91.1 | 100 | 90.2 |
| 7__44__48__148 | 93.7 | 91.4 | 93.9 | 92.1 | 100 | 91.3 |

TABLE 8-8

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 134 | 53.4 | 45.7 | 54.2 | 58.9 | 64.7 | 58.4 |
| 7__134 | 87.3 | 85.7 | 87.5 | 84.2 | 76.5 | 85 |
| 7__134__148 | 92.9 | 88.6 | 93.3 | 91.1 | 100 | 90.2 |
| 7__9__134__148 | 93.7 | 91.4 | 93.9 | 92.1 | 100 | 91.3 |
| 7__134__148__724 | 93.4 | 88.6 | 93.9 | 93.7 | 94.1 | 93.6 |
| 7__22__134__148 | 92.3 | 91.4 | 92.4 | 93.7 | 100 | 93.1 |
| 7__134__148__189 | 92.9 | 88.6 | 93.3 | 91.6 | 100 | 90.8 |
| 7__134__148__714 | 92.6 | 85.7 | 93.3 | 90 | 94.1 | 89.6 |

TABLE 8-9

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 148 | 73.6 | 85.7 | 72.4 | 75.3 | 82.4 | 74.6 |
| 48__148 | 86.3 | 88.6 | 86 | 85.3 | 88.2 | 85 |
| 7__28__148 | 93.7 | 85.7 | 94.5 | 91.6 | 94.1 | 91.3 |
| 7__9__148__726 | 93.7 | 91.4 | 93.9 | 92.1 | 100 | 91.3 |

TABLE 8-9-continued

| SEQ ID NO: | Training cohort ||| Validation cohort |||
| --- | --- | --- | --- | --- | --- | --- |
| | Accuracy (%) | Sensitivity (%) | Specificity (%) | Accuracy (%) | Sensitivity (%) | Specificity (%) |
| 7_9_148_151 | 93.6 | 91.4 | 93.9 | 93.7 | 94.1 | 93.6 |
| 7_9_109_148 | 93.7 | 91.4 | 93.9 | 92.1 | 100 | 91.3 |
| 5_7_9_148 | 92.9 | 91.4 | 93 | 93.2 | 100 | 92.5 |
| 7_9_76_148 | 93.4 | 91.4 | 93.6 | 91.6 | 100 | 90.8 |

TABLE 8-10

| SEQ ID NO: | Training cohort ||| Validation cohort |||
| --- | --- | --- | --- | --- | --- | --- |
| | Accuracy (%) | Sensitivity (%) | Specificity (%) | Accuracy (%) | Sensitivity (%) | Specificity (%) |
| 155 | 60.8 | 65.7 | 60.3 | 58.9 | 64.7 | 58.4 |
| 7_155 | 86.5 | 85.7 | 86.6 | 85.8 | 82.4 | 86.1 |
| 7_148_155 | 90.5 | 85.7 | 91 | 91.6 | 88.2 | 91.9 |
| 7_9_148_155 | 93.4 | 91.4 | 93.6 | 91.6 | 100 | 90.8 |
| 7_38_148_155 | 93.4 | 88.6 | 93.9 | 93.2 | 94.1 | 93.1 |
| 1_9_155_167 | 90 | 94.3 | 89.5 | 92.6 | 100 | 91.9 |
| 1_3_155_715 | 89.7 | 88.6 | 89.8 | 93.2 | 100 | 92.5 |
| 1_3_38_155 | 90 | 88.6 | 90.1 | 93.7 | 94.1 | 93.6 |

TABLE 8-11

| SEQ ID NO: | Training cohort ||| Validation cohort |||
| --- | --- | --- | --- | --- | --- | --- |
| | Accuracy (%) | Sensitivity (%) | Specificity (%) | Accuracy (%) | Sensitivity (%) | Specificity (%) |
| 157 | 70.3 | 71.4 | 70.1 | 68.9 | 94.1 | 66.5 |
| 7_157 | 86.5 | 85.7 | 86.6 | 83.2 | 82.4 | 83.2 |
| 7_148_157 | 91 | 88.6 | 91.3 | 91.6 | 94.1 | 91.3 |
| 7_48_157_714 | 93.9 | 88.6 | 94.5 | 92.6 | 94.1 | 92.5 |
| 7_38_148_157 | 92.3 | 88.6 | 92.7 | 92.6 | 94.1 | 92.5 |
| 1_44_155_157 | 89.4 | 94.3 | 89 | 90.5 | 100 | 89.6 |
| 7_76_157_714 | 92.9 | 82.9 | 93.9 | 90.5 | 94.1 | 90.2 |
| 7_148_157_189 | 91.8 | 88.6 | 92.1 | 92.1 | 94.1 | 91.9 |

TABLE 8-12

| SEQ ID NO: | Training cohort ||| Validation cohort |||
| --- | --- | --- | --- | --- | --- | --- |
| | Accuracy (%) | Sensitivity (%) | Specificity (%) | Accuracy (%) | Sensitivity (%) | Specificity (%) |
| 164 | 72.4 | 82.9 | 71.3 | 65.8 | 76.5 | 64.7 |
| 7_164 | 87.6 | 85.7 | 87.8 | 87.4 | 88.2 | 87.3 |
| 7_148_164 | 91.5 | 85.7 | 92.1 | 92.1 | 94.1 | 91.9 |
| 7_9_148_164 | 92.3 | 91.4 | 92.4 | 91.1 | 94.1 | 90.8 |
| 7_76_164_714 | 91.3 | 85.7 | 91.8 | 94.2 | 94.1 | 94.2 |
| 7_38_164_714 | 92.6 | 82.9 | 93.6 | 90.5 | 82.4 | 91.3 |
| 7_38_148_164 | 92.3 | 88.6 | 92.7 | 91.6 | 94.1 | 91.3 |
| 1_7_164_714 | 90.5 | 85.7 | 91 | 94.2 | 94.1 | 94.2 |

TABLE 8-13

| SEQ ID NO: | Training cohort ||| Validation cohort |||
| --- | --- | --- | --- | --- | --- | --- |
| | Accuracy (%) | Sensitivity (%) | Specificity (%) | Accuracy (%) | Sensitivity (%) | Specificity (%) |
| 167 | 62.1 | 68.6 | 61.4 | 57.4 | 70.6 | 56.1 |
| 7_167 | 89.2 | 85.7 | 89.5 | 87.4 | 82.4 | 87.9 |
| 7_148_167 | 92.1 | 85.7 | 92.7 | 90 | 88.2 | 90.2 |
| 7_9_148_167 | 93.1 | 91.4 | 93.3 | 92.6 | 100 | 91.9 |
| 1_7_167_714 | 92.6 | 85.7 | 93.3 | 94.7 | 100 | 94.2 |
| 7_151_167_714 | 92.9 | 85.7 | 93.6 | 92.1 | 88.2 | 92.5 |

TABLE 8-13-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 7_148_167_189 | 92.9 | 85.7 | 93.6 | 92.6 | 88.2 | 93.1 |
| 7_28_167_714 | 93.4 | 85.7 | 94.2 | 91.1 | 88.2 | 91.3 |

TABLE 8-14

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 172 | 76.8 | 91.4 | 75.4 | 75.8 | 82.4 | 75.1 |
| 7_172 | 86.3 | 85.7 | 86.3 | 83.7 | 76.5 | 84.4 |
| 1_155_172 | 90.2 | 94.3 | 89.8 | 90.5 | 88.2 | 90.8 |
| 7_9_148_172 | 92.1 | 91.4 | 92.1 | 93.2 | 94.1 | 93.1 |
| 7_150_172_714 | 92.1 | 85.7 | 92.7 | 92.1 | 94.1 | 91.9 |
| 7_172_714_715 | 91.3 | 82.9 | 92.2 | 92.1 | 94.1 | 91.9 |
| 7_38_155_172 | 91.3 | 91.4 | 91.3 | 89.5 | 76.5 | 90.8 |
| 1_2_155_172 | 89.7 | 94.3 | 89.2 | 91.6 | 94.1 | 91.3 |

TABLE 8-15

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 214 | 69.5 | 77.1 | 68.7 | 67.4 | 64.7 | 67.6 |
| 7_214 | 89.2 | 85.7 | 89.5 | 87.9 | 82.4 | 88.4 |
| 7_148_214 | 91.5 | 85.7 | 92.1 | 90.5 | 88.2 | 90.8 |
| 7_9_148_214 | 93.4 | 91.4 | 93.6 | 92.6 | 100 | 91.9 |
| 7_148_189_214 | 92.6 | 85.7 | 93.3 | 92.1 | 88.2 | 92.5 |
| 2_7_148_214 | 92.1 | 91.4 | 92.1 | 93.7 | 100 | 93.1 |
| 1_7_214_714 | 91 | 88.6 | 91.3 | 94.7 | 94.1 | 94.8 |
| 7_39_148_214 | 92.1 | 88.6 | 92.4 | 90 | 88.2 | 90.2 |

TABLE 8-16

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 714 | 44.7 | 31.4 | 46.1 | 46.8 | 41.2 | 47.4 |
| 7_714 | 90.2 | 82.9 | 91 | 87.4 | 82.4 | 87.9 |
| 7_157_714 | 92.1 | 85.7 | 92.7 | 91.1 | 94.1 | 90.8 |
| 7_9_148_714 | 93.4 | 91.4 | 93.6 | 92.1 | 94.1 | 91.9 |
| 7_54_148_714 | 93.4 | 88.6 | 93.9 | 95.3 | 94.1 | 95.4 |
| 7_148_151_714 | 94.4 | 88.6 | 95 | 94.2 | 94.1 | 94.2 |
| 7_38_148_714 | 93.4 | 85.7 | 94.2 | 93.2 | 94.1 | 93.1 |
| 7_28_148_714 | 93.9 | 85.7 | 94.8 | 93.7 | 94.1 | 93.6 |

TABLE 8-17

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 715 | 64.2 | 71.4 | 63.5 | 65.8 | 76.5 | 64.7 |
| 7_715 | 87.9 | 85.7 | 88.1 | 86.8 | 94.1 | 86.1 |
| 7_148_715 | 91.8 | 88.6 | 92.1 | 91.1 | 100 | 90.2 |
| 2_7_148_715 | 93.1 | 91.4 | 93.3 | 91.6 | 100 | 90.8 |
| 7_9_148_715 | 93.9 | 91.4 | 94.2 | 93.2 | 100 | 92.5 |
| 7_17_148_715 | 93.7 | 91.4 | 93.9 | 91.1 | 100 | 90.2 |

TABLE 8-17-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 7_38_148_715 | 92.6 | 88.6 | 93 | 91.1 | 100 | 90.2 |
| 7_148_715_725 | 92.3 | 88.6 | 92.7 | 91.6 | 100 | 90.8 |

TABLE 8-18

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 716 | 62.6 | 80 | 60.9 | 58.9 | 70.6 | 57.8 |
| 7_716 | 90.2 | 85.7 | 90.7 | 86.3 | 76.5 | 87.3 |
| 7_148_716 | 91.3 | 85.7 | 91.8 | 91.6 | 88.2 | 91.9 |
| 7_9_148_716 | 93.7 | 91.4 | 93.9 | 92.1 | 100 | 91.3 |
| 7_148_714_716 | 93.1 | 85.7 | 93.9 | 92.1 | 88.2 | 92.5 |
| 2_7_148_716 | 91.8 | 91.4 | 91.8 | 92.6 | 100 | 91.9 |
| 7_38_148_716 | 92.6 | 88.6 | 93 | 92.1 | 94.1 | 91.9 |
| 7_148_715_716 | 91.8 | 88.6 | 92.1 | 91.6 | 100 | 90.8 |

TABLE 8-19

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 717 | 70.3 | 85.7 | 68.7 | 66.3 | 82.4 | 64.7 |
| 7_717 | 86.8 | 85.7 | 86.9 | 84.7 | 82.4 | 85 |
| 7_148_717 | 92.3 | 85.7 | 93 | 90.5 | 88.2 | 90.8 |
| 7_9_148_717 | 93.1 | 91.4 | 93.3 | 92.6 | 100 | 91.9 |
| 7_38_148_717 | 92.3 | 88.6 | 92.7 | 91.6 | 94.1 | 91.3 |
| 7_27_148_717 | 93.1 | 85.7 | 93.9 | 91.6 | 88.2 | 91.9 |
| 7_44_148_717 | 93.1 | 91.4 | 93.3 | 92.1 | 100 | 91.3 |
| 7_148_715_717 | 92.6 | 88.6 | 93 | 91.1 | 100 | 90.2 |

Comparative Example 1

Liver Cancer Discriminant Performance of Existing Tumor Marker in Blood

The concentrations of the existing tumor markers AFP, CEA, CA19-9, and PIVKA-II for detecting liver cancer in blood were measured in the training cohort and the validation cohort obtained in Reference Example 1. When the concentrations of these tumor markers in blood are higher than the reference values described in Non-Patent Literature 5 (AFP: 10 ng/mL, CEA: 5 ng/mL, CA19-9: 37 U/mL, PIVKA-II: 40 mAU/mL), subjects are usually suspected of having cancer. Thus, whether or not the concentration of each tumor marker in blood exceeded its reference value was determined for each sample, and the results were assessed for the ability of these tumor markers to detect cancer in liver cancer patients. The sensitivity of each existing marker in the training cohort and the validation cohort was calculated. The results are shown in Table 5. The sensitivity of AFP, which had the highest sensitivity among the 4 existing tumor markers measured, was as low as 56.3% in the training cohort, and was as low as 53.3% in the validation cohort, demonstrating that neither of the markers are useful in the detection of liver cancer (Table 5).

On the other hand, as shown above in Tables 3 and 6 of Examples 1 and 2, it can be concluded that all of the polynucleotides consisting of the nucleotide sequences represented by SEQ ID NOs: 1 to 183 have combinations of 1 or 2 polynucleotides exhibiting sensitivity beyond the existing liver cancer markers and thus serve as excellent diagnosis markers.

As shown in these Examples and Comparative Example, the kit, etc., and the method of the present invention can detect liver cancer with higher sensitivity than the existing tumor markers and therefore permit early detection of liver cancer. As a result, surgical resection having high potentiality of radical cure can be applied, leading to drastic improvement in survival rate.

INDUSTRIAL APPLICABILITY

According to the present invention, liver cancer can be effectively detected by a simple and inexpensive method. This enables early detection, diagnosis and treatment of liver cancer. The method of the present invention can detect liver cancer with limited invasiveness using the blood of a patient and therefore allows liver cancer to be detected conveniently and rapidly.

All publications, patents, and patent applications cited herein are incorporated herein by reference in their entirety.

The invention claimed is:

1. A method for detecting liver cancer, comprising determining an expression level of hsa-miR-1343-3p in a sample of a subject using a kit comprising a nucleic acid(s), as a primer(s) for PCR, or as a probe(s) for Northern blotting, Southern blotting, or in situ hybridization, capable of specifically binding to hsa-miR-1343-3p, wherein the determining comprises the following steps of:
(a) contacting hsa-miR-1343-3p in the sample or complementary polynucleotide(s) thereof prepared from hsa-miR-1343-3p with the nucleic acid(s);
(b) measuring an expression level of hsa-miR-1343-3p by quantitative RT-PCR using the nucleic acid(s) as the primer(s), or Northern blotting, Southern blotting, or in situ hybridization using the nucleic acids as the probe(s); and
(c) comparing the expression level of hsa-miR-1343-3p measured in step (b) with a control expression level of hsa-miR-1343-3p in a control sample of a healthy subject measured in the same way as in step (b), wherein a lower expression level of hsa-miR-1343-3p in the sample of the subject as compared to the control expression level is detected and is indicative that the subject has liver cancer; and
treating the subject for liver cancer or performing a diagnostic procedure on the liver of the subject, wherein the treatment comprises: surgical resection and/or liver transplantation; local therapy which involves injecting a drug through centesis or performing cauterization to kill cancer; or hepatic arterial embolization; optionally in combination with a drug therapy or radiotherapy, and wherein the diagnostic procedure comprises a palpation or imaging test, wherein the subject is human, and wherein the sample is blood, serum, or plasma.

2. A method for detecting liver cancer, comprising determining an expression level of hsa-miR-1343-3p in a sample of a subject using a device comprising a nucleic acid(s), as a probe(s), capable of specifically binding to hsa-miR-1343-3p, wherein the determining comprises the following steps of:
(a) binding hsa-miR-1343-3p in the sample or cDNA thereof prepared from hsa-miR-1343-3p to the nucleic acid(s) to measure an expression level of hsa-miR-1343-3p by hybridization using the nucleic acid(s); and
(b) comparing the expression level of hsa-miR-1343-3p measured in step (a) with a control expression level of hsa-miR-1343-3p in a control sample of a healthy subject measured in the same way as in step (a), wherein a lower expression level of hsa-miR-1343-3p in the sample of the subject as compared to the control expression level is detected and is indicative that the subject has liver cancer; and
treating the subject for liver cancer or performing a diagnostic procedure on the liver of the subject, wherein the treatment comprises: surgical resection and/or liver transplantation; local therapy which involves injecting a drug through centesis or performing cauterization to kill cancer; or hepatic arterial embolization; optionally in combination with a drug therapy or radiotherapy, and wherein the diagnostic procedure comprises a palpation or imaging test, wherein the subject is human, and wherein the sample is blood, serum, or plasma.

3. The method according to claim 1, wherein step (c) further comprises preparing a discriminant based on a formula.

4. The method according to claim 3, wherein the discriminant is compared to a threshold.

5. The method according to claim 2, wherein step (b) further comprises preparing a discriminant based on a formula.

6. The method according to claim 5, wherein the discriminant is compared to a threshold.

\* \* \* \* \*